United States Patent
Leonard et al.

(10) Patent No.: US 12,091,673 B2
(45) Date of Patent: Sep. 17, 2024

(54) METHODS OF IDENTIFYING, SELECTING, AND PRODUCING SOUTHERN CORN RUST RESISTANT CROPS

(71) Applicants: PIONEER HI-BRED INTERNATIONAL, INC., Johnston, IA (US); HENAN AGRICULTURAL UNIVERSITY, Henan (CN)

(72) Inventors: April L. Leonard, Johnston, IA (US); Jennifer S Jaqueth, Johnston, IA (US); Shawn Thatcher, Johnston, IA (US); Ce Deng, Henan (CN); Meng Lv, Henan (CN); Tangshun Ai, Henan (CN); Junqiang Ding, Henan (CN); Bailin Li, Johnston, IA (US); Girma M. Tabor, Johnston, IA (US)

(73) Assignees: PIONEER HI-BRED INTERNATIONAL, INC., Johnston, IA (US); HENAN AGRICULTURAL UNIVERSITY, Zhengzhou (CN)

( * ) Notice: Subject to any disclaimer, the term of this patent is extended or adjusted under 35 U.S.C. 154(b) by 509 days.

(21) Appl. No.: 17/090,463

(22) Filed: Nov. 5, 2020

(65) Prior Publication Data
US 2021/0222189 A1    Jul. 22, 2021

(30) Foreign Application Priority Data

Nov. 6, 2019 (WO) ................ PCT/CN2019/115925

(51) Int. Cl.
C12N 15/82     (2006.01)
G01N 33/00     (2006.01)

(52) U.S. Cl.
CPC ..... *C12N 15/8282* (2013.01); *C12N 15/8216* (2013.01); *G01N 33/0098* (2013.01); *G01N 2800/60* (2013.01)

(58) Field of Classification Search
None
See application file for complete search history.

(56) References Cited

U.S. PATENT DOCUMENTS

2017/0114356 A1* 4/2017 Li ................. C07K 14/415

FOREIGN PATENT DOCUMENTS

| WO | WO 2010/083178 | 7/2010 |
| WO | WO 2013/098819 | 7/2013 |
| WO | WO 2019/236257 | 12/2019 |

OTHER PUBLICATIONS

Xiuping Wang et al: Gene expression profiles in maize (L.) leaves inoculation with southern corn rust (Underw.), Acta Physiologiae Plantarum, Springer-Verlag, Berlin/Heidelberg, vol. 34, No. 3, Nov. 24, 2011 (Nov. 24, 2011), pp. 997-1006.

Chunjiang Zhou et al. Characterization and fine mapping of RppQ, a resistance gene to southern corn rust in maize , Molecular Genetics and Genomics, Springer, Berlin, DE, vol. 278, No. 6, Oct. 17, 2007 (Oct. 17, 2007), pp. 723-728.

Ya Zhang et al, Mapping of southern corn rust-resistant genes in the W2D inbred line of maize (*Zea mays* L.)11 , Molecular Breeding, Kluwer Academic Pub Li Shers, DO, vol. 25, No. 3, Oct. 8, 2009 (Oct. 8, 2009), pp. 433-439.

CN 106,282,394 A (China Golden Marker (Beijing) Biotech COL TD } Jan. 4, 2017 (Jan. 4, 2017) Especiaiiy Abstract; p. 2, para 5; p. 5, para 1-2; p. 15, para 10.

AC234• 175, Gen Bank Accession No. AC234175, *Zea mays* cultivar 873 chromosome 10 clone CH201-352E9, *** Sequencing in Progress ••• , 22 unordered pieces, Sep. 13, 2014 (Online]. [Retrieved on Jul. 7, 2020). f-letrieved from the internet: <Uf-1L: 11ttps://v1,ww.ncbi.nlm.nih.gov/nuccore/AC234175>).

AC198651, Gen Bank Accession No. AC198651, *Zea mays* cultivar 873 chromosome 10 clone CH201-45H19,  ' Sequencing in Progress* , 11 unordered pieces, Sep. 23, 2013 [online]. [Retrieved on Jul. 7, 2020). f-1etrieved from the internet: <Uf-1L: 11ttps://wNw.ncbi.nlm.nih.gov/nuccore/AC 198651 >).

PCT Search Report and Written Opinion prepared for PCT/US2019/032497, completed Jul. 16, 2019.

C. X. Chen et al, "Molecular tagging and genetic mapping of the disease resistance gene RppQ to southern com rust", Theoretical and Applied Genetics; International Journal of Plant Breeding Research, 1/ol. 108, No. 5, Nov. 18, 2003 (Nov. 18, 2003), p. 945-950.

Wu Xiaojun et al, "Geographic and genetic identification of RppS, a novel locus conferring broad resistance to southern corn rust disease in China", Jan. 30, 2015 (Jan. 30, 2015), vol. 205, No. 1, p. 17-23.

\* cited by examiner

*Primary Examiner* — Mykola V. Kovalenko
*Assistant Examiner* — David R Byrnes
(74) *Attorney, Agent, or Firm* — Barnes & Thornburg LLP

(57) ABSTRACT

The field is related to plant breeding and methods of identifying and selecting plants with resistance to southern corn rust. Provided are methods to identify novel genes that encode proteins providing plant resistance to southern corn rust and uses thereof. These disease resistant genes are useful in the production of resistant plants through breeding, transgenic modification, or genome editing.

3 Claims, No Drawings
Specification includes a Sequence Listing.

SEQUENCE LISTING

```
<160> NUMBER OF SEQ ID NOS: 58

<210> SEQ ID NO 1
<211> LENGTH: 8586
<212> TYPE: DNA
<213> ORGANISM: Zea mays

<400> SEQUENCE: 1
atgtctatcc tggaaaagct cgtccagagc tgttcctttc cagattcatg gcgggggccg     60
```

```
ccagacgctg aggtccaggc tctcatagga tatctcgaag agatacggtc ctccgtcctg    120
gatctttcca aggaggatga ggacgaggat gactctgcta cgtcgtcgtc cacgctgaag    180
atgagcctga cgagccagtt gcaggaactt tgttatgatg ctgaggacta tctggagatg    240
gcgcagcact ctcgtggtgg ctgctcctgg cagatcagtt gggtccggag caaggcgacg    300
aggcagcgcc ccgctctaat cagcgcaaaa gatctctccg gcctcatctc cgtgtgaag     360 ccggcgaaag aaatagccca agcgtacatc aagtctgcta gttcaagaac caccaccaaa    420
gagaatggcc ctaggccaca agaagagcct gcaaaaagca gtagtcgccg tgccgtctat    480
tctgatgata ctctacagcc tgacagccat gacgagcagc tagtcaggtt gctggctttg    540
gaaagtgatc agcagctcaa gacggtggca atccatggcc tgcctggcgt tgggaagaca    600
acacttgcca aagactgta ccactgctat gaagggaggt tccattgcgg ggctttcctt     660
cgggcgtccc gtaacctgca ggacgatacc accaggcttc tcgccaccat gctatccaag    720
attaagggcc aacaagggtg ccgctactgg ggggctccg tgatgagca agatctaatc      780 gacagcatca ggcaacatct acaaggaaaa tcatatttca ttgtgatcga tgatttatgg    840
gctacatcag tgtgggattt cttgagccgt gcttttccca aggataactg tggcagccga    900
atagtaataa ctactcaagt tacagaagtt gcatttgctt gctgtaacaa ccacacagtt    960
gatatattca atatgaaacc tctggacgac gatcagtcac tgcaattgtt ttacagtcga   1020
gtaaagcata taaatggtta taatgctgaa gaatgcaagg ccatatcaca tggaatcgtc   1080
agcaattgtg gtaatctttc accgctagct atcataaata taactggcat gttagcaggc   1140
tgggcggact tcaatatgaa tgattgggag tacgtaagca agtgttgtac gtttacagca   1200
aatcttacta ccgaggaggc gatggagaga tttctgaacc ttatgtacaa caagcttcca   1260
gccaaattga agacgtgcct gctctatctc agtatgtatc cagagggctg tgtcatcgga   1320
aaggatgatt tggtgagaca atgggcagct gaaggtattt tcagtcaagt ggtgaaccca   1380
aaaggtagag aacatgaagt gggttttatt tattttgatg agctcctgaa aagaggattg   1440
atccagcctg tagatacaga ctacaatgat caagtgttgt catgtatagt tcatcaagtg   1500
gtactggaat ttattacaaa gaaatcaatg caggaaaact tcatcactgt cgtggattat   1560
cgtgaaacag ggacagtgct tgatgataat aaggttcatc gactgtctgc caggtttgaa   1620
ggtgccaaaa gtgcacagat accgcggagc ttcagagtac gccaagttcg gtcctttatg   1680 tttctggat tctttaagtc tttaccttcg cttctcaagt attgccttgt ccgagttctg    1740
attcttcgtg tttggagtga tgatcaaggc aagactgtgg ttctagacct ttctccagtt   1800
ggtaatatgc ttcatgtaag gtacctgaag gtggtaagcg acatgatagt caaactccca   1860
ctcattattc gaggcctgcg acacttagag acactcgagg tggatgcaga agaagtcgct   1920
gttccactgg atgttttcat cttgaagagc ctgttgcatc tccgacttcc gagcaaggct   1980
tatcagcttg attcagatat tcaaaggatt ggtttaacaa atacatttcc tttaagtttt   2040
ctgcccttcg tcagaacgtt gtcaatccta ttcctatggc ggtctctcct ctcccatggc   2100
catttgacat cgcttcaaag tcttggctac tttgacctga gcacttgctc cagatatact   2160
gtgcggcaac ttggcaagct gaccaatttg agggatcttc atctaacctg ctctgcagtt   2220
cgttccaggc atcgaattag caacatccaa tgccttgcct ctgttctggg gaaatgcacc   2280
agcctcgaat ctctaactat ccgtggcgaa gcatcttcaa accagagcat ttcttttgat   2340
ggcttaagca gattgtcttc tccaccgtac aacctcgtga gctttgtgct gtccccgagg   2400
```

```
attttcaaaa tggcgaagct ccccaagtgg attgggcaac tcagcaggct cagtacgcta    2460
aagattgctg ttggcgagct gtcaagtgaa gatgttgaca tcctcaaaga actctctgcc    2520
ctcactgctc tttctctcta cgttcgcaga acccctaaga aaggaagctg gatcctattc    2580
agtaagggct tcgcagtgct caagtatttt aagttcactt gcactgcact gtgcgtgaaa    2640
tttagtgaac aagctatgcc tgctgtccaa aggctgaatg tgtgcttcaa tgctaacaca    2700
atgcagcagt acaggccgga agatgcagga atttggtacc tgtcaggcct tcaagttatc    2760
tctgccagaa taggagctgc cggtattgat caagccagca gagaagccgc gaaatctagg    2820
ttgctggacg ccattcttag caaccatcca agcctcctc ctatcagaaa cgtgcaaatg    2880
gtggactggg ttattcatgg cgacacagag gagtgttcaa ccggtgtgat gatacgtaaa    2940
gatgaaagca gccgtgagca tactaggtca tttttaagtc agttcccgtt cagaagacga    3000
cccctgcttc cctccatatt cacaaggcgt ggccaggatg atgagcaaca taaaatcgaa    3060
gaaaatgatg tgctacaaga tagtattatc ttaagggaat cctcttcgct aatgcaaaaa    3120
ccaggttggg tcacccgcag atcaaggagt actggtgttg ccttctgat ggccgtgcga    3180 gggtccacat acatgatcag gcaatatata aaggagccag gattcaatgc agcgaatgag    3240
atggcatcca tcaaccagga gataagacag attggtagaa tggtcatatc aagcaatata    3300
ttggagccgc cggaatggat tctgcaagcc caagacctgg cctgtgatgt gcaggatttc    3360
acggatatct acacatggct gcaaagcaaa tcgcggaggc gtgcccttgc acatataggc    3420
tacatagcgc agctgaagga tcggatcagc agccttcgag agtggcaaca gagaggaggc    3480
agcagcagca gccagcagga gcgtgctgct gccttgtcct tctcgcggcg atcatgcggg    3540
ccttgcgccc ctgaggatgt gctagttggc attgatcagc ccaggaaaga actttcggac    3600
ctcattttcg aaagggagga tgttgtgcaa cagaagccca gggtggtctc tgtcgttggg    3660
tatagtggca ttggcaagac agccctggca agagcagtct actacgaccc tagtgtccgt    3720
tctgccttta cgcgttgc ttgggttgtg catctgaat gcaaccatgg gtgcgacctt    3780
gtaagtaaga tctgccagca ggtcaaggac gaacaagcag ggaacggtgc tgtcgtccct    3840
gactgttata ggttaaaaga gatcatgcgg gataaaaggt tttttatcgt tattgacgac    3900
cttcagggag ctggaatgtg gaacgatata aaaggtgtct tcagtgaaac tcacagtggc    3960
agtcgaataa tcgttaccac gagtattcag tcggtcgccg ctgcctgcac tcctgagccg    4020
cgatacattt acaggatgcc aagtcttggt aatttggact ctgaaaagct actgtggatg    4080
agggtcggca gcatgcaag ccgtacgcct gctctggagc atgctttagg caacgacacc    4140
ttgaaaaaat gcggcggtct acctctggca ctgatcagtg ttgccaatca tttgtgtctt    4200
gggaaagcat tatttgagga gatggacagg gttcttgcca aatgctatga cagcttgcct    4260
gacaatgctc acaggatgtg cttgctgtcc ctgagcacat tccctcaggg tcatgtgatg    4320
aagaggaaga ggctaattag aagatggata gctgaaggat tggctgtcgg agactgtgag    4380
ctcagtgctg aacaagttgc cggtaacata tttgatgtgt tgattgacag gaacgttact    4440
gagcctgtgc tgactgctgg ccacggttct agtagtaagg tcaaggcatg cttagttctt    4500
ggtgtgatca aggacttcat caacaaaacg gcagtctcaa atgagactgt agctataatc    4560
cagaacgatg agcttctcct tcccaacagg atgatgctgg tcgcccatcg tcctgttcgt    4620
cgactgcttg ttcatggagg cacaacaaag aaaagtgaag ctgttgcaaa ggcgatcgga    4680
ctggatcagg tcaggtcgct gacaatctgc aatgctgtgc ccttcgactt ccagggctgc    4740
tggttgctgc gggtcttgga cctggaggct tgccagggga tcgacaagag catccttggc    4800
```

```
agcatatgca agctggtgtt tctcaagtac ctgagcctta ggggcaccga tgtttacgga    4860
atacccaaga aagtaaaaaa gctccagcgt ttggagacgc tggacctcag ggacacacgg    4920
gtggaagaac tgcccatcca agtcttgatg ctcccacggt tggcccatct gtttggcaag    4980
tttgagctac ctccacagct caagcatggt catcgaaccg caaggaggag gaggagtagg    5040
ctgcaggcat ttttctccca gagaagcagg ctgcagactc tttcaggatt cgtcatggtg    5100
gatgatagca acagcttcga gcacatgatg ataaccataa agtcactgag gaaggttaag    5160
gtatggtgca agaattcaat ctcctcccac caagaacgcc atcttgcttc ttcccttcag    5220
caacggctag taggaaacag taatccccta gaatctctgt caattgattt tggcaatgaa    5280
tccatcaatt tcctcaatga tgttggagct accagtgcac ttattggctc tatgaagcta    5340
cagggaaggc taacctcgct ccctagcttc atgacttcgt acgatactac actctcccag    5400
ctgcagctgt cctcaactgg tttgggcata aagccttgt ccctgctgca aatcttacgt     5460
cggctggttt tctgaagct cgctcaggat ggtgatggat tttggggtga ctgcttcgct      5520
gttaacaagg atggatttcc aagccttttta cgcctgtgca ttcaggccag ggagcttccc   5580
cagttgcaca tccatgaagg aggcatgagc tctctcacct ccctcgaact actctgtccc    5640
atgttcgcta gtcgcggtca ctctgactct gactctgact ctgacttggg gaaaacttac    5700
gtggaaaccc attcagagaa gagatccaaa caagttcttt cggtagagaa gcccaaagca    5760
gttgatcccg ggatcagctt caaggaacca agttctgaga caagatcaga aggaactgaa    5820
attcaggaga ttgattcccc taaaacgtcc aaggaggctg gtcccagcat aggcttcaag    5880
gatattattc ttccggagaa cacattcaga agaaactttt cgaaggaagt caaaagtaga    5940
tttgatctga acaacacttt caagggaatg gagtacctcc aatgtctcaa tgagctggta    6000
ctacattgtt ctgttagcga cgaggtattg gatgcctgga caaaacgagc aagcagtcac    6060
atcaataggc caaaggtgac aaggcaatgc acaagagcag cgctgtcgat tggtagaggc    6120
ccgggaacag cgaagcacga aaagaaggg cagcacagaa gccagctcat gaaaaataga    6180
ggttcagaaa cagcaatcca tgaggaggta gcagagcaac acagctcagt aggaacgagc    6240
cgtgaggaag caggattatt ccaagaacag acctcagata caggtcacaa agaagaagaa    6300
gaagaagaag aagaagaatg tacgagtgaa gacagggcat taaatcaacc gtgcgacatg    6360
ctcattggca tggatgtggc aatacgtgaa cttttggagc tggtgaacct ggaagagttt    6420
ggtgtagatg acaaagtgat ctccatcgtg ggatgtccag gtctggggaa gaccacgctc    6480
gcaaaagcat tctctaacct ggaaatgata cgggaaggt tcaacccgcc tgtttgggtt      6540
tcggcatcac aatgccgcag cgcacaggac cttctcatca aggttatccg acaagcttct    6600
catgttcatc cagcacaaat gataagtgct acccccaata tagatctact gcaaactatc    6660
ctagcacagg aaagcttatt gatcatcatc gatgacctac gtgaaactac agcttggaac    6720
tcgatagaga cagccttggg ttcaacaacc tctacgcatg ctggtagcct aataatcgtg    6780
acaacgagga tccaatccat tgctggcaag tgcagcccac acagatacat ctacagaatg    6840
ccaggccttg gccatccgga gtccaaagaa ctattcttga ggacggccta cggtgatgca    6900
catccgacac cgggcgtggc ggacgctgtt gaagaaatct caggggcatg tgatggtctg    6960
ccactggcgt tggttagcgc agctcatgat tggcgtgagc ggcagggca gggttgggaa    7020 ggaagatatg tctttgaaga agtgaacaga gcatttagct ggtggtacga gagtttggcg    7080
gacgcagctc acatgctgtc tctaggcata ttccctatg gccattccat caagcggaag    7140
```

-continued

```
agcctaatta gaagatggat agctgaagga ttggtcagtg aggaaaaaga tggtgatcag      7200
cgattccatg agttggtcga ccagagcatc gtggagcctg tgctaattac tggcagtagt      7260
gatttcaagg tcaagaggtt tcgtcttcgg cgtccggtgc tggagttcat cgtcagggaa      7320
tcagtctcta agaacatggt caaactgctc caaggcgatg agccccttcc aggagaagga      7380
ggaggtcctg tggtgtcgat ttatcaaact acggacacgg aaacatcaag aggaaacatc      7440 atgtccttt ccatattcaa caaggcgtg gctttcgacg acctccaaca atgcacctat         7500
ctccgggtgc tggacctaga acgctgcagg ggggtcgacc acagtgttgt tgctggtata      7560
tgtaaactgt cgcttctcag gtacctgagc ttgaggggca gcgatgtgcg ccacatcccc      7620
agggaaacaa aaggctgaa gtgtctagag accctggaca tccgggagac agtggtgaac         7680
aatctgcctg tggcagccct catgctccca cggctagtcc acctgttcgg caagtttgag      7740
ttgcctcgaa aactcgagga cgagaggata cggggtaagc tcgagagatt cttccgagag      7800
gaaagcagac tacagactct ggctggattg atcatttcta agaacaatgg ctacgagcac      7860
attgtgattc acataaggct actaaggaag attaagatat ggtaccagaa ccacctgctg      7920
cattattcca ccttattgaa cgagcttttt ataagaaaca ctgcactcga ctctttgtcg      7980
gtcgatttcg gggacagctt gatgttccca cacatctctg acatctttgg accctgcatg      8040
ctccgctcca tcaaactgcg aggtcggcat tggccgctgc ctacaattat cgcatcatca      8100
gccaattatc tctccgaggt gcagctgtcc tctactgttc tgccgctcag gtacttgtct      8160
actctgcaga gcttacgccg gctgctttat ctgaagctgg ttgcggatgg atttgtgggt      8220
gacgacaccg acaccttcac tgtgaaaaag gatggattcc caagccttga gaggctctgc      8280
attgaggccc cgaagcttcc acatctgcgc attgttgaag gagccatgcc agctctcacg      8340
tctcttcacc tgctctgtcc gacgatgacg atgatgcctc aacacccggg tcaaatgggc      8400
gaaatcgatg agccggaggc gacatcagaa accaaactgg gcaaggagtg gggaatcgag      8460
tatctcagaa acctcaatga cctggtgttg ccctacactg ttggtgatga acaactcgat      8520
ttctggaagg agaaagcaag gagcaacatg aacaggccaa aggtaaccag gcagccgaag      8580
ccgtaa                                                                 8586
```

<210> SEQ ID NO 2
<211> LENGTH: 5418
<212> TYPE: DNA
<213> ORGANISM: Zea mays

<400> SEQUENCE: 2

```
atggccgtgc gagggtccac atacatgatc aggcaatata taaggagcc aggattcaat         60 gcagcgaatg agatggcatc catcaaccag gagataagac agattggtag aatggtcata      120
tcaagcaata tattggagcc gccggaatgg attctgcaag cccaagacct ggcctgtgat      180
gtgcaggatt tcacggatat ctacacatgg ctgcaaagca atcgcggag gcgtgccctt         240 gcacatatag gctacatagc gcagctgaag gatcggatca gcagccttcg agagtggcaa      300
cagagaggag gcagcagcag cagccagcag gagcgtgctg ctgccttgtc cttctcgcgg      360
cgatcatgcg ggccttgcgc ccctgaggat gtgctagttg cattgatca gcccaggaaa         420 gaactttcgg acctcatttt cgaaagggag gatgttgtgc aacagaagcc agggtggtc         480 tctgtcgttg ggtatagtgg cattggcaag acagccctgg caagagcagt ctactacgac      540
cctagtgtcc gttctgcctt taacggcgtt gcttgggtt tggcatctga atgcaaccat         600
gggtgcgacc ttgtaagtaa gatctgccag caggtcaagg acgaacaagc agggaacggt      660
```

```
gctgtcgtcc ctgactgtta taggttaaaa gagatcatgc gggataaaag gttttttatc    720
gttattgacg accttcaggg agctggaatg tggaacgata taaaaggtgt cttcagtgaa    780
actcacagtg gcagtcgaat aatcgttacc acagtattc agtcggtcgc cgctgcctgc     840
actcctgagc cgcgatacat ttacaggatg ccaagtcttg gtaatttgga ctctgaaaag    900
ctactgtgga tgagggtcgg caggcatgca agccgtacgc ctgctctgga gcatgcttta    960
ggcaacgaca ccttgaaaaa atgcggcggt ctacctctgg cactgatcag tgttgccaat   1020
catttgtgtc ttgggaaagc attatttgag gagatggaca gggttcttgc caaatgctat   1080
gacagcttgc ctgacaatgc tcacaggatg tgcttgctgt ccctgagcac attccctcag   1140
ggtcatgtga tgaagaggaa gaggctaatt agaagatgga tagctgaagg attggctgtc   1200
ggagactgtg agctcagtgc tgaacaagtt gccggtaaca tatttgatgt gttgattgac   1260
aggaacgtta ctgagcctgt gctgactgct ggccacggtt ctagtagtaa ggtcaaggca   1320
tgcttagttc ttggtgtgat caaggacttc atcaacaaaa cggcagtctc aaatgagact   1380
gtagctataa tccagaacga tgagcttctc cttcccaaca ggatgatgct ggtcgcccat   1440
cgtcctgttc gtcgactgct tgttcatgga ggcacaacaa agaaaagtga agctgttgca   1500
aaggcgatcg gactggatca ggtcaggtcg ctgacaatct gcaatgctgt gcccttcgac   1560
ttccagggct gctggttgct gcgggtcttg gacctgaggg cttgccaggg gatcgacaag   1620
agcatccttg gcagcatatg caagctggtg tttctcaagt acctgagcct taggggcacc   1680
gatgtttacg gaatacccaa gaaagtaaaa aagctccagc gttggagac gctggacctc    1740 agggacacac gggtggaaga actgcccatc caagtcttga tgctcccacg gttggcccat   1800
ctgtttggca gtttgagct acctccacag ctcaagcatg gtcatcgaac cgcaaggagg    1860
aggaggagta ggctgcaggc attttttctcc cagagaagca ggctgcagac tctttcagga   1920
ttcgtcatgg tggatgatag caacagcttc gagcacatga tgataaccat aaagtcactg   1980
aggaaggtta aggtatggtg caagaattca atctcctccc accaagaacg ccatcttgct   2040
tcttcccttc agcaacggct agtaggaaac agtaatcccc tagaatctct gtcaattgat   2100
tttggcaatg aatccatcaa tttcctcaat gatgttggag ctaccagtgc acttattggc   2160
tctatgaagc tacagggaag gctaacctcg ctccctagct tcatgacttc gtacgatact   2220
acactctccc agctgcagct gtcctcaact ggtttgggca tagaagcctt gtccctgctg   2280
caaatcttac gtcggctggt ttctctgaag ctcgctcagg atggtgatgg attttggggt   2340
gactgcttcg ctgttaacaa ggatggattt ccaagccttt tacgcctgtg cattcaggcc   2400
agggagcttc cccagttgca catccatgaa ggaggcatga gctctctcac ctccctcgaa   2460
ctactctgtc ccatgttcgc tagtcgcggt cactctgact ctgactctga ctctgacttg   2520
gggaaaactt acgtggaaac ccattcagag aagagatcca acaagttct tcggtagag     2580 aagcccaaag cagttgatcc cgggatcagc ttcaaggaac caagttctga cacaagatca   2640
gaaggaactg aaattcagga gattgattcc cctaaaacgt ccaaggaggc tggtcccagc   2700
ataggcttca aggatattat tcttccggag aacacattca aagaaaactt ttcgaaggaa   2760
gtcaaaagta gatttgatct gaaacaacac ttcaaggga tggagtacct ccaatgtctc    2820
aatgagctgg tactacattg ttctgttagc gacgaggtat tggatgcctg gacaaaacga   2880
gcaagcagtc acatcaatag gccaaaggtg acaaggcaat gcacaagagc agcgctgtcg   2940
attggtagag gcccgggaac agcgaagcac gagaaagaag ggcagcacag aagccagctc   3000
```

```
atgaaaaata gaggttcaga aacagcaatc catgaggagg tagcagagca acacagctca      3060
gtaggaacga gccgtgagga agcaggatta ttccaagaac agacctcaga tacaggtcac      3120
aaagaagaag aagaagaaga agaagaagaa tgtacgagtg aagacagggc attaaatcaa      3180
ccgtgcgaca tgctcattgg catggatgtg gcaatacgtg aacttttgga gctggtgaac      3240
ctggaagagt ttggtgtaga tgacaaagtg atctccatcg tgggatgtcc aggtctgggg      3300
aagaccacgc tcgcaaaagc attctctaac ctggaaatga tacggaaag gttcaacccg       3360 cctgtttggg tttcggcatc acaatgccgc agcgcacagg accttctcat caaggttatc      3420
cgacaagctt ctcatgttca tccagcacaa atgataagtg ctaccoccaa tatagatcta      3480 ctgcaaacta tcctagcaca ggaaagctta ttgatcatca tcgatgacct acgtgaaact      3540
acagcttgga actcgataga gacagccttg ggttcaacaa cctctacgca tgctggtagc      3600
ctaataatcg tgacaacgag gatccaatcc attgctggca agtgcagccc acacagatac      3660
atctacagaa tgccaggcct tggccatccg gagtccaaag aactattctt gaggacggcc      3720
tacggtgatg cacatccgac accgggcgtg gcggacgctg ttgaagaaat ctcagggca       3780 tgtgatggtc tgccactggc gttggttagc gcagctcatg attggcgtga gcggcagggg      3840
cagggttggg aaggaagata tgtctttgaa gaagtgaaca gagcatttag ctggtggtac      3900
gagagtttgg cggacgcagc tcacatgctg tctctaggca tattcccta tggccattcc       3960 atcaagcgga agagcctaat tagaagatgg atagctgaag gattggtcag tgaggaaaaa      4020
gatggtgatc agcgattcca tgagttggtc gaccagagca tcgtggagcc tgtgctaatt      4080
actggcagta gtgatttcaa ggtcaagagg tttcgtcttc ggcgtccggt gctggagttc      4140
atcgtcaggg aatcagtctc taagaacatg gtcaaactgc tccaaggcga tgagcccctt      4200
ccaggagaag gaggaggtcc tgtggtgtcg atttatcaaa ctacggacac ggaaacatca      4260
agaggaaaca tcatgtcctt ttccatattc aacaaggcg tggctttcga cgacctccaa       4320
caatgcacct atctccgggt gctggaccta aacgctgca gggggtcga ccacagtgtt        4380 gttgctggta tatgtaaact gtcgcttctc aggtacctga gcttgagggg cagcgatgtg      4440
cgccacatcc ccagggaaac aaaaaggctg aagtgtctag agaccctgga catccgggag      4500
acagtggtga acaatctgcc tgtggcagcc ctcatgctcc cacggctagt ccacctgttc      4560
ggcaagtttg agttgcctcg aaaactcgag gacgagagga tacggggtaa gctcgagaga      4620
ttcttccgag aggaaagcag actacagact ctggctggat tgatcatttc taagaacaat      4680
ggctacgagc acattgtgat tcacataagg ctactaagga agattaagat atggtaccag      4740
aaccacctgc tgcattattc caccttattg aacgagcttt ttataagaaa cactgcactc      4800
gactctttgt cggtcgattt cggggacagc ttgatgttcc cacacatctc tgacatcttt      4860
ggaccctgca tgctccgctc catcaaactg cgaggtcggc attggccgct gcctacaatt      4920
atcgcatcat cagccaatta tctctccgag gtgcagctgt cctctactgt tctgccgctc      4980
aggtacttgt ctactctgca gagcttacgc cggctgcttt atctgaagct ggttgcggat      5040
ggatttgtgg gtgacgacac cgacaccttc actgtgaaaa aggatggatt cccaagcctt      5100
gagaggctct gcattgaggc cccgaagctt ccacatctgc gcattgttga aggagccatg      5160
ccagctctca cgtctcttca cctgctctgt ccgacgatga cgatgatgcc tcaacacccg      5220
ggtcaaatgg gcgaaatcga tgagccggag gcgacatcag aaaccaaact gggcaaggag      5280
tggggaatcg agtatctcag aaacctcaat gacctggtgt tgcccacac tgttggtgat       5340 gaacaactcg atttctggaa ggagaaagca aggagcaaca tgaacaggcc aaaggtaacc      5400
```

```
aggcagccga agccgtaa                                                   5418

<210> SEQ ID NO 3
<211> LENGTH: 2229
<212> TYPE: DNA
<213> ORGANISM: Zea mays

<400> SEQUENCE: 3
atgctcattg gcatggatgt ggcaatacgt gaacttttgg agctggtgaa cctggaagag     60
tttggtgtag atgacaaagt gatctccatc gtgggatgtc caggtctggg gaagaccacg    120
ctcgcaaaag cattctctaa cctggaaatg atacgggaaa ggttcaaccc gcctgtttgg    180
gtttcggcat cacaatgccg cagcgcacag gaccttctca tcaaggttat ccgacaagct    240
tctcatgttc atccagcaca aatgataagt gctaccccca atatagatct actgcaaact    300
atcctagcac aggaaagctt attgatcatc atcgatgacc tacgtgaaac tacagcttgg    360
aactcgatag agacagcctt gggttcaaca acctctacgc atgctggtag cctaataatc    420
gtgacaacga ggatccaatc cattgctggc aagtgcagcc cacacagata catctacaga    480
atgccaggcc ttggccatcc ggagtccaaa gaactattct tgaggacggc ctacggtgat    540
gcacatccga caccgggcgt ggcggacgct gttgaagaaa tctcaggggc atgtgatggt    600
ctgccactgg cgttggttag cgcagctcat gattggcgtg agcggcaggg gcagggttgg    660
gaaggaagat atgtctttga agaagtgaac agagcattta gctggtggta cgagagtttg    720
gcggacgcag ctcacatgct gtctctaggc atattcccct atggccattc catcaagcgg    780
aagagcctaa ttagaagatg gatagctgaa ggattggtca gtgaggaaaa agatggtgat    840
cagcgattcc atgagttggt cgaccagagc atcgtggagc ctgtgctaat tactggcagt    900
agtgatttca aggtcaagag gtttcgtctt cggcgtccgg tgctggagtt catcgtcagg    960
gaatcagtct ctaagaacat ggtcaaactg ctccaaggcg atgagcccct tccaggagaa   1020
ggaggaggtc ctgtggtgtc gatttatcaa actacggaca cggaaacatc aagaggaaac   1080
atcatgtcct tttccatatt caacaaaggc gtggctttcg acgacctcca acaatgcacc   1140
tatctccggg tgctggacct agaacgctgc aggggggtcg accacagtgt tgttgctggt   1200
atatgtaaac tgtcgcttct caggtacctg agcttgaggg gcagcgatgt gcgccacatc   1260
cccagggaaa caaaaaggct gaagtgtcta gagaccctgg acatccggga gacagtggtg   1320
aacaatctgc ctgtggcagc cctcatgctc ccacggctag tccacctgtt cggcaagttt   1380
gagttgcctc gaaaactcga ggacgagagg atacggggta agctcgagag attcttccga   1440
gaggaaagca gactacagac tctggctgga ttgatcattt ctaagaacaa tggctacgag   1500
cacattgtga ttcacataag gctactaagg aagattaaga tatggtacca gaaccacctg   1560
ctgcattatt ccaccttatt gaacgagctt tttataagaa acactgcact cgactctttg   1620
tcggtcgatt tcggggacag cttgatgttc ccacacatct ctgacatctt ggaccctgc    1680
atgctccgct ccatcaaact gcgaggtcgg cattggccgc tgcctacaat tatcgcatca   1740
tcagccaatt atctctccga ggtgcagctg tcctctactg ttctgccgct caggtacttg   1800
tctactctgc agagcttacg ccggctgctt tatctgaagc tggttgcgga tggatttgtg   1860
ggtgacgaca ccgacaccct cactgtgaaa aaggatggat tcccaagcct tgagaggctc   1920
tgcattgagg ccccgaagct tccacatctg cgcattgttg aaggagccat gccagctctc   1980
acgtctcttc acctgctctg tccgacgatg acgatgatgc ctcaacaccc gggtcaaatg   2040
```

```
ggcgaaatcg atgagccgga ggcgacatca gaaaccaaac tgggcaagga gtggggaatc    2100
gagtatctca gaaaccctca tgacctggtg ttgccctaca ctgttggtga tgaacaactc    2160
gatttctgga aggagaaagc aaggagcaac atgaacaggc caaaggtaac caggcagccg    2220
aagccgtaa                                                            2229
```

<210> SEQ ID NO 4
<211> LENGTH: 3485
<212> TYPE: DNA
<213> ORGANISM: Zea mays

<400> SEQUENCE: 4

```
ctgcgaccta accatcaccc gtgcccggcc cagtggaccc acacagacac agctcgatga      60
ttcgagtata tgaatgtcct cctgagatct caaagtccta cgctgctata ccttccaaca     120
tcctcccaac cagccatacc tgcggatcga actcgagcca agcaacagag agggggggtt     180
ggagagatga caggtgtgga gccagcagtt atcggtgcaa tcgctaagtt ggcggcccct     240
gtcctgccta tagccattaa agggatacaa gatgcactga gaaacggca  agtccgtgac     300 agtgatgttg aaaccctgaa atcccagctt agctacatcc agggcatcat ccgtgatact     360
cggaagacta tcaggagttc ccaagacccg tccgacaggc ttcaatcctg gtctggatac     420
ctcagatgct ggcgtacga  catcgaagac ctaatagcag ccaccgtgt  cggaaccatg     480 acaggtgcga agcttaatgg caagattact atcatccagg atttaatcag atgtgtagag     540
tcctatccgg agtttatggc ggttccgacg aatgaggctc ctagtcaagg cgctgcttct     600
tcctccacta cttcaagcac ccagggcttt ccgctggctg atcttgtggg caagaaggag     660
gacctcgatg agcttctgga cctcctcgtc tggagacccg caatgagct  ggacaaggtc     720 ctcaaggtga tggtgatctc cgtcgtcggc ttcgtggca  tagggagac  caagcttttgc    780 cacacagtgt acacggacgt acaggagagc agaaagttct ccctgcatgc gtatgtcagc     840
gctgctggga aggactgcag catcgttctg aagagataa  tcgagcaatt tagactgcaa     900
gaggatccac tagatagcag tggtggattt tttcacagat cgccggagc  gtttcctggg     960 gctcgtcgta ctgaccaagt tcatgagtta cccgagtatc tccaaaggaa aaggtatttt    1020
gtggtggtgg atggcgtgga gtctgaagaa ctggtgggtg gcatagcatc tgccttcccg    1080
gataatagta tgggcagtag aattatcatg ggtatgagga ccgcagtggg cagggatgca    1140
gagagatgtg tgggtcatcg tcacaagatg tggccacttg aagacaagca gtcggtggtc    1200
tgcttcctaa atgaagcgga gcggcggcg  cggcgacgac gacgcatga  acaagacgac    1260 cactcgtcgt tcattacgtt tcaggaacaa gaccactcat catcctgttt gcacaagata    1320
tgtgatggcg taccacttgc gctggttagc gtatgcgaag tccgcagagg gtccatcatc    1380
actgctgccg ttgaagaaca agaccgctgg ccacacagaa tgcccaaggt gctcgaccac    1440
agctacgatg gtctgcatat ccggggtgct ggggctgtc  cgaaccaata catcccctat    1500
ctccaagcct gcctgctgta ctttgccatg ttccccgcg  gcaatcatgt caagagggga    1560
tccctgatca ggcgatggca ggcggaaggc ctagagttcg gaggcagcaa tatccacaat    1620
caagctgccg aaaacctcaa ggccctcgta gaccggaact tcgtttggcc cctccatgcg    1680
agcctgaatg agcacgccaa gacattccag cctcctggag tggtgctcaa ctacatctcc    1740
cgcaggtctg aagaggagga attcatcctc aggtcttgtc aaccggggga tcttaatccc    1800
aattacagcc gccggctttg tctacatcct gccgaggaag aagaaggtga accccaaccc    1860
ttggtcatca ccaacggttc tgtaccacca cgcctgcgaa ctctggctgt gtcctggggg    1920
```

```
cagcaacagg ccagcaggat tgctgaatgc gagcagctcc gagtgctgga tctggcgtca    1980
tacaacggtc tacagccaga ccagctagag gagatatgca agaaactgaa gcttctcaaa    2040
tatctgagcc tcctgccaga tatcatcact caagttccaa gctcaatgtc taatttgcag    2100
tgcttggaga cactcgagtt gggggaggtc aatggcaggg cggcagttct ggtgcctatc    2160
caagtcttgg aactgccatg cataaaacac ctaatcggaa aatttgagct tattgacaac    2220
ttcaacggag taccaattag ggcttatcca gatgcactag taccaaaggc aatcaaggaa    2280
agcaacctgg agacggtgtc ggggttcttc acccacagag gccaaggatt ccgccactc     2340
atgcgtcaca tgaggcagct caggaaggtg aagatatggt tctacaggga tgcagaaccc    2400
aaatacctag caagctatct cccgaaagcg attacaaaat tcctcaggaa tgacaacgtt    2460
cctcgctccc tgtcacttga cttccaggat ggcccaagac aaacagaaat actgcaggct    2520
tgtgtggctg aagctagggg taatctttac tccctgaagc tgtcgtccgg cacaaatctg    2580
agcaggatcc aactgtcggt tattgccacc aacaagcagc tgactggaat cacaaagcta    2640
tgcctttccc gctggaaaac gataacgttg gatgcagaat ttctgaatga gctgagcaga    2700
ttggtccatc taaggtatct gaagctggat gcagaaacaa taaaaggtac gtacgaccaa    2760
aacccaacac caggaggaaa taaccaagag aaggtcgtca tagagactgg cacattgca     2820
aatctgcggc ggatgtggct tgtggccagg cagacgctgc ccgacataca agtcaagcct    2880
acagctctgc aacgactcgt ttcacttcat ctcatcagtg aaacggacga ttattgtcct    2940
tccgccaacg tcatctgtaa agccaacccc caggacgaca acgagctggc gccgttcacg    3000
agcctccagg aagtctcgct gaatgctacg gtacccgaaa atttaaggga ttcttggcgt    3060
aatgctgcaa gggaccatcc aaagaggcca cgaattctct tcatccaaca ccctcaccgt    3120
gcgggataac ccctatatgt tcttcgtttg aaacctccaa gttcgatctg tcagtttctc    3180
cacgcagtgc tcctgcttct tcaagattga ttcgtctcca tatatactat acttgcctcc    3240
accttcatcc aaataatgtt ttttttaaaag atcaggaggg ggtcatccaa ataatgtttg    3300
attgtattct ttttgtatac tgcggttttg tatccgttga ggtaatttt caagcataaa     3360
tcaacttcca tgctgttttt gtttattcaa ggttttgag gcttctgctg tgacatgtgt     3420
aatcatgtac gatatattac tgcacattat gcttttgtt agtgctgctg agggatgaag      3480
gttgc                                                                3485
```

<210> SEQ ID NO 5
<211> LENGTH: 2861
<212> TYPE: PRT
<213> ORGANISM: Zea mays

<400> SEQUENCE: 5

Met Ser Ile Leu Glu Lys Leu Val Gln Ser Cys Ser Phe Pro Asp Ser
1               5                   10                  15

Trp Arg Gly Pro Pro Asp Ala Glu Val Gln Ala Leu Ile Gly Tyr Leu
            20                  25                  30

Glu Glu Ile Arg Ser Ser Val Leu Asp Leu Ser Lys Glu Asp Glu Asp
        35                  40                  45

Glu Asp Asp Ser Ala Thr Ser Ser Ser Thr Leu Lys Met Ser Leu Thr
    50                  55                  60

Ser Gln Leu Gln Glu Leu Cys Tyr Asp Ala Glu Asp Tyr Leu Glu Met
65                  70                  75                  80

Ala Gln His Ser Arg Gly Gly Cys Ser Trp Gln Ile Ser Trp Val Arg

```
                    85                  90                  95
Ser Lys Ala Thr Arg Gln Arg Pro Ala Leu Ile Ser Ala Lys Asp Leu
                100                 105                 110

Ser Gly Leu Ile Ser Arg Val Lys Pro Ala Lys Glu Ile Ala Gln Ala
                115                 120                 125

Tyr Ile Lys Ser Ala Ser Arg Thr Thr Lys Glu Asn Gly Pro
            130                 135                 140

Arg Pro Gln Glu Glu Pro Ala Lys Ser Ser Arg Arg Ala Val Tyr
145                 150                 155                 160

Ser Asp Asp Thr Leu Gln Pro Asp Ser His Asp Glu Gln Leu Val Arg
                165                 170                 175

Leu Leu Ala Leu Glu Ser Asp Gln Gln Leu Lys Thr Val Ala Ile His
                180                 185                 190

Gly Leu Pro Gly Val Gly Lys Thr Thr Leu Ala Arg Arg Leu Tyr His
                195                 200                 205

Cys Tyr Glu Gly Arg Phe His Cys Gly Ala Phe Leu Arg Ala Ser Arg
        210                 215                 220

Asn Leu Gln Asp Asp Thr Thr Arg Leu Leu Ala Thr Met Leu Ser Lys
225                 230                 235                 240

Ile Lys Gly Gln Gln Gly Cys Arg Tyr Trp Gly Gly Ser Gly Asp Glu
                245                 250                 255

Gln Asp Leu Ile Asp Ser Ile Arg Gln His Leu Gln Gly Lys Ser Tyr
                260                 265                 270

Phe Ile Val Ile Asp Asp Leu Trp Ala Thr Ser Val Trp Asp Phe Leu
            275                 280                 285

Ser Arg Ala Phe Pro Lys Asp Asn Cys Gly Ser Arg Ile Val Ile Thr
        290                 295                 300

Thr Gln Val Thr Glu Val Ala Phe Ala Cys Cys Asn Asn His Thr Val
305                 310                 315                 320

Asp Ile Phe Asn Met Lys Pro Leu Asp Asp Gln Ser Leu Gln Leu
                325                 330                 335

Phe Tyr Ser Arg Val Lys His Ile Asn Gly Tyr Asn Ala Glu Glu Cys
            340                 345                 350

Lys Ala Ile Ser His Gly Ile Val Ser Asn Cys Gly Asn Leu Ser Pro
            355                 360                 365

Leu Ala Ile Ile Asn Ile Thr Gly Met Leu Ala Gly Trp Ala Asp Phe
            370                 375                 380

Asn Met Asn Asp Trp Glu Tyr Val Ser Lys Cys Cys Thr Phe Thr Ala
385                 390                 395                 400

Asn Leu Thr Thr Glu Glu Ala Met Glu Arg Phe Leu Asn Leu Met Tyr
                405                 410                 415

Asn Lys Leu Pro Ala Lys Leu Lys Thr Cys Leu Leu Tyr Leu Ser Met
                420                 425                 430

Tyr Pro Glu Gly Cys Val Ile Gly Lys Asp Asp Leu Val Arg Gln Trp
            435                 440                 445

Ala Ala Glu Gly Ile Phe Ser Gln Val Val Glu Pro Lys Gly Arg Glu
            450                 455                 460

His Glu Val Gly Phe Ile Tyr Phe Asp Glu Leu Leu Lys Arg Gly Leu
465                 470                 475                 480

Ile Gln Pro Val Asp Thr Asp Tyr Asn Asp Gln Val Leu Ser Cys Ile
                485                 490                 495

Val His Gln Val Val Leu Glu Phe Ile Thr Lys Lys Ser Met Gln Glu
                500                 505                 510
```

```
Asn Phe Ile Thr Val Val Asp Tyr Arg Glu Thr Gly Thr Val Leu Asp
            515                 520                 525

Asp Asn Lys Val His Arg Leu Ser Ala Arg Phe Glu Gly Ala Lys Ser
        530                 535                 540

Ala Gln Ile Pro Arg Ser Phe Arg Val Arg Gln Val Arg Ser Phe Met
545                 550                 555                 560

Phe Ser Gly Phe Phe Lys Ser Leu Pro Ser Leu Leu Lys Tyr Cys Leu
                565                 570                 575

Val Arg Val Leu Ile Leu Arg Val Trp Ser Asp Asp Gln Gly Lys Thr
            580                 585                 590

Val Val Leu Asp Leu Ser Pro Val Gly Asn Met Leu His Val Arg Tyr
        595                 600                 605

Leu Lys Val Val Ser Asp Met Ile Val Lys Leu Pro Leu Ile Ile Arg
    610                 615                 620

Gly Leu Arg His Leu Glu Thr Leu Glu Val Asp Ala Glu Glu Val Ala
625                 630                 635                 640

Val Pro Leu Asp Val Phe Ile Leu Lys Ser Leu Leu His Leu Arg Leu
                645                 650                 655

Pro Ser Lys Ala Tyr Gln Leu Asp Ser Asp Ile Gln Arg Ile Gly Leu
            660                 665                 670

Thr Asn Thr Phe Pro Leu Ser Phe Leu Pro Phe Val Arg Thr Leu Ser
        675                 680                 685

Ile Leu Phe Leu Trp Arg Ser Leu Leu Ser His Gly His Leu Thr Ser
    690                 695                 700

Leu Gln Ser Leu Gly Tyr Phe Asp Leu Ser Thr Cys Ser Arg Tyr Thr
705                 710                 715                 720

Val Arg Gln Leu Gly Lys Leu Thr Asn Leu Arg Asp Leu His Leu Thr
                725                 730                 735

Cys Ser Ala Val Arg Ser Arg His Arg Ile Ser Asn Ile Gln Cys Leu
            740                 745                 750

Ala Ser Val Leu Gly Lys Cys Thr Ser Leu Glu Ser Leu Thr Ile Arg
        755                 760                 765

Gly Glu Ala Ser Ser Asn Gln Ser Ile Ser Phe Asp Gly Leu Ser Arg
    770                 775                 780

Leu Ser Ser Pro Pro Tyr Asn Leu Val Ser Phe Val Leu Ser Pro Arg
785                 790                 795                 800

Ile Phe Lys Met Ala Lys Leu Pro Lys Trp Ile Gly Gln Leu Ser Arg
                805                 810                 815

Leu Ser Thr Leu Lys Ile Ala Val Gly Glu Leu Ser Ser Glu Asp Val
            820                 825                 830

Asp Ile Leu Lys Glu Leu Ser Ala Leu Thr Ala Leu Ser Leu Tyr Val
        835                 840                 845

Arg Arg Asn Pro Lys Lys Gly Ser Trp Ile Leu Phe Ser Lys Gly Phe
    850                 855                 860

Ala Val Leu Lys Tyr Phe Lys Phe Thr Cys Thr Ala Leu Cys Val Lys
865                 870                 875                 880

Phe Ser Glu Gln Ala Met Pro Ala Val Gln Arg Leu Asn Val Cys Phe
                885                 890                 895

Asn Ala Asn Thr Met Gln Gln Tyr Arg Pro Glu Asp Ala Gly Ile Trp
            900                 905                 910

Tyr Leu Ser Gly Leu Gln Val Ile Ser Ala Arg Ile Gly Ala Ala Gly
        915                 920                 925
```

-continued

```
Ile Asp Gln Ala Ser Arg Glu Ala Ala Lys Ser Arg Leu Leu Asp Ala
930                 935                 940

Ile Leu Ser Asn His Pro Lys Pro Pro Ile Arg Asn Val Gln Met
945                 950                 955                 960

Val Asp Trp Val Ile His Gly Asp Thr Glu Glu Cys Ser Thr Gly Val
                965                 970                 975

Met Ile Arg Lys Asp Glu Ser Ser Arg Glu His Thr Arg Ser Phe Leu
                980                 985                 990

Ser Gln Phe Pro Phe Arg Arg Arg Pro Leu Leu Pro Ser Ile Phe Thr
                995                 1000                1005

Arg Arg Gly Gln Asp Asp Glu Gln His Lys Ile Glu Glu Asn Asp
    1010                1015                1020

Val Leu Gln Asp Ser Ile Ile Leu Arg Glu Ser Ser Ser Leu Met
    1025                1030                1035

Gln Lys Pro Gly Trp Val Thr Arg Arg Ser Arg Ser Thr Gly Val
    1040                1045                1050

Gly Leu Leu Met Ala Val Arg Gly Ser Thr Tyr Met Ile Arg Gln
    1055                1060                1065

Tyr Ile Lys Glu Pro Gly Phe Asn Ala Ala Asn Glu Met Ala Ser
    1070                1075                1080

Ile Asn Gln Glu Ile Arg Gln Ile Gly Arg Met Val Ile Ser Ser
    1085                1090                1095

Asn Ile Leu Glu Pro Pro Glu Trp Ile Leu Gln Ala Gln Asp Leu
    1100                1105                1110

Ala Cys Asp Val Gln Asp Phe Thr Asp Ile Tyr Thr Trp Leu Gln
    1115                1120                1125

Ser Lys Ser Arg Arg Arg Ala Leu Ala His Ile Gly Tyr Ile Ala
    1130                1135                1140

Gln Leu Lys Asp Arg Ile Ser Ser Leu Arg Glu Trp Gln Gln Arg
    1145                1150                1155

Gly Gly Ser Ser Ser Ser Gln Gln Glu Arg Ala Ala Ala Leu Ser
    1160                1165                1170

Phe Ser Arg Arg Ser Cys Gly Pro Cys Ala Pro Glu Asp Val Leu
    1175                1180                1185

Val Gly Ile Asp Gln Pro Arg Lys Glu Leu Ser Asp Leu Ile Phe
    1190                1195                1200

Glu Arg Glu Asp Val Val Gln Gln Lys Pro Arg Val Val Ser Val
    1205                1210                1215

Val Gly Tyr Ser Gly Ile Gly Lys Thr Ala Leu Ala Arg Ala Val
    1220                1225                1230

Tyr Tyr Asp Pro Ser Val Arg Ser Ala Phe Asn Gly Val Ala Trp
    1235                1240                1245

Val Val Ala Ser Glu Cys Asn His Gly Cys Asp Leu Val Ser Lys
    1250                1255                1260

Ile Cys Gln Gln Val Lys Asp Glu Gln Ala Gly Asn Gly Ala Val
    1265                1270                1275

Val Pro Asp Cys Tyr Arg Leu Lys Glu Ile Met Arg Asp Lys Arg
    1280                1285                1290

Phe Phe Ile Val Ile Asp Asp Leu Gln Gly Ala Gly Met Trp Asn
    1295                1300                1305

Asp Ile Lys Gly Val Phe Ser Glu Thr His Ser Gly Ser Arg Ile
    1310                1315                1320

Ile Val Thr Thr Ser Ile Gln Ser Val Ala Ala Ala Cys Thr Pro
```

```
            1325                    1330                    1335

Glu Pro Arg Tyr Ile Tyr Arg Met Pro Ser Leu Gly Asn Leu Asp
    1340                    1345                    1350

Ser Glu Lys Leu Leu Trp Met Arg Val Gly Arg His Ala Ser Arg
    1355                    1360                    1365

Thr Pro Ala Leu Glu His Ala Leu Gly Asn Asp Thr Leu Lys Lys
    1370                    1375                    1380

Cys Gly Gly Leu Pro Leu Ala Leu Ile Ser Val Ala Asn His Leu
    1385                    1390                    1395

Cys Leu Gly Lys Ala Leu Phe Glu Glu Met Asp Arg Val Leu Ala
    1400                    1405                    1410

Lys Cys Tyr Asp Ser Leu Pro Asp Asn Ala His Arg Met Cys Leu
    1415                    1420                    1425

Leu Ser Leu Ser Thr Phe Pro Gln Gly His Val Met Lys Arg Lys
    1430                    1435                    1440

Arg Leu Ile Arg Arg Trp Ile Ala Glu Gly Leu Ala Val Gly Asp
    1445                    1450                    1455

Cys Glu Leu Ser Ala Glu Gln Val Ala Gly Asn Ile Phe Asp Val
    1460                    1465                    1470

Leu Ile Asp Arg Asn Val Thr Glu Pro Val Leu Thr Ala Gly His
    1475                    1480                    1485

Gly Ser Ser Ser Lys Val Lys Ala Cys Leu Val Leu Gly Val Ile
    1490                    1495                    1500

Lys Asp Phe Ile Asn Lys Thr Ala Val Ser Asn Glu Thr Val Ala
    1505                    1510                    1515

Ile Ile Gln Asn Asp Glu Leu Leu Leu Pro Asn Arg Met Met Leu
    1520                    1525                    1530

Val Ala His Arg Pro Val Arg Arg Leu Leu Val His Gly Gly Thr
    1535                    1540                    1545

Thr Lys Lys Ser Glu Ala Val Ala Lys Ala Ile Gly Leu Asp Gln
    1550                    1555                    1560

Val Arg Ser Leu Thr Ile Cys Asn Ala Val Pro Phe Asp Phe Gln
    1565                    1570                    1575

Gly Cys Trp Leu Leu Arg Val Leu Asp Leu Glu Ala Cys Gln Gly
    1580                    1585                    1590

Ile Asp Lys Ser Ile Leu Gly Ser Ile Cys Lys Leu Val Phe Leu
    1595                    1600                    1605

Lys Tyr Leu Ser Leu Arg Gly Thr Asp Val Tyr Gly Ile Pro Lys
    1610                    1615                    1620

Lys Val Lys Lys Leu Gln Arg Leu Glu Thr Leu Asp Leu Arg Asp
    1625                    1630                    1635

Thr Arg Val Glu Glu Leu Pro Ile Gln Val Leu Met Leu Pro Arg
    1640                    1645                    1650

Leu Ala His Leu Phe Gly Lys Phe Glu Leu Pro Pro Gln Leu Lys
    1655                    1660                    1665

His Gly His Arg Thr Ala Arg Arg Arg Ser Arg Leu Gln Ala
    1670                    1675                    1680

Phe Phe Ser Gln Arg Ser Arg Leu Gln Thr Leu Ser Gly Phe Val
    1685                    1690                    1695

Met Val Asp Asp Ser Asn Ser Phe Glu His Met Met Ile Thr Ile
    1700                    1705                    1710

Lys Ser Leu Arg Lys Val Lys Val Trp Cys Lys Asn Ser Ile Ser
    1715                    1720                    1725
```

-continued

```
Ser His Gln Glu Arg His Leu Ala Ser Ser Leu Gln Gln Arg Leu
    1730                1735                1740

Val Gly Asn Ser Asn Pro Leu Glu Ser Leu Ser Ile Asp Phe Gly
    1745                1750                1755

Asn Glu Ser Ile Asn Phe Leu Asn Asp Val Gly Ala Thr Ser Ala
    1760                1765                1770

Leu Ile Gly Ser Met Lys Leu Gln Gly Arg Leu Thr Ser Leu Pro
    1775                1780                1785

Ser Phe Met Thr Ser Tyr Asp Thr Thr Leu Ser Gln Leu Gln Leu
    1790                1795                1800

Ser Ser Thr Gly Leu Gly Ile Glu Ala Leu Ser Leu Leu Gln Ile
    1805                1810                1815

Leu Arg Arg Leu Val Ser Leu Lys Leu Ala Gln Asp Gly Asp Gly
    1820                1825                1830

Phe Trp Gly Asp Cys Phe Ala Val Asn Lys Asp Gly Phe Pro Ser
    1835                1840                1845

Leu Leu Arg Leu Cys Ile Gln Ala Arg Glu Leu Pro Gln Leu His
    1850                1855                1860

Ile His Glu Gly Gly Met Ser Ser Leu Thr Ser Leu Glu Leu Leu
    1865                1870                1875

Cys Pro Met Phe Ala Ser Arg Gly His Ser Asp Ser Asp Ser Asp
    1880                1885                1890

Ser Asp Leu Gly Lys Thr Tyr Val Glu Thr His Ser Glu Lys Arg
    1895                1900                1905

Ser Lys Gln Val Leu Ser Val Glu Lys Pro Lys Ala Val Asp Pro
    1910                1915                1920

Gly Ile Ser Phe Lys Glu Pro Ser Ser Glu Thr Arg Ser Glu Gly
    1925                1930                1935

Thr Glu Ile Gln Glu Ile Asp Ser Pro Lys Thr Ser Lys Glu Ala
    1940                1945                1950

Gly Pro Ser Ile Gly Phe Lys Asp Ile Ile Leu Pro Glu Asn Thr
    1955                1960                1965

Phe Arg Arg Asn Phe Ser Lys Glu Val Lys Ser Arg Phe Asp Leu
    1970                1975                1980

Lys Gln His Phe Lys Gly Met Glu Tyr Leu Gln Cys Leu Asn Glu
    1985                1990                1995

Leu Val Leu His Cys Ser Val Ser Asp Glu Val Leu Asp Ala Trp
    2000                2005                2010

Thr Lys Arg Ala Ser Ser His Ile Asn Arg Pro Lys Val Thr Arg
    2015                2020                2025

Gln Cys Thr Arg Ala Ala Leu Ser Ile Gly Arg Gly Pro Gly Thr
    2030                2035                2040

Ala Lys His Glu Lys Glu Gly Gln His Arg Ser Gln Leu Met Lys
    2045                2050                2055

Asn Arg Gly Ser Glu Thr Ala Ile His Glu Glu Val Ala Glu Gln
    2060                2065                2070

His Ser Ser Val Gly Thr Ser Arg Glu Glu Ala Gly Leu Phe Gln
    2075                2080                2085

Glu Gln Thr Ser Asp Thr Gly His Lys Glu Glu Glu Glu Glu Glu
    2090                2095                2100

Glu Glu Glu Cys Thr Ser Glu Asp Arg Ala Leu Asn Gln Pro Cys
    2105                2110                2115
```

```
Asp Met Leu Ile Gly Met Asp Val Ala Ile Arg Glu Leu Leu Glu
2120                2125                2130

Leu Val Asn Leu Glu Glu Phe Gly Val Asp Lys Val Ile Ser
    2135                2140                2145

Ile Val Gly Cys Pro Gly Leu Gly Lys Thr Thr Leu Ala Lys Ala
2150                2155                2160

Phe Ser Asn Leu Glu Met Ile Arg Glu Arg Phe Asn Pro Pro Val
    2165                2170                2175

Trp Val Ser Ala Ser Gln Cys Arg Ser Ala Gln Asp Leu Leu Ile
    2180                2185                2190

Lys Val Ile Arg Gln Ala Ser His Val His Pro Ala Gln Met Ile
    2195                2200                2205

Ser Ala Thr Pro Asn Ile Asp Leu Leu Gln Thr Ile Leu Ala Gln
    2210                2215                2220

Glu Ser Leu Leu Ile Ile Ile Asp Asp Leu Arg Glu Thr Thr Ala
    2225                2230                2235

Trp Asn Ser Ile Glu Thr Ala Leu Gly Ser Thr Thr Ser Thr His
    2240                2245                2250

Ala Gly Ser Leu Ile Ile Val Thr Thr Arg Ile Gln Ser Ile Ala
    2255                2260                2265

Gly Lys Cys Ser Pro His Arg Tyr Ile Tyr Arg Met Pro Gly Leu
    2270                2275                2280

Gly His Pro Glu Ser Lys Glu Leu Phe Leu Arg Thr Ala Tyr Gly
    2285                2290                2295

Asp Ala His Pro Thr Pro Gly Val Ala Asp Ala Val Glu Glu Ile
    2300                2305                2310

Ser Gly Ala Cys Asp Gly Leu Pro Leu Ala Leu Val Ser Ala Ala
    2315                2320                2325

His Asp Trp Arg Glu Arg Gln Gly Gln Gly Trp Glu Gly Arg Tyr
    2330                2335                2340

Val Phe Glu Glu Val Asn Arg Ala Phe Ser Trp Trp Tyr Glu Ser
    2345                2350                2355

Leu Ala Asp Ala Ala His Met Leu Ser Leu Gly Ile Phe Pro Tyr
    2360                2365                2370

Gly His Ser Ile Lys Arg Lys Ser Leu Ile Arg Arg Trp Ile Ala
    2375                2380                2385

Glu Gly Leu Val Ser Glu Glu Lys Asp Gly Asp Gln Arg Phe His
    2390                2395                2400

Glu Leu Val Asp Gln Ser Ile Val Glu Pro Val Leu Ile Thr Gly
    2405                2410                2415

Ser Ser Asp Phe Lys Val Lys Arg Phe Arg Leu Arg Arg Pro Val
    2420                2425                2430

Leu Glu Phe Ile Val Arg Glu Ser Val Ser Lys Asn Met Val Lys
    2435                2440                2445

Leu Leu Gln Gly Asp Glu Pro Leu Pro Gly Glu Gly Gly Pro
    2450                2455                2460

Val Val Ser Ile Tyr Gln Thr Thr Asp Thr Glu Thr Ser Arg Gly
    2465                2470                2475

Asn Ile Met Ser Phe Ser Ile Phe Asn Lys Gly Val Ala Phe Asp
    2480                2485                2490

Asp Leu Gln Gln Cys Thr Tyr Leu Arg Val Leu Asp Leu Glu Arg
    2495                2500                2505

Cys Arg Gly Val Asp His Ser Val Val Ala Gly Ile Cys Lys Leu
```

```
                    2510                2515                2520

Ser Leu Leu Arg Tyr Leu Ser Leu Arg Gly Ser Asp Val Arg His
    2525                2530                2535

Ile Pro Arg Glu Thr Lys Arg Leu Lys Cys Leu Glu Thr Leu Asp
    2540                2545                2550

Ile Arg Glu Thr Val Val Asn Asn Leu Pro Val Ala Ala Leu Met
    2555                2560                2565

Leu Pro Arg Leu Val His Leu Phe Gly Lys Phe Glu Leu Pro Arg
    2570                2575                2580

Lys Leu Glu Asp Glu Arg Ile Arg Gly Lys Leu Glu Arg Phe Phe
    2585                2590                2595

Arg Glu Glu Ser Arg Leu Gln Thr Leu Ala Gly Leu Ile Ile Ser
    2600                2605                2610

Lys Asn Asn Gly Tyr Glu His Ile Val Ile His Ile Arg Leu Leu
    2615                2620                2625

Arg Lys Ile Lys Ile Trp Tyr Gln Asn His Leu Leu His Tyr Ser
    2630                2635                2640

Thr Leu Leu Asn Glu Leu Phe Ile Arg Asn Thr Ala Leu Asp Ser
    2645                2650                2655

Leu Ser Val Asp Phe Gly Asp Ser Leu Met Phe Pro His Ile Ser
    2660                2665                2670

Asp Ile Phe Gly Pro Cys Met Leu Arg Ser Ile Lys Leu Arg Gly
    2675                2680                2685

Arg His Trp Pro Leu Pro Thr Ile Ile Ala Ser Ser Ala Asn Tyr
    2690                2695                2700

Leu Ser Glu Val Gln Leu Ser Ser Thr Val Leu Pro Leu Arg Tyr
    2705                2710                2715

Leu Ser Thr Leu Gln Ser Leu Arg Arg Leu Leu Tyr Leu Lys Leu
    2720                2725                2730

Val Ala Asp Gly Phe Val Gly Asp Asp Thr Asp Thr Phe Thr Val
    2735                2740                2745

Lys Lys Asp Gly Phe Pro Ser Leu Glu Arg Leu Cys Ile Glu Ala
    2750                2755                2760

Pro Lys Leu Pro His Leu Arg Ile Val Glu Gly Ala Met Pro Ala
    2765                2770                2775

Leu Thr Ser Leu His Leu Leu Cys Pro Thr Met Thr Met Met Pro
    2780                2785                2790

Gln His Pro Gly Gln Met Gly Glu Ile Asp Glu Pro Glu Ala Thr
    2795                2800                2805

Ser Glu Thr Lys Leu Gly Lys Glu Trp Gly Ile Glu Tyr Leu Arg
    2810                2815                2820

Asn Leu Asn Asp Leu Val Leu Pro Tyr Thr Val Gly Asp Glu Gln
    2825                2830                2835

Leu Asp Phe Trp Lys Glu Lys Ala Arg Ser Asn Met Asn Arg Pro
    2840                2845                2850

Lys Val Thr Arg Gln Pro Lys Pro
    2855                2860

<210> SEQ ID NO 6
<211> LENGTH: 1805
<212> TYPE: PRT
<213> ORGANISM: Zea mays

<400> SEQUENCE: 6
```

```
Met Ala Val Arg Gly Ser Thr Tyr Met Ile Arg Gln Tyr Ile Lys Glu
1               5                   10                  15

Pro Gly Phe Asn Ala Ala Asn Glu Met Ala Ser Ile Asn Gln Glu Ile
            20                  25                  30

Arg Gln Ile Gly Arg Met Val Ile Ser Ser Asn Ile Leu Glu Pro Pro
            35                  40                  45

Glu Trp Ile Leu Gln Ala Gln Asp Leu Ala Cys Asp Val Gln Asp Phe
 50                  55                  60

Thr Asp Ile Tyr Thr Trp Leu Gln Ser Lys Ser Arg Arg Arg Ala Leu
 65                  70                  75                  80

Ala His Ile Gly Tyr Ile Ala Gln Leu Lys Asp Arg Ile Ser Ser Leu
                 85                  90                  95

Arg Glu Trp Gln Gln Arg Gly Gly Ser Ser Ser Gln Gln Glu Arg
                100                 105                 110

Ala Ala Ala Leu Ser Phe Ser Arg Arg Ser Cys Gly Pro Cys Ala Pro
            115                 120                 125

Glu Asp Val Leu Val Gly Ile Asp Gln Pro Arg Lys Glu Leu Ser Asp
            130                 135                 140

Leu Ile Phe Glu Arg Glu Asp Val Val Gln Gln Lys Pro Arg Val Val
145                 150                 155                 160

Ser Val Val Gly Tyr Ser Gly Ile Gly Lys Thr Ala Leu Ala Arg Ala
                165                 170                 175

Val Tyr Tyr Asp Pro Ser Val Arg Ser Ala Phe Asn Gly Val Ala Trp
            180                 185                 190

Val Val Ala Ser Glu Cys Asn His Gly Cys Asp Leu Val Ser Lys Ile
            195                 200                 205

Cys Gln Gln Val Lys Asp Glu Gln Ala Gly Asn Gly Ala Val Val Pro
210                 215                 220

Asp Cys Tyr Arg Leu Lys Glu Ile Met Arg Asp Lys Arg Phe Phe Ile
225                 230                 235                 240

Val Ile Asp Asp Leu Gln Gly Ala Gly Met Trp Asn Asp Ile Lys Gly
            245                 250                 255

Val Phe Ser Glu Thr His Ser Gly Ser Arg Ile Ile Val Thr Thr Ser
            260                 265                 270

Ile Gln Ser Val Ala Ala Ala Cys Thr Pro Glu Pro Arg Tyr Ile Tyr
            275                 280                 285

Arg Met Pro Ser Leu Gly Asn Leu Asp Ser Glu Lys Leu Leu Trp Met
            290                 295                 300

Arg Val Gly Arg His Ala Ser Arg Thr Pro Ala Leu Glu His Ala Leu
305                 310                 315                 320

Gly Asn Asp Thr Leu Lys Lys Cys Gly Gly Leu Pro Leu Ala Leu Ile
            325                 330                 335

Ser Val Ala Asn His Leu Cys Leu Gly Lys Ala Leu Phe Glu Glu Met
            340                 345                 350

Asp Arg Val Leu Ala Lys Cys Tyr Asp Ser Leu Pro Asp Asn Ala His
            355                 360                 365

Arg Met Cys Leu Leu Ser Leu Ser Thr Phe Pro Gln Gly His Val Met
            370                 375                 380

Lys Arg Lys Arg Leu Ile Arg Arg Trp Ile Ala Glu Gly Leu Ala Val
385                 390                 395                 400

Gly Asp Cys Glu Leu Ser Ala Glu Gln Val Ala Gly Asn Ile Phe Asp
            405                 410                 415

Val Leu Ile Asp Arg Asn Val Thr Glu Pro Val Leu Thr Ala Gly His
```

```
            420                 425                 430
Gly Ser Ser Ser Lys Val Lys Ala Cys Leu Val Leu Gly Val Ile Lys
            435                 440                 445
Asp Phe Ile Asn Lys Thr Ala Val Ser Asn Glu Thr Val Ala Ile Ile
450                 455                 460
Gln Asn Asp Glu Leu Leu Pro Asn Arg Met Met Leu Val Ala His
465                 470                 475                 480
Arg Pro Val Arg Arg Leu Leu Val His Gly Gly Thr Thr Lys Lys Ser
                485                 490                 495
Glu Ala Val Ala Lys Ala Ile Gly Leu Asp Gln Val Arg Ser Leu Thr
                500                 505                 510
Ile Cys Asn Ala Val Pro Phe Asp Phe Gln Gly Cys Trp Leu Leu Arg
                515                 520                 525
Val Leu Asp Leu Glu Ala Cys Gln Gly Ile Asp Lys Ser Ile Leu Gly
                530                 535                 540
Ser Ile Cys Lys Leu Val Phe Leu Lys Tyr Leu Ser Leu Arg Gly Thr
545                 550                 555                 560
Asp Val Tyr Gly Ile Pro Lys Lys Val Lys Lys Leu Gln Arg Leu Glu
                565                 570                 575
Thr Leu Asp Leu Arg Asp Thr Arg Val Glu Glu Leu Pro Ile Gln Val
                580                 585                 590
Leu Met Leu Pro Arg Leu Ala His Leu Phe Gly Lys Phe Glu Leu Pro
                595                 600                 605
Pro Gln Leu Lys His Gly His Arg Thr Ala Arg Arg Arg Ser Arg
                610                 615                 620
Leu Gln Ala Phe Phe Ser Gln Arg Ser Arg Leu Gln Thr Leu Ser Gly
625                 630                 635                 640
Phe Val Met Val Asp Asp Ser Asn Ser Phe Glu His Met Met Ile Thr
                645                 650                 655
Ile Lys Ser Leu Arg Lys Val Lys Val Trp Cys Lys Asn Ser Ile Ser
                660                 665                 670
Ser His Gln Glu Arg His Leu Ala Ser Ser Leu Gln Gln Arg Leu Val
                675                 680                 685
Gly Asn Ser Asn Pro Leu Glu Ser Leu Ser Ile Asp Phe Gly Asn Glu
                690                 695                 700
Ser Ile Asn Phe Leu Asn Asp Val Gly Ala Thr Ser Ala Leu Ile Gly
705                 710                 715                 720
Ser Met Lys Leu Gln Gly Arg Leu Thr Ser Leu Pro Ser Phe Met Thr
                725                 730                 735
Ser Tyr Asp Thr Thr Leu Ser Gln Leu Gln Leu Ser Ser Thr Gly Leu
                740                 745                 750
Gly Ile Glu Ala Leu Ser Leu Leu Gln Ile Leu Arg Arg Leu Val Ser
                755                 760                 765
Leu Lys Leu Ala Gln Asp Gly Asp Gly Phe Trp Gly Asp Cys Phe Ala
                770                 775                 780
Val Asn Lys Asp Gly Phe Pro Ser Leu Leu Arg Leu Cys Ile Gln Ala
785                 790                 795                 800
Arg Glu Leu Pro Gln Leu His Ile His Glu Gly Gly Met Ser Ser Leu
                805                 810                 815
Thr Ser Leu Glu Leu Leu Cys Pro Met Phe Ala Ser Arg Gly His Ser
                820                 825                 830
Asp Ser Asp Ser Asp Ser Asp Leu Gly Lys Thr Tyr Val Glu Thr His
                835                 840                 845
```

```
Ser Glu Lys Arg Ser Lys Gln Val Leu Ser Val Lys Pro Lys Ala
850                 855                 860

Val Asp Pro Gly Ile Ser Phe Lys Glu Pro Ser Ser Glu Thr Arg Ser
865                 870                 875                 880

Glu Gly Thr Glu Ile Gln Glu Ile Asp Ser Pro Lys Thr Ser Lys Glu
                885                 890                 895

Ala Gly Pro Ser Ile Gly Phe Lys Asp Ile Ile Leu Pro Glu Asn Thr
            900                 905                 910

Phe Arg Arg Asn Phe Ser Lys Glu Val Lys Ser Arg Phe Asp Leu Lys
        915                 920                 925

Gln His Phe Lys Gly Met Glu Tyr Leu Gln Cys Leu Asn Glu Leu Val
    930                 935                 940

Leu His Cys Ser Val Ser Asp Glu Val Leu Asp Ala Trp Thr Lys Arg
945                 950                 955                 960

Ala Ser Ser His Ile Asn Arg Pro Lys Val Thr Arg Gln Cys Thr Arg
                965                 970                 975

Ala Ala Leu Ser Ile Gly Arg Gly Pro Gly Thr Ala Lys His Glu Lys
            980                 985                 990

Glu Gly Gln His Arg Ser Gln Leu Met Lys Asn Arg Gly Ser Glu Thr
        995                 1000                1005

Ala Ile His Glu Glu Val Ala Glu Gln His Ser Ser Val Gly Thr
    1010                1015                1020

Ser Arg Glu Glu Ala Gly Leu Phe Gln Glu Gln Thr Ser Asp Thr
    1025                1030                1035

Gly His Lys Glu Glu Glu Glu Glu Glu Glu Glu Cys Thr Ser
    1040                1045                1050

Glu Asp Arg Ala Leu Asn Gln Pro Cys Asp Met Leu Ile Gly Met
    1055                1060                1065

Asp Val Ala Ile Arg Glu Leu Leu Glu Leu Val Asn Leu Glu Glu
    1070                1075                1080

Phe Gly Val Asp Asp Lys Val Ile Ser Ile Val Gly Cys Pro Gly
    1085                1090                1095

Leu Gly Lys Thr Thr Leu Ala Lys Ala Phe Ser Asn Leu Glu Met
    1100                1105                1110

Ile Arg Glu Arg Phe Asn Pro Pro Val Trp Val Ser Ala Ser Gln
    1115                1120                1125

Cys Arg Ser Ala Gln Asp Leu Leu Ile Lys Val Ile Arg Gln Ala
    1130                1135                1140

Ser His Val His Pro Ala Gln Met Ile Ser Ala Thr Pro Asn Ile
    1145                1150                1155

Asp Leu Leu Gln Thr Ile Leu Ala Gln Glu Ser Leu Leu Ile Ile
    1160                1165                1170

Ile Asp Asp Leu Arg Glu Thr Thr Ala Trp Asn Ser Ile Glu Thr
    1175                1180                1185

Ala Leu Gly Ser Thr Thr Ser Thr His Ala Gly Ser Leu Ile Ile
    1190                1195                1200

Val Thr Thr Arg Ile Gln Ser Ile Ala Gly Lys Cys Ser Pro His
    1205                1210                1215

Arg Tyr Ile Tyr Arg Met Pro Gly Leu Gly His Pro Glu Ser Lys
    1220                1225                1230

Glu Leu Phe Leu Arg Thr Ala Tyr Gly Asp Ala His Pro Thr Pro
    1235                1240                1245
```

```
Gly Val Ala Asp Ala Val Glu Glu Ile Ser Gly Ala Cys Asp Gly
    1250                1255                1260

Leu Pro Leu Ala Leu Val Ser Ala Ala His Asp Trp Arg Glu Arg
    1265                1270                1275

Gln Gly Gln Gly Trp Glu Gly Arg Tyr Val Phe Glu Glu Val Asn
    1280                1285                1290

Arg Ala Phe Ser Trp Trp Tyr Glu Ser Leu Ala Asp Ala Ala His
    1295                1300                1305

Met Leu Ser Leu Gly Ile Phe Pro Tyr Gly His Ser Ile Lys Arg
    1310                1315                1320

Lys Ser Leu Ile Arg Arg Trp Ile Ala Glu Gly Leu Val Ser Glu
    1325                1330                1335

Glu Lys Asp Gly Asp Gln Arg Phe His Glu Leu Val Asp Gln Ser
    1340                1345                1350

Ile Val Glu Pro Val Leu Ile Thr Gly Ser Ser Asp Phe Lys Val
    1355                1360                1365

Lys Arg Phe Arg Leu Arg Arg Pro Val Leu Glu Phe Ile Val Arg
    1370                1375                1380

Glu Ser Val Ser Lys Asn Met Val Lys Leu Leu Gln Gly Asp Glu
    1385                1390                1395

Pro Leu Pro Gly Glu Gly Gly Pro Val Val Ser Ile Tyr Gln
    1400                1405                1410

Thr Thr Asp Thr Glu Thr Ser Arg Gly Asn Ile Met Ser Phe Ser
    1415                1420                1425

Ile Phe Asn Lys Gly Val Ala Phe Asp Asp Leu Gln Gln Cys Thr
    1430                1435                1440

Tyr Leu Arg Val Leu Asp Leu Glu Arg Cys Arg Gly Val Asp His
    1445                1450                1455

Ser Val Val Ala Gly Ile Cys Lys Leu Ser Leu Leu Arg Tyr Leu
    1460                1465                1470

Ser Leu Arg Gly Ser Asp Val Arg His Ile Pro Arg Glu Thr Lys
    1475                1480                1485

Arg Leu Lys Cys Leu Glu Thr Leu Asp Ile Arg Glu Thr Val Val
    1490                1495                1500

Asn Asn Leu Pro Val Ala Ala Leu Met Leu Pro Arg Leu Val His
    1505                1510                1515

Leu Phe Gly Lys Phe Glu Leu Pro Arg Lys Leu Glu Asp Glu Arg
    1520                1525                1530

Ile Arg Gly Lys Leu Glu Arg Phe Phe Arg Glu Glu Ser Arg Leu
    1535                1540                1545

Gln Thr Leu Ala Gly Leu Ile Ile Ser Lys Asn Asn Gly Tyr Glu
    1550                1555                1560

His Ile Val Ile His Ile Arg Leu Leu Arg Lys Ile Lys Ile Trp
    1565                1570                1575

Tyr Gln Asn His Leu Leu His Tyr Ser Thr Leu Leu Asn Glu Leu
    1580                1585                1590

Phe Ile Arg Asn Thr Ala Leu Asp Ser Leu Ser Val Asp Phe Gly
    1595                1600                1605

Asp Ser Leu Met Phe Pro His Ile Ser Asp Ile Phe Gly Pro Cys
    1610                1615                1620

Met Leu Arg Ser Ile Lys Leu Arg Gly Arg His Trp Pro Leu Pro
    1625                1630                1635

Thr Ile Ile Ala Ser Ser Ala Asn Tyr Leu Ser Glu Val Gln Leu
```

```
            1640                1645                1650

Ser  Ser  Thr  Val  Leu  Pro  Leu  Arg  Tyr  Leu  Ser  Thr  Leu  Gln  Ser
    1655                1660                1665

Leu  Arg  Arg  Leu  Leu  Tyr  Leu  Lys  Leu  Val  Ala  Asp  Gly  Phe  Val
    1670                1675                1680

Gly  Asp  Asp  Thr  Asp  Thr  Phe  Thr  Val  Lys  Lys  Asp  Gly  Phe  Pro
    1685                1690                1695

Ser  Leu  Glu  Arg  Leu  Cys  Ile  Glu  Ala  Pro  Lys  Leu  Pro  His  Leu
    1700                1705                1710

Arg  Ile  Val  Glu  Gly  Ala  Met  Pro  Ala  Leu  Thr  Ser  Leu  His  Leu
    1715                1720                1725

Leu  Cys  Pro  Thr  Met  Thr  Met  Met  Pro  Gln  His  Pro  Gly  Gln  Met
    1730                1735                1740

Gly  Glu  Ile  Asp  Glu  Pro  Glu  Ala  Thr  Ser  Glu  Thr  Lys  Leu  Gly
    1745                1750                1755

Lys  Glu  Trp  Gly  Ile  Glu  Tyr  Leu  Arg  Asn  Leu  Asn  Asp  Leu  Val
    1760                1765                1770

Leu  Pro  Tyr  Thr  Val  Gly  Asp  Glu  Gln  Leu  Asp  Phe  Trp  Lys  Glu
    1775                1780                1785

Lys  Ala  Arg  Ser  Asn  Met  Asn  Arg  Pro  Lys  Val  Thr  Arg  Gln  Pro
    1790                1795                1800

Lys  Pro
    1805

<210> SEQ ID NO 7
<211> LENGTH: 742
<212> TYPE: PRT
<213> ORGANISM: Zea mays

<400> SEQUENCE: 7

Met  Leu  Ile  Gly  Met  Asp  Val  Ala  Ile  Arg  Glu  Leu  Leu  Glu  Leu  Val
1                  5                   10                  15

Asn  Leu  Glu  Glu  Phe  Gly  Val  Asp  Asp  Lys  Val  Ile  Ser  Ile  Val  Gly
            20                  25                  30

Cys  Pro  Gly  Leu  Gly  Lys  Thr  Thr  Leu  Ala  Lys  Ala  Phe  Ser  Asn  Leu
        35                  40                  45

Glu  Met  Ile  Arg  Glu  Arg  Phe  Asn  Pro  Pro  Val  Trp  Val  Ser  Ala  Ser
50                  55                  60

Gln  Cys  Arg  Ser  Ala  Gln  Asp  Leu  Leu  Ile  Lys  Val  Ile  Arg  Gln  Ala
65                  70                  75                  80

Ser  His  Val  His  Pro  Ala  Gln  Met  Ile  Ser  Ala  Thr  Pro  Asn  Ile  Asp
            85                  90                  95

Leu  Leu  Gln  Thr  Ile  Leu  Ala  Gln  Glu  Ser  Leu  Leu  Ile  Ile  Ile  Asp
        100                 105                 110

Asp  Leu  Arg  Glu  Thr  Thr  Ala  Trp  Asn  Ser  Ile  Glu  Thr  Ala  Leu  Gly
    115                 120                 125

Ser  Thr  Thr  Ser  Thr  His  Ala  Gly  Ser  Leu  Ile  Ile  Val  Thr  Thr  Arg
130                 135                 140

Ile  Gln  Ser  Ile  Ala  Gly  Lys  Cys  Ser  Pro  His  Arg  Tyr  Ile  Tyr  Arg
145                 150                 155                 160

Met  Pro  Gly  Leu  Gly  His  Pro  Glu  Ser  Lys  Glu  Leu  Phe  Leu  Arg  Thr
            165                 170                 175

Ala  Tyr  Gly  Asp  Ala  His  Pro  Thr  Pro  Gly  Val  Ala  Asp  Ala  Val  Glu
        180                 185                 190
```

```
Glu Ile Ser Gly Ala Cys Asp Gly Leu Pro Leu Ala Leu Val Ser Ala
            195                 200                 205

Ala His Asp Trp Arg Glu Arg Gln Gly Gln Gly Trp Glu Gly Arg Tyr
    210                 215                 220

Val Phe Glu Glu Val Asn Arg Ala Phe Ser Trp Trp Tyr Glu Ser Leu
225                 230                 235                 240

Ala Asp Ala Ala His Met Leu Ser Leu Gly Ile Phe Pro Tyr Gly His
                245                 250                 255

Ser Ile Lys Arg Lys Ser Leu Ile Arg Arg Trp Ile Ala Glu Gly Leu
            260                 265                 270

Val Ser Glu Lys Asp Gly Asp Gln Arg Phe His Glu Leu Val Asp
    275                 280                 285

Gln Ser Ile Val Glu Pro Val Leu Ile Thr Gly Ser Ser Asp Phe Lys
290                 295                 300

Val Lys Arg Phe Arg Leu Arg Arg Pro Val Leu Glu Phe Ile Val Arg
305                 310                 315                 320

Glu Ser Val Ser Lys Asn Met Val Lys Leu Leu Gln Gly Asp Glu Pro
                325                 330                 335

Leu Pro Gly Glu Gly Gly Pro Val Val Ser Ile Tyr Gln Thr Thr
            340                 345                 350

Asp Thr Glu Thr Ser Arg Gly Asn Ile Met Ser Phe Ser Ile Phe Asn
                355                 360                 365

Lys Gly Val Ala Phe Asp Asp Leu Gln Gln Cys Thr Tyr Leu Arg Val
            370                 375                 380

Leu Asp Leu Glu Arg Cys Arg Gly Val Asp His Ser Val Val Ala Gly
385                 390                 395                 400

Ile Cys Lys Leu Ser Leu Leu Arg Tyr Leu Ser Leu Arg Gly Ser Asp
                405                 410                 415

Val Arg His Ile Pro Arg Glu Thr Lys Arg Leu Lys Cys Leu Glu Thr
            420                 425                 430

Leu Asp Ile Arg Glu Thr Val Val Asn Asn Leu Pro Val Ala Ala Leu
            435                 440                 445

Met Leu Pro Arg Leu Val His Leu Phe Gly Lys Phe Glu Leu Pro Arg
450                 455                 460

Lys Leu Glu Asp Glu Arg Ile Arg Gly Lys Leu Glu Arg Phe Phe Arg
465                 470                 475                 480

Glu Glu Ser Arg Leu Gln Thr Leu Ala Gly Leu Ile Ile Ser Lys Asn
                485                 490                 495

Asn Gly Tyr Glu His Ile Val Ile His Ile Arg Leu Leu Arg Lys Ile
            500                 505                 510

Lys Ile Trp Tyr Gln Asn His Leu Leu His Tyr Ser Thr Leu Leu Asn
            515                 520                 525

Glu Leu Phe Ile Arg Asn Thr Ala Leu Asp Ser Leu Ser Val Asp Phe
530                 535                 540

Gly Asp Ser Leu Met Phe Pro His Ile Ser Asp Ile Phe Gly Pro Cys
545                 550                 555                 560

Met Leu Arg Ser Ile Lys Leu Arg Gly Arg His Trp Pro Leu Pro Thr
                565                 570                 575

Ile Ile Ala Ser Ser Ala Asn Tyr Leu Ser Glu Val Gln Leu Ser Ser
                580                 585                 590

Thr Val Leu Pro Leu Arg Tyr Leu Ser Thr Leu Gln Ser Leu Arg Arg
            595                 600                 605

Leu Leu Tyr Leu Lys Leu Val Ala Asp Gly Phe Val Gly Asp Asp Thr
```

-continued

```
                610                 615                 620
Asp Thr Phe Thr Val Lys Lys Asp Gly Phe Pro Ser Leu Glu Arg Leu
625                 630                 635                 640

Cys Ile Glu Ala Pro Lys Leu Pro His Leu Arg Ile Val Glu Gly Ala
                645                 650                 655

Met Pro Ala Leu Thr Ser Leu His Leu Leu Cys Pro Thr Met Thr Met
                660                 665                 670

Met Pro Gln His Pro Gly Gln Met Gly Glu Ile Asp Glu Pro Glu Ala
                675                 680                 685

Thr Ser Glu Thr Lys Leu Gly Lys Glu Trp Gly Ile Glu Tyr Leu Arg
690                 695                 700

Asn Leu Asn Asp Leu Val Leu Pro Tyr Thr Val Gly Asp Glu Gln Leu
705                 710                 715                 720

Asp Phe Trp Lys Glu Lys Ala Arg Ser Asn Met Asn Arg Pro Lys Val
                725                 730                 735

Thr Arg Gln Pro Lys Pro
                740

<210> SEQ ID NO 8
<211> LENGTH: 1019
<212> TYPE: PRT
<213> ORGANISM: Zea mays

<400> SEQUENCE: 8

Met Asn Val Leu Leu Arg Ser Gln Ser Pro Thr Leu Leu Tyr Leu Pro
1               5                   10                  15

Thr Ser Ser Gln Pro Ala Ile Pro Ala Asp Arg Thr Arg Ala Lys Gln
                20                  25                  30

Gln Arg Gly Gly Val Gly Glu Met Thr Gly Val Glu Pro Ala Val Ile
            35                  40                  45

Gly Ala Ile Ala Lys Leu Ala Ala Pro Val Leu Pro Ile Ala Ile Lys
        50                  55                  60

Gly Ile Gln Asp Ala Leu Lys Lys Arg Gln Val Arg Asp Ser Asp Val
65                  70                  75                  80

Glu Thr Leu Lys Ser Gln Leu Ser Tyr Ile Gln Gly Ile Ile Arg Asp
                85                  90                  95

Thr Arg Lys Thr Ile Arg Ser Ser Gln Asp Pro Ser Asp Arg Leu Gln
                100                 105                 110

Ser Trp Ser Gly Tyr Leu Arg Cys Leu Ala Tyr Asp Ile Glu Asp Leu
            115                 120                 125

Ile Ala Gly His Arg Val Gly Thr Met Thr Gly Ala Lys Leu Asn Gly
        130                 135                 140

Lys Ile Thr Ile Ile Gln Asp Leu Ile Arg Cys Val Glu Ser Tyr Pro
145                 150                 155                 160

Glu Phe Met Ala Val Pro Thr Asn Glu Ala Pro Ser Gln Gly Ala Ala
                165                 170                 175

Ser Ser Ser Thr Thr Ser Ser Thr Gln Gly Phe Pro Leu Ala Asp Leu
            180                 185                 190

Val Gly Lys Lys Glu Asp Leu Asp Glu Leu Leu Asp Leu Leu Val Trp
        195                 200                 205

Arg Pro Asp Asn Glu Leu Asp Lys Val Leu Lys Val Met Val Ile Ser
210                 215                 220

Val Val Gly Phe Gly Gly Ile Gly Glu Thr Lys Leu Cys His Thr Val
225                 230                 235                 240
```

```
Tyr Thr Asp Val Gln Glu Ser Arg Lys Phe Ser Leu His Ala Tyr Val
            245                 250                 255

Ser Ala Ala Gly Lys Asp Cys Ser Ile Val Leu Glu Glu Ile Ile Glu
        260                 265                 270

Gln Phe Arg Leu Gln Glu Asp Pro Leu Asp Ser Ser Gly Gly Phe Phe
    275                 280                 285

His Arg Phe Ala Gly Ala Phe Pro Gly Ala Arg Arg Thr Asp Gln Val
290                 295                 300

His Glu Leu Pro Glu Tyr Leu Gln Arg Lys Arg Tyr Phe Val Val Val
305                 310                 315                 320

Asp Gly Val Glu Ser Glu Glu Leu Val Gly Gly Ile Ala Ser Ala Phe
            325                 330                 335

Pro Asp Asn Ser Met Gly Ser Arg Ile Ile Met Gly Met Arg Thr Ala
            340                 345                 350

Val Gly Arg Asp Ala Glu Arg Cys Val Gly His Arg His Lys Met Trp
        355                 360                 365

Pro Leu Glu Asp Lys Gln Ser Val Val Cys Phe Leu Asn Glu Ala Glu
    370                 375                 380

Arg Arg Arg Arg Arg Arg Arg His Glu Gln Asp Asp His Ser Ser
385                 390                 395                 400

Phe Ile Thr Phe Gln Glu Gln Asp His Ser Ser Ser Cys Leu His Lys
            405                 410                 415

Ile Cys Asp Gly Val Pro Leu Ala Leu Val Ser Val Cys Glu Val Arg
            420                 425                 430

Arg Gly Ser Ile Ile Thr Ala Ala Val Glu Glu Gln Asp Arg Trp Pro
        435                 440                 445

His Arg Met Pro Lys Val Leu Asp His Ser Tyr Asp Gly Leu His Ile
    450                 455                 460

Arg Gly Ala Gly Gly Cys Pro Asn Gln Tyr Ile Pro Tyr Leu Gln Ala
465                 470                 475                 480

Cys Leu Leu Tyr Phe Ala Met Phe Pro Arg Gly Asn His Val Lys Arg
            485                 490                 495

Gly Ser Leu Ile Arg Arg Trp Gln Ala Glu Gly Leu Glu Phe Gly Gly
            500                 505                 510

Ser Asn Ile His Asn Gln Ala Ala Glu Asn Leu Lys Ala Leu Val Asp
        515                 520                 525

Arg Asn Phe Val Trp Pro Leu His Ala Ser Leu Asn Glu His Ala Lys
    530                 535                 540

Thr Phe Gln Pro Pro Gly Val Val Leu Asn Tyr Ile Ser Arg Arg Ser
545                 550                 555                 560

Glu Glu Glu Glu Phe Ile Leu Arg Ser Cys Pro Thr Gly Asp Leu Asn
            565                 570                 575

Pro Asn Tyr Ser Arg Arg Leu Cys Leu His Pro Ala Glu Glu Glu Glu
            580                 585                 590

Gly Glu Pro Gln Pro Leu Val Ile Thr Asn Gly Ser Val Pro Pro Arg
        595                 600                 605

Leu Arg Thr Leu Ala Val Ser Trp Gly Gln Gln Gln Ala Ser Arg Ile
    610                 615                 620

Ala Glu Cys Glu Gln Leu Arg Val Leu Asp Leu Ala Ser Tyr Asn Gly
625                 630                 635                 640

Leu Gln Pro Asp Gln Leu Glu Glu Ile Cys Lys Lys Leu Lys Leu Leu
            645                 650                 655

Lys Tyr Leu Ser Leu Leu Pro Asp Ile Ile Thr Gln Val Pro Ser Ser
```

```
                    660              665              670
Met Ser Asn Leu Gln Cys Leu Glu Thr Leu Glu Leu Gly Glu Val Asn
            675              680              685

Gly Arg Ala Ala Val Leu Val Pro Ile Gln Val Leu Glu Leu Pro Cys
        690              695              700

Ile Lys His Leu Ile Gly Lys Phe Glu Leu Ile Asp Asn Phe Asn Gly
705             710              715              720

Val Pro Ile Arg Ala Tyr Pro Asp Ala Leu Val Pro Lys Ala Ile Lys
                725              730              735

Glu Ser Asn Leu Glu Thr Val Ser Gly Phe Phe Thr His Arg Gly Gln
            740              745              750

Gly Phe Pro Pro Leu Met Arg His Met Arg Gln Leu Arg Lys Val Lys
        755              760              765

Ile Trp Phe Tyr Arg Asp Ala Glu Pro Lys Tyr Leu Ala Ser Tyr Leu
    770              775              780

Pro Lys Ala Ile Thr Lys Phe Leu Arg Asn Asp Asn Val Pro Arg Ser
785             790              795              800

Leu Ser Leu Asp Phe Gln Asp Gly Pro Arg Gln Thr Glu Ile Leu Gln
                805              810              815

Ala Cys Val Ala Glu Ala Arg Gly Asn Leu Tyr Ser Leu Lys Leu Ser
            820              825              830

Ser Gly Thr Asn Leu Ser Arg Ile Gln Leu Ser Val Ile Ala Thr Asn
        835              840              845

Lys Gln Leu Thr Gly Ile Thr Lys Leu Cys Leu Ser Arg Trp Lys Thr
    850              855              860

Ile Thr Leu Asp Ala Glu Phe Leu Asn Glu Leu Ser Arg Leu Val His
865             870              875              880

Leu Arg Tyr Leu Lys Leu Asp Ala Glu Thr Ile Lys Gly Thr Tyr Asp
                885              890              895

Gln Asn Pro Thr Pro Gly Gly Asn Asn Gln Glu Lys Val Val Ile Glu
            900              905              910

Thr Gly His Ile Ala Asn Leu Arg Arg Met Trp Leu Val Ala Arg Gln
        915              920              925

Thr Leu Pro Asp Ile Gln Val Lys Pro Thr Ala Leu Gln Arg Leu Val
    930              935              940

Ser Leu His Leu Ile Ser Glu Thr Asp Tyr Cys Pro Ser Ala Asn
945             950              955              960

Val Ile Cys Lys Ala Asn Pro Gln Asp Asn Glu Leu Ala Pro Phe
                965              970              975

Thr Ser Leu Gln Glu Val Ser Leu Asn Ala Thr Val Pro Glu Asn Leu
            980              985              990

Arg Asp Ser Trp Arg Asn Ala Ala  Arg Asp His Pro Lys  Arg Pro Arg
        995              1000             1005

Ile Leu  Phe Ile Gln His Pro  His Arg Ala Gly
   1010              1015

<210> SEQ ID NO 9
<211> LENGTH: 42516
<212> TYPE: DNA
<213> ORGANISM: Zea mays

<400> SEQUENCE: 9
ctaggccgga ccgtgccggg tacgatgggc ttaacacggg tgatggttag gtcgcagccc      60
atcagagtgg agctgtcatg gtgctagaag ataatgcatc tcatctcatc tcagtcactt     120
```

```
cccccacccg gcgaccagaa actcctgcac cggctgctga tggagtcttg acaagtgatt      180
cttgtcgatc ggccaggcaa gttctcgtcg tcagtggagg agcgaaatat gctccctgcc      240
tagctaatta actgatcatg catacatact cttccgttcc atgtgtgtcc gcagctacgg      300
cggcggtggc cacgaaacga tggaagctgc ttctgtttag gctcccatgt ctatcctgga      360
aaagctcgtc cagagctgtt cctttccaga ttcatggcgg gggccgccag acgctgaggt      420
ccaggctctc ataggatatc tcgaagagat acggtcctcc gtcctggatc tttccaagga      480
ggatgaggac gaggatgact ctgctacgtc gtcgtccacg ctgaagatga gcctgacgag      540
ccagttgcag gaactttgtt atgatgctga ggactatctg gagatggcgc agcactctcg      600
tggtggctgc tcctggcaga tcagttgggt ccggagcaag gcgacgaggc agcgccccgc      660
tctaatcagc gcaaaagatc tctccggcct catctcccgt gtgaagccgg cgaaagaaat      720
agcccaagcg tacatcaagt ctgctagttc aagaaccacc accaaagaga atggccctag      780
gccacaagaa gagcctgcaa aaagcagtag tcgccgtgcc gtctattctg atgatactct      840
acagcctgac agccatgacg agcagctagt caggttgctg gctttggaaa gtgatcagca      900
gctcaagacg gtggcaatcc atggcctgcc tggcgttggg aagacaacac ttgccagaag      960
actgtaccac tgctatgaag ggaggttcca ttgcggggct ttccttcggg cgtcccgtaa     1020
cctgcaggac gataccacca ggcttctcgc caccatgcta tccaagatta agggccaaca     1080
agggtgccgc tactgggggg gctccggtga tgagcaagat ctaatcgaca gcatcaggca     1140
acatctacaa ggaaaatcgt aagtgctact gcatgcctca gttagttcat aagaaaaacg     1200
gcgcagcttt atttcacgct ctttgatgca tgtgtgtgcc cgcccactag tctctctact     1260
actaaaaaga ctctaaaaga ccctagtaaa tatatcttac acatatggca taaaggtcac     1320
acactagatt aagtaaacga gataatgcat aaaatcaata aatcgtttgc gtaaaatgtg     1380
aatagaaata tcataaatag acaaatagat ggaaacggag ccaggaactg aaatatatgt     1440
cataaaaacc tattgacatt ggcataaata tgtaaacaaa atagcataaa aataggatcg     1500
ccgccctgtg gaaccgccgc ctcgcatctg ggatgtgcca ccacttcgtg cctaaggaag     1560
gctgtcgtcg tcgctcgcgc ctagggaagt ctgtcatcgt cgctcccacc ttggatggca     1620
tcgcagtcgt acgcgctcag gggtcgaccc tcgcgcgcgt gcatcccgag atccgtcgca     1680
tcagccgctt ccacctcgcc gtcatgcaag ccttaggggt gccgtcattg ctcacgtgcc     1740
cccgatatca gtcgtcgcgt cgctgcagcc gctcccacct caccgttgtg cgcacctcaa     1800
ggggtcactg ccacgtgcac ctcagggaga agctgtcgcg cttgtgtccc ctgggatcca     1860
ccaccgcggc cactgccacc tcaccgtcgc gcacacctca tggggtcgcc gccgcgtgcg     1920
tgccctcggg attcgatgcc gcagccgctc ccacctcacc gtcgtgcgcg cctcaagggg     1980
gccatcgccg catgctggcc tcaaggatcc atcgccgtga gcgtgtcccc cggatccgcc     2040
gtcgcgcgct tgctcccagg atccgccgcc acgcgtgcct ctcaggggtg ggggcgtaac     2100
tgtcgtcatc gctaaaactg aaccctagcg atctggagct tcttttatag acgcttcgga     2160
cctggtgcgg ctgaaccggt tggcaacatc gggtaagggc tttcgcccag ctattagaag     2220
cccaggactc catatacata tactatatat atacacagag agagagagag ctagattctt     2280
gtacaacttg gtaaccaact tgaaatcgac tcggtgtctt tcatgtaaat gttgtctctc     2340
cttaggatgt aaaaggaggg ttgagaaacc cctcaagatc aagatacaac tgttgtctct     2400
ccttcgatgt cctcaatcca cctactttga agagcctctt gaatcgtcct tgttttgct      2460
```

```
attctgcttg gaacaacagc gagcggcctt ggggctgtat cccccagtct atgcccatgc    2520
agccacttgc cggtccaaaa aaggtagatg atccattacc aacctcaaac atcagtaccg    2580
tgttgaagaa atcctaggtt ttgctaggaa cctgaatggg aagcgatgac caaggaagat    2640
gggtcatttt tttaatccat agccaacgca tacataatgc ccaacataat tactttagat    2700
tggaaatgcc caatccacca agatgtaaag gtctgtacac ccttctctaa gcaacaagac    2760
aatgccctcc ttttgcgcct ttacgacctc tccaaagaaa acctctgtgg atcttatcaa    2820
tggttttgag agtacattgt ggaacatcaa ttttcattgc caaatatacc atcatacaag    2880
tgaggatata ttggacttgc actctccttc cgactctagt catcaaattt gccttctatc    2940
ctgtccataa ttggttgagt ttgctcctta aaaattttat ggagagaaag aggtaggccc    3000
aaatatcagc aaggaaagga agaatactcg caaggaacaa atcctaggtc acatccacat    3060
cttattcagg gcactggata tgaaacacac tagatttcta gttatgcagt cctgaagctg    3120
ctccaaataa gcttagaatt tccaaggtag caacaatatc agttcttgag ggatgcaaga    3180
agatagccac attgtcagca taaatagata tctgattgta cctatgtatg tttattagca    3240
cctgcagcaa gccatcctct tcggctttag acaagagata gcccaagaca tccataacca    3300
taatgaaaac catgggagaa agaggattcc cttgacgtag ccctcttttg tggacaataa    3360
catctcccgt aaaccattc agcaatactt gagtggaaga tgaagccaac aacccacata    3420
taatctccct ccaaaccagt ccaaagccta acttttgaga acctcaataa ggaagggcca    3480
agagaccgaa tcaaatgcct tggtaatgtc aagtttaagt agtaatctag cattttctgc    3540
tgatggaaga atttagttgt ttgctgcaca tgcatgaaat tttcctagat aaaacagcct    3600
ctaatgaaag cactttggtt ttgggagatc atacccttta aactcttggc caaccctaaa    3660
gccagctgat cccccgggcc ctcgtgaaca ctaaaacata tcacgagccg cctaacgggc    3720
ttcttgctga gtcaccctat gggatgggcc agctggacgt agccaactta ggtgagcccg    3780
atccaagctg acaagaccg acgcccgagt taagcgccac taaagcacag atgtgtcagg    3840
tgatgcagtt gcaaacacct gaagggttat gccctcggcg ataactcggg cggataggcg    3900
atcaagactt tggatatgca gggatacagt ttgcgacaat gaaggagata agcaagtaga    3960
tagtaatcac aacttgtaat gggttaacta tctttggtcg tgtatataag gccgagggggg    4020 acccccctacg attccatctc atcaccaatc actccagctc atctttaacc acaaaccacc    4080
agcttgtaat ccttgtactc caaagatcaa tatcaaacca caacaggaag tagcatatta    4140
cgcaattcta agcggcccga gcctgtataa ttctgtgagt gatcctagcg tgtctctgca    4200
caaaccatcg agtcgcgatc aacgatgtcg tcctaccctg aagcccacgt gggtaacccc    4260
gtggtgcgca gtcgggtcac aaacaccaaa accagcagct tggtaaagag cttagcaaag    4320
ttatgtacaa ggctaattgg tctgaaatct ttaacttgat tagcctcttc tttctttggc    4380
aaaaggataa tgtaagttgt gttcagtttg ccaagattgc taaacttgtg acccccatatg    4440 gttacaacag tcgccataac atcaccccctt gatgatactc cagcatgttt tataaaatct    4500
cccagtgaaa ctgtctggac caggtgcttt ggaagcacta gatcaactat ccatgatttt    4560
atttaatcca atatgcaaat cgttctccaa ccatggttta actttatac tattgttttt    4620 ttagataacg gaaccaagt ttcggctttg tccccccaaaa ggagggtaca accaggcata    4680
caaactgaca ataaacgacc cgcactctca acatagagtg aagtcccaca ccacaaacct    4740
aaaacggaca cccaacagaa aggctgaaaa cctaaaaatg taatcttatt cataaaactc    4800
caaccaaaac gagagaaaat ttgcatagat gttgcttcga tccgtcgaca catctccatt    4860
```

```
attatctcct tgtcctcacc cctctacaaa agtccccaga acctaagcca attggtcgcc    4920
caaaacaaaa actgcaaaaa agtaaccatc gggtaattat taaacactaa gtcattccga    4980
cttatccaga taacccaaca taacgttgca gcacctgcga taatcaaatt tttagctttg    5040
ggatgcaccc catgcaacca agatccaaaa atatgtttca ttgatctcga ggtacttaaa    5100
ccaaaacaac aatataaaag tctctaaaag aatctagcat agtgacattt aaaaaaaatt    5160
ggtcttgttt agattcattt gagtcacaaa acacacactt ttgacttccc tgtcaactac    5220
gcttagctag attgtctttc gagaaccacc cctctaatga gataccacat aaagatctta    5280 attttagag gtaattttag cttccataga ggtttgaaat aaaaaacttg gcattattaa      5340
taagagcatt gtacatcgat cggaccgtga aaagcctcaa ggctgacaaa ctccatttga    5400
actcatctct cgcactagat agatcagtat gaataataat cgaaccaat ctattccaac      5460 ataatagatt atcacccaca agcgctctac ggaaagaaat gtttagagaa attctattaa    5520
aaacattcgc cactgtatcg cttttcttac gagctaaatt atataaggat ggaaatttta    5580
gcatcaaagg ttgtttaccc atccaagagt cctcccaaaa tctaatctgc ttcccatctt    5640
taagagtaaa gaaaccaaga ctaaggaatt ggtctttaac tttcattagc acagaccaaa    5700
aataagagta acccaatttt ctaattacct ttgacaaggt actagatttt aggtatttgt    5760
tcctaagtag cttctaccat aggttgtcct cattaatcaa tttaaacaac catttaccaa    5820
gcaaacactt attttggacc tcttggtctt taggttggca aagaatgtcc catcatgcaa    5880
gcctatactt ctttttatga tgatctccta tccataagaa tcttgaacga aagtagtcta    5940
ttttttctag tacacccta ggcacttcaa aaaaagaca acacaaacat aactaaactt      6000
gtcaggacag gattaatcaa gactaaccga cctcctactg agaacttgaa agggaagctt    6060
tatctttatg gttttccaat cattattact taactttcta taatgcattg ggatgtccaa    6120
gtacttgaat gggaagatag tgtttcttta tggttttcca atcattatga taattaattt     6180
ttatgggaag ctttatcttt atggttttcc aatctttatc tttatggttt tccaatcatt    6240
attacttgac acctaaacag agaaagatag tgtttcttcc tcctcagata gaccaaaaca    6300
aaaagctcac ttttatgata attaattttt aaccctaaaa catgttcgaa ggttaacaat    6360
aagggcttta aatttgccga tttcgctaag tcgtggtcca aaaaaagaat tatgtcatct    6420
gcatattgca gaatggatag accccatcc actaaatgtg ggatgagacc atcgagttga     6480
tcctcctctt ttgctctatt caccaaaata gcaagcatgt ctacaactat attgaataat    6540
aaaggagaaa gagggtccac cgacgtaaac ctttagaagt ctagaaattt gcaccaattt    6600
ggtcagtcat gccaacatga ccacccgttg tgactgaatt aatcgaggaa caccactttt    6660
tagaaaaatc tttcatatgt aatgtttgtt gtacaaaaag tccatttgat tttatcataa    6720
gctttctcaa aatcaagctt caaaatcacc ccacaatcct ttttctatgt agctcatgaa    6780
tagtctcgtg taaaaccact gcaccttcca tgatatttct acctgttaca aaagctgttt    6840
ggtagaggcc tattacctta cttgctaccc ccgagactcg atttgtaaat actttggtaa    6900
agattttaaa acttacgttt agtaaacaaa tcggtctgta ctgttgtata gacatagcat    6960
ctttacattt aggcaggagt ataatggtgc caaaattaag gctaaaaga ggtagctctc      7020 ccttattgaa agcatcaaac gaagacacaa atcatcttcc ataacattcc aaaacacctg    7080
ataaaattcc gccagaaagt catttggccc cggggcttta ttgtgttcta tctggaaaat    7140
tgcttccctg atttcgtttt caataaacac cgacatcaga taaaaattct catcctctta    7200
```

```
ataaaagagg gatttttttt gcactcgtca ctgactttcc attttttgtc caccctctta    7260
agtgctgcct aagctcttgc catcactagg tttctatgtt tatacattta taatcttagc    7320
cttacagttt tttattttg caaaaaaaaa atcatcctgc agatatttca ttgtgatcga    7380
tgatttatgg gctacatcag tgtgggattt cttgagccgt gcttttccca aggataactg    7440
tggcagccga atagtaataa ctactcaagt tacagaagtt gcatttgctt gctgtaacaa    7500
ccacacagtt gatatattca atatgaaacc tctggacgac gatcagtcac tgcaattgtt    7560
ttacagtcga gtaaagcata taaatggtta taatgctgaa gaatgcaagg ccatatcaca    7620
tggaatcgtc agcaattgtg gtaatctttc accgctagct atcataaata taactggcat    7680
gttagcaggc tgggcggact tcaatatgaa tgattgggag tacgtaagca agtgttgtac    7740
gtttacagca aatcttacta ccgaggaggc gatggagaga tttctgaacc ttatgtacaa    7800
caagcttcca gccaaattga agacgtgcct gctctatctc agtatgtatc cagagggctg    7860
tgtcatcgga aaggatgatt tggtgagaca atgggcagct gaaggtattt tcagtcaagt    7920
ggtggaacca aaaggtagag aacatgaagt gggtttttatt tatttgatg agctcctgaa    7980 aagaggattg atccagcctg tagatacaga ctacaatgat caagtgttgt catgtatagt    8040
tcatcaagtg gtactggaat ttattacaaa gaaatcaatg caggaaaact tcatcactgt    8100
cgtggattat cgtgaaacag gacagtgct tgatgataat aaggttcatc gactgtctgc    8160
caggtttgaa ggtgccaaaa gtgcacagat accgcggagc ttcagagtac gccaagttcg    8220
gtcctttatg ttttctggat tctttaagtc tttaccttcg cttctcaagt attgccttgt    8280
ccgagttctg attcttcgtg tttggagtga tgatcaaggc aagactgtgg ttctagacct    8340
ttctccagtt ggtaatatgc ttcatgtaag gtacctgaag gtggtaagcg acatgatagt    8400
caaactccca ctcattattc gaggcctgcg acacttagag acactcgagg tggatgcaga    8460
agaagtcgct gttccactgg atgttttcat cttgaagagc ctgttgcatc tccgacttcc    8520
gagcaaggct tatcagcttg attcagatat tcaaaggatt ggtttaacaa atacatttcc    8580
tttaagtttt ctgcccttcg tcagaacgtt gtcaatccta ttcctatggc ggtctctcct    8640
ctcccatggc catttgacat cgcttcaaag tcttggctac tttgacctga gcacttgctc    8700
cagatatact gtgcggcaac ttggcaagct gaccaatttg agggatcttc atctaacctg    8760
ctctgcagtt cgttccaggc atcgaattag caacatccaa tgccttgcct ctgttctggg    8820
gaaatgcacc agcctcgaat tctaactat ccgtggcgaa gcatcttcaa accagagcat    8880
ttcttttgat ggcttaagca gattgtcttc tccaccgtac aacctcgtga gctttgtgct    8940
gtccccgagg attttcaaaa tggcgaagct ccccaagtgg attgggcaac tcagcaggct    9000
cagtacgcta aagattgctg ttggcgagct gtcaagtgaa gatgttgaca tcctcaaaga    9060
actctctgcc ctcactgctc tttctctcta cgttcgcaga aaccctaaga aggaagctg    9120 gatcctattc agtaagggct tcgcagtgct caagtatttt aagttcactt gcactgcact    9180
gtgcgtgaaa tttagtgaac aagctatgcc tgctgtccaa aggctgaatg tgtgcttcaa    9240
tgctaacaca atgcagcagt acaggccgga agatgcagga atttggtacc tgtcaggcct    9300
tcaagttatc tctgccagaa taggagctgc cggtattgat caagccagca gagaagccgc    9360
gaaatctagg ttgctggacg ccattcttag caaccatcca aagcctcctc ctatcagaaa    9420
cgtgcaaatg gtggactggg ttattcatgg cgacacagag gagtgttcaa ccggtgtgat    9480
gatacgtaaa gatgaaagca gccgtgagca tactaggtca ttttttaagtc agttcccgtt    9540 cagaagacga cccctgcttc cctccatatt cacaaggcgt ggccaggatg atgagcaaca    9600
```

```
taaaatcgaa gaaaatgatg tgctacaaga tagtattatc ttaagggaat cctcttcgct   9660
aatgcaaaaa ccaggtactc tccattctta tatatgctta ttaataatta ttttacacca   9720
tatatatagt gttttagtat aagctttgtt atctctacaa acataatagt ttactttatc   9780
tgaaaactta accacgcgat tgggaaaata gttttttgttc ctcatgctag ctagctactg   9840
aatcgacata aatgtcaagg aacttggatt atgtgatgca acccatgccc ttacacgagc   9900
taaaatctta cgagtcatca gcattaatta gttactatta atatctctat ctaataaaaa   9960
aattacattt aacaacgctt ttcactttta ccattttatt tcacgataga catacgctg   10020 aaaccgactg aactgcggat agagaggcac atgagagtat ttctagcttt ggggtttagg  10080
tttactgttg gtctgatcat attgatcaat ctggtcctga ccaattggag tgccttaaac  10140
cacatggtcc tgatctaagt aaacatccca aactcaaaaa ttgagccttt acaaataagc  10200
ggacatacaa ctccgtctat gttgaacttg gtctcaagcc ccggtaaagg aggggatgtt  10260
aggcttagcg agccaacctc tacttagtca tttgtggaaa tgaaacccat gataagtttg  10320
taggagtgta accctcttaa tagcatcgtg ccacatcgga atccgggtac ggtgttaaat  10380
gggcaagggc cggatcgtcg ccctcttagg gacacgctgt gttgtggtct aggcaaggtg  10440
ttaagtgaac aaggatgggg tcatcatttc cttagtggtg tgctacatcc gcgcccgggt  10500
gtagtgaaaa gtgagcaagg gtcttcatat ctctctcgac gggtgcgaag gataaggaag  10560
ttagtcgaac caactaggtt tcgtgtaggc agttagaacg tagggtcccc tataggtaag  10620
ttaggaaagc taattgatgt agcaattaag atgcgtgtaa tataatatcc tatgcgttca  10680
agagactaaa tggaagggac aaaatatgga ggaggtggag gatattggct tcatgctttg  10740
caacatagga gcaacttcga gtaggaacgg tattggtacc ttgattggca agagccttaa  10800
ggatggagtc gctgatgtta ggaatcaagg tgactggatt accctagtcc ggctggtagt  10860
tggagattcg gctatgaatg tgatcagtgc ctatgcccct caggtaggtc ttagtgagag  10920
caccaagtgg cagttttggg aagatctgga tagcatggtt agtaccatgc ctaccagtga  10980
gagactcttc ataggagaag acctcaacag ccatgtgtgt gtgactaatg taggttgcaa  11040
actagtgcac aggggttcag gtacggtagt aggacacaag aggaggagga tggtttggaa  11100
ttcgcgttag cctacaacct attgatagag aatacccctct ttaggaagag ggaatctcat  11160
ctaatgacct ttcacaatgg acaacacttg agtcagatcg actttatcct tacaagaagg  11220
gaggatagac atgcttgcgt agattgtaag gtaatgccta ggtaatgtgt tgtccctcta  11280
cataagcttg tggcggcgaa cattcgtttt taggtacgtg tccactggga caaatgtacc  11340
aagatcgcga gaacggagtg gtgaaagctt agagggaac cgacacaaat gtttaaggac  11400
aggatgctag gtgaaaaagc cttcggaaga aggagaacat gcaaacaaca tctggctaaa  11460
gatggcaaca tgttttcaaa agatggctt ggaagtgttt ggtgtgagta ggggaggcaa  11520
gcaggaggcg aaagacaccc tagtggtgga atgacaaggt gcaaagggtt attaaggata  11580
cgaaggtgtg tttcaagtgc ctcctccttg acaaaggtgc ggccaacatc gagggattta  11640
aaatagagaa gagggttgta aagcgagcta tgagtgtagc aaagggaccg acgtatgatg  11700
atctttatca gcggctaggc acaaggagg aagagaatga catttatagg atggctagga  11760
tacatgagag gaagacaagg gacatcaacc aaatcaaatg cgtcaaggat gagacagatc  11820
gacttcttgt gaaatataag gagatcaagg acaaatggtg agagtacttc gacaagttgt  11880
ttaatgggga gaatgatggt cctaccctca agttggatga ctcatttgat gatacgaaca  11940
```

```
tacactttgt aaggataaat catgaggcaa agatcatgga ggctttgaaa agcatgaagt    12000
ggggtaaagc gatggccctg atggcattcc tattgaggtg tggagatgcc taggtaccaa    12060
agcgataata tggttaacta agcttttaa cctcatcttt cagtcaaaca agatgcttaa     12120
aggaatggag aagtatattt gtatcggttt ttaagaacaa gggagatgtt caaatttgta    12180
ctaactacca tgggattaag ttgacgagtc atacgatcaa actctaggag agggttatcg    12240
agcatcgcct aataagagtg acaactgaca agtgtgaccc taaactaatt tgggttcatg    12300
cctagaaggt tgaccatgga ggcaattttc ctaatatgac aattgatgga gacatataga    12360
gagttgaagg acttacacat ggtctttatt gactttgaga aggcgtatga caaagtacca    12420
agaaatgtca tgtgatgggc cttggaaaag caaaaagtcc caattaagta tattatcctc    12480
atcaaggata tggatgcgat gacatttgtg tcacacccgg attttaggga tccaaagccc    12540
gggcgcgaac ataaacacca ggtgtgctgg gaccaagtct cacacatatg atgcatagtg    12600
gcacaggatc gaatgtcaca tctttactat ataacaggag ttctatacaa ataattaaa    12660 taattacatc atatgaggaa atgatccagc aacccaaagt tgactgggag acgacgacct    12720
agatctctca cgaactcatc gcagcatcct ccaagctcct catcctgtgg tacctgctat    12780
tgacctgtgg gggggtgtg agacagcaag agtgagctca catacgttca tcgctcaaca    12840
agttgtgggg aataatgtgc atgaactcgc caaggtggg agctcacgtg aagtgtaagg    12900
cttaccaaag aggatggttg aagctgagca ttgcttttaa agttggtcaa aattttatta    12960
gcaattacta agtataagta aataccaacc caattaagta gtagaacaag agtaacaaca    13020
tcacctgcga tgcaatgcat atgacaaatt gaatttaagt tccataaatt aatcatgtga    13080
gggtccgagc tgctcatgac cgtgagcacg gctagtatac cagtttaca ctctgcagag    13140 gtggcgcttc tttacccaca agtcatgtta cccatctgcc aagggatcgc gacttcccat    13200
acacctctac cgaggaggcg aggcagggta acactacgag gcctttacaa agttccacta    13260
gcttcagaaa acccgctaca gtttatagga agctccaatg caggaattcc cttgcaggac    13320
cgccatcgca gcaaaatcct cccgagggtc tccctacact gaccactccc ctactgccct    13380 tgccccttc gggtaaggta gtcctccact agctttccta attaatcagc caagggcgtc    13440
ccattatacc cttgtggtag cactgttttc ccgggtggtc gctccatgtt ccaattaaca    13500
taatgatctt atcatgaacg ataaatagca acggataaca aaagtataat catgtgtaat    13560
gtatcttcat acccaaaacc acataaagca ctagcaagta ctacccaaaa agttcagtgg    13620
tatcaaggta taaagatatt caaactaggg taacctattg ggtcccatca aaattaacct    13680
atgcagatca ttatgattaa tcagaacatg gctgggtaaa aagaagtgat caagggcaca    13740
acttgcctgg gacttgagat tccaggtacc aggatgatct tcaggtgaca cgtgaccctca   13800 cgctagtcgt agcaatacaa acaagcagtg tataggcaaa attaacatca caccaaacat    13860
gtaaacaaaa tacataatag taatctactc attaaaataa gattctagga acagaaatca    13920
ttaattttgg agttacggat tctaagttat gaatttctga agttaataag catctagagt    13980
agattaatcc aaatgaataa ttttaattta agttttatgg ttaaacaatg ttactagttg    14040
atagacaata ttaatacaaa tttattgaaa ctggaatgga tcaatttgga cttaatatga    14100
attttctacg aattaaacaa gtttctggaa ttattttgt attaaaaatc attttctata     14160
attaattttc tatttcaatt gttctctgga ctgggcataa ataacagaaa gacacagggg    14220
ctaatgtata aaaatatccc agactcagat tctacccgcg gtggacggcg ggtttataca    14280
aagaaaagat agggtctctt tagtaaatat gccgaggcga agaggtatgg tttaatctcg    14340
```

```
ggcgctggat cagacttgga cgcgccagat tagaacgatg tatacgcgaa ccggtaagga   14400
atcgcgtccg ttggatccat cagatgcggc ccggatttaa ttaccccga ttccatccta   14460 tccactggtg actagatcta cggtcaggat ttctcgctcg aagggtaag ctatgccta    14520 atccgcaccg cagatcgcac gatcgacggc acacattgcc tcttccttcc ctcgccgcgc   14580
agctacggtg gagactaatc cccacccgac ggcgctgagc agaggcacgg cggcgccatc   14640 gccgacccc cccaaaccat tggcccgagc accaatccat gacccggaca gtgctacacg    14700
aactatggag caaggtgaat taaataaggt gatcctcacc gtcgattggg acgcgaagaa   14760
tcacagccac ggagatgcgt agcactatag tggagaaagg attcctatga gaaatcccgc   14820
ggtcacctgt gctccacgac tctcccagca agttccgagt cgatccccga gagctcgtca   14880
ccggcggaaa atccttcttc tctttcttct cttcccatgg tttcgctcag cctgtgctcg   14940
gcttggtgct gtccgctccg acctggccta cctgtagagg gggcgatggt gctcgagttt   15000
tatacccggt gattagcctg tggttcgcca aatcccaaca acctggacga ataccccgga   15060
atccgcgcac cagagtgacg gggtttgtta cgcgagatcc acggaatctg ttggtgctca   15120
ccccggttcg tgacgacgaa ggagacgagt attacaagtg gccccacat gcaagagaca    15180 catagagcca cacacggagg tgagcagtca ctgggcacta ggacccaccc gacagtggtt   15240
cgaagcgcag accaggagca agccgcgtgg gccgcgcgtg ggaaatacga tattgggccg   15300
aggcaagggt gagggtgagc tatccgaccg gaaatttggc ccaagcaatg ttttttttcct  15360 ttttccttgt ttttttctgt tttccttttt gttttttctat tttcagttc cttgattcaa   15420 attaaattta gtttttcag atttgaacga atttcaaact cacgcataat gcaccatcaa    15480
gtaaaattca acatgtaatg caaagtcatc tatatgtaca tgttagttat tttatttatt   15540
taggcacaac ttctccatgt acaattcatg aaagaatagt tttactcaat cttaataaaa   15600
taaatctttt tatcatctct ttctgagttt gaaatattaa acttaaaagg tcaattctat   15660
atttgcgata tcaaaattta atgatacttc tcatctatct ttatgtactt cctaattcag   15720
attctagttt ctagatctat tcttagcttt gaataaccaa agaaaaattt aatcttatta   15780
cttttttaga aaatgatctc aaaccaataa aatccttatt aaaagacatt ttaatctaaa   15840
tactttgaag aacttttccc agtaatcaag gcacgatttt tttagggtgt tacaaatcct   15900 accccctta acaagaatct cgtcccgaga ttcgtaagaa atgggatata ggaagtcaaa    15960
ggcttaggtt gcagtttagc ttcgattttt ttatctaagt ggctttaagc acaaatgttt   16020
tcataatgat ttttttttata aggaattgat taggaacaca tgggtatatt tatgtatatc   16080
cactttacta tgtagggtaa aaaaaatgtc tttaaagcat agataggtct gggtaagaaa   16140
aagtggggta aggaaaagact ccatccaaga ttgtggatct tgactaatct tggtgatcac   16200
acttgatcct tgaagacttg agtttgtgct catcctttct tgatcatctt ctccaggctt   16260
gtctcattga ttaggagtta gtgtatatta tcgggctggg aaatatgttt aagatagaca   16320
tggatgagat agactacatg atgtaggtca gaagtttgtg tttggtgtca ggtgggggtt   16380
gatagattat gcaatccatc aagactctat tggttgggtt ggtctccttt ggcctttatt   16440
tcttggagtt gtcatccgag ttaaggacat atggctagga catatgtggg taggatggat   16500
tgtatggtgt aggtaggtta gaatctctga tgggttgaaa cagagggtta tgcaactatc   16560
agatggttaa ggtattaact ggttaagtga ctgaccttag gttagctcaa cttaaggtta   16620
gacttcgtta ggttagatta atctatcaca ttagatcatg gttgttactt taggatgaga   16680
```

```
taagtaaagt ggttaggata agaagaaccc ttcaagataa gatgaatcta ttaagataag    16740
agagaatctt ttaagatagg atgaattggt tagaatggga tcttttagga taagataaat    16800
ctcttaaact agatatattt caatggggat aatctagttt gtctagttat tttgatgagc    16860
attttttcct atatgtatat gcagatgtaa ttgtggacat tactccacaa ctaattacac    16920
tcaatcaaag atccaaatca gacaaatatc ataagaacaa acactcaagc atataaataa    16980
aatagttttg tttttgttcc taagagcagg tctcctattc ctaaagtcac tttaggtacg    17040
ggatttcaaa gtgtgaactc cacatttgtc tttagagtga aaaggtaaga ataatcagag    17100
taaaggggaa atagatgaga aaagattaag aaaagtttag ggaagaatcc gagttgcaaa    17160
ggtaaggtta atcagagtag aacagtagaa ggtgggactg gatcaaggaa agtatagaaa    17220
gaatcagagt aaggtaagta tgtaatggtt gtccagttct atctaggttt tgtcctacag    17280
tcaacattcc tctgatacca cttctgtcac acccggattt tagggatcca aagcccgggc    17340
gcgaacataa acaccaggtg tgctgggacc aagtctcaca catatgatgc atagtggcac    17400
aggatcgaat gtcacatctt tactatataa caggagttct atacaaaata attaaataat    17460
tacatcatat gaggaaatga tccagcaacc caaagttgac tgggagacga cgacctagat    17520
ctctcacgaa ctcatcgcag catcctccaa gctcctcatc ctgtggtacc tgctattgac    17580
ctgtgggggg ggtgtgagac agcaagagtg agctcacata cgttcatcgc tcaacaagtt    17640
gtggggaata atgtgcatga actcgccaaa ggtgggagct cacgtgaagt gtaaggctta    17700
ccaaagagga tggttgaagc tgagcattgc tttttaaagtt ggtcaaaatt ttattagcaa    17760
ttactaagta taagtaaata ccaacccaat taagtagtag aacaagagta acaacatcac    17820
ctgcgatgca atgcatatga caaattgaat ttaagttcca taaattaatc atgtgagggt    17880
ccgagctgct catgaccgtg agcacggcta gtataccagt tttacactct gcagaggtgg    17940
cgcttcttta cccacaagtc atgttaccca tctgccaagg gatcgcgact tcccgtacac    18000
ctctaccgag gaggcgaggc agggtaacac tacgaggcct ttacaaagtt ccactagctt    18060
cagaaaaccc gctacagttt ataggaagct ccaatgcagg aattcccttg caggaccgcc    18120
atcgcagcaa atcctcccg agggtctccc tacactgacc actcccctac tgcccttgcc    18180
cctttcgggt aaggtagtcc tccactagct ttcctaatta atcagccaag ggcgtcccat    18240
tatacccttg tggtagcact gttttcccgg gtggtcgctc catgttccaa ttaacataat    18300
gatcttatca tgaacgataa atagcaacgg ataacaaaag tataatcatg tgtaatgtat    18360
cttcataccc aaaaccacat aaagcactag caagtactac ccaaaaagtt cagtggtatc    18420
aaggtataaa gatattcaaa ctagggtaac ctattgggtc ccatcaaaat taacctatgc    18480
agatcattat gattaatcag aacatggctg ggtaaaaaga agtgatcaag ggcacaactt    18540
gcctgggact tgagattcca ggtaccagga tgatcttcag gtgacacgtg acctcacgct    18600
agtcgtagca atacaaacaa gcagtgtata ggcaaaatta acatcacacc aaacatgtaa    18660
acaaaataca taatagtaat ctactcatta aaataagatt ctaggaacag aaatcattaa    18720
ttttggagtt acggattcta agttatgaat ttctgaagtt aataagcatc tagagtagat    18780
taatccaaat gaataatttt aatttaagtt ttatggttaa acaatgttac tagttgatag    18840
acaatattaa tacaaattta ttgaaactgg aatggatcaa tttggactta atatgaattt    18900
tctacgaatt aaacaagttt ctggaattat ttttgtatta aaaatcattt tctataatta    18960
attttctatt tcaattgttc tctggactgg gcataaaata cagaaagaca caggggctaa    19020
tgtataaaaa tatcccagac tcagattcta cccgcggtgg acggcgggtt tatacaaaga    19080
```

```
aaagatagggg tctctttagt aaatatgccg aggcgaagag gtatggttta atctcgggcg    19140
ctggatcaga cttggacgcg ccagattaga acgatgtata cgcgaaccgg taaggaatcg    19200
cgtccgttgg atccatcaga tgcggcccgg atttaattac ccccgattcc atcctatcca    19260
ctggtgacta gatctacggt caggattcct cgctcgaagg ggtaagctat gccctaatcc    19320
gcaccgcaga tcgcacgatc gacggcacac attgcctctt ccttccctcg ccgcgcagct    19380
acggtggaga ctaatcccca cccgacggcg ctgagcagag gcacggcggc gccatcgccg    19440
accccgccca aaccattggc ccgagcacca atccatgacc cggacagtgc tacacgaact    19500
atggagcaag gtgaattaaa taaggtgatc ctcaccgtcg attgggacgc gaagaatcac    19560
agccacggag atgcgtagca ctatagtgga gaaaggattc ctatgagaaa tcccgcggtc    19620
acctgtgctc cacgactctc ccagcaagtt ccgagtcgat ccccgagagc tcgtcaccgg    19680
cggaaaatcc ttcttctctt tcttctcttc ccatggtttc gctcagcctg tgctcggctt    19740
ggtgctgtcc gctccgacct ggcctacctg tagagggggc gatggtgctc gagttttata    19800
cccggtgatt agcctgtggt tcaccaaatc ccaacaacct ggacgaatac cccggaatcc    19860
gcgcaccaga gtgacggggt tgttacgcg agatccacgg aatctgttgg tgctcaccccc    19920 ggttcgtgac gacgaaggag acgagtatta caagtgggcc ccacatgcaa gagacacata    19980
gagccacaca cggaggtgag cagtcactgg gcactaggac ccacccgaca gtggttcgaa    20040
gcgcagacca ggagcaagcc gcgtgggccg cgcgtgggaa atacgatatt gggccgaggc    20100
aagggtgagg gtgagctatc cgaccggaaa tttggcccaa gcaatgtttt tttccttttt    20160
ccttgttttt ttctgttttc cttttgttt ttctattttc agtttccttg attcaaatta    20220
aatttagttt tttcagattt gaacgaattt caaactcacg cataatgcac catcaagtaa    20280
aattcaacat gtaatgcaaa gtcatctata tgtacatgtt agttattta tttatttagg    20340 cacaacttct ccatgtacaa ttcatgaaag aatagtttta ctcaatctta ataaaataaa    20400 tcttttatc atctctttct gagtttgaaa tattaaactt aaaaggtcaa ttctatattt    20460
gcgatatcaa aatttaatga tacttctcat ctatctttat gtacttccta attcagattc    20520
tagtttctag atctattctt agctttgaat aaccaaagaa aaatttaatc ttattacttt    20580
tttagaaaat gatctcaaac caataaaatc cttattaaaa gacattttaa tctaaatact    20640
ttgaagaact tttcccagta atcaaggcac gatttttta gggtgttaca atttgtccgt    20700
acatgtgatg atgacattag tgactttttc aattaaaata ggactacatc aagggtcatc    20760
attgagcctt tatttatttt ctttgtgatg gatgactgga cgaggtcgta agagacatac    20820
atggtgataa aacgacttgg tcaagctcca tgggcttcca tgccggagtt ttgagtgtca    20880 gatcctttt gaactcaatc cccaagtccc gccttgctcc tcgctcaggc gccctcgctt    20940
tctactagtg gctttgtttg gtcattgtaa gttttgactc gagccctctt cggttggctt    21000
cgtggtccaa ttggccattg gtggcttggc tttggatttc taggtggtct aactctctga    21060
tagggttttt cactttgttg tctcttctcg gtaggtgggg ttctctgtct actggctttg    21120
ttggtttgac tgcaatgagt ttaaggtttt ctttcaccttt tggagcttgg gccgcccttt    21180
gtggcaacat gagctatttt cttggtggag aaggctgagg agtctctgta gcaaagagtc    21240
aaggaaaagt tttgaccggc ctctgatata ttttggtgg caaatttggt tggaaagcaa    21300
tcatatagtg ttccagggac agcaaaaaat gtagagcagg ttgcgctctc tgtgaaagag    21360
ttttttttga tactaaatat catatctgaa aagggcggca tgaacagcaa aattcaaaat    21420
```

```
catagtaaga atcaactcgg ttatagtttc aagagtgtca tgggccatat tgatcacatt    21480
aaactcggtt atagtttcgt ctgacgaccc ttaacggaaa aacaggttgg atgaatttca    21540
aaaaacatgt cgttatcttg tgtaaattta tggacagaaa gaagatgctt ggagatatct    21600
gggacataca agacattacg tagtgcaagt gggcgatcaa cagaattaat tgtagaatga    21660
ccagtgttta agatctgcaa acccgcacca ttgctgactt ggacttgctc accaccatga    21720
tagcgttcac gaagcatcag tcggtcaaga tcactagtga tgtgatctgt tgctcccatg    21780
tcgacgtacc aatttggatc aattttggtc gaggaggtgg ccgccaatgc cgccatggga    21840
gaatcagtgt tgtagctgtc gtcattcctg tgccagcaat ggatggtggt aggaccctcc    21900
ttgcgacaga tctggcaggg cggtcgtgcg tttgagccat gaccacaatt gtcactgatg    21960
cgggacaaag gtccagcacg gccgcgccag cggacacggg caccacgtcc cctgtcgtgg    22020
tcaccacgac cgccacggcc tgcgtagttg gcagacgatc cgaacgcaag ctgatggttc    22080
atctgatgtt taatttgcct cgcctcaaat gccatgagat aggcatatac atcatcaagc    22140
gagagggagt cgcccttggt tgtcattgaa gtaacaaagg ggtcatactc gactggcaaa    22200
cctacaagca gataagcaat caccctcgtcg tcacgaagag aggaaccagc aacaaccatc    22260
tcagttgcca agcccttgat tttgcgaaaa taatctgacg tcgtaagatc gagtttcttt    22320
gccgtggcaa gctcgacgcg gatctagaga gtacgcgctc gtgtggagga agtgaactgc    22380
gtctgtaagg aatcccagac ttccttggta gtcgtggcca taaccacgtc acggaggag    22440 tcctccgaca tggacgacaa caatccgctc aggagttgct agtcttgatc ataccacttg    22500
atatacgcag ggttgataac ttgtgcagca cctggcgcag tggacgcagt gatcatccgt    22560
gctggtgccg gtgtggtccc atctaggaac ccgatcaacc tagagctctg cgggtagggg    22620
agaagttgag cacgccataa caggtaattg ctcttgttta gacgaatggt taccgcgtga    22680
tggagcggca ccatgggagg tgtgggctcg gaagaaaaac tgttggccat ggtgatctga    22740
ggagaggagg aagacgtaag ggaagatgtg gtggacgagt ttgacatcta ttggatcaat    22800
agctctggta ccatgttgaa tggcgcaagg caatcagcct ccctgctgtt agcgtattaa    22860
tataggaaga gatacatgca tggcgtatag aaagggacgc aacaataggc aacaaccatg    22920
cctagaaagg aggcacaggt ccaacagaat caggcgcaca agccttacct aacaaggaga    22980
tattttcaat cttaacagaa tttaggaggg gggaggggga gaaggatttt tcagtcccac    23040
cgttaaggaa accatgaacc agttcaatgg gactgagata ccctttttgtg gtgttgagtt    23100 tttggccaag tgacaaagga aagtgtttca gtgattttgg ggcatttcac caatctagct    23160
aacgtatgcg aattctggag ttttaatgta ggccctgggc aggatccaag ttttgtgttt    23220
tactacatgt gctgagattc atctctatgc aggtgtctat tcaagttgat ctgcagatag    23280
ttgttggtct atattttca gttttcctc tccttcccgc catctagtgt ctaccatatc    23340
ttgttcattt tttacctcta ctaatatatt gtagaggcaa agttttgcc acttcctttc    23400 aaaaaaactt aagcgttaga aggtttaatg tagactctag cgttagaggg gataaacaag    23460
tagtttccgc cttttatca agttaatcaa ctcagaaagt tgtttcttct cagtttttat    23520
taaccctgct tcttctcagt ttttattaac cctgctgaat tctttgccca ccacttaga    23580 tattgccgta gaaacctaat cttattccgc gatacttgta cggcggtttc ttctctattt    23640
tttgttgcca aatagaacta atcatatcat taaaaaccct ctctaatatc ctatgtgttt    23700
gatttctagt gactaatttt tattctctcc attttggtcc ctaaattgct aaacacatga    23760
actaaaatag aaaaaatctc tatttttggtc catgtgttta gcaatttagg gactaaaaat    23820
```

```
tactaaacta gagggacaga aaattagttc atttaaacca aacatcctct taatatgtgc   23880
atcaaacgga tcatgtgcat ttgatattgt tagcagaaac ggcaggaaaa acaaagtaga   23940
tcaaccaaca aaacacagag cacgacacac agatttacgt ggaaaaccat tcaatgtgaa   24000
ggaaaaaacc acggacacga attaagcgaa accttcacta tgtgtggagt gtttaaagaa   24060
cgccgtccgt tgacgacacg acttacaaga ggagtaaatg acgacacacg acaaattcta   24120
attagggtta ctaatatata tcgcgggggg ctctgcccccc ataccccccg cgtacagggc   24180
tgccaacgtg gtctctatat gcagaattta gatcacagac taaacagata tgttccctag   24240
attagaatat aattggtcca aaatttcagt ctagtatgat gatcttttaa taattttttaa  24300 aacaatggaa ctgcaggttg ggtcacccgc agatcaagga gtactggtgt tggccttctg   24360
atggccgtgc gagggtccac atacatgatc aggcaatata taaaggagcc aggattcaat   24420
gcagcgaatg agatggcatc catcaaccag gagataagac agattggtag aatggtcata   24480
tcaagcaata tattggagcc gccggaatgg attctgcaag cccaagacct ggcctgtgat   24540
gtgcaggatt tcacggatat ctacacatgg ctgcaaagca aatcgcggag gcgtgcccttt  24600 gcacatatag gctacatagc gcagctgaag gatcggatca gcagccttcg agagtggcaa   24660
cagagaggag gcagcagcag cagccagcag gagcgtgctg ctgccttgtc cttctcgcgg   24720
cgatcatgcg ggccttgcgc ccctgaggat gtgctagttg gcattgatca gcccaggaaa   24780
gaactttcgg acctcatttt cgaaagggag gatgttgtgc aacagaagcc cagggtggtc   24840
tctgtcgttg ggtatagtgg cattggcaag acagccctgg caagagcagt ctactacgac   24900
cctagtgtcc gttctgcctt taacggcgtt gcttgggttg tggcatctga atgcaaccat   24960
gggtgcgacc ttgtaagtaa gatctgccag caggtcaagg acgaacaagc agggaacggt   25020
gctgtcgtcc ctgactgtta taggttaaaa gagatcatgc gggataaaag gtatatataa   25080
tgtatagctt attttctttc tctgctcccc cgaccaaaaa aaaattaagt tttgtttctc   25140
ttttcttctt ctgctaggtt ttttatcgtt attgacgacc ttcagggagc tggaatgtgg   25200
aacgatataa aaggtgtctt cagtgaaact cacagtggca gtcgaataat cgttaccacg   25260
agtattcagt cggtcgccgc tgcctgcact cctgagccgc gatacattta caggatgcca   25320
agtcttggta atttggactc tgaaaagcta ctgtggatga gggtcggcag gcatgcaagc   25380
cgtacgcctg ctctggagca tgctttaggc aacgacacct tgaaaaaatg cggcggtcta   25440
cctctggcac tgatcagtgt tgccaatcat ttgtgtcttg ggaaagcatt atttgaggag   25500
atggacaggg ttcttgccaa atgctatgac agcttgcctg acaatgctca caggatgtgc   25560
ttgctgtccc tgagcacatt ccctcagggt catgtgatga agaggaagag gctaattaga   25620
agatggatag ctgaaggatt ggctgtcgga gactgtgagc tcagtgctga acaagttgcc   25680
ggtaacatat ttgatgtgtt gattgacagg aacgttactg agcctgtgct gactgctggc   25740
cacggttcta gtagtaaggt caaggcatgc ttagttcttg gtgtgatcaa ggacttcatc   25800
aacaaaacgg cagtctcaaa tgagactgta gctataatcc agaacgatga gcttctcctt   25860
cccaacagga tgatgctggt cgcccatcgt cctgttcgtc gactgcttgt tcatggaggc   25920
acaacaaaga aaagtgaagc tgttgcaaag gcgatcggac tggatcaggt caggtcgctg   25980
acaatctgca atgctgtgcc cttcgacttc cagggctgct ggttgctgcg ggtcttggac   26040
ctggaggctt gccaggggat cgacaagagc atccttggca gcatatgcaa gctggtgtttt  26100 ctcaagtacc tgagccttag gggcaccgat gtttacggaa tacccaagaa agtaaaaaag   26160
```

```
ctccagcgtt tggagacgct ggacctcagg gacacacggg tggaagaact gcccatccaa    26220
gtcttgatgc tcccacggtt ggcccatctg tttggcaagt ttgagctacc tccacagctc    26280
aagcatggtc atcgaaccgc aaggaggagg aggagtaggc tgcaggcatt tttctcccag    26340
agaagcaggc tgcagactct ttcaggattc gtcatggtgg atgatagcaa cagcttcgag    26400
cacatgatga taaccataaa gtcactgagg aaggttaagg tatggtgcaa gaattcaatc    26460
tcctcccacc aagaacgcca tcttgcttct tcccttcagc aacggctagt aggaaacagt    26520
aatcccctag aatctctgtc aattgatttt ggcaatgaat ccatcaattt cctcaatgat    26580
gttggagcta ccagtgcact tattggctct atgaagctac agggaaggct aacctcgctc    26640
cctagcttca tgacttcgta cgatactaca ctctcccagc tgcagctgtc ctcaactggt    26700 ttggcatag aagccttgtc cctgctgcaa atcttacgtc ggctggtttc tctgaagctc    26760
gctcaggatg gtgatggatt tgggggtgac tgcttcgctg ttaacaagga tggatttcca    26820
agccttttac gcctgtgcat tcaggccagg gagcttcccc agttgcacat ccatgaagga    26880
ggcatgagct ctctcacctc cctcgaacta ctctgtccca tgttcgctag tcgcggtcac    26940
tctgactctg actctgactc tgacttgggg aaaacttacg tggaaaccca ttcagagaag    27000
agatccaaac aagttctttc ggtagagaag cccaaagcag ttgatcccgg gatcagcttc    27060
aaggaaccaa gttctgagac aagatcagaa ggaactgaaa ttcaggagat tgattcccct    27120
aaaacgtcca aggaggctgg tcccagcata ggcttcaagg atattattct tccggagaac    27180
acattcagaa gaaacttttc gaaggaagtc aaaagtagat ttgatctgaa acaacacttc    27240
aagggaatgg agtacctcca atgtctcaat gagctggtac tacattgttc tgttagcgac    27300
gaggtattgg atgcctggac aaaacgagca agcagtcaca tcaataggcc aaaggtgaca    27360
aggtaagcag tcacctccgt tcttttttt ttatttgtcg cgttttagtc caaaaatgaa    27420
ctaaatattc gagagaactt atgtagtagt ttacaaatag ttttgcagtt taccttctct    27480
acttttagta atcactcaat tcgacaggca atgcacaaga gcagcgctgt cgattggtag    27540
aggcccggga acagcgaagc acgagaaaga agggcagcac agaagccagc tcatgaaaaa    27600
tagaggttca gaaacagcaa tccatgagga ggtagcagag caacacagct cagtaggaac    27660
gagccgtgag gaagcaggat tattccaaga acagacctca ggtaaacagc tagaagcatg    27720
ccaaagacct atatgtacat tttttgtggt tccatatatt tgtagtctga ctagttccta    27780
tctttgttta atcggaagat acaggtcaca aagaagaaga agaagaagaa gaagaagaat    27840
gtacgagtga agacagggca ttaaatcaac cgtgcgacat gctcattggc atggatgtgg    27900
caatacgtga acttttggag ctggtgaacc tggaagagtt tggtgtagat gacaaagtga    27960
tctccatcgt gggatgtcca ggtctgggga agaccacgct cgcaaaagca ttctctaacc    28020
tggaaatgat acgggaaagg ttcaacccgc ctgtttgggt ttcggcatca caatgccgca    28080
gcgcacagga ccttctcatc aaggttatcc gacaagcttc tcatgttcat ccagcacaaa    28140
tgataagtgc taccccaat atagatctac tgcaaactat cctagcacag gaaaggtact    28200
cgctccacac caccacccgt gcttattacc tctatatcca ccctgcctgg gtttacttct    28260
ctcagtcatg cacacaaaaa ttgtttaaca aaaagaataa gtagagcaat tcagctttta    28320
caaaaggaaa tgtttgaaaa tatgcatcaa gtagttatat agaattttaa tatttagaaa    28380
aggcacaatt tttattgtt atgaatagaa cttgtattcg atataaggcc ctaaggccaa    28440
cgtatatgca ctggtacact atagagtcct acctatatat agttgggaat cagcaaaaaa    28500
catagattcc tatctatata catcttgata aaaaaaatga cttatatatt atgagggctc    28560
```

```
cagatccaaa tatataaaag tacatgagat tacaaatatg gaaaacgaaa tacaaatata    28620
gacacgtatc tacaaatatg gacatatatc gcgaacacct cctcaaactc aaggtggatc    28680
cagaacacta agtttggaaa ggtaaaaccg acgctgagcc tgggtctctg ccttggtgga    28740
gaaatctgtc ggctgaagct ctaacgacgc atatcaaaga gaaacaacac catcatgtat    28800
ctgtgctagt gtataatgag tgttaacacc aacatgcttg gtaagctcat gctttaccgg    28860
gtctcaagca atactaatag cacatgtact gtcagacaaa agagaagtcg gtatacaaat    28920
agagacacca aaatcctcaa gcaaaggaa atgtttgaaa atatgcatca tgttttttta    28980
agtacaggtt atatagaatt ttaatattta gaaaaggcac attttttat tgttacgaat    29040 agaacttgta ttcgatataa ggccctaagg ccagcatata tacactggta cagtatagag    29100
tcctacctat atatagttgg gaatcagcaa aaagcataga ttcctatcta tatacatctt    29160
gataaaaaaa aatatgactt atatattgtg agggctccag acccaaatat ataaaagtac    29220
aggagattac aaatatgaaa aacgaaatac aaatatagac atgtatctac aaatatggac    29280
atatatcacg aacacccct caaactcaag gtggatccag aacactaagt ttcgaaaggt    29340
aaaaccgacg ctgagcctgg gtctctgcct tggtgaagaa atctgtcggc tgaagctctg    29400
acgacgcaca ccgaagagag aaacaacacc atgcatcatg tatttgtgct cgtgtataat    29460
gagcgtcaac accaatatgt ttggtaacct catgctttac cgggtcatga gcaatactaa    29520
tagcacatgt actgtcagac aaaagaggag tcggcataca aatagaaaca ccaaaatcct    29580
caagcaacca gcaaaccaag taacatccgc agtcacaaga gccatatcac gtaactcagc    29640
ctctacactc gaacgagaaa ccgctacctc tttcttagtc ttcgtagcag tgagggaacc    29700
accaagaaaa acacgatagg aagaaaggga acaatgatca aaggaatcac tagcccaagt    29760
agcatcacaa tatgcctaga gctaaaaaga gttggatcgt ggaaagaata aacgatgaga    29820
gacagttcca cgaagataac atagaaccca caacaagtga ctatagtgaa gctaagcgag    29880
ggcggaaaca aactgactaa gagtgtgcac agagtaggag atatcaggac gagtaacacc    29940
aaggtaaaca agactcccaa cagtgtgaca ataacgagga tcctcaagag gttcaccatc    30000
cgtggcatga agatgaacat tgagttccat aggactgtca actgtttgtt gttcagtaag    30060
agagacccga tcaagaagat ccaaaatgta cttctcttga gacagataaa accctcaga    30120 tgaagagcaa aactctatcc caagaaaata acgaagagga ccaagatcag acatgagaaa    30180
ctgctcacta agacgtgcct ttacgaaggc aatatactca ggatcatctc cagtgatgat    30240
catatcatca acataaagaa ggagaagagt ccaaccacga gataaagtat gtacaaaaaa    30300
cgcaggatca tgagcgttgc agaaaaccca gacgcagtga ccacagacgc aaaccgctga    30360
aaccaagctc gtggagcttg cttgagacca taaagagagc ggtgaagacg acaaaccata    30420
ccctcaggaa caaatatct aggcagtggt tgcatgtaga cctcttcacg cagctcacct    30480
ttaagaaagg cattcttgat atcaagctga gagatgcacc actcacgaac agaggccacg    30540
acaagaagag tgtgaacagt cgtcatgtga acaaccggag taaaagtctc atcataatcg    30600
tggccttgta cctgctggaa accacgaaca accaagcgag cctttagcgc tcaagagaac    30660
cattcgagcg ggtcttaacc ttataaaccc acttacgcgt gataggacga acacgtggtg    30720
gacaaggtat gagttcccat gtgtcagtgc gctctagtgc agcgatctca tcagccatcg    30780
catgccgcca ttcttgatga aggatggcat cacaataaga agctggctca ggaagagtgg    30840
tagtcacaaa acagaaggag aatactgatc agtaggccga tgaagacggt gactacgtgt    30900
```

```
aagaaatggc tctggtgtag aagcagaaag gtaaaatgga tcagcgaaag aggacaactc   30960
aacaggaaca gatgactcac aaggagatgc cgatacatca agagaagatg aagcagcagg   31020
agatggctca ccatcataag atggcgtatc agaagtgtag gaaacaggtg acgcctaaga   31080 ggggggggtga attaggactt ctaaaacttt tactaaacta ggccacaatt aaatccctag   31140
agcaaaacct atgcaaataa tcaaactaga gagtgcaatc taggttttgt ctaagtgttg   31200
ctatctctac cgcaatggct aaatttaaat ctacactata taagtatgaa tacaagattg   31260
aaacttaaat gcttaatata aatgcggaaa cttaagagc aaagtagaga agcaaactct    31320
cgaggatgac gccggtattt ttaccgaggt atccggaacc acgcaaggtc ccgactaatc   31380
ctcgttggtg cccctacgca aagggaagcc cacgcgaggg ccaagcacca cggtcaagta   31440
actccgtaga gagccgcggg ccttctccac acgcaagtgg tgctccgctt ccggctcctc   31500
tcggacgctc cccgccgtct ccactatcga gcttccgacc aaaacgccgc gggcctcgtt   31560
ccctccggta cacggtggcg gccgtgcac aaacgcggtt gtcacggtct cgcaagactc    31620 tcgcccact cggtacaatt acaacgactc acgcaagagc cgagggggttg tgtggtttta    31680 caaaactcac tcaactaact agggttcacc tagagcaagc gctaaagcgg tctaactaac   31740
ttaagcactt cgcaaagcac ctacgctaat caccgagtga ttctattaag cacttgggtg   31800
tttgagctct tggaaatgtg cactatatgc cttggtatgt tgcttgggct cccacacttg   31860
agaatggccg gttggggtgg tatttatagc ctccaatccc caaactagca gttggacaga   31920
aagtagcaac tttctgtcgt cgggtgcacc ggacagtccg gtgcaccacc ggacagccac   31980
tgtgcagtgt ccggtgcacg ccacgtcagc cgaccgttgg cgcctgtagc agtcgaccgt   32040
tgccgtctgt ccgatgcgca ccggacagtc cggtgttgac tgtccggtgc accactggac   32100
agaccggtgc tacagcctga gagcgcctgt ctgtggcctc tctgcgcaga ctgtccggtt   32160
gtcccaccgg atagtccggt gcgcaccgga caggtactgt tcactgtccg gtgcgccacc   32220
aggcgctggc tgacagccct cttcaaggtt tcttcgttga tttctccggg cttcttttgt   32280
tcttgagtct tggacttatg tgcatcattt tatgtcttct tttgaggtgt tgctttcctc   32340
aattcctaag tccaagtaaa tattgcatcc tgtgaactac aaacacaaac actagaaaac   32400
ttattagttc acggattgtg ttgttcatca acaccaaaa ctcgattaac caaatggctc     32460
ggggtccatt ttccttacaa tctccccctt tttggtgatt gatgacaaca caaccaaagc   32520
aagcagataa tacaagtatt tgaatgaaaa tatgcaatct acttgctagg atgcatgttt   32580
gtccccacaa tgtgaagtta tggacttaag cctcccccta actccataat tcacttactt   32640
cctattttag aaccaaataa ccaaaaccac ttgaaaaacc atttgtagat ataaaatttt   32700
aaattggtgg tgtttggtgt ttgatataga tttcatttct ttggtcccta aacttctccc   32760
ctttggcatc aaccaccgaa aaggaagaca ttaaaagcat gtaggaagta aataaaagct   32820
taccctcatt gagaattcta tcagatgata ccacttgaag aatactaaat taaaccacat   32880
gaatgatatc agttgaaagg attactcccc ctaaacgagt gttctcttta gagagaattt   32940
tctccccctt tttagagatg aagaaatact cccctgaca gagatcctct acttaggaaa    33000
aagcatgtga aaattagagg tgcaagacat gatttgaaaa gactaacttc ccatatgcat   33060
aggtaacaga atatgagtta agtacttatg cattttagc aacatggaag tatatgatat     33120
gaaatatagt ctaatcaaat gttggagaag acctgtaaat gatattaaat gtagtctcat   33180
aagataccaa ttgaaagtca atggcgagct tgagagacat gagagttctt ggagattttg   33240
cagtggaaga ttgttgtctt tctccgggga cttcattttc cttacaatga gactatcacg   33300
```

```
tgaaatagac ttgaaaaggt gttagtctca aagtattaga ttatagagta acctccccct   33360
gaaggtgtgc atataagttt tgaatacttg taggagactt gcactttgat ttgatatcaa   33420
gaaggaaaat ttatccataa tccgaacttt ggaacatata agttaaatga tacaacttgt   33480
agaaatcaaa attttaatt gatgcatcat ttactatgga gtgatataaa agctatgtgt    33540
catgctttaa ctaaacattt taaaccatgt aggtttgctt aagtatatga attgaaaacg   33600
agcaatccta ccatgtgatt tacctagtat gcatgatttt aaacaaaagt aaataacaaa   33660
tgtaatacta ggcaagaaag gtaaactaga taaaaggtaa atagatacgc atatctaaaa   33720
acaagaaata caataaatct agttaccta gtcatgggtg ggaaatttgg gtccaaaatt    33780
ttcactaacc cacttggcaa taaacttgat ccaatatgat gtatcccatg atatacttct   33840
cgaatttgcc aagtctccaa attttcgat gaccttgtt ccactcactt ccctttcggg     33900
atccaaacct tcttggtgct tttcatggtt gaaattattt cctttggcac ccagatgcgt   33960
ttggctcctt ttcctttgtt ggccttgatt gctatcacct ttccattctt tttcttcttg   34020
atcaaatatg gtgtagcatc cttttgttc acctttttga tgtaggtgtt ggagattttg     34080
cttgatggct tttgcttgag cttttgcctt tgtttatccc cggtcattgc cttgcattgg   34140
aaagacttgt ggccttccat gtggcatagc ctataaatca cagtttctcc ctccataggc   34200
ttgttcactc ccgcagtggt gttatcctgt ggaggtcgga tttgtttgac tttgcctttc    34260
ttgtcataca aagtctttcc aaggcgagcc acttcttgct ttaattgttc attttctttt   34320
gcaacctcat ccgaacatgt ttctacaaca atattctcaa caagaactta gttgcagggg   34380
ttagaatcat caattaaatc aaagtaggaa gtagaagcat ctttcttaat aatttcaggt    34440
atttcaacta aagatgatgc tggggtgcta ccaatgtttt ctagcttagt agttagctca   34500
ttattgtgta tgctaagaat ttccatttc tctagcaaat tttcaatagc ttcttgggag     34560
ctagctaact ttgccttaag ttttcattc ttttaataa ggctatcatc ggtagcagtg      34620
gatggagcac tagattctaa tagctcaatt ttagttgata gctcactatt taagtttaca   34680
aaagtttcaa atttttctag caaacctttg taatcatttt gagagctaac caacttattt   34740
ttcaaagttt taagttgagc ttttttgctt agtgcaaaca tcctggaaaa attctacggc   34800
ttccgcaagc tcatctagag agggttttcc ctcaccttca tcatcactac tactttcatc   34860 actgaagat ggaatgcttt tgttacccct tgtcataagg catttgtgtg atgactgtga     34920
tgagcgtgac gaggaccggt ggctgcgcgt ccttggaggt tcatcttcac ttgaagaatc   34980
atccaaagtt ctaacacttg ttagtgcctt gcctttgctc ctctccttt tgggtttggc     35040 catatttgga cagttgtccc tgaagtggcc cttctcccca catgcgaagc atcctctctt   35100
cctttgcttt ttcctgtcaa tgttaaagag aagatcctcg acctgcaggg gcacacccat   35160
tagattaatc ttgcggatca tcctcattac ctttccgacg cgtcggattg tttcttcgtc   35220
ctcggaggat gatgtgcatg gttgattatc ttcatcatca tcactttctt cttcttcctc   35280
ttcttcgctt gaggaacttg gagtgggagc cttctttttg cccttccttt catcacatgc   35340
aaaagcatat ggccttgagg aagttggctc ctctccccga ctcattttc gtgacatctc     35400 aaaggccgcg attttcccaa tcacaatggt cggggtcatg ttgctcaaat cctccatatt   35460
gtgaaggatg gtgatgatgc tcccatatct ttgttgtggt agcagggaga taatcttcct   35520
cataatgtcc gcgtcaccta gcttattaat gtcaatagat ttgagctcat tgataattag   35580
attcaaatga gaatacatgt ctctaacaag ctcatcatct ttcatagcaa aagaattata   35640
```

```
ataatttaag actaggcaat gttttttgctc acggacattg gatgtgccgt catggagctc    35700 atgcaattttt agccaaatct cattagcagt tttcaagata aatacttgat taaaaatatc    35760
catgctaaga gattcataca agcaattttt ggctctagca tttaaatgaa tttattttc     35820 ctcactcgtg gtgggtttct cgggattctt gaggggtttc atcccgtcac gagtgactct    35880
ccaaacacct agatcaacgg cctctaggta acaagccatt ctagcactat aatatgggaa    35940
gttagtgccg tcgaagtgtg gtggcctatg ggtatccatc ccttcctcta aaaagcgtcg    36000
gctcttttag cggtgaagct aaagcgtttc aaatgagcca aaccggcctt tgataccact    36060
tgtaggaaat gggcgacgcc taagaggggg ggtgaattag gacttctaaa acttttacta    36120
aactaggcca caattaaatc cctagagcaa aacctatgca aataatcaaa ctagagagtg    36180
caatctaggt tttgtctaag tgttgctatc tctaccgcaa tggctaaatt tcaatctata    36240
ctatataagc atgaatacaa gattgaaact taaatgctta atataaatgc ggaaacttaa    36300
agagcaaagt agagaagcaa actctcgtgg atgacgccgg tatttttacc gaggtatccg    36360
gaaccacgca aggtcccgac taatcctcgt tggtgcccct acgcaaaggg aagcccacgc    36420
gagggccaag caccacggtc aagtaactcc gtagagagcc acgggccttc tccacgcgta    36480
agtggtgctc cgcttccagc tcctctcgga cgctccccgt cgtctccact atcgagcttc    36540
cggccgaaac gccgcgggcc tcgttccctc cggtacacgg tggcggccgt gacacaaacg    36600
cggttgtcac ggtctcgcaa gactctcgcc ccactcggta caattacaac gactcacgca    36660
agagccgagg ggttgtgtgg ttttacaaaa ctcactcaac taactagggt tcacctagag    36720
caagcgctaa agcggtctaa ctaacctaag cacttcgcaa agcacctacg ctaatcaccg    36780
agtgattcta ttaagcactt gggtgtttga gctcttggaa atgtgcacta tatgccttgg    36840
tatgttgctt gggctcccac acttgagaat ggccggttgg ggtggtattt atagcctcca    36900
atccccaaac tagcagttgg acagaaagca gcaactttct gtcgtcgggt gcaccggaca    36960
gtccgatgca ccaccggaca gccactgtgc agtgtctggt gcacgccacg tcagccgacc    37020
gttggcgcct gtagcagtcg accgttggat ccgaccgttg ccgtctgtcc ggtgcgcacc    37080
gaacagtccg gtgccgactg tccgatgcac caccggacaa atcggtgcta cagcccgaga    37140
gcgcctgtct gtggcctctc tgcgcagatt gttcggttgt cccaccggac agtccggtgc    37200
gcaccggaca ggtactgttc actgtccggt gcgccaccag gcgctagctg acatccctct    37260
tcaaggtttc ttcattgatt tcttcgggct tcttttgttc ttgagtcttg gacttatgtg    37320
catcatttta tgtcttcttt tgaggtgttg ctttcctcaa ttccttagtt caagtaaata    37380
ttgcatcctg tgaactacaa acataaacac tagaaaactt attagttcac ggattatgtt    37440
gttcatcata caccaaaact cgattaacca aatggcctgg ggtccatttt tcttacaaga    37500
agggatagtg gttcagcgag tgtaaaccaa tgtcactgga ggcttcatgg aataataaga    37560
aagaaaagaa gactccaaag aaggcacata acaagattgt gacaaatgtg aagctggtat    37620
agtagaagta ggggtatcag gaaagaacaa aaggacatgg ggtcaactaa tgacacgaaa    37680
gaagcatcag acgagggacg aggatagaaa ggacgggcct catcaaaaac cacaaactga    37740
gatgtcctca tctgacgagc gaccatatcc caacaatgat accccttatg ctcagcattg    37800
tacccaatga aaacacactc aacatactga gccgccagct tggttcgctc acgcggtgaa    37860
agcaacacat agcacacacg accaaaaaga cgaagactag aatagtcatg catattacca    37920
caaaaacgct caaaaggaat cccacccaa agagcggaag aaggaaataa tttgctgtag    37980
aaacagcttc ggtccaaaaa tgaggggaga caggaaacga gtataagagc acgagcagtc    38040
```

```
taaaaatatg atgatgcttg ctctcagcaa cactagtctg agcatgagtg ccaagacaag    38100
aaaactgagc aagagtacct tgcgtagaaa gaaactggcg aagagcatca gaaaggtatt    38160
ttccttttag aattagcacg aaaaacacaa atagaagtgt caaactgagt gcgaaccata    38220
gaagagaacc cctaatagat agctaaaacc tcactacagt gtttcataaa gtatatccat    38280
gtgtgatgag taaaatcatc tataaaatg atgaagtatt tatgacctcc tttggaaaca    38340
atagagcagg acccccataca tatgaatgaa caagatcaaa aggactatgg gacactaact    38400
cattagaatg ataaggatgt tgacctgct tgcctaaacg acaaccctga cactgatgca     38460
aggactcatg acctaaaact gaacctaaaa tacctcgatg aattaacgta gatagacgag    38520
agccacaaag atgacctaga cgatggtgcc actgagcaaa cgatgaggta gaagtagcag     38580
aagcggatct agcaagacca gtgggcatag cggaaggaat acgaagccag tcaaagctcc    38640
caaagacgct gagaaactaa tagtagtgac cactaaaagc gagacgctaa aaccaagccc    38700
gagtagcctg cttgaggcca taagagaat gacgaaggca acaaaccata ccctcgagaa     38760
cagaatagcc atgtggtggc tgcatataaa ccacctcaca caactcacca ttaagaaagg    38820
cattcttgac atccgctatt gagagatggg ccactcatga acagaagcca tagcaaggag    38880
ggtgcgaata gtggtcatgt gagcaacaag agcaaaagtg tcatcataat cacggccatg    38940
ttcctgctag aaaccacgag caacaagaca agccttataa cgctcaagag aatcattaga    39000
gtgggtctta accctataga tccacttaca tgtgatagga cgaacatatg gtggacaagg     39060
tacaagttcc catgtgctag cgcgctctag agcagcaatc tccttagcca ttgcatgttg    39120
ccatttctaa caaagattag catcacgggc tcagaaagaa cattagtcac aaaagcagaa    39180
ggagagtaac aaccagtagg atgacaaagt caatgactat gtctaagaga tgactccagt    39240
gtagagtagg agaggaaact ggctcaacag gaatagatga catactagga gataccgatg    39300
ctttaggaga acatcattga tcagtagaag gagatagctc atcagacgaa gatggtgtat    39360
cagaagatgg aatcacagtg cagtgtgtgt caacttgtgt taccgtaggc ttcgtggaat    39420
aatcaggaaa caaagaagaa ggctccaaag aaaacataga agaagaatgc aacaggcgtg    39480
aaaccgatcc agtagaagta gaggcatcat gaaagaaaag aaagaagggt caaccaatga    39540
tgctaaagaa gtctcataaa aaggacaagt ctcataaaaa ccatatcccg agaagtcctc    39600
attcgatgaa caaccggatc ccaacaatga taccccatgt ggttaacatt gtacccaagg    39660
ggaatacaca ttcagtagac taaggcatca atttggttca ctcacatggt gaaagcaaca    39720
tgtagcacac acaaccaaat agaatcccac cctgaagagt cgaagatatt ttggctcaca    39780
aaggaccatt gtctatgact tcccctacct cttcgtgata ttttggcgga ttgaccatga    39840
catcaaatgg actaggcttg atgttgcttg accatatgcc ttttgtctcc attaacaatg    39900
tattgcaact gctcctggtc gaccatttct ccaagtattc ctttgattaa gctaccaagt    39960
tcagtctggg aagacatcat catggacttt gtattccctc gcatcaacgt taagtcggtg    40020
gtcgaccatt tctccaagta cacatacttt ctaccccta ggccatccat acaccgccat     40080
ctcttcatcg tcaaagcatt cttcgacaac attgtcaagc ttcatggtgt ctcatgctcc    40140
atctcagcga ttttcatccg ctctacataa cttttatat gtatgtacta tctatatatc     40200
taaaaaaaca atgatctata tataataatt tgtgtacata tagctagttc tattaaagat    40260
ggaatatatt tgtttggttg gttgacttat taaaagtgta cgtggtctaa atatcctatt    40320
tggcttcttg cttgctagct tattgatcat catcgatgac ctacgtgaaa ctacagcttg    40380
```

-continued

| | |
|---|---|
| gaactcgata gagacagcct tgggttcaac aacctctacg catgctggta gcctaataat | 40440 |
| cgtgacaacg aggatccaat ccattgctgg caagtgcagc ccacacagat acatctacag | 40500 |
| aatgccaggc cttggccatc cggagtccaa agaactattc ttgaggacgg cctacggtga | 40560 |
| tgcacatccg acaccgggcg tggcggacgc tgttgaagaa atctcagggg catgtgatgg | 40620 |
| tctgccactg gcgttggtta gcgcagctca tgattggcgt gagcggcagg ggcagggttg | 40680 |
| ggaaggaaga tatgtctttg aagaagtgaa cagagcattt agctggtggt acgagagttt | 40740 |
| ggcggacgca gctcacatgc tgtctctagg catattcccc tatggccatt ccatcaagcg | 40800 |
| gaagagccta attagaagat ggatagctga aggattggtc agtgaggaaa agatggtga | 40860 |
| tcagcgattc catgagttgg tcgaccagag catcgtggag cctgtgctaa ttactggcag | 40920 |
| tagtgatttc aaggtcaaga ggtttcgtct tcggcgtccg gtgctggagt tcatcgtcag | 40980 |
| ggaatcagtc tctaagaaca tggtcaaact gctccaaggc gatgagcccc ttccaggaga | 41040 |
| aggaggaggt cctgtggtgt cgatttatca aactacggac acggaaacat caagaggaaa | 41100 |
| catcatgtcc ttttccatat tcaacaaagg cgtggctttc gacgacctcc aacaatgcac | 41160 |
| ctatctccgg gtgctggacc tagaacgctg caggggggtc gaccacagtg ttgttgctgg | 41220 |
| tatatgtaaa ctgtcgcttc tcaggtacct gagcttgagg ggcagcgatg tgcgccacat | 41280 |
| ccccagggaa acaaaaaggc tgaagtgtct agagaccctg gacatccggg agacagtggt | 41340 |
| gaacaatctg cctgtggcag ccctcatgct cccacggcta gtccacctgt tcggcaagtt | 41400 |
| tgagttgcct cgaaaactcg aggacgagag gatacggggt aagctcgaga gattcttccg | 41460 |
| agaggaaagc agactacaga ctctggctgg attgatcatt tctaagaaca atggctacga | 41520 |
| gcacattgtg attcacataa ggctactaag gaagattaag atatggtacc agaaccacct | 41580 |
| gctgcattat tccaccttat tgaacgagct ttttataaga aacactgcac tcgactcttt | 41640 |
| gtcggtcgat ttcggggaca gcttgatgtt cccacacatc tctgacatct ttggaccctg | 41700 |
| catgctccgc tccatcaaac tgcgaggtcg gcattggccg ctgcctacaa ttatcgcatc | 41760 |
| atcagccaat tatctctccg aggtgcagct gtcctctact gttctgccgc tcaggtactt | 41820 |
| gtctactctg cagagcttac gccggctgct ttatctgaag ctggttgcgg atggattgt | 41880 |
| gggtgacgac accgacacct tcactgtgaa aaaggatgga ttcccaagcc ttgagaggct | 41940 |
| ctgcattgag gccccgaagc ttccacatct gcgcattgtt gaaggagcca tgccagctct | 42000 |
| cacgtctctt cacctgctct gtccgacgat gacgatgatg cctcaacacc cgggtcaaat | 42060 |
| gggcgaaatc gatgagccgg aggcgacatc agaaaccaaa ctgggcaagg agtggggaat | 42120 |
| cgagtatctc agaaacctca atgacctggt gttgccctac actgttggtg atgaacaact | 42180 |
| cgatttctgg aaggagaaag caaggagcaa catgaacagg ccaaaggtaa ccaggcagcc | 42240 |
| gaagccgtaa tctgctgtca tttccccct gcgcatgcac atgaattttt gtatgacatt | 42300 |
| ttatttgttc ctggtgtatc gtcgtttgtg tatatatggc ttcctaatct gctgtcattc | 42360 |
| acgtttcgca tgcgcatcaa tttttaagac attcattact ggtggcaggt gtctgtatta | 42420 |
| tataatcata atactgtcat taattgtgga tccaacttta tataatcatg gatgctaata | 42480 |
| atgcattcat gcatgaagaa gtgaatccat ccagct | 42516 |

<210> SEQ ID NO 10
<211> LENGTH: 3301
<212> TYPE: DNA
<213> ORGANISM: Zea mays

<400> SEQUENCE: 10

```
atgaatgtcc tcctgagatc tcaaagtcct acgctgctat accttccaac atcctcccaa     60
ccagccatac ctgcggatcg aactcgagcc aagcaacaga gagggggggt tggagagatg    120
acaggtgtgg agccagcagt tatcggtgca atcgctaagt tggcggcccc tgtcctgcct    180
atagccatta aagggataca agatgcactg aagaaacggc aagtccgtga cagtgatgtt    240
gaaaccctga atcccagct tagctacatc cagggcatca tccgtgatac tcggaagact    300
atcaggagtt cccaagaccc gtccgacagg cttcaatcct ggtctggata cctcagatgc    360
ttggcgtacg acatcgaaga cctaatagca ggccaccgtg tcggaaccat gacaggtgcg    420
aagcttaatg gcaagattac tatcatccag gatttaatca gatgtgtaga gtcctatccg    480
gagtttatgg cggttccgac gaatgaggct cctagtcaag gcgctgcttc ttcctccact    540
acttcaagca cccagggctt tccgctggct gatcttgtgg gcaagaagga ggacctcgat    600
gagcttctgg acctcctcgt ctggagaccc gacaatgagc tggacaaggt cctcaaggtg    660
atggtgatct ccgtcgtcgg cttcggtggc ataggggaga ccaagctttg ccacacagtg    720
tacacggacg tacaggagag cagaaagttc tccctgcatg cgtatgtcag cgctgctggg    780
aaggactgca gcatcgttct ggaagagata atcgagcaat ttagactgca agaggatcca    840
ctagatagca gtggtggatt ttttcacagg tgagccgtca tattttcagc cgcatgcata    900
tttgttctaa aatctacctt ctgaatttgt atttcgaaac cgcgtttatt agattcgccg    960
gagcgtttcc tggggctcgt cgtactgacc aagttcatga gttacccgag tatctccaaa   1020
ggaaaaggtg atttcttttg ggttttttaa attggtgccc tcagttttgg tggtgtgctc   1080
accttccact tttctgtgcg taatttgctg attaattaac tattccctct atatattgat   1140 ctttttttc tccttcgttt cctgtttata tatgtatata tataggtatt ttgtggtggt   1200
ggatggcgtg gagtctgaag aactggtggg tggcatagca tctgccttcc cggataatag   1260
tatgggcagt agaattatca tgggtatgag gaccgcagtg ggcagggatg cagagagatg   1320
tgtgggtcat cgtcacaaga tgtggccact tgaagacaag cagtcggtgg tctgcttcct   1380
aaatgaagcg gagcggcggc ggcggcgacg acgacgacat gaacaagacg accactcgtc   1440
gttcattacg tttcaggaac aagaccactc atcatcctgt tgcacaaga tatgtgatgg   1500 cgtaccactt gcgctggtta gcgtatgcga agtccgcaga gggtccatca tcactgctgc   1560
cgttgaagaa caagaccgct ggccacacag aatgcccaag gtgctcgacc acagctacga   1620
tggtctgcat atccggggtg ctggggctg tccgaaccaa tacatcccct atctccaagc   1680
ctgcctgctg tactttgcca tgttcccccg cggcaatcat gtcaagaggg gatccctgat   1740
caggcgatgg caggcggaag gcctagagtt cggaggcagc aatatccaca atcaagctgc   1800
cgaaaacctc aaggccctcg tagaccggaa cttcgtttgg cccctccatg cgagcctgaa   1860
tgagcacgcc aagacattcc agcctcctgg agtggtgctc aactacatct cccgcaggtc   1920
tgaagaggag gaattcatcc tcaggtcttg tccaaccggg atcttaatc ccaattacag   1980 ccgccggctt tgtctacatc ctgccgagga agaagaaggt gaaccccaac ccttggtcat   2040
caccaacggt tctgtaccac cacgcctgcg aactctggct gtgtcctggg ggcagcaaca   2100
ggccagcagg attgctgaat gcgagcagct ccgagtgctg gatctggcgt catacaacgg   2160
tctacagcca gaccagctag aggagatatg caagaaactg aagcttctca aatatctgag   2220
cctcctgcca gatatcatca ctcaagttcc aagctcaatg tctaatttgc agtgcttgga   2280
gacactcgag ttgggggagg tcaatggcag ggcggcagtt ctggtgccta tccaagtctt   2340
```

```
ggaactgcca tgcataaaac acctaatcgg aaaatttgag cttattgaca acttcaacgg    2400
agtaccaatt agggcttatc cagatgcact agtaccaaag gcaatcaagg aaagcaacct    2460
ggagacggtg tcggggttct tcacccacag aggccaagga tttccgccac tcatgcgtca    2520
catgaggcag ctcaggaagg tgaagatatg gttctacagg gatgcagaac ccaaatacct    2580
agcaagctat ctcccgaaag cgattacaaa attcctcagg aatgacaacg ttcctcgctc    2640
cctgtcactt gacttccagg atggcccaag acaaacagaa atactgcagg cttgtgtggc    2700
tgaagctagg ggtaatcttt actccctgaa gctgtcgtcc ggcacaaatc tgagcaggat    2760
ccaactgtcg gttattgcca ccaacaagca gctgactgga atcacaaagc tatgcctttc    2820
ccgctggaaa acgataacgt tggatgcaga atttctgaat gagctgagca gattggtcca    2880
tctaaggtat ctgaagctgg atgcagaaac aataaaaggt acgtacgacc aaaacccaac    2940
accaggagga aataaccaag agaaggtcgt catagagact gggcacattg caaatctgcg    3000
gcggatgtgg cttgtggcca ggcagacgct gcccgacata caagtcaagc ctacagctct    3060
gcaacgactc gtttcacttc atctcatcag tgaaacggac gattattgtc cttccgccaa    3120
cgtcatctgt aaagccaacc cccaggacga caacgagctg gcgccgttca cgagcctcca    3180
ggaagtctcg ctgaatgcta cggtacccga aaatttaagg gattcttggc gtaatgctgc    3240
aagggaccat ccaaagaggc cacgaattct cttcatccaa caccctcacc gtgcgggata    3300
a                                                                    3301

<210> SEQ ID NO 11
<211> LENGTH: 199
<212> TYPE: DNA
<213> ORGANISM: Zea mays
<220> FEATURE:
<221> NAME/KEY: misc_feature
<222> LOCATION: (99)..(99)
<223> OTHER INFORMATION: n is a, c, g, or t

<400> SEQUENCE: 11
cgggcaaagg aagagcaccc gaggtcatca aaacagccta agaaaataa cagggatagg    60 aggagatcct atactcctga tgatataaat gatcgccgng gtgcagacaa tggtcgtgat    120
gagtaagttc tgttccttga ctgttggtac atgtctatgg gttagtctag ttatgtttttg    180 aagtagtgat attgtgcat                                                 199

<210> SEQ ID NO 12
<211> LENGTH: 121
<212> TYPE: DNA
<213> ORGANISM: Zea mays
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t

<400> SEQUENCE: 12
agggagtatt acacgacgga ctagatgttg ccatcaagaa gttancagtc tctgatgata    60
ntcaagagag gcgcctgcaa cttgagctta atattcgtgc aaagcttgaa catggaaaca    120
t                                                                    121

<210> SEQ ID NO 13
<211> LENGTH: 19
```

```
<212> TYPE: DNA
<213> ORGANISM: Zea mays

<400> SEQUENCE: 13
ggtggagcgg gagtccgga                                                      19

<210> SEQ ID NO 14
<211> LENGTH: 23
<212> TYPE: DNA
<213> ORGANISM: Zea mays

<400> SEQUENCE: 14
ctgctgatgt ctggaagaac cct                                                 23

<210> SEQ ID NO 15
<211> LENGTH: 21
<212> TYPE: DNA
<213> ORGANISM: Zea mays

<400> SEQUENCE: 15
agcatcatgc cagcaggttt t                                                   21

<210> SEQ ID NO 16
<211> LENGTH: 23
<212> TYPE: DNA
<213> ORGANISM: Zea mays

<400> SEQUENCE: 16
atctctccct cgctctcctt ctc                                                 23

<210> SEQ ID NO 17
<211> LENGTH: 20
<212> TYPE: DNA
<213> ORGANISM: Zea mays

<400> SEQUENCE: 17
agcagcaggt tggtcgaatg                                                     20

<210> SEQ ID NO 18
<211> LENGTH: 431
<212> TYPE: DNA
<213> ORGANISM: Zea mays
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t

<400> SEQUENCE: 18
aacatatgag ctattggcat gtgcactcga gaaggataat agagctgagg aagcacatar          60
aatctggcag aataaagtgg gccacgatct gcattcggty ccttggcgtt tctgccgtct         120
tatgttggct atctactacc gaaacaatag gctagacagr ctcgtgaagg tttggacaca         180
gacccngtaa ctttrtgatg cactttatan ttttacttt acrtactttc catttgataa          240
tgtgccttac aygaatkact ttacctgccy cttatgmcga tttagctctt caaagaactc         300
gaagcttgtg gycgtaaacc tccaagcaaa gacattgtgc ggaaagtcga agatgcrtac         360
```

```
gaaacrcttg gattactaga agataaaaag rynttgcttg ataaatacaa ggatttatac    420
aacaaaccgt c                                                         431
```

<210> SEQ ID NO 19
<211> LENGTH: 101
<212> TYPE: DNA
<213> ORGANISM: Zea mays

<400> SEQUENCE: 19

```
tccaaccaca agacacatct acagatggca atgggaaccc aaatacccaa cgggttttac    60
ccgatatgaa ggtgggtacg agatgatttc tctacccgcg g                        101
```

<210> SEQ ID NO 20
<211> LENGTH: 62
<212> TYPE: DNA
<213> ORGANISM: Zea mays
<220> FEATURE:
<221> NAME/KEY: misc_feature
<222> LOCATION: (24)..(24)
<223> OTHER INFORMATION: n is a, c, g, or t

<400> SEQUENCE: 20

```
atgcatggta gattcgttca taangggggct ttagttttttt ttttttttgca tgatggttga   60 tg                                                                    62
```

<210> SEQ ID NO 21
<211> LENGTH: 101
<212> TYPE: DNA
<213> ORGANISM: Zea mays
<220> FEATURE:
<221> NAME/KEY: misc_feature
<222> LOCATION: (51)..(51)
<223> OTHER INFORMATION: n is a, c, g, or t

<400> SEQUENCE: 21

```
aggggatgaa gaacattatg actatgcaat atatgtggaa tgataaagtc ntagctcagt    60
tctatgctac tctctggata aagaaggtgg atgaggaagc t                        101
```

<210> SEQ ID NO 22
<211> LENGTH: 101
<212> TYPE: DNA
<213> ORGANISM: Zea mays
<220> FEATURE:
<221> NAME/KEY: misc_feature
<222> LOCATION: (51)..(51)
<223> OTHER INFORMATION: n is a, c, g, or t

<400> SEQUENCE: 22

```
gacctcatca tcctacgacg acctagagca gaagagcttc ggttcgagaa ngagaaggag    60
aagggcccgg cggccagacc gagcagtccg ccgaggagcg g                        101
```

<210> SEQ ID NO 23
<211> LENGTH: 56
<212> TYPE: DNA
<213> ORGANISM: Zea mays
<220> FEATURE:
<221> NAME/KEY: misc_feature
<222> LOCATION: (25)..(25)
<223> OTHER INFORMATION: n is a, c, g, or t

<400> SEQUENCE: 23

```
ttcctttgga tcaccatcac tctcntagcc agcacgacag ctgcattcgt aggatc        56
```

```
<210> SEQ ID NO 24
<211> LENGTH: 62
<212> TYPE: DNA
<213> ORGANISM: Zea mays
<220> FEATURE:
<221> NAME/KEY: misc_feature
<222> LOCATION: (32)..(32)
<223> OTHER INFORMATION: n is a, c, g, or t

<400> SEQUENCE: 24
tgtttgttta cctctcaact tatttaaact tngtgaggtt aataatatgt catgtatgga      60
tt                                                                    62

<210> SEQ ID NO 25
<211> LENGTH: 62
<212> TYPE: DNA
<213> ORGANISM: Zea mays
<220> FEATURE:
<221> NAME/KEY: misc_feature
<222> LOCATION: (26)..(26)
<223> OTHER INFORMATION: n is a, c, g, or t

<400> SEQUENCE: 25
tagttattac tattcggctg ccacanttat ccttgggaaa agcacggctc aagaaatccc      60
ac                                                                    62

<210> SEQ ID NO 26
<211> LENGTH: 66
<212> TYPE: DNA
<213> ORGANISM: Zea mays
<220> FEATURE:
<221> NAME/KEY: misc_feature
<222> LOCATION: (26)..(26)
<223> OTHER INFORMATION: n is a, c, g, or t

<400> SEQUENCE: 26
ttagcgaaat cggcaaattt aaagcnctta ttgttaacct tcgaacatgt tttagggtta      60
aaaatt                                                                66

<210> SEQ ID NO 27
<211> LENGTH: 66
<212> TYPE: DNA
<213> ORGANISM: Zea mays
<220> FEATURE:
<221> NAME/KEY: misc_feature
<222> LOCATION: (26)..(26)
<223> OTHER INFORMATION: n is a, c, g, or t

<400> SEQUENCE: 27
tgagcttatt gacaacttca acggantacc aattagggct tatccagatg cactagtacc      60
aaaggc                                                                66

<210> SEQ ID NO 28
<211> LENGTH: 61
<212> TYPE: DNA
<213> ORGANISM: Zea mays
<220> FEATURE:
<221> NAME/KEY: misc_feature
<222> LOCATION: (35)..(35)
<223> OTHER INFORMATION: n is a, c, g, or t

<400> SEQUENCE: 28
ctattggaag gtgtccttct ctcttttatt tctgncttat tccaagtttc ttttggcctt      60
t                                                                     61
```

```
<210> SEQ ID NO 29
<211> LENGTH: 69
<212> TYPE: DNA
<213> ORGANISM: Zea mays
<220> FEATURE:
<221> NAME/KEY: misc_feature
<222> LOCATION: (46)..(46)
<223> OTHER INFORMATION: n is a, c, g, or t

<400> SEQUENCE: 29
gtgcagcatt cagcaccttg agaatattgg ggaccactac tacacnaccc taatgaactg      60
gagggacaa                                                             69

<210> SEQ ID NO 30
<211> LENGTH: 101
<212> TYPE: DNA
<213> ORGANISM: Zea mays
<220> FEATURE:
<221> NAME/KEY: misc_feature
<222> LOCATION: (51)..(51)
<223> OTHER INFORMATION: n is a, c, g, or t

<400> SEQUENCE: 30
tgtcgtttac cggatatgga ttcagatact tttatattcg ggacgaatac ngatagtatc      60
tagatagcac accttcagat tctggtctga ttcagagcga a                        101

<210> SEQ ID NO 31
<211> LENGTH: 69
<212> TYPE: DNA
<213> ORGANISM: Zea mays
<220> FEATURE:
<221> NAME/KEY: misc_feature
<222> LOCATION: (26)..(26)
<223> OTHER INFORMATION: n is a, c, g, or t

<400> SEQUENCE: 31
ttgttgcatc gaatatgtca aacagngcca tgtaatagaa caacatctct cgaaaacgtg      60
acaggaagg                                                             69

<210> SEQ ID NO 32
<211> LENGTH: 79
<212> TYPE: DNA
<213> ORGANISM: Zea mays
<220> FEATURE:
<221> NAME/KEY: misc_feature
<222> LOCATION: (30)..(30)
<223> OTHER INFORMATION: n is a, c, g, or t

<400> SEQUENCE: 32
ttgtttcaga tcaaatctac ttttgacttn cttcgaaaag tttcttctga atgtgttctc      60
cggaagaata atatccttg                                                  79

<210> SEQ ID NO 33
<211> LENGTH: 4164
<212> TYPE: DNA
<213> ORGANISM: Zea mays

<400> SEQUENCE: 33
atggccgtgc gagggtccac atacatgatc aggcaatata taaggagcc aggattcaat      60 gcagcgaatg agatggcatc catcaaccag gagataagac agattggtag aatggtcata    120
tcaagcaata tattggagcc gccggaatgg attctgcaag cccaagacct ggcctgtgat    180
gtgcaggatt tcacggatat ctacacatgg ctgcaaagca atcgcggag gcgtgccctt    240
```

```
gcacatatag gctacatagc gcagctgaag gatcggatca gcagccttcg agagtggcaa    300
cagagaggag gcagcagcag cagccagcag gagcgtgctg ctgccttgtc cttctcgcgg    360
cgatcatgcg ggccttgcgc ccctgaggat gtgctagttg gcattgatca gcccaggaaa    420
gaactttcgg acctcatttt cgaaaggggag gatgttgtgc aacagaagcc cagggtggtc    480
tctgtcgttg ggtatagtgg cattggcaag acagccctgg caagagcagt ctactacgac    540
cctagtgtcc gttctgcctt taacggcgtt gcttgggttg tggcatctga atgcaaccat    600
gggtgcgacc ttgtaagtaa gatctgccag caggtcaagg acgaacaagc agggaacggt    660
gctgtcgtcc ctgactgtta taggttaaaa gagatcatgc gggataaaag gtttttatc    720 gttattgacg accttcaggg agctggaatg tggaacgata taaaggtgt cttcagtgaa    780 actcacagtg gcagtcgaat aatcgttacc acgagtattc agtcggtcgc cgctgcctgc    840
actcctgagc cgcgatacat ttacaggatg ccaagtcttg gtaatttgga ctctgaaaag    900
ctactgtgga tgagggtcgg caggcatgca agccgtacgc ctgctctgga gcatgcttta    960
ggcaacgaca ccttgaaaaa atgcggcggt ctacctctgg cactgatcag tgttgccaat   1020
catttgtgtc ttgggaaagc attatttgag gagatggaca gggttcttgc caaatgctat   1080
gacagcttgc ctgacaatgc tcacaggatg tgcttgctgt ccctgagcac attccctcag   1140
ggtcatgtga tgaagaggaa gaggctaatt agaagatgga tagctgaagg attggctgtc   1200
ggagactgtg agctcagtgc tgaacaagtt gccggtaaca tatttgatgt gttgattgac   1260
aggaacgtta ctgagcctgt gctgactgct ggccacggtt ctagtagtaa ggtcaaggca   1320
tgcttagttc ttggtgtgat caaggacttc atcaacaaaa cggcagtctc aaatgagact   1380
gtagctataa tccagaacga tgagcttctc cttcccaaca ggatgatgct ggtcgcccat   1440
cgtcctgttc gtcgactgct tgttcatgga ggcacaacaa agaaaagtga agctgttgca   1500
aaggcgatcg gactggatca ggtcaggtcg ctgacaatct gcaatgctgt gcccttcgac   1560
ttccagggct gctggttgct gcgggtcttg gacctggagg cttgccaggg gatcgacaag   1620
agcatccttg gcagcatatg caagctggtg tttctcaagt acctgagcct tagggggcacc   1680 gatgtttacg gaatacccaa gaaagtaaaa aagctccagc gtttggagac gctggacctc   1740
agggacacac gggtggaaga actgcccatc caagtcttga tgctcccacg gttggcccat   1800
ctgtttggca agtttgagct acctccacag ctcaagcatg gtcatcgaac cgcaaggagg   1860
aggaggagta ggctgcaggc atttttctcc cagagaagca ggctgcagac tctttcagga   1920
ttcgtcatgg tggatgatag caacagcttc gagcacatga tgataaccat aaagtcactg   1980
aggaaggtta aggtatggtg caagaattca atctcctccc accaagaacg ccatcttgct   2040
tcttcccttc agcaacggct agtaggaaac agtaatcccc tagaatctct gtcaattgat   2100
tttggcaatg aatccatcaa tttcctcaat gatgttggag ctaccagtgc acttattggc   2160
tctatgaagc tacagggaag gctaacctcg ctccctagct tcatgacttc gtacgatact   2220
acactctccc agctgcagct gtcctcaact ggtttgggca tagaagcctt gtccctgctg   2280
caaatcttac gtcggctggt ttctctgaag ctcgctcagg atggtgatgg attttggggt   2340
gactgcttcg ctgttaacaa ggatggattt ccaagccttt tacgcctgtg cattcaggcc   2400
agggagcttc cccagttgca catccatgaa ggaggcatga gctctctcac ctccctcgaa   2460
ctactctgtc ccatgttcgc tagtcgcggt cactctgact ctgactctga ctctgacttg   2520
gggaaaactt acgtggaaac ccattcagag aagagatcca aacaagttct ttcggtagag   2580
```

| | |
|---|---|
| aagcccaaag cagttgatcc cgggatcagc ttcaaggaac caagttctga gacaagatca | 2640 |
| gaaggaactg aaattcagga gattgattcc cctaaaacgt ccaaggaggc tggtcccagc | 2700 |
| ataggcttca aggatattat tcttccggag aacacattca gaagaaactt ttcgaaggaa | 2760 |
| gtcaaaagta gatttgatct gaaacaacac ttcaagggaa tggagtacct ccaatgtctc | 2820 |
| aatgagctgg tactacattg ttctgttagc gacgaggtat tggatgcctg acaaaacga | 2880 |
| gcaagcagtc acatcaatag gccaaaggtg acaaggcaat gcacaagagc agcgctgtcg | 2940 |
| attggtagag gcccgggaac agcgaagcac gagaaagaag ggcagcacag aagccagctc | 3000 |
| atgaaaaata gaggttcaga aacagcaatc catgaggagg tagcagagca acacagctca | 3060 |
| gtaggaacga gccgtgagga agcaggatta ttccaagaac agacctcaga tacaggtcac | 3120 |
| aaagaagaag aagaagaaga agaagaagaa tgtacgagtg aagacagggc attaaatcaa | 3180 |
| ccgtgcgaca tgctcattgg catggatgtg gcaatacgtg aacttttgga gctggtgaac | 3240 |
| ctggaagagt ttggtgtaga tgacaaagtg atctccatcg tgggatgtcc aggtctgggg | 3300 |
| aagaccacgc tcgcaaaagc attctctaac ctggaaatga tacgggaaag gttcaacccg | 3360 |
| cctgtttggg tttcggcatc acaatgccgc agcgcacagg accttctcat caaggttatc | 3420 |
| cgacaagctt ctcatgttca tccagcacaa atgataagtg ctaccccaa tatagatcta | 3480 |
| ctgcaaacta tcctagcaca ggaaagctta ttgatcatca tcgatgacct acgtgaaact | 3540 |
| acagcttgga actcgataga acagccttg ggttcaacaa cctctacgca tgctggtagc | 3600 |
| ctaataatcg tgacaacgag gatccaatcc attgctggca agtgcagccc acacagatac | 3660 |
| atctacagaa tgccaggcct tggccatccg gagtccaaag aactattctt gaggacggcc | 3720 |
| tacggtgatg cacatccgac accgggcgtg gcggacgctg ttgaagaaat ctcaggggca | 3780 |
| tgtgatggtc tgccactggc gttggttagc gcagctcatg attggcgtga gcggcagggg | 3840 |
| cagggttggg aaggaagata tgtctttgaa gaagtgaaca gagcatttag ctggtggtac | 3900 |
| gagagtttgg cggacgcagc tcacatgctg tctctaggca tattcccta tggccattcc | 3960 |
| atcaagcgga agagcctaat tagaagatgg atagctgaag gattggtcag tgaggaaaaa | 4020 |
| gatggtgatc agcgattcca tgagttggtc gaccagagca tcgtggagcc tgtgctaatt | 4080 |
| actggcagta gtgatttcaa ggtcaagagg tttcgtcttc gggcgtccgg tgctggagtt | 4140 |
| catcgtcagg gaatcagtct ctaa | 4164 |

<210> SEQ ID NO 34
<211> LENGTH: 6339
<212> TYPE: DNA
<213> ORGANISM: Zea mays

<400> SEQUENCE: 34

| | |
|---|---|
| atgtctatcc tggaaaagct cgtccagagc tgttcctttc cagattcatg gcggggggccg | 60 |
| ccagacgctg aggtccaggc tctcatagga tatctcgaag agatacggtc ctccgtcctg | 120 |
| gatcttttcca aggaggatga ggacgaggat gactctgcta cgtcgtcgtc cacgctgaag | 180 |
| atgagcctga cgagccagtt gcaggaactt tgttatgatg ctgaggacta tctggagatg | 240 |
| gcgcagcact ctcgtggtgg ctgctcctgg cagatcagtt gggtccggag caaggcgacg | 300 |
| aggcagcgcc ccgctctaat cagcgcaaaa gatctctccg gcctcatctc ccgtgtgaag | 360 |
| ccggcgaaag aaatagccca agcgtacatc aagtctgcta gttcaagaac caccaccaaa | 420 |
| gagaatggcc ctaggccaca agaagagcct gcaaaaagca gtagtcgccg tgccgtctat | 480 |
| tctgatgata ctctacagcc tgacagccat gacgagcagc tagtcaggtt gctggctttg | 540 |

```
gaaagtgatc agcagctcaa gacggtggca atccatggcc tgcctggcgt tgggaagaca      600
acacttgcca gaagactgta ccactgctat gaagggaggt tccattgcgg ggctttcctt      660
cgggcgtccc gtaacctgca ggacgatacc accaggcttc tcgccaccat gctatccaag      720
attaagggcc aacaagggtg ccgctactgg gggggctccg gtgatgagca agatctaatc      780
gacagcatca ggcaacatct acaaggaaaa tcatatttca ttgtgatcga tgatttatgg      840
gctacatcag tgtgggattt cttgagccgt gcttttccca aggataactg tggcagccga      900
atagtaataa ctactcaagt tacagaagtt gcatttgctt gctgtaacaa ccacacagtt      960
gatatattca atatgaaacc tctggacgac gatcagtcac tgcaattgtt ttacagtcga     1020
gtaaagcata taaatggtta taatgctgaa gaatgcaagg ccatatcaca tggaatcgtc     1080
agcaattgtg gtaatctttc accgctagct atcataaata taactggcat gttagcaggc     1140
tgggcggact tcaatatgaa tgattgggag tacgtaagca agtgttgtac gtttacagca     1200
aatcttacta ccgaggaggc gatggagaga tttctgaacc ttatgtacaa caagcttcca     1260
gccaaattga agacgtgcct gctctatctc agtatgtatc cagagggctg tgtcatcgga     1320
aaggatgatt tggtgagaca atgggcagct gaaggtattt tcagtcaagt ggtgaaacca     1380
aaaggtagag aacatgaagt gggttttatt tattttgatg agctcctgaa aagaggattg     1440
atccagcctg tagatacaga ctacaatgat caagtgttgt catgtatagt tcatcaagtg     1500
gtactggaat ttattacaaa gaaatcaatg caggaaaact tcatcactgt cgtggattat     1560
cgtgaaacag ggacagtgct tgatgataat aaggttcatc gactgtctgc caggtttgaa     1620
ggtgccaaaa gtgcacagat accgcggagc ttcagagtac gccaagttcg gtcctttatg     1680
ttttctggat tctttaagtc tttaccttcg cttctcaagt attgccttgt ccgagttctg     1740
attcttcgtg tttggagtga tgatcaaggc aagactgtgg ttctagacct ttctccagtt     1800
ggtaatatgc ttcatgtaag gtacctgaag gtggtaagcg acatgatagt caaactccca     1860
ctcattattc gaggcctgcg acacttagag acactcgagg tggatgcaga agaagtcgct     1920
gttccactgg atgttttcat cttgaagagc ctgttgcatc tccgacttcc gagcaaggct     1980
tatcagcttg attcagatat tcaaaggatt ggtttaacaa atacatttcc tttaagtttt     2040
ctgcccttcg tcagaacgtt gtcaatccta ttcctatggc ggtctctcct ctcccatggc     2100
catttgacat cgcttcaaag tcttggctac tttgacctga gcacttgctc cagatatact     2160
gtgcggcaac ttggcaagct gaccaatttg agggatcttc atctaacctg ctctgcagtt     2220
cgttccaggc atcgaattag caacatccaa tgccttgcct ctgttctggg gaaatgcacc     2280
agcctcgaat ctctaactat ccgtggcgaa gcatcttcaa accagagcat ttcttttgat     2340
ggcttaagca gattgtcttc tccaccgtac aacctcgtga gctttgtgct gtccccgagg     2400 atttttcaaaa tggcgaagct ccccaagtgg attgggcaac tcagcaggct cagtacgcta     2460
aagattgctg ttggcgagct gtcaagtgaa gatgttgaca tcctcaaaga actctctgcc     2520
ctcactgctc tttctctcta cgttcgcaga aaccctaaga aggaagctg gatcctattc      2580 agtaagggct tcgcagtgct caagtatttt aagttcactt gcactgcact gtgcgtgaaa     2640
tttagtgaac aagctatgcc tgctgtccaa aggctgaatg tgtgcttcaa tgctaacaca     2700
atgcagcagt acaggccgga agatgcagga atttggtacc tgtcaggcct tcaagttatc     2760
tctgccagaa taggagctgc cggtattgat caagccagca gagaagccgc gaaatctagg     2820
ttgctggacg ccattcttag caaccatcca aagcctcctc ctatcagaaa cgtgcaaatg     2880
```

```
gtggactggg ttattcatgg cgacacagag gagtgttcaa ccggtgtgat gatacgtaaa    2940
gatgaaagca gccgtgagca tactaggtca tttttaagtc agttcccgtt cagaagacga    3000
cccctgcttc cctccatatt cacaaggcgt ggccaggatg atgagcaaca taaaatcgaa    3060
gaaaatgatg tgctacaaga tagtattatc ttaagggaat cctcttcgct aatgcaaaaa    3120
ccaggttggg tcacccgcag atcaaggagt actggtgttg gccttctgat ggccgtgcga    3180
gggtccacat acatgatcag gcaatatata aaggagccag gattcaatgc agcgaatgag    3240
atggcatcca tcaaccagga gataagacag attggtagaa tggtcatatc aagcaatata    3300
ttggagccgc cggaatggat tctgcaagcc caagacctgg cctgtgatgt gcaggatttc    3360
acggatatct acacatggct gcaaagcaaa tcgcggaggc gtgcccttgc acatataggc    3420
tacatagcgc agctgaagga tcggatcagc agccttcgag agtggcaaca gagaggaggc    3480
agcagcagca gccagcagga gcgtgctgct gccttgtcct tctcgcggcg atcatgcggg    3540
ccttgcgccc ctgaggatgt gctagttggc attgatcagc ccaggaaaga actttcggac    3600
ctcattttcg aaagggagga tgttgtgcaa cagaagccca gggtggtctc tgtcgttggg    3660
tatagtggca ttggcaagac agccctggca agagcagtct actacgaccc tagtgtccgt    3720
tctgcctttta acgcgttgc ttgggttgtg gcatctgaat gcaaccatgg gtgcgacctt    3780
gtaagtaaga tctgccagca ggtcaaggac gaacaagcag ggaacggtgc tgtcgtccct    3840
gactgttata ggttaaaaga gatcatgcgg gataaaaggt tttttatcgt tattgacgac    3900
cttcagggag ctggaatgtg gaacgatata aaaggtgtct tcagtgaaac tcacagtggc    3960
agtcgaataa tcgttaccac gagtattcag tcggtcgccg ctgcctgcac tcctgagccg    4020
cgatacattt acaggatgcc aagtcttggt aatttggact ctgaaaagct actgtggatg    4080
agggtcggca ggcatgcaag ccgtacgcct gctctggagc atgctttagg caacgacacc    4140
ttgaaaaaat gcggcggtct acctctggca ctgatcagtg ttgccaatca tttgtgtctt    4200
gggaaagcat tatttgagga gatggacagg gttcttgcca aatgctatga cagcttgcct    4260
gacaatgctc acaggatgtg cttgctgtcc ctgagcacat tccctcaggg tcatgtgatg    4320
aagaggaaga ggctaattag aagatggata gctgaaggat tggctgtcgg agactgtgag    4380
ctcagtgctg aacaagttgc cggtaacata tttgatgtgt tgattgacag gaacgttact    4440
gagcctgtgc tgactgctgg ccacggttct agtagtaagg tcaaggcatg cttagttctt    4500
ggtgtgatca aggacttcat caacaaaacg gcagtctcaa atgagactgt agctataatc    4560
cagaacgatg agcttctcct tcccaacagg atgatgctgg tcgcccatcg tcctgttcgt    4620
cgactgcttg ttcatggagg cacaacaaag aaaagtgaag ctgttgcaaa ggcgatcgga    4680
ctggatcagg tcaggtcgct gacaatctgc aatgctgtgc ccttcgactt ccagggctgc    4740
tggttgctgc gggtcttgga cctggaggct tgccagggga tcgacaagag catccttggc    4800
agcatatgca agctggtgtt tctcaagtac ctgagcctta ggggcaccga tgtttacgga    4860
atacccaaga aagtaaaaaa gctccagcgt ttggagacgc tggacctcag ggacacacgg    4920
gtggaagaac tgcccatcca agtcttgatg ctcccacggt tggcccatct gtttggcaag    4980
tttgagctac ctccacagct caagcatggt catcgaaccg caaggaggag gaggagtagg    5040
ctgcaggcat ttttctccca gagaagcagg ctgcagactc tttcaggatt cgtcatggtg    5100
gatgatagca acagcttcga gcacatgatg ataaccataa agtcactgag gaaggttaag    5160
gtatggtgca agaattcaat ctcctcccac caagaacgcc atcttgcttc ttcccttcag    5220
caacggctag taggaaacag taatcccctc gaatctctgt caattgattt tggcaatgaa    5280
```

```
tccatcaatt tcctcaatga tgttggagct accagtgcac ttattggctc tatgaagcta    5340
cagggaaggc taacctcgct ccctagcttc atgacttcgt acgatactac actctcccag    5400
ctgcagctgt cctcaactgg tttgggcata gaagccttgt ccctgctgca aatcttacgt    5460
cggctggttt ctctgaagct cgctcaggat ggtgatggat tttggggtga ctgcttcgct    5520
gttaacaagg atggatttcc aagcctttta cgcctgtgca ttcaggccag ggagcttccc    5580
cagttgcaca tccatgaagg aggcatgagc tctctcacct ccctcgaact actctgtccc    5640
atgttcgcta gtcgcggtca ctctgactct gactctgact ctgacttggg gaaaacttac    5700
gtggaaaccc attcagagaa gagatccaaa caagttcttt cggtagagaa gcccaaagca    5760
gttgatcccg ggatcagctt caaggaacca agttctgaga caagatcaga aggaactgaa    5820
attcaggaga ttgattcccc taaaacgtcc aaggaggctg gtcccagcat aggcttcaag    5880
gatattattc ttccggagaa cacattcaga agaaactttt cgaaggaagt caaaagtaga    5940
tttgatctga acaacacttt caagggaatg gagtacctcc aatgtctcaa tgagctggta    6000
ctacattgtt ctgttagcga cgaggtattg gatgcctgga caaaacgagc aagcagtcac    6060
atcaataggc caaaggtgac aaggcaatgc acaagagcag cgctgtcgat ggtagaggc     6120 ccgggaacag cgaagcacga aaagaaggg cagcacagaa gccagctcat gaaaaataga    6180
ggttcagaaa cagcaatcca tgaggaggta gcagagcaac acagctcagt aggaacgagc    6240
cgtgaggaag caggattatt ccaagaacag actctacagg tcacaaagaa gaagaagaag    6300
aagaagaaga agaatgtacg agtgaagaca gggcattaa                           6339
```

<210> SEQ ID NO 35
<211> LENGTH: 6777
<212> TYPE: DNA
<213> ORGANISM: Zea mays

<400> SEQUENCE: 35

```
atgtctatcc tggaaaagct cgtccagagc tgttcctttc agattcatg gcggggggccg     60 ccagacgctg aggtccaggc tctcatagga tatctcgaag agatacggtc ctccgtcctg    120
gatctttcca aggaggatga ggacgaggat gactctgcta cgtcgtcgtc cacgctgaag    180
atgagcctga cgagccagtt gcaggaactt tgttatgatg ctgaggacta tctggagatg    240
gcgcagcact ctcgtggtgg ctgctcctgg cagatcagtt gggtccggag caaggcgacg    300
aggcagcgcc ccgctctaat cagcgcaaaa gatctctccg gcctcatctc ccgtgtgaag    360
ccggcgaaag aaatagccca agcgtacatc aagtctgcta gttcaagaac caccaccaaa    420
gagaatggcc ctaggccaca agaagagcct gcaaaaagca gtagtcgccg tgccgtctat    480
tctgatgata ctctacagcc tgacagccat gacgagcagc tagtcaggtt gctggctttg    540
gaaagtgatc agcagctcaa gacggtggca atccatggcc tgcctggcgt tgggaagaca    600
acacttgcca gagactgta ccactgctat aagggaggt tccattgcgg ggcttttcctt    660 cgggcgtccc gtaacctgca ggacgatacc accaggcttc tcgccaccat gctatccaag    720
attaagggcc aacaagggtg ccgctactgg gggggctccg gtgatgagca agatctaatc    780
gacagcatca ggcaacatct acaaggaaaa tcatatttca ttgtgatcga tgatttatgg    840
gctacatcag tgtgggattt cttgagccgt gcttttccca aggataactg tggcagccga    900
atagtaataa ctactcaagt tacagaagtt gcatttgctt gctgtaacaa ccacacagtt    960
gatatattca atatgaaacc tctggacgac gatcagtcac tgcaattgtt ttacagtcga   1020
```

-continued

```
gtaaagcata taaatggtta taatgctgaa gaatgcaagg ccatatcaca tggaatcgtc    1080
agcaattgtg gtaatctttc accgctagct atcataaata taactggcat gttagcaggc    1140
tgggcggact tcaatatgaa tgattgggag tacgtaagca agtgttgtac gtttacagca    1200
aatcttacta ccgaggaggc gatggagaga tttctgaacc ttatgtacaa caagcttcca    1260
gccaaattga agacgtgcct gctctatctc agtatgtatc cagagggctg tgtcatcgga    1320
aaggatgatt tggtgagaca atgggcagct gaaggtattt tcagtcaagt ggtgaaacca    1380
aaaggtagag aacatgaagt gggttttatt tattttgatg agctcctgaa aagaggattg    1440
atccagcctg tagatacaga ctacaatgat caagtgttgt catgtatagt tcatcaagtg    1500
gtactggaat ttattacaaa gaaatcaatg caggaaaact tcatcactgt cgtggattat    1560
cgtgaaacag ggacagtgct tgatgataat aaggttcatc gactgtctgc caggtttgaa    1620
ggtgccaaaa gtgcacagat accgcggagc ttcagagtac gccaagttcg gtcctttatg    1680
ttttctggat tctttaagtc tttaccttcg cttctcaagt attgccttgt ccgagttctg    1740
attcttcgtg tttggagtga tgatcaaggc aagactgtgg ttctagacct ttctccagtt    1800
ggtaatatgc ttcatgtaag gtacctgaag gtggtaagcg acatgatagt caaactccca    1860
ctcattattc gaggcctgcg acacttagag acactcgagg tggatgcaga agaagtcgct    1920
gttccactgg atgttttcat cttgaagagc ctgttgcatc tccgacttcc gagcaaggct    1980
tatcagcttg attcagatat tcaaaggatt ggtttaacaa atacatttcc tttaagttt    2040 ctgcccttcg tcagaacgtt gtcaatccta ttcctatggc ggtctctcct ctcccatggc    2100
catttgacat cgcttcaaag tcttggctac tttgacctga gcacttgctc cagatatact    2160
gtgcggcaac ttgcaagct gaccaatttg agggatcttc atctaacctg ctctgcagtt    2220
cgttccaggc atcgaattag caacatccaa tgccttgcct ctgttctggg gaaatgcacc    2280
agcctcgaat ctctaactat ccgtggcgaa gcatcttcaa accagagcat ttcttttgat    2340
ggcttaagca gattgtcttc tccaccgtac aacctcgtga gctttgtgct gtccccgagg    2400 atttttcaaaa tggcgaagct ccccaagtgg attgggcaac tcagcaggct cagtacgcta    2460
aagattgctg ttggcgagct gtcaagtgaa gatgttgaca tcctcaaaga actctctgcc    2520
ctcactgctc tttctctcta cgttcgcaga aaccctaaga aggaagctg gatcctattc    2580 agtaagggct tcgcagtgct caagtatttt aagttcactt gcactgcact gtgcgtgaaa    2640
tttagtgaac aagctatgcc tgctgtccaa aggctgaatg tgtgcttcaa tgctaacaca    2700
atgcagcagt acaggccgga agatgcagga atttggtacc tgtcaggcct tcaagttatc    2760
tctgccagaa taggagctgc cggtattgat caagccagca gagaagccgc gaaatctagg    2820
ttgctggacg ccattcttag caaccatcca aagcctcctc ctatcagaaa cgtgcaaatg    2880
gtggactggg ttattcatgg cgacacagag gagtgttcaa ccggtgtgat gatacgtaaa    2940
gatgaaagca gccgtgagca tactaggtca tttttaagtc agttcccgtt cagaagacga    3000 ccctgcttc cctccatatt cacaaggcgt ggccaggatg atgagcaaca taaaatcgaa    3060
gaaaatgatg tgctacaaga tagtattatc ttaagggaat cctcttcgct aatgcaaaaa    3120
ccaggttggg tcacccgcag atcaaggagt actggtgttg gccttctgat ggccgtgcga    3180
gggtccacat acatgatcag gcaatatata aaggagccag gattcaatgc agcgaatgag    3240
atggcatcca tcaaccagga gataagacag attggtagaa tggtcatatc aagcaatata    3300
ttggagccgc cggaatggat tctgcaagcc caagacctgg cctgtgatgt gcaggatttc    3360
acggatatct acacatggct gcaaagcaaa tcgcggaggc gtgcccttgc acatataggc    3420
```

```
tacatagcgc agctgaagga tcggatcagc agccttcgag agtggcaaca gagaggaggc   3480
agcagcagca gccagcagga gcgtgctgct gccttgtcct tctcgcggcg atcatgcggg   3540
ccttgcgccc ctgaggatgt gctagttggc attgatcagc ccaggaaaga actttcggac   3600
ctcattttcg aaagggagga tgttgtgcaa cagaagccca gggtggtctc tgtcgttggg   3660
tatagtggca ttggcaagac agccctggca agagcagtct actacgaccc tagtgtccgt   3720
tctgccttta acggcgttgc ttgggttgtg catctgaat gcaaccatgg gtgcgacctt   3780
gtaagtaaga tctgccagca ggtcaaggac gaacaagcag ggaacggtgc tgtcgtccct   3840
gactgttata ggttaaaaga gatcatgcgg gataaaaggt tttttatcgt tattgacgac   3900
cttcagggag ctggaatgtg gaacgatata aaaggtgtct tcagtgaaac tcacagtggc   3960
agtcgaataa tcgttaccac gagtattcag tcggtcgccg ctgcctgcac tcctgagccg   4020
cgatacattt acaggatgcc aagtcttggt aatttggact ctgaaaagct actgtggatg   4080
agggtcggca ggcatgcaag ccgtacgcct gctctggagc atgctttagg caacgacacc   4140
ttgaaaaaat gcggcggtct acctctggca ctgatcagtg ttgccaatca tttgtgtctt   4200
gggaaagcat tatttgaggg gatggacagg gttcttgcca aatgctatga cagcttgcct   4260
gacaatgctc acaggatgtg cttgctgtcc ctgagcacat tccctcaggg tcatgtgatg   4320
aagaggaaga ggctaattag aagatggata gctgaaggat tggctgtcgg agactgtgag   4380
ctcagtgttg aacaagttgc cggtaacata tttgatgtgt tgattgacag gaacgttact   4440
gagcctgtgc tgactgctgg ccacggttct agtagtaagg tcaaggcatg cttagttctt   4500
ggtgtgatca aggacttcat caacaaaacg gcagtctcaa atgagactgt agctataatc   4560
cagaacgatg agcttctcct tcccaacagg atgatgctgg tcgcccatcg tcctgttcgt   4620
cgactgcttg ttcatggagg cacaacaaag aaaagtgaag ctgttgcaaa ggcgatcgga   4680
ctggatcagg tcaggtcgct gacaatctgc aatgctgtgc ccttcgactt ccagggctgc   4740
tggttgctgc gggtcttgga cctggaggct tgccagggga tcgacaagag catccttggc   4800
agcatatgca agctggtgtt tctcaagtac ctgagcctta ggggcaccga tgtttacgga   4860
atacccaaga aagtaaaaaa gctccagcgt ttggagacgc tggacctcag ggacacacgg   4920
gtggaagaac tgcccatcca agtcttgatg ctcccacggt tggcccatct gtttggcaag   4980
tttgagctac ctccacagct caagcatggt catcgaaccg caaggaggag gaggagtagg   5040
ctgcaggcat ttttctccca gagaagcagg ctgcagactc tttcaggatt cgtcatggtg   5100
gatgatagca acagcttcga gcacatgatg ataaccataa agtcactgag gaaggttaag   5160
gtatggtgca agaattcaat ctcctcccac caagaacgcc atcttgcttc ttcccttcag   5220
caacggctag taggaaacag taatccccta gaatctctgt caattgattt tggcaatgaa   5280
tccatcaatt tcctcaatga tgttggagct accagtgcac ttattggctc tatgaagcta   5340
cagggaaggc taacctcgct ccctagcttc atgacttcgt acgatactac actctcccag   5400
ctgcagctgt cctcaactgg tttgggcata gaagccttgt ccctgctgca aatcttacgt   5460
cggctggttt ctctgaagct cgctcaggat ggtgatggat tttggggtga ctgcttcgct   5520
gttaacaagg atggatttcc aagcctttta cgcctgtgca ttcaggccag ggagcttccc   5580
cagttgcaca tccatgaagg aggcatgagc tctctcacct ccctcgaact actctgtccc   5640
atgttcgcta gtcgcggtca ctctgactct gactctgact ctgacttggg gaaaacttac   5700
gtggaaaccc attcagagaa gagatccaaa caagttcttt cggtagagaa gcccaaagca   5760
```

| | |
|---|---:|
| gttgatcccg ggatcagctt caaggaacca agttctgaga caagatcaga aggaactgaa | 5820 |
| attcaggaga ttgattcccc taaaacgtcc aaggaggctg gtcccagcat aggcttcaag | 5880 |
| gatattattc ttccggagaa cacattcaga agaaactttt cgaaggaagt caaaagtaga | 5940 |
| tttgatctga acaacactt caagggaatg gagtacctcc aatgtctcaa tgagctggta | 6000 |
| ctacattgtt ctgttagcga cgaggtattg gatgcctgga caaaacgagc aagcagtcac | 6060 |
| atcaataggc caaggtgac aaggcaatgc acaagagcag cgctgtcgat tggtagaggc | 6120 |
| ccgggaacag cgaagcacga aaagaaggg cagcacagaa gccagctcat gaaaaataga | 6180 |
| ggttcagaaa cagcaatcca tgaggaggta gcagagcaac acagctcagt aggaacgagc | 6240 |
| cgtgaggaag caggattatt ccaagaacag acctcaggtc acaaagaaga agaagaagaa | 6300 |
| gaagaagaag aatgtacgag tgaagacagg gcattaaatc aaccgtgcga catgctcatt | 6360 |
| ggcatggatg tggcaatacg tgaactttg gagctggtga acctggaaga gtttggtgta | 6420 |
| gatgacaaag tgatctccat cgtgggatgt ccaggtctgg ggaagaccac gctcgcaaaa | 6480 |
| gcattctcta acctggaaat gatacgggaa aggttcaacc cgcctgtttg ggtttcggca | 6540 |
| tcacaatgcc gcagcgcaca ggaccttctc atcaaggtta ccgacaagc ttctcatgtt | 6600 |
| catccagcac aaatgataag tgctaccccc aatatagatc tactgcaaac tatcctagca | 6660 |
| caggaaaggt actcgctcca caccaccacc cgtgcttatt acctctatat ccaccctgcc | 6720 |
| tgggtttact tctctcagtc atgcacacaa aaattgttta acaaaagaa taagtag | 6777 |

<210> SEQ ID NO 36
<211> LENGTH: 6282
<212> TYPE: DNA
<213> ORGANISM: Zea mays

<400> SEQUENCE: 36

| | |
|---|---:|
| atgtctatcc tggaaaagct cgtccagagc tgttcctttc cagattcatg gcggggccg | 60 |
| ccagacgctg aggtccaggc tctcatagga tatctcgaag agatacggtc ctccgtcctg | 120 |
| gatcttttcca aggaggatga ggacgaggat gactctgcta cgtcgtcgtc cacgctgaag | 180 |
| atgagcctga cgagccagtt gcaggaactt tgttatgatg ctgaggacta tctggagatg | 240 |
| gcgcagcact ctcgtggtgg ctgctcctgg cagatcagtt gggtccggag caaggcgacg | 300 |
| aggcagcgcc ccgctctaat cagcgcaaaa gatctctccg gcctcatctc ccgtgtgaag | 360 |
| ccggcgaaag aaatagccca agcgtacatc aagtctgcta gttcaagaac caccaccaaa | 420 |
| gagaatggcc ctaggccaca agaagagcct gcaaaaagca gtagtcgccg tgccgtctat | 480 |
| tctgatgata ctctacagcc tgacagccat gacgagcagc tagtcaggtt gctggctttg | 540 |
| gaaagtgatc agcagctcaa gacggtggca atccatggcc tgcctggcgt tgggaagaca | 600 |
| acacttgcca gaagactgta ccactgctat gaagggaggt tccattgcgg ggctttcctt | 660 |
| cgggcgtccc gtaacctgca ggacgatacc accaggcttc tcgccaccat gctatccaag | 720 |
| attaagggcc aacaagggtg ccgctactgg gggggctccg gtgatgagca agatctaatc | 780 |
| gacagcatca ggcaacatct acaaggaaaa tcatatttca ttgtgatcga tgatttatgg | 840 |
| gctacatcag tgtgggattt cttgagccgt gcttttccca aggataactg tggcagccga | 900 |
| atagtaataa ctactcaagt tacagaagtt gcatttgctt gctgtaacaa ccacacagtt | 960 |
| gatatattca atatgaaacc tctggacgac gatcagtcac tgcaattgtt ttacagtcga | 1020 |
| gtaaagcata taaatggtta taatgctgaa gaatgcaagg ccatatcaca tggaatcgtc | 1080 |
| agcaattgtg gtaatctttc accgctagct atcataaata taactggcat gttagcaggc | 1140 |

```
tgggcggact tcaatatgaa tgattgggag tacgtaagca agtgttgtac gtttacagca    1200
aatcttacta ccgaggaggc gatggagaga tttctgaacc ttatgtacaa caagcttcca    1260
gccaaattga agacgtgcct gctctatctc agtatgtatc cagagggctg tgtcatcgga    1320
aaggatgatt tggtgagaca atgggcagct gaaggtattt tcagtcaagt ggtggaacca    1380
aaaggtagag aacatgaagt gggttttatt tattttgatg agctcctgaa aagaggattg    1440
atccagcctg tagatacaga ctacaatgat caagtgttgt catgtatagt tcatcaagtg    1500
gtactggaat ttattacaaa gaaatcaatg caggaaaact tcatcactgt cgtggattat    1560
cgtgaaacag ggacagtgct tgatgataat aaggttcatc gactgtctgc caggtttgaa    1620
ggtgccaaaa gtgcacagat accgcggagc ttcagagtac gccaagttcg gtcctttatg    1680
ttttctggat tctttaagtc tttaccttcg cttctcaagt attgccttgt ccgagttctg    1740
attcttcgtg tttggagtga tgatcaaggc aagactgtgg ttctagacct ttctccagtt    1800
ggtaatatgc ttcatgtaag gtacctgaag gtggtaagcg acatgatagt caaactccca    1860
ctcattattc gaggcctgcg acacttagag acactcgagg tggatgcaga agaagtcgct    1920
gttccactgg atgttttcat cttgaagagc ctgttgcatc tccgacttcc gagcaaggct    1980
tatcagcttg attcagatat tcaaaggatt ggtttaacaa atacatttcc tttaagtttt    2040
ctgcccttcg tcagaacgtt gtcaatccta ttcctatggc ggtctctcct ctcccatggc    2100
catttgacat cgcttcaaag tcttggctac tttgacctga gcacttgctc cagatatact    2160
gtgcggcaac ttggcaagct gaccaatttg agggatcttc atctaacctg ctctgcagtt    2220
cgttccaggc atcgaattag caacatccaa tgccttgcct ctgttctggg gaaatgcacc    2280
agcctcgaat ctctaactat ccgtggcgaa gcatcttcaa accagagcat ttcttttgat    2340
ggcttaagca gattgtcttc tccaccgtac aacctcgtga gctttgtgct gtccccgagg    2400
attttcaaaa tggcgaagct cccccaagtgg attgggcaac tcagcaggct cagtacgcta    2460
aagattgctg ttggcgagct gtcaagtgaa gatgttgaca tcctcaaaga actctctgcc    2520
ctcactgctc tttctctcta cgttcgcaga aaccctaaga aaggaagctg atcctattc     2580 agtaagggct tcgcagtgct caagtatttt aagttcactt gcactgcact gtgcgtgaaa    2640
tttagtgaac aagctatgcc tgctgtccaa aggctgaatg tgtgcttcaa tgctaacaca    2700
atgcagcagt acaggccgga agatgcagga atttggtacc tgtcaggcct tcaagttatc    2760
tctgccagaa taggagctgc cggtattgat caagccagca gagaagccgc gaaatctagg    2820
ttgctggacg ccattcttag caaccatcca agcctcctc ctatcagaaa cgtgcaaatg     2880
gtggactggg ttattcatgg cgacacagag gagtgttcaa ccggtgtgat gatacgtaaa    2940
gatgaaagca gccgtgagca tactaggtca tttttaagtc agttcccgtt cagaagacga    3000
cccctgcttc cctccatatt cacaaggcgt ggccaggatg atgagcaaca taaaatcgaa    3060
gaaaatgatg tgctacaaga tagtattatc ttaagggaat cctcttcgct aatgcaaaaa    3120
ccaggttggg tcacccgcag atcaaggagt actggtgttg gccttctgat ggccgtgcga    3180
gggtccacat acatgatcag gcaatatata aaggagccag gattcaatgc agcgaatgag    3240
atggcatcca tcaaccagga gataagacag attggtagaa tggtcatatc aagcaatata    3300
ttggagccgc cggaatggat tctgcaagcc caagacctgg cctgtgatgt gcaggatttc    3360
acggatatct acacatggct gcaaagcaaa tcgcggaggc gtgcccttgc acatataggc    3420
tacatagcgc agctgaagga tcggatcagc agccttcgag agtggcaaca gagaggaggc    3480
```

```
agcagcagca gccagcagga gcgtgctgct gccttgtcct tctcgcggcg atcatgcggg    3540
ccttgcgccc ctgaggatgt gctagttggc attgatcagc ccaggaaaga actttcggac    3600
ctcattttcg aaagggagga tgttgtgcaa cagaagccca gggtggtctc tgtcgttggg    3660
tatagtggca ttggcaagac agccctggca agagcagtct actacgaccc tagtgtccgt    3720
tctgccttta acggcgttgc ttgggttgtg gcatctgaat gcaaccatgg gtgcgacctt    3780
gtaagtaaga tctgccagca ggtcaaggac gaacaagcag ggaacggtgc tgtcgtccct    3840
gactgttata ggttaaaaga gatcatgcgg gataaaaggt tttttatcgt tattgacgac    3900
cttcagggag ctggaatgtg gaacgatata aaaggtgtct tcagtgaaac tcacagtggc    3960
agtcgaataa tcgttaccac gagtattcag tcggtcgccg ctgcctgcac tcctgagccg    4020
cgatacattt acaggatgcc aagtcttggt aatttggact ctgaaaagct actgtggatg    4080
agggtcggca ggcatgcaag ccgtacgcct gctctggagc atgctttagg caacgacacc    4140
ttgaaaaaat gcggcggtct acctctggca ctgatcagtg ttgccaatca tttgtgtctt    4200
gggaaagcat tatttgagga gatggacagg gttcttgcca aatgctatga cagcttgcct    4260
gacaatgctc acaggatgtg cttgctgtcc ctgagcacat tccctcaggg tcatgtgatg    4320
aagaggaaga ggctaattag aagatggata gctgaaggat tggctgtcgg agactgtgag    4380
ctcagtgctg aacaagttgc cggtaacata tttgatgtgt tgattgacag gaacgttact    4440
gagcctgtgc tgactgctgg ccacggttct agtagtaagg tcaaggcatg cttagttctt    4500
ggtgtgatca aggacttcat caacaaaacg gcagtctcaa atgagactgt agctataatc    4560
cagaacgatg agcttctcct tcccaacagg atgatgctgg tcgcccatcg tcctgttcgt    4620
cgactgcttg ttcatggagg cacaacaaag aaaagtgaag ctgttgcaaa ggcgatcgga    4680
ctggatcagg tcaggtcgct gacaatctgc aatgctgtgc ccttcgactt ccagggctgc    4740
tggttgctgc gggtcttgga cctggaggct tgccagggga tcgacaagag catccttggc    4800
agcatatgca agctggtgtt tctcaagtac ctgagcctta ggggcaccga tgtttacgga    4860
atacccaaga agtaaaaaa gctccagcgt ttggagacgc tggacctcag ggacacacgg    4920
gtggaagaac tgcccatcca agtcttgatg ctcccacggt tggcccatct gtttggcaag    4980
tttgagctac ctccacagct caagcatggt catcgaaccg caaggaggag gaggagtagg    5040
ctgcaggcat ttttctccca gagaagcagg ctgcagactc tttcaggatt cgtcatggtg    5100
gatgatagca acagcttcga gcacatgatg ataaccataa agtcactgag gaaggttaag    5160
gtatggtgca agaattcaat ctcctcccac caagaacgcc atcttgcttc ttcccttcag    5220
caacggctag taggaaacag taatccccta gaatctctgt caattgattt tggcaatgaa    5280
tccatcaatt tcctcaatga tgttggagct accagtgcac ttattggctc tatgaagcta    5340
cagggaaggc taacctcgct ccctagcttc atgacttcgt acgatactac actctcccag    5400
ctgcagctgt cctcaactgg tttgggcata aagccttgt ccctgctgca atcttacgt    5460 cggctggttt ctctgaagct cgctcaggat ggtgatggat tttggggtga ctgcttcgct    5520
gttaacaagg atggatttcc aagccttta cgcctgtgca ttcaggccag ggagcttccc    5580
cagttgcaca tccatgaagg aggcatgagc tctctcacct ccctcgaact actctgtccc    5640
atgttcgcta gtcgcggtca ctctgactct gactctgact ctgacttggg gaaaacttac    5700
gtggaacccc attcagagaa gagatccaaa caagttcttt cggtagagaa gcccaaagca    5760
gttgatcccg ggatcagctt caaggaacca agttctgaga caagatcaga aggaactgaa    5820
attcaggaga ttgattcccc taaaacgtcc aaggaggctg gtcccagcat aggcttcaag    5880
```

| | |
|---|---|
| gatattattc ttccggagaa cacattcaga agaaactttt cgaaggaagt caaaagtaga | 5940 |
| tttgatctga aacaacactt caagggaatg gagtacctcc aatgtctcaa tgagctggta | 6000 |
| ctacattgtt ctgttagcga cgaggtattg gatgcctgga caaaacgagc aagcagtcac | 6060 |
| atcaataggc caaaggtgac aaggcaatgc acaagagcag cgctgtcgat tggtagaggc | 6120 |
| ccgggaacag cgaagcacga aaagaaggg cagcacagaa gccagctcat gaaaaataga | 6180 |
| ggttcagaaa cagcaatcca tgaggaggta gcagagcaac acagctcagt aggaacgagc | 6240 |
| cgtgaggaag caggattatt ccaagaacag acctcaggtc ac | 6282 |

<210> SEQ ID NO 37
<211> LENGTH: 3633
<212> TYPE: DNA
<213> ORGANISM: Zea mays

<400> SEQUENCE: 37

| | |
|---|---|
| atgcctgctg tccaaaggct gaatgtgtgc ttcaatgcta acacaatgca gcagtacagg | 60 |
| ccggaagatg caggaatttg gtacctgtca ggccttcaag ttatctctgc cagaatagga | 120 |
| gctgccggta ttgatcaagc cagcagagaa gccgcgaaat ctaggttgct ggacgccatt | 180 |
| cttagcaacc atccaaagcc tcctcctatc agaaacgtgc aaatggtgga ctgggttatt | 240 |
| catggcgaca cagaggagtg ttcaaccggt gtgatgatac gtaaagatga aagcagccgt | 300 |
| gagcatacta ggtcattttt aagtcagttc ccgttcagaa gacgacccct gcttccctcc | 360 |
| atattcacaa ggcgtggcca ggatgatgag caacataaaa tcgaagaaaa tgatgtgcta | 420 |
| caagatagta ttatcttaag ggaatcctct tcgctaatgc aaaaaccagg ttgggtcacc | 480 |
| cgcagatcaa ggagtactgg tgttggcctt ctgatggccg tgcgagggtc cacatacatg | 540 |
| atcaggcaat atataaagga gccaggattc aatgcagcga atgagatggc atccatcaac | 600 |
| caggagataa gacagattgg tagaatggtc atatcaagca atatattgga gccgccggaa | 660 |
| tggattctgc aagcccaaga cctggcctgt gatgtgcagg atttcacgga tatctacaca | 720 |
| tggctgcaaa gcaaatcgcg gaggcgtgcc cttgcacata taggctacat agcgcagctg | 780 |
| aaggatcgga tcagcagcct tcgagagtgg caacagagag gaggcagcag cagcagccag | 840 |
| caggagcgtg ctgctgcctt gtccttctcg cggcgatcat gcgggccttg cgcccctgag | 900 |
| gatgtgctag ttggcattga tcagcccagg aaagaacttt cggacctcat tttcgaaagg | 960 |
| gaggatgttg tgcaacagaa gcccagggtg gtctctgtcg ttgggtatag tggcattggc | 1020 |
| aagacagccc tggcaagagc agtctactac gaccctagtg tccgttctgc ctttaacggc | 1080 |
| gttgcttggg ttgtggcatc tgaatgcaac catgggtgcg accttgtaag taagatctgc | 1140 |
| cagcaggtca aggacgaaca agcagggaac ggtgctgtcg tccctgactg ttataggtta | 1200 |
| aaagagatca tgcgggataa aaggtttttt atcgttattg acgaccttca gggagctgga | 1260 |
| atgtggaacg atataaaagg tgtcttcagt gaaactcaca gtggcagtcg aataatcgtt | 1320 |
| accacgagta ttcagtcggt cgccgctgcc tgcactcctg agccgcgata catttacagg | 1380 |
| atgccaagtc ttggtaattt ggactctgaa aagctactgt ggatgagggt cggcaggcat | 1440 |
| gcaagccgta cgcctgctct ggagcatgct ttaggcaacg acaccttgaa aaaatgcggc | 1500 |
| ggtctacctc tggcactgat cagtgttgcc aatcatttgt gtcttgggaa agcattattt | 1560 |
| gaggagatgg acagggttct tgccaaatgc tatgacagct tgcctgacaa tgctcacagg | 1620 |
| atgtgcttgc tgtccctgag cacattccct cagggtcatg tgatgaagag gaagaggcta | 1680 |

```
attagaagat ggatagctga aggattggct gtcggagact gtgagctcag tgctgaacaa    1740
gttgccggta acatatttga tgtgttgatt gacaggaacg ttactgagcc tgtgctgact    1800
gctggccacg gttctagtag taaggtcaag gcatgcttag ttcttggtgt gatcaaggac    1860
ttcatcaaca aaacggcagt ctcaaatgag actgtagcta taatccagaa cgatgagctt    1920
ctccttccca acaggatgat gctggtcgcc catcgtcctg ttcgtcgact gcttgttcat    1980
ggaggcacaa caaagaaaag tgaagctgtt gcaaaggcga tcggactgga tcaggtcagg    2040
tcgctgacaa tctgcaatgc tgtgcccttc gacttccagg gctgctggtt gctgcgggtc    2100
ttggacctgg aggcttgcca ggggatcgac aagagcatcc ttggcagcat atgcaagctg    2160
gtgtttctca agtacctgag ccttaggggc accgatgttt acggaatacc caagaaagta    2220
aaaaagctcc agcgtttgga gacgctggac ctcaggggaca cacggggtgga agaactgccc   2280 atccaagtct tgatgctccc acggttggcc catctgtttg gcaagtttga gctacctcca    2340
cagctcaagc atggtcatcg aaccgcaagg aggaggagga gtaggctgca ggcattttc    2400 tcccagagaa gcaggctgca gactctttca ggattcgtca tggtggatga tagcaacagc    2460
ttcgagcaca tgatgataac cataaagtca ctgaggaagg ttaaggtatg gtgcaagaat    2520
tcaatctcct cccaccaaga acgccatctt gcttcttccc ttcagcaacg gctagtagga    2580
aacagtaatc ccctagaatc tctgtcaatt gattttggca atgaatccat caatttcctc    2640
aatgatgttg gagctaccag tgcacttatt ggctctatga agctacaggg aaggctaacc    2700
tcgctcccta gcttcatgac ttcgtacgat actacactct cccagctgca gctgtcctca    2760 actggttttgg gcatagaagc cttgtccctg ctgcaaatct tacgtcggct ggtttctctg    2820
aagctcgctc aggatggtga tggattttgg ggtgactgct tcgctgttaa caaggatgga    2880
tttccaagcc ttttacgcct gtgcattcag gccaggagc ttccccagtt gcacatccat    2940
gaaggaggca tgagctctct cacctccctc gaactactct gtcccatgtt cgctagtcgc    3000
ggtcactctg actctgactc tgactctgac ttggggaaaa cttacgtgga aacccattca    3060
gagaagagat ccaaacaagt tctttcggta gagaagccca aagcagttga tcccgggatc    3120
agcttcaagg aaccaagttc tgagacaaga tcagaaggaa ctgaaattca ggagattgat    3180
tcccctaaaa cgtccaagga ggctggtccc agcataggct tcaaggatat tattcttccg    3240
gagaacacat tcagaagaaa cttttcgaag gaagtcaaaa gtagatttga tctgaaacaa    3300
cacttcaagg gaatggagta cctccaatgt ctcaatgagc tggtactaca ttgttctgtt    3360
agcgacgagg tattggatgc ctggacaaaa cgagcaagca gtcacatcaa taggccaaag    3420
gtgacaaggc aatgcacaag agcagcgctg tcgattggta gaggcccggg aacagcgaag    3480
cacgagaaag aagggcagca cagaagccag ctcatgaaaa atagaggttc agaaacagca    3540
atccatgagg aggtagcaga gcaacacagc tcagtaggaa cgaccgtga ggaagcagga    3600 ttattccaag aacagacctc agatacaggt cac                                 3633
```

<210> SEQ ID NO 38
<211> LENGTH: 2412
<212> TYPE: DNA
<213> ORGANISM: Zea mays

<400> SEQUENCE: 38

```
atgaaaaata gaggttcaga aacagcaatc catgaggagg tagcagagca acacagctca      60
gtaggaacga gccgtgagga agcaggatta ttccaagaac agacctcagg tcacaaagaa     120
gaagaagaag aagaagaaga agaatgtacg agtgaagaca gggcattaaa tcaaccgtgc     180
```

```
gacatgctca ttggcatgga tgtggcaata cgtgaacttt tggagctggt gaacctggaa    240
gagtttggtg tagatgacaa agtgatctcc atcgtgggat gtccaggtct ggggaagacc    300
acgctcgcaa aagcattctc taacctggaa atgatacggg aaaggttcaa cccgcctgtt    360
tgggtttcgg catcacaatg ccgcagcgca caggaccttc tcatcaaggt tatccgacaa    420
gcttctcatg ttcatccagc acaaatgata agtgctaccc ccaatataga tctactgcaa    480
actatcctag cacaggaaag cttattgatc atcatcgatg acctacgtga aactacagct    540
tggaactcga tagagacagc cttgggttca acaacctcta cgcatgctgg tagcctaata    600
atcgtgacaa cgaggatcca atccattgct ggcaagtgca gcccacacag atacatctac    660
agaatgccag gccttggcca tccggagtcc aaagaactat tcttgaggac ggcctacggt    720
gatgcacatc cgacaccggg cgtggcggac gctgttgaag aaatctcagg gcatgtgat     780 ggtctgccac tggcgttggt tagcgcagct catgattggc gtgagcggca ggggcagggt    840
tgggaaggaa gatatgtctt tgaagaagtg aacagagcat ttagctggtg gtacgagagt    900
ttggcggacg cagctcacat gctgtctcta ggcatattcc cctatggcca ttccatcaag    960
cggaagagcc taattagaag atggatagct gaaggattgg tcagtgagga aaaagatggt   1020
gatcagcgat tccatgagtt ggtcgaccag agcatcgtgg agcctgtgct aattactggc   1080
agtagtgatt tcaaggtcaa gaggtttcgt cttcggcgtc cggtgctgga gttcatcgtc   1140
agggaatcag tctctaagaa catggtcaaa ctgctccaag gcgatgagcc ccttccagga   1200
gaaggaggag gtcctgtggt gtcgatttat caaactacgg acacgaaaac atcaaggaga   1260
aacatcatgt ccttttccat attcaacaaa ggcgtggctt tcgacgacct ccaacaatgc   1320
acctatctcc gggtgctgga cctagaacgc tgcaggggg tcgaccacag tgttgttgct    1380
ggtatatgta aactgtcgct tctcaggtac ctgagcttga ggggcagcga tgtgcgccac   1440
atccccaggg aaacaaaaag gctgaagtgt ctagagaccc tggacatccg ggagacagtg   1500
gtgaacaatc tgcctgtggc agccctcatg ctcccacggc tagtccacct gttcggcaag   1560
tttgagttgc ctcgaaaact cgaggacgag aggatacggg gtaagctcga gagattcttc   1620
cgagaggaaa gcagactaca gactctggct ggattgatca tttctaagaa caatggctac   1680
gagcacattg tgattcacat aaggctacta aggaagatta agatatggta ccagaaccac   1740
ctgctgcatt attccaccTT attgaacgag cttttttataa gaaacactgc actcgactct   1800
ttgtcggtcg atttcgggga cagcttgatg ttcccacaca tctctgacat ctttggaccc   1860
tgcatgctcc gctccatcaa actgcgaggt cggcattggc cgctgcctac aattatcgca   1920
tcatcagcca attatctctc cgaggtgcag ctgtcctcta ctgttctgcc gctcaggtac   1980
ttgtctactc tgcagagctt acgccggctg ctttatctga agctggttgc ggatggattt   2040
gtgggtgacg acaccgacac cttcactgtg aaaaaggatg gattcccaag ccttgagagg   2100
ctctgcattg aggccccgaa gcttccacat ctgcgcattg ttgaaggagc catgccagct   2160
ctcacgtctc ttcacctgct ctgtccgacg atgacgatga tgcctcaaca cccgggtcaa   2220
atgggcgaaa tcgatgagcc ggaggcgaca tcagaaacca aactgggcaa ggagtgggga   2280
atcgagtatc tcagaaacct caatgacctg gtgttgccct acactgttgg tgatgaacaa   2340
ctcgatttct ggaaggagaa agcaaggagc aacatgaaca ggccaaaggt aaccaggcag   2400
ccgaagccgt aa                                                        2412
```

<210> SEQ ID NO 39

```
<211> LENGTH: 8580
<212> TYPE: DNA
<213> ORGANISM: Zea mays

<400> SEQUENCE: 39
atgtctatcc tggaaaagct cgtccagagc tgttcctttc cagattcatg gcggggggccg      60 ccagacgctg aggtccaggc tctcatagga tatctcgaag agatacggtc ctccgtcctg     120
gatctttcca aggaggatga ggacgaggat gactctgcta cgtcgtcgtc cacgctgaag     180
atgagcctga cgagccagtt gcaggaactt tgttatgatg ctgaggacta tctggagatg     240
gcgcagcact ctcgtggtgg ctgctcctgg cagatcagtt gggtccggag caaggcgacg     300
aggcagcgcc ccgctctaat cagcgcaaaa gatctctccg gcctcatctc ccgtgtgaag     360
ccggcgaaag aaatagccca agcgtacatc aagtctgcta gttcaagaac caccaccaaa     420
gagaatggcc ctaggccaca agaagagcct gcaaaaagca gtagtcgccg tgccgtctat     480
tctgatgata ctctacagcc tgacagccat gacgagcagc tagtcaggtt gctggctttg     540
gaaagtgatc agcagctcaa gacggtggca atccatggcc tgcctggcgt tgggaagaca     600
acacttgcca gaagactgta ccactgctat gaagggaggt tccattgcgg ggctttcctt     660
cgggcgtccc gtaacctgca ggacgatacc accaggcttc tcgccaccat gctatccaag     720
attaagggcc aacaagggtg ccgctactgg gggggctccg gtgatgagca agatctaatc     780
gacagcatca gcaacatct acaaggaaaa tcatatttca ttgtgatcga tgatttatgg     840
gctacatcag tgtgggattt cttgagccgt gcttttccca aggataactg tggcagccga     900
atagtaataa ctactcaagt tacagaagtt gcatttgctt gctgtaacaa ccacacagtt     960
gatatattca atatgaaacc tctggacgac gatcagtcac tgcaattgtt ttacagtcga    1020
gtaaagcata taaatggtta taatgctgaa gaatgcaagg ccatatcaca tggaatcgtc    1080
agcaattgtg gtaatctttc accgctagct atcataaata taactggcat gttagcaggc    1140
tgggcggact tcaatatgaa tgattgggag tacgtaagca agtgttgtac gtttacagca    1200
aatcttacta ccgaggaggc gatggagaga tttctgaacc ttatgtacaa caagcttcca    1260
gccaaattga gacgtgcct gctctatctc agtatgtatc cagagggctg tgtcatcgga    1320
aaggatgatt tggtgagaca atgggcagct gaaggtattt tcagtcaagt ggtggaacca    1380
aaaggtagag aacatgaagt gggttttatt tattttgatg agctcctgaa aagaggattg    1440
atccagcctg tagatacaga ctacaatgat caagtgttgt catgtatagt tcatcaagtg    1500
gtactggaat ttattacaaa gaaatcaatg caggaaaact tcatcactgt cgtggattat    1560
cgtgaaacag ggacagtgct tgatgataat aaggttcatc gactgtctgc caggtttgaa    1620
ggtgccaaaa gtgcacagat accgcggagc ttcagagtac gccaagttcg gtcctttatg    1680
ttttctggat tctttaagtc tttaccttcg cttctcaagt attgccttgt ccgagttctg    1740
attcttcgtg tttggagtga tgatcaaggc aagactgtgg ttctagacct ttctccagtt    1800
ggtaatatgc ttcatgtaag gtacctgaag gtggtaagcg acatgatagt caaactccca    1860
ctcattattc gaggcctgcg acacttagag acactcgagg tggatgcaga agaagtcgct    1920
gttccactgg atgttttcat cttgaagagc ctgttgcatc tccgacttcc gagcaaggct    1980
tatcagcttg attcagatat tcaaaggatt ggtttaacaa atacatttcc tttaagtttt    2040
ctgcccttcg tcagaacgtt gtcaatccta ttcctatggc ggtctctcct ctcccatggc    2100
catttgacat cgcttcaaag tcttggctac tttgacctga gcacttgctc cagatatact    2160
gtgcggcaac ttggcaagct gaccaatttg agggatcttc atctaacctg ctctgcagtt    2220
```

```
cgttccaggc atcgaattag caacatccaa tgccttgcct ctgttctggg gaaatgcacc    2280
agcctcgaat ctctaactat ccgtggcgaa gcatcttcaa accagagcat ttcttttgat    2340
ggcttaagca gattgtcttc tccaccgtac aacctcgtga gctttgtgct gtccccgagg    2400
attttcaaaa tggcgaagct ccccaagtgg attgggcaac tcagcaggct cagtacgcta    2460
aagattgctg ttggcgagct gtcaagtgaa gatgttgaca tcctcaaaga actctctgcc    2520
ctcactgctc tttctctcta cgttcgcaga aaccctaaga aggaagctg atcctattc     2580 agtaagggct tcgcagtgct caagtatttt aagttcactt gcactgcact gtgcgtgaaa    2640
tttagtgaac aagctatgcc tgctgtccaa aggctgaatg tgtgcttcaa tgctaacaca    2700
atgcagcagt acaggccgga agatgcagga atttggtacc tgtcaggcct tcaagttatc    2760
tctgccagaa taggagctgc cggtattgat caagccagca gagaagccgc gaaatctagg    2820
ttgctggacg ccattcttag caaccatcca aagcctcctc ctatcagaaa cgtgcaaatg    2880
gtggactggg ttattcatgg cgacacagag gagtgttcaa ccggtgtgat gatacgtaaa    2940
gatgaaagca gccgtgagca tactaggtca tttttaagtc agttcccgtt cagaagacga    3000
cccctgcttc cctccatatt cacaaggcgt ggccaggatg atgagcaaca taaaatcgaa    3060
gaaaatgatg tgctacaaga tagtattatc ttaagggaat cctcttcgct aatgcaaaaa    3120
ccaggttggg tcacccgcag atcaaggagt actggtgttg gccttctgat ggccgtgcga    3180
gggtccacat acatgatcag gcaatatata aaggagccag gattcaatgc agcgaatgag    3240
atggcatcca tcaaccagga gataagacag attggtagaa tggtcatatc aagcaatata    3300
ttggagccgc cggaatggat tctgcaagcc caagacctgg cctgtgatgt gcaggatttc    3360
acggatatct acacatggct gcaaagcaaa tcgcggaggc gtgcccttgc acatataggc    3420
tacatagcgc agctgaagga tcggatcagc agccttcgag agtggcaaca gagaggaggc    3480
agcagcagca gccagcagga gcgtgctgct gccttgtcct tctcgcggcg atcatgcggg    3540
ccttgcgccc ctgaggatgt gctagttggc attgatcagc ccaggaaaga actttcggac    3600
ctcattttcg aaaggsagga tgttgtgcaa cagaagccca gggtggtctc tgtcgttggg    3660
tatagtggca ttggcaagac agccctggca agagcagtct actacgaccc tagtgtccgt    3720
tctgccttta cggcgttgc ttgggttgtg gcatctgaat gcaaccatgg gtgcgaccttt   3780 gtaagtaaga tctgccagca ggtcaaggac gaacaagcag ggaacggtgc tgtcgtccct    3840
gactgttata ggttaaaaga gatcatgcgg gataaaaggt ttttatcgt tattgacgac    3900 cttcagggag ctggaatgtg gaacgatata aaaggtgtct tcagtgaaac tcacagtggc    3960
agtcgaataa tcgttaccac gagtattcag tcggtcgccg ctgcctgcac tcctgagccg    4020
cgatacattt acaggatgcc aagtcttggt aatttggact ctgaaaagct actgtggatg    4080
agggtcggca ggcatgcaag ccgtacgcct gctctggagc atgctttagg caacgacacc    4140
ttgaaaaaat gcgcggtct acctctggca ctgatcagtg ttgccaatca tttgtgtctt    4200
gggaaagcat tatttgagga gatggacagg gttcttgcca aatgctatga cagcttgcct    4260
gacaatgctc acaggatgtg cttgctgtcc ctgagcacat tccctcaggg tcatgtgatg    4320
aagaggaaga ggctaattag aagatggata gctgaaggat tggctgtcgg agactgtgag    4380
ctcagtgctg aacaagttgc cggtaacata tttgatgtgt tgattgacag gaacgttact    4440
gagcctgtgc tgactgctgg ccacggttct agtagtaagg tcaaggcatg cttagttctt    4500
ggtgtgatca aggacttcat caacaaaacg gcagtctcaa atgagactgt agctataatc    4560
```

```
cagaacgatg agcttctcct tcccaacagg atgatgctgg tcgcccatcg tcctgttcgt   4620
cgactgcttg ttcatggagg cacaacaaag aaaagtgaag ctgttgcaaa ggcgatcgga   4680
ctggatcagg tcaggtcgct gacaatctgc aatgctgtgc ccttcgactt ccagggctgc   4740
tggttgctgc gggtcttgga cctggaggct tgccagggga tcgacaagag catccttggc   4800
agcatatgca agctggtgtt tctcaagtac ctgagcctta ggggcaccga tgtttacgga   4860
atacccaaga agtaaaaaaa gctccagcgt ttggagacgc tggacctcag gacacacgg    4920
gtggaagaac tgcccatcca agtcttgatg ctcccacggt tggcccatct gtttggcaag   4980
tttgagctac ctccacagct caagcatggt catcgaaccg caaggaggag gaggagtagg   5040
ctgcaggcat ttttctccca gagaagcagg ctgcagactc tttcaggatt cgtcatggtg   5100
gatgatagca acagcttcga gcacatgatg ataaccataa agtcactgag gaaggttaag   5160
gtatggtgca agaattcaat ctcctcccac caagaacgcc atcttgcttc ttcccttcag   5220
caacggctag taggaaacag taatccccta gaatctctgt caattgattt tggcaatgaa   5280
tccatcaatt tcctcaatga tgttggagct accagtgcac ttattggctc tatgaagcta   5340
cagggaaggc taacctcgct ccctagcttc atgacttcgt acgatactac actctcccag   5400
ctgcagctgt cctcaactgg tttgggcata aagccttgt ccctgctgca aatcttacgt    5460
cggctggttt ctctgaagct cgctcaggat ggtgatggat tttggggtga ctgcttcgct   5520
gttaacaagg atggatttcc aagcctttta cgcctgtgca ttcaggccag ggagcttccc   5580
cagttgcaca tccatgaagg aggcatgagc tctctcacct ccctcgaact actctgtccc   5640
atgttcgcta gtcgcggtca ctctgactct gactctgact ctgacttggg gaaaacttac   5700
gtggaaccc attcagagaa gagatccaaa caagttcttt cggtagagaa gcccaaagca    5760
gttgatcccg ggatcagctt caaggaacca agttctgaga caagatcaga aggaactgaa   5820
attcaggaga ttgattcccc taaaacgtcc aaggaggctg gtcccagcat aggcttcaag   5880
gatattattc ttccggagaa cacattcaga agaaacttttt cgaaggaagt caaaagtaga   5940
tttgatctga acaacacactt caagggaatg gagtacctcc aatgtctcaa tgagctggta   6000
ctacattgtt ctgttagcga cgaggtattg gatgcctgga caaaacgagc aagcagtcac   6060
atcaataggc caaaggtgac aaggcaatgc acaagagcag cgctgtcgat tggtagaggc   6120
ccgggaacag cgaagcacga gaaagaaggg cagcacagaa gccagctcat gaaaaataga   6180
ggttcagaaa cagcaatcca tgaggaggta gcagagcaac acagctcagt aggaacgagc   6240
cgtgaggaag caggattatt ccaagaacag acctcaggtc acaaagaaga agaagaagaa   6300
gaagaagaag aatgtacgag tgaagacagg gcattaaatc aaccgtgcga catgctcatt   6360
ggcatggatg tggcaatacg tgaacttttg gagctggtga acctgaaga gtttggtgta    6420
gatgacaaag tgatctccat cgtgggatgt ccaggtctgg ggaagaccac gctcgcaaaa   6480
gcattctcta acctgaaat gatacgggaa aggttcaacc cgcctgtttg ggtttcggca    6540
tcacaatgcc gcagcgcaca ggaccttctc atcaaggtta ccgacaagc ttctcatgtt    6600
catccagcac aaatgataag tgctaccccc aatatagatc tactgcaaac tatcctagca   6660
caggaaagct tattgatcat catcgatgac ctacgtgaaa ctacagcttg aactcgata    6720
gagacagcct tgggttcaac aacctctacg catgctggta gcctaataat cgtgacaacg   6780
aggatccaat ccattgctgg caagtgcagc ccacacagat acatctacag aatgccaggc   6840
cttggccatc cggagtccaa agaactattc ttgaggacgg cctacggtga tgcacatccg   6900
acaccgggcg tggcggacgc tgttgaagaa atctcagggg catgtgatgg tctgccactg   6960
```

-continued

| | |
|---|---|
| gcgttggtta gcgcagctca tgattggcgt gagcggcagg ggcagggttg ggaaggaaga | 7020 |
| tatgtctttg aagaagtgaa cagagcattt agctggtggt acgagagttt ggcggacgca | 7080 |
| gctcacatgc tgtctctagg catattcccc tatggccatt ccatcaagcg aagagccta | 7140 |
| attagaagat ggatagctga aggattggtc agtgaggaaa aagatggtga tcagcgattc | 7200 |
| catgagttgg tcgaccagag catcgtggag cctgtgctaa ttactggcag tagtgatttc | 7260 |
| aaggtcaaga ggtttcgtct tcggcgtccg gtgctggagt tcatcgtcag ggaatcagtc | 7320 |
| tctaagaaca tggtcaaact gctccaaggc gatgagcccc ttccaggaga aggaggaggt | 7380 |
| cctgtggtgt cgatttatca aactacggac acggaaacat caagaggaaa catcatgtcc | 7440 |
| ttttccatat tcaacaaagg cgtggctttc gacgacctcc aacaatgcac ctatctccgg | 7500 |
| gtgctggacc tagaacgctg caggggggtc gaccacagtg ttgttgctgg tatatgtaaa | 7560 |
| ctgtcgcttc tcaggtacct gagcttgagg ggcagcgatg tgcgccacat ccccagggaa | 7620 |
| acaaaaaggc tgaagtgtct agagaccctg gacatccggg agacagtggt gaacaatctg | 7680 |
| cctgtggcag ccctcatgct cccacggcta gtccacctgt tcggcaagtt tgagttgcct | 7740 |
| cgaaaactcg aggacgagag gatacggggt aagctcgaga gattcttccg agaggaaagc | 7800 |
| agactacaga ctctggctgg attgatcatt tctaagaaca atggctacga gcacattgtg | 7860 |
| attcacataa ggctactaag gaagattaag atatggtacc agaaccacct gctgcattat | 7920 |
| tccaccttat tgaacgagct ttttataaga aacactgcac tcgactcttt gtcggtcgat | 7980 |
| ttcggggaca gcttgatgtt cccacacatc tctgacatct ttggaccctg catgctccgc | 8040 |
| tccatcaaac tgcgaggtcg gcattggccg ctgcctacaa ttatcgcatc atcagccaat | 8100 |
| tatctctccg aggtgcagct gtcctctact gttctgccgc tcaggtactt gtctactctg | 8160 |
| cagagcttac gccggctgct ttatctgaag ctggttgcgg atggatttgt gggtgacgac | 8220 |
| accgacacct tcactgtgaa aaaggatgga ttcccaagcc ttgagaggct ctgcattgag | 8280 |
| gccccgaagc ttccacatct gcgcattgtt gaaggagcca tgccagctct cacgtctctt | 8340 |
| cacctgctct gtccgacgat gacgatgatg cctcaacacc cgggtcaaat gggcgaaatc | 8400 |
| gatgagccgg aggcgacatc agaaaccaaa ctgggcaagg agtggggaat cgagtatctc | 8460 |
| agaaacctca atgacctggt gttgccctac actgttggtg atgaacaact cgatttctgg | 8520 |
| aaggagaaag caaggagcaa catgaacagg ccaaaggtaa ccaggcagcc gaagccgtaa | 8580 |

<210> SEQ ID NO 40
<211> LENGTH: 5412
<212> TYPE: DNA
<213> ORGANISM: Zea mays

<400> SEQUENCE: 40

| | |
|---|---|
| atggccgtgc gagggtccac atacatgatc aggcaatata taaaggagcc aggattcaat | 60 |
| gcagcgaatg agatggcatc catcaaccag gagataagac agattggtag aatggtcata | 120 |
| tcaagcaata tattggagcc gccggaatgg attctgcaag cccaagacct ggcctgtgat | 180 |
| gtgcaggatt tcacggatat ctacacatgg ctgcaaagca atcgcggag gcgtgcccctt | 240 |
| gcacatatag gctacatagc gcagctgaag gatcggatca gcagccttcg agagtggcaa | 300 |
| cagagaggag gcagcagcag cagccagcag gagcgtgctg ctgccttgtc cttctcgcgg | 360 |
| cgatcatgcg ggccttgcgc ccctgaggat gtgctagttg gcattgatca gcccaggaaa | 420 |
| gaactttcgg acctcatttt cgaaagggag gatgttgtgc aacagaagcc cagggtggtc | 480 |

```
tctgtcgttg ggtatagtgg cattggcaag acagccctgg caagagcagt ctactacgac      540
cctagtgtcc gttctgcctt taacggcgtt gcttgggttg tggcatctga atgcaaccat      600
gggtgcgacc ttgtaagtaa gatctgccag caggtcaagg acgaacaagc agggaacggt      660
gctgtcgtcc ctgactgtta taggttaaaa gagatcatgc gggataaaag gttttttatc      720
gttattgacg accttcaggg agctggaatg tggaacgata taaaggtgt cttcagtgaa       780 actcacagtg gcagtcgaat aatcgttacc acgagtattc agtcggtcgc cgctgcctgc      840
actcctgagc cgcgatacat ttacaggatg ccaagtcttg gtaatttgga ctctgaaaag      900
ctactgtgga tgagggtcgg caggcatgca agccgtacgc ctgctctgga gcatgcttta     960
ggcaacgaca ccttgaaaaa atgcggcggt ctacctctgg cactgatcag tgttgccaat     1020
catttgtgtc ttgggaaagc attatttgag gagatggaca gggttcttgc caaatgctat     1080
gacagcttgc ctgacaatgc tcacaggatg tgcttgctgt ccctgagcac attccctcag     1140
ggtcatgtga tgaagaggaa gaggctaatt agaagatgga tagctgaagg attggctgtc     1200
ggagactgtg agctcagtgc tgaacaagtt gccggtaaca tatttgatgt gttgattgac     1260
aggaacgtta ctgagcctgt gctgactgct ggccacggtt ctagtagtaa ggtcaaggca     1320
tgcttagttc ttggtgtgat caaggacttc atcaacaaaa cggcagtctc aaatgagact     1380
gtagctataa tccagaacga tgagcttctc cttcccaaca ggatgatgct ggtcgcccat     1440
cgtcctgttc gtcgactgct tgttcatgga ggcacaacaa agaaaagtga agctgttgca     1500
aaggcgatcg gactggatca ggtcaggtcg ctgacaatct gcaatgctgt gcccttcgac     1560
ttccagggct gctggttgct gcgggtcttg gacctggagg cttgccaggg gatcgacaag     1620
agcatccttg gcagcatatg caagctggtg tttctcaagt acctgagcct tagggcacc     1680 gatgtttacg gaatacccaa gaaagtaaaa aagctccagc gttggagac gctggacctc      1740 agggacacac gggtggaaga actgcccatc caagtcttga tgctcccacg gttggcccat     1800
ctgtttggca gtttgagct acctccacag ctcaagcatg gtcatcgaac cgcaaggagg      1860
aggaggagta ggctgcaggc attttttctcc cagagaagca ggctgcagac tctttcagga     1920
ttcgtcatgt tggatgatag caacagcttc gagcacatga tgataaccat aaagtcactg     1980
aggaaggtta aggtatggtg caagaattca atctcctccc accaagaacg ccatcttgct     2040
tcttcccttc agcaacggct agtaggaaac agtaatcccc tagaatctct gtcaattgat     2100
tttggcaatg aatccatcaa tttcctcaat gatgttggag ctaccagtgc acttattggc     2160
tctatgaagc tacagggaag gctaacctcg ctccctagct tcatgacttc gtacgatact     2220
acactctccc agctgcagct gtcctcaact ggtttgggca tagaagcctt gtccctgctg     2280
caaatcttac gtcggctggt ttctctgaag ctcgctcagg atggtgatgg attttggggt    2340
gactgcttcg ctgttaacaa ggatggattt ccaagccttt tacgcctgtg cattcaggcc     2400
agggagcttc cccagttgca catccatgaa ggaggcatga gctctctcac ctccctcgaa     2460
ctactctgtc ccatgttcgc tagtcgcggt cactctgact ctgactctga ctctgacttg     2520
gggaaaactt acgtggaaac ccattcagag aagagatcca acaagttct tcggtagag      2580 aagcccaaag cagttgatcc cgggatcagc ttcaaggaac caagttctga cacaagatca     2640
gaaggaactg aaattcagga gattgattcc cctaaaacgt ccaaggaggc tggtcccagc     2700
ataggcttca aggatattat tcttccggag aacacattca agagaaactt ttcgaaggaa     2760
gtcaaaagta gatttgatct gaaacaacac ttcaagggaa tggagtacct ccaatgtctc     2820
aatgagctgg tactacattg ttctgttagc gacgaggtat tggatgcctg gacaaaacga     2880
```

```
gcaagcagtc acatcaatag gccaaaggtg acaaggcaat gcacaagagc agcgctgtcg    2940
attggtagag gcccgggaac agcgaagcac gagaaagaag ggcagcacag aagccagctc    3000
atgaaaaata gaggttcaga aacagcaatc catgaggagg tagcagagca acacagctca    3060
gtaggaacga gccgtgagga agcaggatta ttccaagaac agacctcagg tcacaaagaa    3120
gaagaagaag aagaagaaga agaatgtacg agtgaagaca gggcattaaa tcaaccgtgc    3180
gacatgctca ttggcatgga tgtggcaata cgtgaacttt tggagctggt gaacctggaa    3240
gagtttggtg tagatgacaa agtgatctcc atcgtgggat gtccaggtct ggggaagacc    3300
acgctcgcaa aagcattctc taacctggaa atgatacggg aaaggttcaa cccgcctgtt    3360
tgggtttcgg catcacaatg ccgcagcgca caggaccttc tcatcaaggt tatccgacaa    3420
gcttctcatg ttcatccagc acaaatgata agtgctaccc ccaatataga tctactgcaa    3480
actatcctag cacaggaaag cttattgatc atcatcgatg acctacgtga aactacagct    3540
tggaactcga tagagacagc cttgggttca acaacctcta cgcatgctgg tagcctaata    3600
atcgtgacaa cgaggatcca atccattgct ggcaagtgca gcccacacag atacatctac    3660
agaatgccag gccttggcca tccggagtcc aaagaactat tcttgaggac ggcctacggt    3720
gatgcacatc cgacaccggg cgtggcggac gctgttgaag aaatctcagg gcatgtgat    3780 ggtctgccac tggcgttggt tagcgcagct catgattggc gtgagcggca ggggcagggt    3840
tgggaaggaa gatatgtctt tgaagaagtg aacagagcat ttagctggtg gtacgagagt    3900
ttggcggacg cagctcacat gctgtctcta ggcatattcc cctatggcca ttccatcaag    3960
cggaagagcc taattagaag atggatagct gaaggattgg tcagtgagga aaaagatggt    4020
gatcagcgat tccatgagtt ggtcgaccag agcatcgtgg agcctgtgct aattactggc    4080
agtagtgatt tcaaggtcaa gaggtttcgt cttcggcgtc cggtgctgga gttcatcgtc    4140
agggaatcag tctctaagaa catggtcaaa ctgctccaag gcgatgagcc ccttccagga    4200
gaaggaggag gtcctgtggt gtcgatttat caaactacgg acacggaaac atcaagagga    4260
aacatcatgt cctttccat attcaacaaa ggcgtggctt cgacgaccct caacaatgc     4320 acctatctcc gggtgctgga cctagaacgc tgcagggggg tcgaccacag tgttgttgct    4380
ggtatatgta aactgtcgct tctcaggtac ctgagcttga ggggcagcga tgtgcgccac    4440
atccccaggg aaacaaaaag gctgaagtgt ctagagaccc tggacatccg ggagacagtg    4500
gtgaacaatc tgcctgtggc agccctcatg ctcccacggc tagtccacct gttcggcaag    4560
tttgagttgc ctcgaaaact cgaggacgag aggatacggg gtaagctcga gagattcttc    4620
cgagaggaaa gcagactaca gactctggct ggattgatca tttctaagaa caatggctac    4680
gagcacattg tgattcacat aaggctacta aggaagatta agatatggta ccagaaccac    4740
ctgctgcatt attccaccct tattgaacgag ctttttataa gaaacactgc actcgactct    4800
ttgtcggtcg atttcgggga cagcttgatg ttcccacaca tctctgacat cttggaccc     4860 tgcatgctcc gctccatcaa actgcgaggt cggcattggc cgctgcctac aattatcgca    4920
tcatcagcca attatctctc cgaggtgcag ctgtcctcta ctgttctgcc gctcaggtac    4980
ttgtctactc tgcagagctt acgccggctg ctttatctga agctggttgc ggatggattt    5040
gtgggtgacg acaccgacac cttcactgtg aaaaaggatg gattcccaag ccttgagagg    5100
ctctgcattg aggccccgaa gcttccacat ctgcgcattg ttgaaggagc catgccagct    5160
ctcacgtctc ttcacctgct ctgtccgacg atgacgatga tgcctcaaca cccgggtcaa    5220
```

```
atgggcgaaa tcgatgagcc ggaggcgaca tcagaaacca aactgggcaa ggagtgggga      5280
atcgagtatc tcagaaacct caatgacctg gtgttgccct acactgttgg tgatgaacaa      5340
ctcgatttct ggaaggagaa agcaaggagc aacatgaaca ggccaaaggt aaccaggcag      5400
ccgaagccgt aa                                                          5412

<210> SEQ ID NO 41
<211> LENGTH: 3960
<212> TYPE: DNA
<213> ORGANISM: Zea mays

<400> SEQUENCE: 41
atgccttgcc tctgttctgg ggaaatgcac cagcctcgaa tctctaacta tccgtgcgaa        60
gcatcttcaa accagagcat ttcttttgat ggcttaagca gattgtcttc tccaccgtac       120
aacctcgtga gctttgtgct gtccccgagg attttcaaaa tggcgaagct ccccaagtgg       180
attgggcaac tcagcaggct cagtacgcta aagattgctg ttggcgagct gtcaagtgaa       240
gatgttgaca tcctcaaaga actctctgcc ctcactgctc tttctctcta cgttcgcaga       300
aaccctaaga aggaagctg atcctattc agtaagggct cgcagtgct caagtatttt        360 aagttcactt gcactgcact gtgcgtgaaa tttagtgaac aagctatgcc tgctgtccaa       420
aggctgaatg tgtgcttcaa tgctaacaca atgcagcagt acaggccgga agatgcagga       480
atttggtacc tgtcaggcct tcaagttatc tctgccagaa taggagctgc cggtattgat       540
caagccagca gagaagccgc gaaatctagg ttgctggacg ccattcttag caaccatcca       600
aagcctcctc ctatcagaaa cgtgcaaatg gtggactggg ttattcatgg cgacacagag       660
gagtgttcaa ccggtgtgat gatacgtaaa gatgaaagca gccgtgagca tactaggtca       720 ttttaagtc agttcccgtt cagaagacga ccctgcttc cctccatatt cacaaggcgt       780
ggccaggatg atgagcaaca taaaatcgaa gaaaatgatg tgctacaaga tagtattatc       840
ttaagggaat cctcttcgct aatgcaaaaa ccaggttggg tcacccgcag atcaaggagt       900
actggtgttg gccttctgat ggccgtgcga gggtccacat acatgatcag gcaatatata       960
aaggagccag gattcaatgc agcgaatgag atggcatcca tcaaccagga gataagacag      1020
attggtagaa tggtcatatc aagcaatata ttggagccgc cggaatggat tctgcaagcc      1080
caagacctgg cctgtgatgt gcaggatttc acggatatct acacatggct gcaaagcaaa      1140
tcgcggaggc gtgcccttgc acatataggc tacatagcgc agctgaagga tcggatcagc      1200
agccttcgag agtggcaaca gagaggaggc agcagcagca gccagcagga gcgtgctgct      1260
gccttgtcct tctcgcggcg atcatgcggg ccttgcgccc ctgaggatgt gctagttggc      1320
attgatcagc ccaggaaaga actttcggac ctcattttcg aaaggggagga tgttgtgcaa      1380 cagaagccca gggtggtctc tgtcgttggg tatagtggca ttggcaagac agccctggca      1440
agagcagtct actacgaccc tagtgtccgt tctgccttta acggcgttgc ttgggttgtg      1500
gcatctgaat gcaaccatgg ggtgcgacct tgtaagtaaga tctgccagca ggtcaaggac      1560
gaacaagcag ggaacggtgc tgtcgtccct gactgttata ggttaaaaga gatcatgcgg      1620
gataaaaggt tttttatcgt tattgacgac cttcagggag ctggaatgtg aacgatata      1680 aaaggtgtct tcagtgaaac tcacagtggc agtcgaataa tcgttaccac gagtattcag      1740
tcggtcgccg ctgcctgcac tcctgagccg cgatacattt acaggatgcc aagtcttggt      1800
aatttggact ctgaaaagct actgtggatg agggtcggca ggcatgcaag ccgtacgcct      1860
gctctggagc atgctttagg caacgacacc ttgaaaaaat gcggcggtct acctctggca      1920
```

```
ctgatcagtg ttgccaatca tttgtgtctt gggaaagcat tatttgagga gatggacagg    1980
gttcttgcca aatgctatga cagcttgcct gacaatgctc acaggatgtg cttgctgtcc    2040
ctgagcacat tccctcaggg tcatgtgatg aagaggaaga ggctaattag aagatggata    2100
gctgaaggat tggctgtcgg agactgtgag ctcagtgctg aacaagttgc cggtaacata    2160
tttgatgtgt tgattgacag gaacgttact gagcctgtgc tgactgctgg ccacggttct    2220
agtagtaagg tcaaggcatg cttagttctt ggtgtgatca aggacttcat caacaaaacg    2280
gcagtctcaa atgagactgt agctataatc cagaacgatg agcttctcct tcccaacagg    2340
atgatgctgg tcgcccatcg tcctgttcgt cgactgcttg ttcatggagg cacaacaaag    2400
aaaagtgaag ctgttgcaaa ggcgatcgga ctggatcagg tcaggtcgct gacaatctgc    2460
aatgctgtgc ccttcgactt ccagggctgc tggttgctgc gggtcttgga cctggaggct    2520
tgccagggga tcgacaagag catccttggc agcatatgca agctggtgtt tctcaagtac    2580
ctgagcctta ggggcaccga tgtttacgga tacccaagaa agtaaaaaaa gctccagcgt    2640
ttggagacgc tggacctcag ggacacacgg gtggaagaac tgcccatcca agtcttgatg    2700
ctcccacggt tggcccatct gtttggcaag tttgagctac ctccacagct caagcatggt    2760
catcgaaccg caaggaggag gaggagtagg ctgcaggcat ttttctccca gagaagcagg    2820
ctgcagactc tttcaggatt cgtcatggtg gatgatagca acagcttcga gcacatgatg    2880
ataaccataa agtcactgag gaaggttaag gtatggtgca agaattcaat ctcctcccac    2940
caagaacgcc atcttgcttc ttcccttcag caacggctag taggaaacag taatccccta    3000
gaatctctgt caattgattt tggcaatgaa tccatcaatt tcctcaatga tgttggagct    3060
accagtgcac ttattggctc tatgaagcta cagggaaggc taacctcgct ccctagcttc    3120
atgacttcgt acgatactac actctcccag ctgcagctgt cctcaactgg tttgggcata    3180
gaagccttgt ccctgctgca aatcttacgt cggctggttt ctctgaagct cgctcaggat    3240
ggtgatggat tttggggtga ctgcttcgct gttaacaagg atggatttcc aagcctttta    3300
cgcctgtgca ttcaggccag ggagcttccc cagttgcaca tccatgaagg aggcatgagc    3360
tctctcacct ccctcgaact actctgtccc atgttcgcta gtcgcggtca ctctgactct    3420
gactctgact ctgacttggg gaaaacttac gtggaaaccc attcagagaa gagatccaaa    3480
caagttcttt cggtagagaa gcccaaagca gttgatcccg ggatcagctt caaggaacca    3540
agttctgaga caagatcaga aggaactgaa attcaggaga ttgattcccc taaaacgtcc    3600
aaggaggctg gtcccagcat aggcttcaag gatattattc ttccggagaa cacattcaga    3660
agaaactttt cgaaggaagt caaaagtaga tttgatctga acaacactt caagggaatg    3720 gagtacctcc aatgtctcaa tgagctggta ctacattgtt ctgttagcga cgaggtattg    3780
gatgcctgga caaaacgagc aagcagtcac atcaataggc caaggtgac aaggcaatgc    3840 acaagagcag cgctgtcgat tggtagaggc ccgggaacag cgaagcacga aaagaaggg    3900 cagcacagaa gccagctcat gaaaatagag gttcagaaac agcaatccat gaggaggtag    3960
```

<210> SEQ ID NO 42
<211> LENGTH: 3099
<212> TYPE: DNA
<213> ORGANISM: Zea mays

<400> SEQUENCE: 42

```
atggtgatgg attttggggg tgactgcttc gctgttaaca aggatggatt tccaagcctt      60
```

-continued

```
ttacgcctgt gcattcaggc cagggagctt ccccagttgc acatccatga aggaggcatg      120
agctctctca cctccctcga actactctgt cccatgttcg ctagtcgcgg tcactctgac      180
tctgactctg actctgactt ggggaaaact tacgtggaaa cccattcaga gaagagatcc      240
aaacaagttc tttcggtaga gaagcccaaa gcagttgatc ccgggatcag cttcaaggaa      300
ccaagttctg agacaagatc agaaggaact gaaattcagg agattgattc ccctaaaacg      360
tccaaggagc tggtcccag cataggcttc aaggatatta ttcttccgga gaacacattc      420
agaagaaact tttcgaagga agtcaaaagt agatttgatc tgaaacaaca cttcaaggga      480
atggagtacc tccaatgtct caatgagctg gtactacatt gttctgttag cgacgaggta      540
ttggatgcct ggacaaaacg agcaagcagt cacatcaata ggccaaaggt gacaaggcaa      600
tgcacaagag cagcgctgtc gattggtaga ggcccgggaa cagcgaagca cgagaaagaa      660
gggcagcaca gaagccagct catgaaaaat agaggttcag aaacagcaat ccatgaggag      720
gtagcagagc aacacagctc agtaggaacg agccgtgagg aagcaggatt attccaagaa      780
cagacctcag atacaggtca caagaagaa gaagaagaa aagaagaaga atgtacgagt      840
gaagacaggg cattaaatca accgtgcgac atgctcattg gcatggatgt ggcaatacgt      900
gaacttttgg agctggtgaa cctggaagag tttggtgtag atgacaaagt gatctccatc      960
gtgggatgtc caggtctggg gaagaccacg ctcgcaaaag cattctctaa cctggaaatg     1020
atacgggaaa ggttcaaccc gcctgtttgg gtttcggcat cacaatgccg cagcgcacag     1080
gaccttctca tcaaggttat ccgacaagct tctcatgttc atccagcaca aatgataagt     1140
gctaccccca atatagatct actgcaaact atcctagcac aggaaagctt attgatcatc     1200
atcgatgacc tacgtgaaac tacagcttgg aactcgatag agacagcctt gggttcaaca     1260
acctctacga atgctggtag cctaataatc gtgacaacga ggatccaatc cattgctggc     1320
aagtgcagcc cacacagata catctacaga atgccaggcc ttggccatcc ggagtccaaa     1380
gaactattct tgaggacggc ctacggtgat gcacatccga caccgggcgt ggcggacgct     1440
gttgaagaaa tctcaggggc atgtgatggt ctgccactgg cgttggttag cgcagctcat     1500
gattggcgtg agcggcaggg gcagggttgg gaaggaagat atgtctttga agaagtgaac     1560
agagcattta gctggtggta cgagagtttg gcggacgcag ctcacatgct gtctctaggc     1620
atattcccct atggccattc catcaagcgg aagagcctaa ttagaagatg gatagctgaa     1680
ggattggtca gtgaggaaaa agatggtgat cagcgattcc atgagttggt cgaccagagc     1740
atcgtggagc ctgtgctaat tactggcagt agtgatttca aggtcaagag gtttcgtctt     1800
cggcgtccgg tgctggagtt catcgtcagg gaatcagtct ctaagaacat ggtcaaactg     1860
ctccaaggcg atgagcccct tccaggagaa ggaggaggtc ctgtggtgtc gatttatcaa     1920
actacggaca cggaaacatc aagaggaaac atcatgtcct tttccatatt caacaaaggc     1980
gtggctttcg acgacctcca acaatgcacc tatctccggg tgctggacct agaacgctgc     2040 agggggtcg accacagtgt tgttgctggt atatgtaaac tgtcgcttct caggtacctg     2100
agcttgaggg gcagcgatgt gcgccacatc cccaggaaa caaaaaggct gaagtgtcta     2160
gagaccctgg catccggga gacagtggtg aacaatctgc ctgtggcagc cctcatgctc     2220
ccacggctag tccacctgtt cggcaagttt gagttgcctc gaaaactcga ggacgagagg     2280
atacggggta agctcgagag attcttccga gaggaaagca gactacagac tctggctgga     2340
ttgatcattt ctaagaacaa tggctacgag cacattgtga ttcacataag gctactaagg     2400
aagattaaga tatggtacca gaaccacctg ctgcattatt ccaccttatt gaacgagctt     2460
```

-continued

```
tttataagaa acactgcact cgactctttg tcggtcgatt tcggggacag cttgatgttc    2520
ccacacatct ctgacatctt tggaccctgc atgctccgct ccatcaaact gcgaggtcgg    2580
cattggccgc tgcctacaat tatcgcatca tcagccaatt atctctccga ggtgcagctg    2640
tcctctactg ttctgccgct caggtacttg tctactctgc agagcttacg ccggctgctt    2700
tatctgaagc tggttgcgga tggatttgtg ggtgacgaca ccgacaccTt cactgtgaaa    2760
aaggatggat tcccaagcct tgagaggctc tgcattgagg ccccgaagct tccacatctg    2820
cgcattgttg aaggagccat gccagctctc acgtctcttc acctgctctg tccgacgatg    2880
acgatgatgc tcaacacccc gggtcaaatg ggcgaaatcg atgagccgga ggcgacatca    2940
gaaaccaaac tgggcaagga gtggggaatc gagtatctca gaaacctcaa tgacctggtg    3000
ttgccctaca ctgttggtga tgaacaactc gatttctgga aggagaaagc aaggagcaac    3060
atgaacaggc caaaggtaac caggcagccg aagccgtaa                          3099
```

<210> SEQ ID NO 43
<211> LENGTH: 2424
<212> TYPE: DNA
<213> ORGANISM: Zea mays

<400> SEQUENCE: 43

```
atgcgggata aaaggttttt tatcgttatt gacgaccttc agggagctgg aatgtggaac     60
gatataaaag gtgtcttcag tgaaactcac agtggcagtc gaataatcgt taccacgagt    120
attcagtcgg tcgccgctgc ctgcactcct gagccgcgat acatttacag gatgccaagt    180
cttggtaatt tggactctga aaagctactg tggatgaggg tcggcaggca tgcaagccgt    240
acgcctgctc tggagcatgc tttaggcaac gacaccttga aaaatgcgg cggtctacct    300 ctggcactga tcagtgttgc caatcatttg tgtcttggga agcattatt tgaggagatg    360 gacagggttc ttgccaaatg ctatgacagc ttgcctgaca atgctcacag gatgtgcttg    420
ctgtccctga gcacattccc tcagggtcat gtgatgaaga ggaagaggct aattagaaga    480
tggatagctg aaggattggc tgtcggagac tgtgagctca gtgctgaaca agttgccggt    540
aacatatttg atgtgttgat tgacaggaac gttactgagc ctgtgctgac tgctggccac    600
ggttctagta gtaaggtcaa ggcatgctta gttcttggtg tgatcaagga cttcatcaac    660
aaaacggcag tctcaaatga gactgtagct ataatccaga acgatgagct tctccttccc    720
aacaggatga tgctggtcgc ccatcgtcct gttcgtcgac tgcttgttca tggaggcaca    780
acaaagaaaa gtgaagctgt tgcaaaggcg atcggactgg atcaggtcag gtcgctgaca    840
atctgcaatg ctgtgccctt cgacttccag ggctgctggt tgctgcgggt cttggacctg    900
gaggcttgcc aggggatcga caagagcatc cttggcagca tgcaagct ggtgtttctc    960 aagtacctga gccttagggg caccgatgtt tacggaatac ccaagaaagt aaaaaagctc   1020
cagcgtttgg agacgctgga cctcagggac acacgggtgg aagaactgcc catccaagtc   1080
ttgatgctcc cacggttggc ccatctgttt ggcaagtttg agctacctcc acagctcaag   1140
catggtcatc gaaccgcaag gaggaggagg agtaggctgc aggcattttt ctcccagaga   1200
agcaggctgc agactctttc aggattcgtc atggtggatg atagcaacag cttcgagcac   1260
atgatgataa ccataaagtc actgaggaag gttaaggtat ggtgcaagaa ttcaatctcc   1320
tcccaccaag aacgccatct tgcttcttcc cttcagcaac ggctagtagg aaacagtaat   1380
cccctagaat ctctgtcaat tgattttggc aatgaatcca tcaatttcct caatgatgtt   1440
```

| | |
|---|---|
| ggagctacca gtgcacttat tggctctatg aagctacagg gaaggctaac ctcgctccct | 1500 |
| agcttcatga cttcgtacga tactacactc tcccagctgc agctgtcctc aactggtttg | 1560 |
| ggcatagaag ccttgtccct gctgcaaatc ttacgtcggc tggtttctct gaagctcgct | 1620 |
| caggatggtg atggattttg gggtgactgc ttcgctgtta acaaggatgg atttccaagc | 1680 |
| cttttacgcc tgtgcattca ggccagggag cttccccagt tgcacatcca tgaaggaggc | 1740 |
| atgagctctc tcacctccct cgaactactc tgtcccatgt tcgctagtcg cggtcactct | 1800 |
| gactctgact ctgactctga cttggggaaa acttacgtgg aaacccattc agagaagaga | 1860 |
| tccaaacaag ttctttcggt agagaagccc aaagcagttg atcccgggat cagcttcaag | 1920 |
| gaaccaagtt ctgagacaag atcagaagga actgaaattc aggagattga ttcccctaaa | 1980 |
| acgtccaagg aggctggtcc cagcataggc ttcaaggata ttattcttcc ggagaacaca | 2040 |
| ttcagaagaa acttttcgaa ggaagtcaaa agtagatttg atctgaaaca cacttcaag | 2100 |
| ggaatggagt acctccaatg tctcaatgag ctggtactac attgttctgt tagcgacgag | 2160 |
| gtattggatg cctggacaaa acgagcaagc agtcacatca ataggccaaa ggtgacaagg | 2220 |
| caatgcacaa gagcagcgct gtcgattggt agaggcccgg aacagcgaa gcacgagaaa | 2280 |
| gaagggcagc acagaagcca gctcatgaaa aatagaggtt cagaaacagc aatccatgag | 2340 |
| gaggtagcag agcaacacag ctcagtagga acgagccgtg aggaagcagg attattccaa | 2400 |
| gaacagacct cagatacagg tcac | 2424 |

<210> SEQ ID NO 44
<211> LENGTH: 1494
<212> TYPE: DNA
<213> ORGANISM: Zea mays

<400> SEQUENCE: 44

| | |
|---|---|
| atgctgtctc taggcatatt cccctatggc cattccatca agcggaagag cctaattaga | 60 |
| agatggatag ctgaaggatt ggtcagtgag gaaaaagatg gtgatcagcg attccatgag | 120 |
| ttggtcgacc agagcatcgt ggagcctgtg ctaattactg gcagtagtga tttcaaggtc | 180 |
| aagaggtttc gtcttcggcg tccggtgctg gagttcatcg tcagggaatc agtctctaag | 240 |
| aacatggtca aactgctcca aggcgatgag ccccttccag gagaaggagg aggtcctgtg | 300 |
| gtgtcgattt atcaaactac ggacacggaa acatcaagag gaaacatcat gtcctttcc | 360 |
| atattcaaca aaggcgtggc tttcgacgac ctccaacaat gcacctatct ccgggtgctg | 420 |
| gacctagaac gctgcagggg ggtcgaccac agtgttgttg ctggtatatg taaactgtcg | 480 |
| cttctcaggt acctgagctt gagggggcagc gatgtgcgcc acatcccag ggaaacaaaa | 540 |
| aggctgaagt gtctagagac cctggacatc cgggagacag tggtgaacaa tctgcctgtg | 600 |
| gcagccctca tgctcccacg gctagtccac ctgttcggca gtttgagtt gcctcgaaaa | 660 |
| ctcgaggacg agaggatacg gggtaagctc gagagattct tccgagagga aagcagacta | 720 |
| cagactctgg ctggattgat catttctaag aacaatggct acgagcacat tgtgattcac | 780 |
| ataaggctac taaggaagat taagatatgg taccagaacc acctgctgca ttattccacc | 840 |
| ttattgaacg agcttttat aagaaacact gcactgact ctttgtcggt cgatttcggg | 900 |
| gacagcttga tgttcccaca catctctgac atctttggac cctgcatgct ccgctccatc | 960 |
| aaactgcgag gtcggcattg gccgctgcct acaattatcg catcatcagc caattatctc | 1020 |
| tccgaggtgc agctgtcctc tactgttctg ccgtcaggt acttgtctac tctgcagagc | 1080 |
| ttacgccggc tgctttatct gaagctggtt gcggatggat ttgtgggtga cgacaccgac | 1140 |

```
accttcactg tgaaaaagga tggattccca agccttgaga ggctctgcat tgaggccccg    1200
aagcttccac atctgcgcat tgttgaagga gccatgccag ctctcacgtc tcttcacctg    1260
ctctgtccga cgatgacgat gatgcctcaa cacccgggtc aaatgggcga aatcgatgag    1320
ccggaggcga catcagaaac caaactgggc aaggagtggg gaatcgagta tctcagaaac    1380
ctcaatgacc tggtgttgcc ctacactgtt ggtgatgaac aactcgattt ctggaaggag    1440
aaagcaagga gcaacatgaa caggccaaag gtaaccaggc agccgaagcc gtaa           1494

<210> SEQ ID NO 45
<211> LENGTH: 1341
<212> TYPE: DNA
<213> ORGANISM: Zea mays

<400> SEQUENCE: 45
atgctcccac ggttggccca tctgtttggc aagtttgagc tacctccaca gctcaagcat      60
ggtcatcgaa ccgcaaggag gaggaggagt aggctgcagg cattttttctc ccagagaagc    120 aggctgcaga ctctttcagg attcgtcatg gtggatgata gcaacagctt cgagcacatg    180
atgataacca taaagtcact gaggaaggtt aaggtatggt gcaagaattc aatctcctcc    240
caccaagaac gccatcttgc ttcttccctt cagcaacggc tagtaggaaa cagtaatccc    300
ctagaatctc tgtcaattga ttttggcaat gaatccatca atttcctcaa tgatgttgga    360
gctaccagtg cacttattgg ctctatgaag ctacaggaa ggctaacctc gctccctagc     420
ttcatgactt cgtacgatac tacactctcc cagctgcagc tgtcctcaac tggtttgggc    480
atagaagcct tgtccctgct gcaaatctta cgtcggctgg tttctctgaa gctcgctcag    540
gatggtgatg attttggggg tgactgcttc gctgttaaca aggatggatt tccaagcctt    600
ttacgcctgt gcattcaggc cagggagctt ccccagttgc acatccatga aggaggcatg    660
agctctctca cctcccctcga actactctgt cccatgttcg ctagtcgcgg tcactctgac    720
tctgactctg actctgactt ggggaaaact tacgtggaaa cccattcaga gaagagatcc    780
aaacaagttc tttcggtaga aagcccaaa gcagttgatc ccgggatcag cttcaaggaa     840
ccaagttctg agacaagatc agaaggaact gaaattcagg agattgattc ccctaaaacg    900
tccaaggagg ctggtcccag cataggcttc aaggatatta ttcttccgga aacacattc     960 agaagaaact tttcgaagga agtcaaaagt agatttgatc tgaaacaaca cttcaaggga   1020
atggagtacc tccaatgtct caatgagctg gtactacatt gttctgttag cgacgaggta   1080
ttggatgcct ggacaaaacg agcaagcagt cacatcaata ggccaaaggt gacaaggcaa   1140
tgcacaagag cagcgctgtc gattggtaga ggcccgggaa cagcgaagca cgagaaagaa   1200
gggcagcaca gaagccagct catgaaaaat agaggttcag aaacagcaat ccatgaggag   1260
gtagcagagc aacacagctc agtaggaacg agccgtgagg aagcaggatt attccaagaa   1320
cagacctcag atacaggtca c                                              1341

<210> SEQ ID NO 46
<211> LENGTH: 1387
<212> TYPE: PRT
<213> ORGANISM: Zea mays

<400> SEQUENCE: 46

Met Ala Val Arg Gly Ser Thr Tyr Met Ile Arg Gln Tyr Ile Lys Glu
1               5                   10                  15

Pro Gly Phe Asn Ala Ala Asn Glu Met Ala Ser Ile Asn Gln Glu Ile
```

```
                20                  25                  30
Arg Gln Ile Gly Arg Met Val Ile Ser Ser Asn Ile Leu Glu Pro Pro
            35                  40                  45

Glu Trp Ile Leu Gln Ala Gln Asp Leu Ala Cys Asp Val Gln Asp Phe
        50                  55                  60

Thr Asp Ile Tyr Thr Trp Leu Gln Ser Lys Ser Arg Arg Arg Ala Leu
65                  70                  75                  80

Ala His Ile Gly Tyr Ile Ala Gln Leu Lys Asp Arg Ile Ser Ser Leu
                85                  90                  95

Arg Glu Trp Gln Gln Arg Gly Gly Ser Ser Ser Gln Gln Glu Arg
            100                 105                 110

Ala Ala Ala Leu Ser Phe Ser Arg Arg Ser Cys Gly Pro Cys Ala Pro
            115                 120                 125

Glu Asp Val Leu Val Gly Ile Asp Gln Pro Arg Lys Glu Leu Ser Asp
            130                 135                 140

Leu Ile Phe Glu Arg Glu Asp Val Val Gln Gln Lys Pro Arg Val Val
145                 150                 155                 160

Ser Val Val Gly Tyr Ser Gly Ile Gly Lys Thr Ala Leu Ala Arg Ala
                165                 170                 175

Val Tyr Tyr Asp Pro Ser Val Arg Ser Ala Phe Asn Gly Val Ala Trp
            180                 185                 190

Val Val Ala Ser Glu Cys Asn His Gly Cys Asp Leu Val Ser Lys Ile
            195                 200                 205

Cys Gln Gln Val Lys Asp Glu Gln Ala Gly Asn Gly Ala Val Val Pro
            210                 215                 220

Asp Cys Tyr Arg Leu Lys Glu Ile Met Arg Asp Lys Arg Phe Phe Ile
225                 230                 235                 240

Val Ile Asp Asp Leu Gln Gly Ala Gly Met Trp Asn Asp Ile Lys Gly
                245                 250                 255

Val Phe Ser Glu Thr His Ser Gly Ser Arg Ile Ile Val Thr Thr Ser
            260                 265                 270

Ile Gln Ser Val Ala Ala Ala Cys Thr Pro Glu Pro Arg Tyr Ile Tyr
            275                 280                 285

Arg Met Pro Ser Leu Gly Asn Leu Asp Ser Glu Lys Leu Leu Trp Met
            290                 295                 300

Arg Val Gly Arg His Ala Ser Arg Thr Pro Ala Leu Glu His Ala Leu
305                 310                 315                 320

Gly Asn Asp Thr Leu Lys Lys Cys Gly Gly Leu Pro Leu Ala Leu Ile
                325                 330                 335

Ser Val Ala Asn His Leu Cys Leu Gly Lys Ala Leu Phe Glu Glu Met
            340                 345                 350

Asp Arg Val Leu Ala Lys Cys Tyr Asp Ser Leu Pro Asp Asn Ala His
            355                 360                 365

Arg Met Cys Leu Leu Ser Leu Ser Thr Phe Pro Gln Gly His Val Met
            370                 375                 380

Lys Arg Lys Arg Leu Ile Arg Arg Trp Ile Ala Glu Gly Leu Ala Val
385                 390                 395                 400

Gly Asp Cys Glu Leu Ser Ala Glu Gln Val Ala Gly Asn Ile Phe Asp
                405                 410                 415

Val Leu Ile Asp Arg Asn Val Thr Glu Pro Val Leu Thr Ala Gly His
            420                 425                 430

Gly Ser Ser Ser Lys Val Lys Ala Cys Leu Val Leu Gly Val Ile Lys
            435                 440                 445
```

-continued

```
Asp Phe Ile Asn Lys Thr Ala Val Ser Asn Glu Thr Val Ala Ile Ile
    450                 455                 460
Gln Asn Asp Glu Leu Leu Pro Asn Arg Met Met Leu Val Ala His
465                 470                 475                 480
Arg Pro Val Arg Arg Leu Leu Val His Gly Gly Thr Thr Lys Lys Ser
                485                 490                 495
Glu Ala Val Ala Lys Ala Ile Gly Leu Asp Gln Val Arg Ser Leu Thr
                500                 505                 510
Ile Cys Asn Ala Val Pro Phe Asp Phe Gln Gly Cys Trp Leu Leu Arg
            515                 520                 525
Val Leu Asp Leu Glu Ala Cys Gln Gly Ile Asp Lys Ser Ile Leu Gly
    530                 535                 540
Ser Ile Cys Lys Leu Val Phe Leu Lys Tyr Leu Ser Leu Arg Gly Thr
545                 550                 555                 560
Asp Val Tyr Gly Ile Pro Lys Lys Val Lys Lys Leu Gln Arg Leu Glu
                565                 570                 575
Thr Leu Asp Leu Arg Asp Thr Arg Val Glu Glu Leu Pro Ile Gln Val
                580                 585                 590
Leu Met Leu Pro Arg Leu Ala His Leu Phe Gly Lys Phe Glu Leu Pro
    595                 600                 605
Pro Gln Leu Lys His Gly His Arg Thr Ala Arg Arg Arg Ser Arg
    610                 615                 620
Leu Gln Ala Phe Phe Ser Gln Arg Ser Arg Leu Gln Thr Leu Ser Gly
625                 630                 635                 640
Phe Val Met Val Asp Asp Ser Asn Ser Phe Glu His Met Met Ile Thr
                645                 650                 655
Ile Lys Ser Leu Arg Lys Val Lys Val Trp Cys Lys Asn Ser Ile Ser
            660                 665                 670
Ser His Gln Glu Arg His Leu Ala Ser Ser Leu Gln Gln Arg Leu Val
    675                 680                 685
Gly Asn Ser Asn Pro Leu Glu Ser Leu Ser Ile Asp Phe Gly Asn Glu
    690                 695                 700
Ser Ile Asn Phe Leu Asn Asp Val Gly Ala Thr Ser Ala Leu Ile Gly
705                 710                 715                 720
Ser Met Lys Leu Gln Gly Arg Leu Thr Ser Leu Pro Ser Phe Met Thr
                725                 730                 735
Ser Tyr Asp Thr Thr Leu Ser Gln Leu Gln Leu Ser Ser Thr Gly Leu
            740                 745                 750
Gly Ile Glu Ala Leu Ser Leu Leu Gln Ile Leu Arg Arg Leu Val Ser
    755                 760                 765
Leu Lys Leu Ala Gln Asp Gly Asp Gly Phe Trp Gly Asp Cys Phe Ala
    770                 775                 780
Val Asn Lys Asp Gly Phe Pro Ser Leu Leu Arg Leu Cys Ile Gln Ala
785                 790                 795                 800
Arg Glu Leu Pro Gln Leu His Ile His Glu Gly Gly Met Ser Ser Leu
                805                 810                 815
Thr Ser Leu Glu Leu Leu Cys Pro Met Phe Ala Ser Arg Gly His Ser
            820                 825                 830
Asp Ser Asp Ser Asp Ser Asp Leu Gly Lys Thr Tyr Val Glu Thr His
        835                 840                 845
Ser Glu Lys Arg Ser Lys Gln Val Leu Ser Val Glu Lys Pro Lys Ala
    850                 855                 860
```

```
Val Asp Pro Gly Ile Ser Phe Lys Glu Pro Ser Ser Glu Thr Arg Ser
865                 870                 875                 880

Glu Gly Thr Glu Ile Gln Glu Ile Asp Ser Pro Lys Thr Ser Lys Glu
            885                 890                 895

Ala Gly Pro Ser Ile Gly Phe Lys Asp Ile Ile Leu Pro Glu Asn Thr
                900                 905                 910

Phe Arg Arg Asn Phe Ser Lys Glu Val Lys Ser Arg Phe Asp Leu Lys
            915                 920                 925

Gln His Phe Lys Gly Met Glu Tyr Leu Gln Cys Leu Asn Glu Leu Val
        930                 935                 940

Leu His Cys Ser Val Ser Asp Glu Val Leu Asp Ala Trp Thr Lys Arg
945                 950                 955                 960

Ala Ser Ser His Ile Asn Arg Pro Lys Val Thr Arg Gln Cys Thr Arg
                965                 970                 975

Ala Ala Leu Ser Ile Gly Arg Gly Pro Gly Thr Ala Lys His Glu Lys
            980                 985                 990

Glu Gly Gln His Arg Ser Gln Leu Met Lys Asn Arg Gly Ser Glu Thr
        995                 1000                1005

Ala Ile His Glu Glu Val Ala Glu Gln His Ser Ser Val Gly Thr
    1010                1015                1020

Ser Arg Glu Glu Ala Gly Leu Phe Gln Glu Gln Thr Ser Asp Thr
    1025                1030                1035

Gly His Lys Glu Glu Glu Glu Glu Glu Glu Glu Cys Thr Ser
    1040                1045                1050

Glu Asp Arg Ala Leu Asn Gln Pro Cys Asp Met Leu Ile Gly Met
    1055                1060                1065

Asp Val Ala Ile Arg Glu Leu Leu Glu Leu Val Asn Leu Glu Glu
    1070                1075                1080

Phe Gly Val Asp Asp Lys Val Ile Ser Ile Val Gly Cys Pro Gly
    1085                1090                1095

Leu Gly Lys Thr Thr Leu Ala Lys Ala Phe Ser Asn Leu Glu Met
    1100                1105                1110

Ile Arg Glu Arg Phe Asn Pro Pro Val Trp Val Ser Ala Ser Gln
    1115                1120                1125

Cys Arg Ser Ala Gln Asp Leu Leu Ile Lys Val Ile Arg Gln Ala
    1130                1135                1140

Ser His Val His Pro Ala Gln Met Ile Ser Ala Thr Pro Asn Ile
    1145                1150                1155

Asp Leu Leu Gln Thr Ile Leu Ala Gln Glu Ser Leu Leu Ile Ile
    1160                1165                1170

Ile Asp Asp Leu Arg Glu Thr Thr Ala Trp Asn Ser Ile Glu Thr
    1175                1180                1185

Ala Leu Gly Ser Thr Thr Ser Thr His Ala Gly Ser Leu Ile Ile
    1190                1195                1200

Val Thr Thr Arg Ile Gln Ser Ile Ala Gly Lys Cys Ser Pro His
    1205                1210                1215

Arg Tyr Ile Tyr Arg Met Pro Gly Leu Gly His Pro Glu Ser Lys
    1220                1225                1230

Glu Leu Phe Leu Arg Thr Ala Tyr Gly Asp Ala His Pro Thr Pro
    1235                1240                1245

Gly Val Ala Asp Ala Val Glu Glu Ile Ser Gly Ala Cys Asp Gly
    1250                1255                1260

Leu Pro Leu Ala Leu Val Ser Ala Ala His Asp Trp Arg Glu Arg
```

```
                    1265                1270                1275

Gln Gly Gln Gly Trp Glu Gly Arg Tyr Val Phe Glu Glu Val Asn
        1280                1285                1290

Arg Ala Phe Ser Trp Trp Tyr Glu Ser Leu Ala Asp Ala Ala His
    1295                1300                1305

Met Leu Ser Leu Gly Ile Phe Pro Tyr Gly His Ser Ile Lys Arg
1310                1315                1320

Lys Ser Leu Ile Arg Arg Trp Ile Ala Glu Gly Leu Val Ser Glu
1325                1330                1335

Glu Lys Asp Gly Asp Gln Arg Phe His Glu Leu Val Asp Gln Ser
1340                1345                1350

Ile Val Glu Pro Val Leu Ile Thr Gly Ser Ser Asp Phe Lys Val
1355                1360                1365

Lys Arg Phe Arg Leu Arg Ala Ser Gly Ala Gly Val His Arg Gln
1370                1375                1380

Gly Ile Ser Leu
1385

<210> SEQ ID NO 47
<211> LENGTH: 2112
<212> TYPE: PRT
<213> ORGANISM: Zea mays

<400> SEQUENCE: 47

Met Ser Ile Leu Glu Lys Leu Val Gln Ser Cys Ser Phe Pro Asp Ser
1               5                   10                  15

Trp Arg Gly Pro Pro Asp Ala Glu Val Gln Ala Leu Ile Gly Tyr Leu
            20                  25                  30

Glu Glu Ile Arg Ser Ser Val Leu Asp Leu Ser Lys Glu Asp Glu Asp
        35                  40                  45

Glu Asp Asp Ser Ala Thr Ser Ser Ser Thr Leu Lys Met Ser Leu Thr
    50                  55                  60

Ser Gln Leu Gln Glu Leu Cys Tyr Asp Ala Glu Asp Tyr Leu Glu Met
65                  70                  75                  80

Ala Gln His Ser Arg Gly Gly Cys Ser Trp Gln Ile Ser Trp Val Arg
                85                  90                  95

Ser Lys Ala Thr Arg Gln Arg Pro Ala Leu Ile Ser Ala Lys Asp Leu
            100                 105                 110

Ser Gly Leu Ile Ser Arg Val Lys Pro Ala Lys Glu Ile Ala Gln Ala
        115                 120                 125

Tyr Ile Lys Ser Ala Ser Ser Arg Thr Thr Lys Glu Asn Gly Pro
    130                 135                 140

Arg Pro Gln Glu Glu Pro Ala Lys Ser Ser Arg Arg Ala Val Tyr
145                 150                 155                 160

Ser Asp Asp Thr Leu Gln Pro Asp Ser His Asp Glu Gln Leu Val Arg
                165                 170                 175

Leu Leu Ala Leu Glu Ser Asp Gln Gln Leu Lys Thr Val Ala Ile His
            180                 185                 190

Gly Leu Pro Gly Val Gly Lys Thr Thr Leu Ala Arg Arg Leu Tyr His
        195                 200                 205

Cys Tyr Glu Gly Arg Phe His Cys Gly Ala Phe Leu Arg Ala Ser Arg
    210                 215                 220

Asn Leu Gln Asp Asp Thr Thr Arg Leu Leu Ala Thr Met Leu Ser Lys
225                 230                 235                 240
```

-continued

```
Ile Lys Gly Gln Gln Gly Cys Arg Tyr Trp Gly Gly Ser Gly Asp Glu
                245                 250                 255

Gln Asp Leu Ile Asp Ser Ile Arg Gln His Leu Gln Gly Lys Ser Tyr
            260                 265                 270

Phe Ile Val Ile Asp Asp Leu Trp Ala Thr Ser Val Trp Asp Phe Leu
        275                 280                 285

Ser Arg Ala Phe Pro Lys Asp Asn Cys Gly Ser Arg Ile Val Ile Thr
    290                 295                 300

Thr Gln Val Thr Glu Val Ala Phe Ala Cys Asn Asn His Thr Val
305                 310                 315                 320

Asp Ile Phe Asn Met Lys Pro Leu Asp Asp Gln Ser Leu Gln Leu
                325                 330                 335

Phe Tyr Ser Arg Val Lys His Ile Asn Gly Tyr Asn Ala Glu Glu Cys
            340                 345                 350

Lys Ala Ile Ser His Gly Ile Val Ser Asn Cys Gly Asn Leu Ser Pro
        355                 360                 365

Leu Ala Ile Ile Asn Ile Thr Gly Met Leu Ala Gly Trp Ala Asp Phe
    370                 375                 380

Asn Met Asn Asp Trp Glu Tyr Val Ser Lys Cys Cys Thr Phe Thr Ala
385                 390                 395                 400

Asn Leu Thr Thr Glu Glu Ala Met Glu Arg Phe Leu Asn Leu Met Tyr
                405                 410                 415

Asn Lys Leu Pro Ala Lys Leu Lys Thr Cys Leu Leu Tyr Leu Ser Met
            420                 425                 430

Tyr Pro Glu Gly Cys Val Ile Gly Lys Asp Asp Leu Val Arg Gln Trp
        435                 440                 445

Ala Ala Glu Gly Ile Phe Ser Gln Val Val Glu Pro Lys Gly Arg Glu
    450                 455                 460

His Glu Val Gly Phe Ile Tyr Phe Asp Glu Leu Leu Lys Arg Gly Leu
465                 470                 475                 480

Ile Gln Pro Val Asp Thr Asp Tyr Asn Asp Gln Val Leu Ser Cys Ile
                485                 490                 495

Val His Gln Val Val Leu Glu Phe Ile Thr Lys Lys Ser Met Gln Glu
            500                 505                 510

Asn Phe Ile Thr Val Val Asp Tyr Arg Glu Thr Gly Thr Val Leu Asp
        515                 520                 525

Asp Asn Lys Val His Arg Leu Ser Ala Arg Phe Glu Gly Ala Lys Ser
    530                 535                 540

Ala Gln Ile Pro Arg Ser Phe Arg Val Arg Gln Val Arg Ser Phe Met
545                 550                 555                 560

Phe Ser Gly Phe Phe Lys Ser Leu Pro Ser Leu Leu Lys Tyr Cys Leu
                565                 570                 575

Val Arg Val Leu Ile Leu Arg Val Trp Ser Asp Asp Gln Gly Lys Thr
            580                 585                 590

Val Val Leu Asp Leu Ser Pro Val Gly Asn Met Leu His Val Arg Tyr
        595                 600                 605

Leu Lys Val Val Ser Asp Met Ile Val Lys Leu Pro Leu Ile Ile Arg
    610                 615                 620

Gly Leu Arg His Leu Glu Thr Leu Glu Val Asp Ala Glu Glu Val Ala
625                 630                 635                 640

Val Pro Leu Asp Val Phe Ile Leu Lys Ser Leu Leu His Leu Arg Leu
                645                 650                 655

Pro Ser Lys Ala Tyr Gln Leu Asp Ser Asp Ile Gln Arg Ile Gly Leu
```

```
                     660                665                670
Thr Asn Thr Phe Pro Leu Ser Phe Leu Pro Phe Val Arg Thr Leu Ser
                675                680                685
Ile Leu Phe Leu Trp Arg Ser Leu Leu Ser His Gly His Leu Thr Ser
690                695                700
Leu Gln Ser Leu Gly Tyr Phe Asp Leu Ser Thr Cys Ser Arg Tyr Thr
705                710                715                720
Val Arg Gln Leu Gly Lys Leu Thr Asn Leu Arg Asp Leu His Leu Thr
                725                730                735
Cys Ser Ala Val Arg Ser Arg His Arg Ile Ser Asn Ile Gln Cys Leu
                740                745                750
Ala Ser Val Leu Gly Lys Cys Thr Ser Leu Glu Ser Leu Thr Ile Arg
                755                760                765
Gly Glu Ala Ser Ser Asn Gln Ser Ile Ser Phe Asp Gly Leu Ser Arg
                770                775                780
Leu Ser Ser Pro Pro Tyr Asn Leu Val Ser Phe Val Leu Ser Pro Arg
785                790                795                800
Ile Phe Lys Met Ala Lys Leu Pro Lys Trp Ile Gly Gln Leu Ser Arg
                805                810                815
Leu Ser Thr Leu Lys Ile Ala Val Gly Glu Leu Ser Ser Glu Asp Val
                820                825                830
Asp Ile Leu Lys Glu Leu Ser Ala Leu Thr Ala Leu Ser Leu Tyr Val
                835                840                845
Arg Arg Asn Pro Lys Lys Gly Ser Trp Ile Leu Phe Ser Lys Gly Phe
                850                855                860
Ala Val Leu Lys Tyr Phe Lys Phe Thr Cys Thr Ala Leu Cys Val Lys
865                870                875                880
Phe Ser Glu Gln Ala Met Pro Ala Val Gln Arg Leu Asn Val Cys Phe
                885                890                895
Asn Ala Asn Thr Met Gln Gln Tyr Arg Pro Glu Asp Ala Gly Ile Trp
                900                905                910
Tyr Leu Ser Gly Leu Gln Val Ile Ser Ala Arg Ile Gly Ala Ala Gly
                915                920                925
Ile Asp Gln Ala Ser Arg Glu Ala Ala Lys Ser Arg Leu Leu Asp Ala
                930                935                940
Ile Leu Ser Asn His Pro Lys Pro Pro Ile Arg Asn Val Gln Met
945                950                955                960
Val Asp Trp Val Ile His Gly Asp Thr Glu Glu Cys Ser Thr Gly Val
                965                970                975
Met Ile Arg Lys Asp Glu Ser Ser Arg Glu His Thr Arg Ser Phe Leu
                980                985                990
Ser Gln Phe Pro Phe Arg Arg Arg Pro Leu Leu Pro Ser Ile Phe Thr
                995                1000               1005
Arg Arg Gly Gln Asp Asp Glu Gln His Lys Ile Glu Glu Asn Asp
                1010               1015               1020
Val Leu Gln Asp Ser Ile Ile Leu Arg Glu Ser Ser Leu Met
        1025               1030               1035
Gln Lys Pro Gly Trp Val Thr Arg Arg Ser Arg Ser Thr Gly Val
        1040               1045               1050
Gly Leu Leu Met Ala Val Arg Gly Ser Thr Tyr Met Ile Arg Gln
        1055               1060               1065
Tyr Ile Lys Glu Pro Gly Phe Asn Ala Ala Asn Glu Met Ala Ser
        1070               1075               1080
```

```
Ile Asn Gln Glu Ile Arg Gln Ile Gly Arg Met Val Ile Ser Ser
    1085            1090                1095

Asn Ile Leu Glu Pro Pro Glu Trp Ile Leu Gln Ala Gln Asp Leu
    1100            1105                1110

Ala Cys Asp Val Gln Asp Phe Thr Asp Ile Tyr Thr Trp Leu Gln
    1115            1120                1125

Ser Lys Ser Arg Arg Arg Ala Leu Ala His Ile Gly Tyr Ile Ala
    1130            1135                1140

Gln Leu Lys Asp Arg Ile Ser Ser Leu Arg Glu Trp Gln Gln Arg
    1145            1150                1155

Gly Gly Ser Ser Ser Ser Gln Gln Glu Arg Ala Ala Ala Leu Ser
    1160            1165                1170

Phe Ser Arg Arg Ser Cys Gly Pro Cys Ala Pro Glu Asp Val Leu
    1175            1180                1185

Val Gly Ile Asp Gln Pro Arg Lys Glu Leu Ser Asp Leu Ile Phe
    1190            1195                1200

Glu Arg Glu Asp Val Val Gln Gln Lys Pro Arg Val Val Ser Val
    1205            1210                1215

Val Gly Tyr Ser Gly Ile Gly Lys Thr Ala Leu Ala Arg Ala Val
    1220            1225                1230

Tyr Tyr Asp Pro Ser Val Arg Ser Ala Phe Asn Gly Val Ala Trp
    1235            1240                1245

Val Val Ala Ser Glu Cys Asn His Gly Cys Asp Leu Val Ser Lys
    1250            1255                1260

Ile Cys Gln Gln Val Lys Asp Glu Gln Ala Gly Asn Gly Ala Val
    1265            1270                1275

Val Pro Asp Cys Tyr Arg Leu Lys Glu Ile Met Arg Asp Lys Arg
    1280            1285                1290

Phe Phe Ile Val Ile Asp Asp Leu Gln Gly Ala Gly Met Trp Asn
    1295            1300                1305

Asp Ile Lys Gly Val Phe Ser Glu Thr His Ser Gly Ser Arg Ile
    1310            1315                1320

Ile Val Thr Thr Ser Ile Gln Ser Val Ala Ala Ala Cys Thr Pro
    1325            1330                1335

Glu Pro Arg Tyr Ile Tyr Arg Met Pro Ser Leu Gly Asn Leu Asp
    1340            1345                1350

Ser Glu Lys Leu Leu Trp Met Arg Val Gly Arg His Ala Ser Arg
    1355            1360                1365

Thr Pro Ala Leu Glu His Ala Leu Gly Asn Asp Thr Leu Lys Lys
    1370            1375                1380

Cys Gly Gly Leu Pro Leu Ala Leu Ile Ser Val Ala Asn His Leu
    1385            1390                1395

Cys Leu Gly Lys Ala Leu Phe Glu Glu Met Asp Arg Val Leu Ala
    1400            1405                1410

Lys Cys Tyr Asp Ser Leu Pro Asp Asn Ala His Arg Met Cys Leu
    1415            1420                1425

Leu Ser Leu Ser Thr Phe Pro Gln Gly His Val Met Lys Arg Lys
    1430            1435                1440

Arg Leu Ile Arg Arg Trp Ile Ala Glu Gly Leu Ala Val Gly Asp
    1445            1450                1455

Cys Glu Leu Ser Ala Glu Gln Val Ala Gly Asn Ile Phe Asp Val
    1460            1465                1470
```

```
Leu Ile Asp Arg Asn Val Thr Glu Pro Val Leu Thr Ala Gly His
1475                1480                1485

Gly Ser Ser Ser Lys Val Lys Ala Cys Leu Val Leu Gly Val Ile
1490                1495                1500

Lys Asp Phe Ile Asn Lys Thr Ala Val Ser Asn Glu Thr Val Ala
1505                1510                1515

Ile Ile Gln Asn Asp Glu Leu Leu Leu Pro Asn Arg Met Met Leu
1520                1525                1530

Val Ala His Arg Pro Val Arg Arg Leu Leu Val His Gly Gly Thr
1535                1540                1545

Thr Lys Lys Ser Glu Ala Val Ala Lys Ala Ile Gly Leu Asp Gln
1550                1555                1560

Val Arg Ser Leu Thr Ile Cys Asn Ala Val Pro Phe Asp Phe Gln
1565                1570                1575

Gly Cys Trp Leu Leu Arg Val Leu Asp Leu Glu Ala Cys Gln Gly
1580                1585                1590

Ile Asp Lys Ser Ile Leu Gly Ser Ile Cys Lys Leu Val Phe Leu
1595                1600                1605

Lys Tyr Leu Ser Leu Arg Gly Thr Asp Val Tyr Gly Ile Pro Lys
1610                1615                1620

Lys Val Lys Lys Leu Gln Arg Leu Glu Thr Leu Asp Leu Arg Asp
1625                1630                1635

Thr Arg Val Glu Glu Leu Pro Ile Gln Val Leu Met Leu Pro Arg
1640                1645                1650

Leu Ala His Leu Phe Gly Lys Phe Glu Leu Pro Pro Gln Leu Lys
1655                1660                1665

His Gly His Arg Thr Ala Arg Arg Arg Ser Arg Leu Gln Ala
1670                1675                1680

Phe Phe Ser Gln Arg Ser Arg Leu Gln Thr Leu Ser Gly Phe Val
1685                1690                1695

Met Val Asp Asp Ser Asn Ser Phe Glu His Met Met Ile Thr Ile
1700                1705                1710

Lys Ser Leu Arg Lys Val Lys Val Trp Cys Lys Asn Ser Ile Ser
1715                1720                1725

Ser His Gln Glu Arg His Leu Ala Ser Ser Leu Gln Gln Arg Leu
1730                1735                1740

Val Gly Asn Ser Asn Pro Leu Glu Ser Leu Ser Ile Asp Phe Gly
1745                1750                1755

Asn Glu Ser Ile Asn Phe Leu Asn Asp Val Gly Ala Thr Ser Ala
1760                1765                1770

Leu Ile Gly Ser Met Lys Leu Gln Gly Arg Leu Thr Ser Leu Pro
1775                1780                1785

Ser Phe Met Thr Ser Tyr Asp Thr Thr Leu Ser Gln Leu Gln Leu
1790                1795                1800

Ser Ser Thr Gly Leu Gly Ile Glu Ala Leu Ser Leu Leu Gln Ile
1805                1810                1815

Leu Arg Arg Leu Val Ser Leu Lys Leu Ala Gln Asp Gly Asp Gly
1820                1825                1830

Phe Trp Gly Asp Cys Phe Ala Val Asn Lys Asp Gly Phe Pro Ser
1835                1840                1845

Leu Leu Arg Leu Cys Ile Gln Ala Arg Glu Leu Pro Gln Leu His
1850                1855                1860

Ile His Glu Gly Gly Met Ser Ser Leu Thr Ser Leu Glu Leu Leu
```

```
              1865                1870                1875

Cys Pro Met Phe Ala Ser Arg Gly His Ser Asp Ser Asp Ser Asp
        1880                1885                1890

Ser Asp Leu Gly Lys Thr Tyr Val Glu Thr His Ser Glu Lys Arg
        1895                1900                1905

Ser Lys Gln Val Leu Ser Val Glu Lys Pro Lys Ala Val Asp Pro
        1910                1915                1920

Gly Ile Ser Phe Lys Glu Pro Ser Ser Glu Thr Arg Ser Glu Gly
        1925                1930                1935

Thr Glu Ile Gln Glu Ile Asp Ser Pro Lys Thr Ser Lys Glu Ala
        1940                1945                1950

Gly Pro Ser Ile Gly Phe Lys Asp Ile Ile Leu Pro Glu Asn Thr
        1955                1960                1965

Phe Arg Arg Asn Phe Ser Lys Glu Val Lys Ser Arg Phe Asp Leu
        1970                1975                1980

Lys Gln His Phe Lys Gly Met Glu Tyr Leu Gln Cys Leu Asn Glu
        1985                1990                1995

Leu Val Leu His Cys Ser Val Ser Asp Glu Val Leu Asp Ala Trp
        2000                2005                2010

Thr Lys Arg Ala Ser Ser His Ile Asn Arg Pro Lys Val Thr Arg
        2015                2020                2025

Gln Cys Thr Arg Ala Ala Leu Ser Ile Gly Arg Gly Pro Gly Thr
        2030                2035                2040

Ala Lys His Glu Lys Glu Gly Gln His Arg Ser Gln Leu Met Lys
        2045                2050                2055

Asn Arg Gly Ser Glu Thr Ala Ile His Glu Val Ala Glu Gln
        2060                2065                2070

His Ser Ser Val Gly Thr Ser Arg Glu Glu Ala Gly Leu Phe Gln
        2075                2080                2085

Glu Gln Thr Leu Gln Val Thr Lys Lys Lys Lys Lys Lys Lys Lys
        2090                2095                2100

Lys Asn Val Arg Val Lys Thr Gly His
        2105                2110

<210> SEQ ID NO 48
<211> LENGTH: 2258
<212> TYPE: PRT
<213> ORGANISM: Zea mays

<400> SEQUENCE: 48

Met Ser Ile Leu Glu Lys Leu Val Gln Ser Cys Ser Phe Pro Asp Ser
1               5                   10                  15

Trp Arg Gly Pro Pro Asp Ala Glu Val Gln Ala Leu Ile Gly Tyr Leu
            20                  25                  30

Glu Glu Ile Arg Ser Ser Val Leu Asp Leu Ser Lys Glu Asp Glu Asp
        35                  40                  45

Glu Asp Asp Ser Ala Thr Ser Ser Ser Thr Leu Lys Met Ser Leu Thr
    50                  55                  60

Ser Gln Leu Gln Glu Leu Cys Tyr Asp Ala Glu Asp Tyr Leu Glu Met
65                  70                  75                  80

Ala Gln His Ser Arg Gly Gly Cys Ser Trp Gln Ile Ser Trp Val Arg
                85                  90                  95

Ser Lys Ala Thr Arg Gln Arg Pro Ala Leu Ile Ser Ala Lys Asp Leu
            100                 105                 110
```

```
Ser Gly Leu Ile Ser Arg Val Lys Pro Ala Lys Glu Ile Ala Gln Ala
            115                 120                 125

Tyr Ile Lys Ser Ala Ser Ser Arg Thr Thr Thr Lys Glu Asn Gly Pro
            130                 135                 140

Arg Pro Gln Glu Glu Pro Ala Lys Ser Ser Arg Arg Ala Val Tyr
145                 150                 155                 160

Ser Asp Asp Thr Leu Gln Pro Asp Ser His Asp Glu Gln Leu Val Arg
            165                 170                 175

Leu Leu Ala Leu Glu Ser Asp Gln Gln Leu Lys Thr Val Ala Ile His
            180                 185                 190

Gly Leu Pro Gly Val Gly Lys Thr Thr Leu Ala Arg Arg Leu Tyr His
            195                 200                 205

Cys Tyr Glu Gly Arg Phe His Cys Gly Ala Phe Leu Arg Ala Ser Arg
            210                 215                 220

Asn Leu Gln Asp Asp Thr Thr Arg Leu Leu Ala Thr Met Leu Ser Lys
225                 230                 235                 240

Ile Lys Gly Gln Gln Gly Cys Arg Tyr Trp Gly Gly Ser Gly Asp Glu
            245                 250                 255

Gln Asp Leu Ile Asp Ser Ile Arg Gln His Leu Gln Gly Lys Ser Tyr
            260                 265                 270

Phe Ile Val Ile Asp Asp Leu Trp Ala Thr Ser Val Trp Asp Phe Leu
            275                 280                 285

Ser Arg Ala Phe Pro Lys Asp Asn Cys Gly Ser Arg Ile Val Ile Thr
            290                 295                 300

Thr Gln Val Thr Glu Val Ala Phe Ala Cys Cys Asn Asn His Thr Val
305                 310                 315                 320

Asp Ile Phe Asn Met Lys Pro Leu Asp Asp Gln Ser Leu Gln Leu
            325                 330                 335

Phe Tyr Ser Arg Val Lys His Ile Asn Gly Tyr Asn Ala Glu Glu Cys
            340                 345                 350

Lys Ala Ile Ser His Gly Ile Val Ser Asn Cys Gly Asn Leu Ser Pro
            355                 360                 365

Leu Ala Ile Ile Asn Ile Thr Gly Met Leu Ala Gly Trp Ala Asp Phe
            370                 375                 380

Asn Met Asn Asp Trp Glu Tyr Val Ser Lys Cys Cys Thr Phe Thr Ala
385                 390                 395                 400

Asn Leu Thr Thr Glu Glu Ala Met Glu Arg Phe Leu Asn Leu Met Tyr
                    405                 410                 415

Asn Lys Leu Pro Ala Lys Leu Lys Thr Cys Leu Leu Tyr Leu Ser Met
            420                 425                 430

Tyr Pro Glu Gly Cys Val Ile Gly Lys Asp Asp Leu Val Arg Gln Trp
            435                 440                 445

Ala Ala Glu Gly Ile Phe Ser Gln Val Val Glu Pro Lys Gly Arg Glu
            450                 455                 460

His Glu Val Gly Phe Ile Tyr Phe Asp Glu Leu Leu Lys Arg Gly Leu
465                 470                 475                 480

Ile Gln Pro Val Asp Thr Asp Tyr Asn Asp Gln Val Leu Ser Cys Ile
            485                 490                 495

Val His Gln Val Val Leu Glu Phe Ile Thr Lys Lys Ser Met Gln Glu
            500                 505                 510

Asn Phe Ile Thr Val Val Asp Tyr Arg Glu Thr Gly Thr Val Leu Asp
            515                 520                 525

Asp Asn Lys Val His Arg Leu Ser Ala Arg Phe Glu Gly Ala Lys Ser
```

```
                530             535             540
Ala Gln Ile Pro Arg Ser Phe Arg Val Arg Gln Val Arg Ser Phe Met
545                 550             555                 560

Phe Ser Gly Phe Phe Lys Ser Leu Pro Ser Leu Leu Lys Tyr Cys Leu
                565             570             575

Val Arg Val Leu Ile Leu Arg Val Trp Ser Asp Asp Gln Gly Lys Thr
            580             585             590

Val Val Leu Asp Leu Ser Pro Val Gly Asn Met Leu His Val Arg Tyr
            595             600             605

Leu Lys Val Val Ser Asp Met Ile Val Lys Leu Pro Leu Ile Ile Arg
        610             615             620

Gly Leu Arg His Leu Glu Thr Leu Glu Val Asp Ala Glu Glu Val Ala
625             630             635             640

Val Pro Leu Asp Val Phe Ile Leu Lys Ser Leu Leu His Leu Arg Leu
                645             650             655

Pro Ser Lys Ala Tyr Gln Leu Asp Ser Asp Ile Gln Arg Ile Gly Leu
            660             665             670

Thr Asn Thr Phe Pro Leu Ser Phe Leu Pro Phe Val Arg Thr Leu Ser
        675             680             685

Ile Leu Phe Leu Trp Arg Ser Leu Leu Ser His Gly His Leu Thr Ser
    690             695             700

Leu Gln Ser Leu Gly Tyr Phe Asp Leu Ser Thr Cys Ser Arg Tyr Thr
705             710             715             720

Val Arg Gln Leu Gly Lys Leu Thr Asn Leu Arg Asp Leu His Leu Thr
                725             730             735

Cys Ser Ala Val Arg Ser Arg His Arg Ile Ser Asn Ile Gln Cys Leu
            740             745             750

Ala Ser Val Leu Gly Lys Cys Thr Ser Leu Glu Ser Leu Thr Ile Arg
        755             760             765

Gly Glu Ala Ser Ser Asn Gln Ser Ile Ser Phe Asp Gly Leu Ser Arg
    770             775             780

Leu Ser Ser Pro Pro Tyr Asn Leu Val Ser Phe Val Leu Ser Pro Arg
785             790             795             800

Ile Phe Lys Met Ala Lys Leu Pro Lys Trp Ile Gly Gln Leu Ser Arg
                805             810             815

Leu Ser Thr Leu Lys Ile Ala Val Gly Glu Leu Ser Ser Glu Asp Val
            820             825             830

Asp Ile Leu Lys Glu Leu Ser Ala Leu Thr Ala Leu Ser Leu Tyr Val
        835             840             845

Arg Arg Asn Pro Lys Lys Gly Ser Trp Ile Leu Phe Ser Lys Gly Phe
850             855             860

Ala Val Leu Lys Tyr Phe Lys Phe Thr Cys Thr Ala Leu Cys Val Lys
865             870             875             880

Phe Ser Glu Gln Ala Met Pro Ala Val Gln Arg Leu Asn Val Cys Phe
                885             890             895

Asn Ala Asn Thr Met Gln Gln Tyr Arg Pro Glu Asp Ala Gly Ile Trp
            900             905             910

Tyr Leu Ser Gly Leu Gln Val Ile Ser Ala Arg Ile Gly Ala Ala Gly
        915             920             925

Ile Asp Gln Ala Ser Arg Glu Ala Ala Lys Ser Arg Leu Leu Asp Ala
    930             935             940

Ile Leu Ser Asn His Pro Lys Pro Pro Ile Arg Asn Val Gln Met
945             950             955             960
```

-continued

```
Val Asp Trp Val Ile His Gly Asp Thr Glu Glu Cys Ser Thr Gly Val
            965                 970                 975

Met Ile Arg Lys Asp Glu Ser Ser Arg Glu His Thr Arg Ser Phe Leu
            980                 985                 990

Ser Gln Phe Pro Phe Arg Arg Arg Pro Leu Leu Pro Ser Ile Phe Thr
            995                1000                1005

Arg Arg Gly Gln Asp Asp Glu Gln His Lys Ile Glu Glu Asn Asp
        1010                1015                1020

Val Leu Gln Asp Ser Ile Ile Leu Arg Glu Ser Ser Ser Leu Met
        1025                1030                1035

Gln Lys Pro Gly Trp Val Thr Arg Arg Ser Arg Ser Thr Gly Val
        1040                1045                1050

Gly Leu Leu Met Ala Val Arg Gly Ser Thr Tyr Met Ile Arg Gln
        1055                1060                1065

Tyr Ile Lys Glu Pro Gly Phe Asn Ala Ala Asn Glu Met Ala Ser
        1070                1075                1080

Ile Asn Gln Glu Ile Arg Gln Ile Gly Arg Met Val Ile Ser Ser
        1085                1090                1095

Asn Ile Leu Glu Pro Pro Glu Trp Ile Leu Gln Ala Gln Asp Leu
        1100                1105                1110

Ala Cys Asp Val Gln Asp Phe Thr Asp Ile Tyr Thr Trp Leu Gln
        1115                1120                1125

Ser Lys Ser Arg Arg Ala Leu Ala His Ile Gly Tyr Ile Ala
        1130                1135                1140

Gln Leu Lys Asp Arg Ile Ser Ser Leu Arg Glu Trp Gln Gln Arg
        1145                1150                1155

Gly Gly Ser Ser Ser Ser Gln Glu Arg Ala Ala Ala Leu Ser
        1160                1165                1170

Phe Ser Arg Arg Ser Cys Gly Pro Cys Ala Pro Glu Asp Val Leu
        1175                1180                1185

Val Gly Ile Asp Gln Pro Arg Lys Glu Leu Ser Asp Leu Ile Phe
        1190                1195                1200

Glu Arg Glu Asp Val Val Gln Gln Lys Pro Arg Val Val Ser Val
        1205                1210                1215

Val Gly Tyr Ser Gly Ile Gly Lys Thr Ala Leu Ala Arg Ala Val
        1220                1225                1230

Tyr Tyr Asp Pro Ser Val Arg Ser Ala Phe Asn Gly Val Ala Trp
        1235                1240                1245

Val Val Ala Ser Glu Cys Asn His Gly Cys Asp Leu Val Ser Lys
        1250                1255                1260

Ile Cys Gln Gln Val Lys Asp Glu Gln Ala Gly Asn Gly Ala Val
        1265                1270                1275

Val Pro Asp Cys Tyr Arg Leu Lys Glu Ile Met Arg Asp Lys Arg
        1280                1285                1290

Phe Phe Ile Val Ile Asp Asp Leu Gln Gly Ala Gly Met Trp Asn
        1295                1300                1305

Asp Ile Lys Gly Val Phe Ser Glu Thr His Ser Gly Ser Arg Ile
        1310                1315                1320

Ile Val Thr Thr Ser Ile Gln Ser Val Ala Ala Ala Cys Thr Pro
        1325                1330                1335

Glu Pro Arg Tyr Ile Tyr Arg Met Pro Ser Leu Gly Asn Leu Asp
        1340                1345                1350
```

```
Ser Glu Lys Leu Leu Trp Met Arg Val Gly Arg His Ala Ser Arg
    1355                1360                1365

Thr Pro Ala Leu Glu His Ala Leu Gly Asn Asp Thr Leu Lys Lys
    1370                1375                1380

Cys Gly Gly Leu Pro Leu Ala Leu Ile Ser Val Ala Asn His Leu
    1385                1390                1395

Cys Leu Gly Lys Ala Leu Phe Glu Gly Met Asp Arg Val Leu Ala
    1400                1405                1410

Lys Cys Tyr Asp Ser Leu Pro Asp Asn Ala His Arg Met Cys Leu
    1415                1420                1425

Leu Ser Leu Ser Thr Phe Pro Gln Gly His Val Met Lys Arg Lys
    1430                1435                1440

Arg Leu Ile Arg Arg Trp Ile Ala Glu Gly Leu Ala Val Gly Asp
    1445                1450                1455

Cys Glu Leu Ser Val Glu Gln Val Ala Gly Asn Ile Phe Asp Val
    1460                1465                1470

Leu Ile Asp Arg Asn Val Thr Glu Pro Val Leu Thr Ala Gly His
    1475                1480                1485

Gly Ser Ser Ser Lys Val Lys Ala Cys Leu Val Leu Gly Val Ile
    1490                1495                1500

Lys Asp Phe Ile Asn Lys Thr Ala Val Ser Asn Glu Thr Val Ala
    1505                1510                1515

Ile Ile Gln Asn Asp Glu Leu Leu Pro Asn Arg Met Met Leu
    1520                1525                1530

Val Ala His Arg Pro Val Arg Arg Leu Leu Val His Gly Gly Thr
    1535                1540                1545

Thr Lys Lys Ser Glu Ala Val Ala Lys Ala Ile Gly Leu Asp Gln
    1550                1555                1560

Val Arg Ser Leu Thr Ile Cys Asn Ala Val Pro Phe Asp Phe Gln
    1565                1570                1575

Gly Cys Trp Leu Leu Arg Val Leu Asp Leu Glu Ala Cys Gln Gly
    1580                1585                1590

Ile Asp Lys Ser Ile Leu Gly Ser Ile Cys Lys Leu Val Phe Leu
    1595                1600                1605

Lys Tyr Leu Ser Leu Arg Gly Thr Asp Val Tyr Gly Ile Pro Lys
    1610                1615                1620

Lys Val Lys Lys Leu Gln Arg Leu Glu Thr Leu Asp Leu Arg Asp
    1625                1630                1635

Thr Arg Val Glu Glu Leu Pro Ile Gln Val Leu Met Leu Pro Arg
    1640                1645                1650

Leu Ala His Leu Phe Gly Lys Phe Glu Leu Pro Pro Gln Leu Lys
    1655                1660                1665

His Gly His Arg Thr Ala Arg Arg Arg Ser Arg Leu Gln Ala
    1670                1675                1680

Phe Phe Ser Gln Arg Ser Arg Leu Gln Thr Leu Ser Gly Phe Val
    1685                1690                1695

Met Val Asp Asp Ser Asn Ser Phe Glu His Met Met Ile Thr Ile
    1700                1705                1710

Lys Ser Leu Arg Lys Val Lys Val Trp Cys Lys Asn Ser Ile Ser
    1715                1720                1725

Ser His Gln Glu Arg His Leu Ala Ser Ser Leu Gln Gln Arg Leu
    1730                1735                1740

Val Gly Asn Ser Asn Pro Leu Glu Ser Leu Ser Ile Asp Phe Gly
```

-continued

```
            1745                1750                1755
Asn Glu Ser Ile Asn Phe Leu Asn Asp Val Gly Ala Thr Ser Ala
            1760                1765                1770
Leu Ile Gly Ser Met Lys Leu Gln Gly Arg Leu Thr Ser Leu Pro
            1775                1780                1785
Ser Phe Met Thr Ser Tyr Asp Thr Thr Leu Ser Gln Leu Gln Leu
            1790                1795                1800
Ser Ser Thr Gly Leu Gly Ile Glu Ala Leu Ser Leu Leu Gln Ile
            1805                1810                1815
Leu Arg Arg Leu Val Ser Leu Lys Leu Ala Gln Asp Gly Asp Gly
            1820                1825                1830
Phe Trp Gly Asp Cys Phe Ala Val Asn Lys Asp Gly Phe Pro Ser
            1835                1840                1845
Leu Leu Arg Leu Cys Ile Gln Ala Arg Glu Leu Pro Gln Leu His
            1850                1855                1860
Ile His Glu Gly Gly Met Ser Ser Leu Thr Ser Leu Glu Leu Leu
            1865                1870                1875
Cys Pro Met Phe Ala Ser Arg Gly His Ser Asp Ser Asp Ser Asp
            1880                1885                1890
Ser Asp Leu Gly Lys Thr Tyr Val Glu Thr His Ser Glu Lys Arg
            1895                1900                1905
Ser Lys Gln Val Leu Ser Val Glu Lys Pro Lys Ala Val Asp Pro
            1910                1915                1920
Gly Ile Ser Phe Lys Glu Pro Ser Ser Glu Thr Arg Ser Glu Gly
            1925                1930                1935
Thr Glu Ile Gln Glu Ile Asp Ser Pro Lys Thr Ser Lys Glu Ala
            1940                1945                1950
Gly Pro Ser Ile Gly Phe Lys Asp Ile Ile Leu Pro Glu Asn Thr
            1955                1960                1965
Phe Arg Arg Asn Phe Ser Lys Glu Val Lys Ser Arg Phe Asp Leu
            1970                1975                1980
Lys Gln His Phe Lys Gly Met Glu Tyr Leu Gln Cys Leu Asn Glu
            1985                1990                1995
Leu Val Leu His Cys Ser Val Ser Asp Glu Val Leu Asp Ala Trp
            2000                2005                2010
Thr Lys Arg Ala Ser Ser His Ile Asn Arg Pro Lys Val Thr Arg
            2015                2020                2025
Gln Cys Thr Arg Ala Ala Leu Ser Ile Gly Arg Gly Pro Gly Thr
            2030                2035                2040
Ala Lys His Glu Lys Glu Gly Gln His Arg Ser Gln Leu Met Lys
            2045                2050                2055
Asn Arg Gly Ser Glu Thr Ala Ile His Glu Glu Val Ala Glu Gln
            2060                2065                2070
His Ser Ser Val Gly Thr Ser Arg Glu Glu Ala Gly Leu Phe Gln
            2075                2080                2085
Glu Gln Thr Ser Gly His Lys Glu Glu Glu Glu Glu Glu Glu Glu
            2090                2095                2100
Glu Cys Thr Ser Glu Asp Arg Ala Leu Asn Gln Pro Cys Asp Met
            2105                2110                2115
Leu Ile Gly Met Asp Val Ala Ile Arg Glu Leu Leu Glu Leu Val
            2120                2125                2130
Asn Leu Glu Glu Phe Gly Val Asp Asp Lys Val Ile Ser Ile Val
            2135                2140                2145
```

```
Gly Cys Pro Gly Leu Gly Lys Thr Thr Leu Ala Lys Ala Phe Ser
    2150                2155                2160

Asn Leu Glu Met Ile Arg Glu Arg Phe Asn Pro Val Trp Val
    2165                2170                2175

Ser Ala Ser Gln Cys Arg Ser Ala Gln Asp Leu Leu Ile Lys Val
    2180                2185                2190

Ile Arg Gln Ala Ser His Val His Pro Ala Gln Met Ile Ser Ala
    2195                2200                2205

Thr Pro Asn Ile Asp Leu Leu Gln Thr Ile Leu Ala Gln Glu Arg
    2210                2215                2220

Tyr Ser Leu His Thr Thr Arg Ala Tyr Tyr Leu Tyr Ile His
    2225                2230                2235

Pro Ala Trp Val Tyr Phe Ser Gln Ser Cys Thr Gln Lys Leu Phe
    2240                2245                2250

Asn Lys Lys Asn Lys
    2255

<210> SEQ ID NO 49
<211> LENGTH: 2094
<212> TYPE: PRT
<213> ORGANISM: Zea mays

<400> SEQUENCE: 49

Met Ser Ile Leu Glu Lys Leu Val Gln Ser Cys Ser Phe Pro Asp Ser
1               5                   10                  15

Trp Arg Gly Pro Pro Asp Ala Glu Val Gln Ala Leu Ile Gly Tyr Leu
                20                  25                  30

Glu Glu Ile Arg Ser Ser Val Leu Asp Leu Ser Lys Glu Asp Glu Asp
            35                  40                  45

Glu Asp Asp Ser Ala Thr Ser Ser Ser Thr Leu Lys Met Ser Leu Thr
        50                  55                  60

Ser Gln Leu Gln Glu Leu Cys Tyr Asp Ala Glu Asp Tyr Leu Glu Met
65                  70                  75                  80

Ala Gln His Ser Arg Gly Gly Cys Ser Trp Gln Ile Ser Trp Val Arg
                85                  90                  95

Ser Lys Ala Thr Arg Gln Arg Pro Ala Leu Ile Ser Ala Lys Asp Leu
                100                 105                 110

Ser Gly Leu Ile Ser Arg Val Lys Pro Ala Lys Glu Ile Ala Gln Ala
            115                 120                 125

Tyr Ile Lys Ser Ala Ser Ser Arg Thr Thr Lys Glu Asn Gly Pro
        130                 135                 140

Arg Pro Gln Glu Glu Pro Ala Lys Ser Ser Arg Arg Ala Val Tyr
145                 150                 155                 160

Ser Asp Asp Thr Leu Gln Pro Asp Ser His Asp Glu Gln Leu Val Arg
                165                 170                 175

Leu Leu Ala Leu Glu Ser Asp Gln Gln Leu Lys Thr Val Ala Ile His
            180                 185                 190

Gly Leu Pro Gly Val Gly Lys Thr Thr Leu Ala Arg Arg Leu Tyr His
        195                 200                 205

Cys Tyr Glu Gly Arg Phe His Cys Gly Ala Phe Leu Arg Ala Ser Arg
    210                 215                 220

Asn Leu Gln Asp Asp Thr Thr Arg Leu Leu Ala Thr Met Leu Ser Lys
225                 230                 235                 240

Ile Lys Gly Gln Gln Gly Cys Arg Tyr Trp Gly Gly Ser Gly Asp Glu
```

-continued

```
                245                 250                 255
Gln Asp Leu Ile Asp Ser Ile Arg Gln His Leu Gln Gly Lys Ser Tyr
            260                 265                 270
Phe Ile Val Ile Asp Asp Leu Trp Ala Thr Ser Val Trp Asp Phe Leu
            275                 280                 285
Ser Arg Ala Phe Pro Lys Asp Asn Cys Gly Ser Arg Ile Val Ile Thr
        290                 295                 300
Thr Gln Val Thr Glu Val Ala Phe Ala Cys Cys Asn Asn His Thr Val
305                 310                 315                 320
Asp Ile Phe Asn Met Lys Pro Leu Asp Asp Gln Ser Leu Gln Leu
                325                 330                 335
Phe Tyr Ser Arg Val Lys His Ile Asn Gly Tyr Asn Ala Glu Glu Cys
                340                 345                 350
Lys Ala Ile Ser His Gly Ile Val Ser Asn Cys Gly Asn Leu Ser Pro
                355                 360                 365
Leu Ala Ile Ile Asn Ile Thr Gly Met Leu Ala Gly Trp Ala Asp Phe
            370                 375                 380
Asn Met Asn Asp Trp Glu Tyr Val Ser Lys Cys Cys Thr Phe Thr Ala
385                 390                 395                 400
Asn Leu Thr Thr Glu Glu Ala Met Glu Arg Phe Leu Asn Leu Met Tyr
                    405                 410                 415
Asn Lys Leu Pro Ala Lys Leu Lys Thr Cys Leu Leu Tyr Leu Ser Met
                420                 425                 430
Tyr Pro Glu Gly Cys Val Ile Gly Lys Asp Asp Leu Val Arg Gln Trp
            435                 440                 445
Ala Ala Glu Gly Ile Phe Ser Gln Val Val Glu Pro Lys Gly Arg Glu
        450                 455                 460
His Glu Val Gly Phe Ile Tyr Phe Asp Glu Leu Leu Lys Arg Gly Leu
465                 470                 475                 480
Ile Gln Pro Val Asp Thr Asp Tyr Asn Asp Gln Val Leu Ser Cys Ile
                485                 490                 495
Val His Gln Val Val Leu Glu Phe Ile Thr Lys Lys Ser Met Gln Glu
                500                 505                 510
Asn Phe Ile Thr Val Val Asp Tyr Arg Glu Thr Gly Thr Val Leu Asp
            515                 520                 525
Asp Asn Lys Val His Arg Leu Ser Ala Arg Phe Glu Gly Ala Lys Ser
        530                 535                 540
Ala Gln Ile Pro Arg Ser Phe Arg Val Arg Gln Val Arg Ser Phe Met
545                 550                 555                 560
Phe Ser Gly Phe Phe Lys Ser Leu Pro Ser Leu Leu Lys Tyr Cys Leu
                565                 570                 575
Val Arg Val Leu Ile Leu Arg Val Trp Ser Asp Gln Gly Lys Thr
                580                 585                 590
Val Val Leu Asp Leu Ser Pro Val Gly Asn Met Leu His Val Arg Tyr
            595                 600                 605
Leu Lys Val Val Ser Asp Met Ile Val Lys Leu Pro Leu Ile Ile Arg
        610                 615                 620
Gly Leu Arg His Leu Glu Thr Leu Glu Val Asp Ala Glu Glu Val Ala
625                 630                 635                 640
Val Pro Leu Asp Val Phe Ile Leu Lys Ser Leu Leu His Leu Arg Leu
                645                 650                 655
Pro Ser Lys Ala Tyr Gln Leu Asp Ser Asp Ile Gln Arg Ile Gly Leu
                660                 665                 670
```

```
Thr Asn Thr Phe Pro Leu Ser Phe Leu Pro Phe Val Arg Thr Leu Ser
        675                 680                 685

Ile Leu Phe Leu Trp Arg Ser Leu Leu Ser His Gly His Leu Thr Ser
    690                 695                 700

Leu Gln Ser Leu Gly Tyr Phe Asp Leu Ser Thr Cys Ser Arg Tyr Thr
705                 710                 715                 720

Val Arg Gln Leu Gly Lys Leu Thr Asn Leu Arg Asp Leu His Leu Thr
                725                 730                 735

Cys Ser Ala Val Arg Ser Arg His Arg Ile Ser Asn Ile Gln Cys Leu
            740                 745                 750

Ala Ser Val Leu Gly Lys Cys Thr Ser Leu Glu Ser Leu Thr Ile Arg
            755                 760                 765

Gly Glu Ala Ser Ser Asn Gln Ser Ile Ser Phe Asp Gly Leu Ser Arg
770                 775                 780

Leu Ser Ser Pro Pro Tyr Asn Leu Val Ser Phe Val Leu Ser Pro Arg
785                 790                 795                 800

Ile Phe Lys Met Ala Lys Leu Pro Lys Trp Ile Gly Gln Leu Ser Arg
                805                 810                 815

Leu Ser Thr Leu Lys Ile Ala Val Gly Glu Leu Ser Ser Glu Asp Val
            820                 825                 830

Asp Ile Leu Lys Glu Leu Ser Ala Leu Thr Ala Leu Ser Leu Tyr Val
        835                 840                 845

Arg Arg Asn Pro Lys Lys Gly Ser Trp Ile Leu Phe Ser Lys Gly Phe
850                 855                 860

Ala Val Leu Lys Tyr Phe Lys Phe Thr Cys Thr Ala Leu Cys Val Lys
865                 870                 875                 880

Phe Ser Glu Gln Ala Met Pro Ala Val Gln Arg Leu Asn Val Cys Phe
                885                 890                 895

Asn Ala Asn Thr Met Gln Gln Tyr Arg Pro Glu Asp Ala Gly Ile Trp
            900                 905                 910

Tyr Leu Ser Gly Leu Gln Val Ile Ser Ala Arg Ile Gly Ala Ala Gly
        915                 920                 925

Ile Asp Gln Ala Ser Arg Glu Ala Ala Lys Ser Arg Leu Leu Asp Ala
    930                 935                 940

Ile Leu Ser Asn His Pro Lys Pro Pro Ile Arg Asn Val Gln Met
945                 950                 955                 960

Val Asp Trp Val Ile His Gly Asp Thr Glu Glu Cys Ser Thr Gly Val
                965                 970                 975

Met Ile Arg Lys Asp Glu Ser Ser Arg Glu His Thr Arg Ser Phe Leu
            980                 985                 990

Ser Gln Phe Pro Phe Arg Arg Arg  Pro Leu Leu Pro Ser  Ile Phe Thr
        995                 1000                1005

Arg Arg  Gly Gln Asp Asp Glu  Gln His Lys Ile Glu  Glu Asn Asp
    1010                1015                1020

Val Leu  Gln Asp Ser Ile Ile  Leu Arg Glu Ser  Ser Leu Met
    1025                1030                1035

Gln Lys  Pro Gly Trp Val Thr  Arg Arg Ser Arg Ser  Thr Gly Val
    1040                1045                1050

Gly Leu  Leu Met Ala Val Arg  Gly Ser Thr Tyr Met  Ile Arg Gln
    1055                1060                1065

Tyr Ile  Lys Glu Pro Gly Phe  Asn Ala Ala Asn Glu  Met Ala Ser
    1070                1075                1080
```

```
Ile Asn Gln Glu Ile Arg Gln Ile Gly Arg Met Val Ile Ser Ser
1085                1090                1095

Asn Ile Leu Glu Pro Pro Glu Trp Ile Leu Gln Ala Gln Asp Leu
1100                1105                1110

Ala Cys Asp Val Gln Asp Phe Thr Asp Ile Tyr Thr Trp Leu Gln
1115                1120                1125

Ser Lys Ser Arg Arg Arg Ala Leu Ala His Ile Gly Tyr Ile Ala
1130                1135                1140

Gln Leu Lys Asp Arg Ile Ser Ser Leu Arg Glu Trp Gln Gln Arg
1145                1150                1155

Gly Gly Ser Ser Ser Ser Gln Glu Arg Ala Ala Ala Leu Ser
1160                1165                1170

Phe Ser Arg Arg Ser Cys Gly Pro Cys Ala Pro Glu Asp Val Leu
1175                1180                1185

Val Gly Ile Asp Gln Pro Arg Lys Glu Leu Ser Asp Leu Ile Phe
1190                1195                1200

Glu Arg Glu Asp Val Val Gln Gln Lys Pro Arg Val Val Ser Val
1205                1210                1215

Val Gly Tyr Ser Gly Ile Gly Lys Thr Ala Leu Ala Arg Ala Val
1220                1225                1230

Tyr Tyr Asp Pro Ser Val Arg Ser Ala Phe Asn Gly Val Ala Trp
1235                1240                1245

Val Val Ala Ser Glu Cys Asn His Gly Cys Asp Leu Val Ser Lys
1250                1255                1260

Ile Cys Gln Gln Val Lys Asp Glu Gln Ala Gly Asn Gly Ala Val
1265                1270                1275

Val Pro Asp Cys Tyr Arg Leu Lys Glu Ile Met Arg Asp Lys Arg
1280                1285                1290

Phe Phe Ile Val Ile Asp Asp Leu Gln Gly Ala Gly Met Trp Asn
1295                1300                1305

Asp Ile Lys Gly Val Phe Ser Glu Thr His Ser Gly Ser Arg Ile
1310                1315                1320

Ile Val Thr Thr Ser Ile Gln Ser Val Ala Ala Ala Cys Thr Pro
1325                1330                1335

Glu Pro Arg Tyr Ile Tyr Arg Met Pro Ser Leu Gly Asn Leu Asp
1340                1345                1350

Ser Glu Lys Leu Leu Trp Met Arg Val Gly Arg His Ala Ser Arg
1355                1360                1365

Thr Pro Ala Leu Glu His Ala Leu Gly Asn Asp Thr Leu Lys Lys
1370                1375                1380

Cys Gly Gly Leu Pro Leu Ala Leu Ile Ser Val Ala Asn His Leu
1385                1390                1395

Cys Leu Gly Lys Ala Leu Phe Glu Glu Met Asp Arg Val Leu Ala
1400                1405                1410

Lys Cys Tyr Asp Ser Leu Pro Asp Asn Ala His Arg Met Cys Leu
1415                1420                1425

Leu Ser Leu Ser Thr Phe Pro Gln Gly His Val Met Lys Arg Lys
1430                1435                1440

Arg Leu Ile Arg Arg Trp Ile Ala Glu Gly Leu Ala Val Gly Asp
1445                1450                1455

Cys Glu Leu Ser Ala Glu Gln Val Ala Gly Asn Ile Phe Asp Val
1460                1465                1470

Leu Ile Asp Arg Asn Val Thr Glu Pro Val Leu Thr Ala Gly His
```

```
              1475                1480                1485

Gly  Ser  Ser  Ser  Lys  Val  Lys  Ala  Cys  Leu  Val  Leu  Gly  Val  Ile
          1490                1495                1500

Lys  Asp  Phe  Ile  Asn  Lys  Thr  Ala  Val  Ser  Asn  Glu  Thr  Val  Ala
          1505                1510                1515

Ile  Ile  Gln  Asn  Asp  Glu  Leu  Leu  Pro  Asn  Arg  Met  Met  Leu
          1520                1525                1530

Val  Ala  His  Arg  Pro  Val  Arg  Arg  Leu  Leu  Val  His  Gly  Gly  Thr
          1535                1540                1545

Thr  Lys  Lys  Ser  Glu  Ala  Val  Ala  Lys  Ala  Ile  Gly  Leu  Asp  Gln
          1550                1555                1560

Val  Arg  Ser  Leu  Thr  Ile  Cys  Asn  Ala  Val  Pro  Phe  Asp  Phe  Gln
          1565                1570                1575

Gly  Cys  Trp  Leu  Leu  Arg  Val  Leu  Asp  Leu  Glu  Ala  Cys  Gln  Gly
          1580                1585                1590

Ile  Asp  Lys  Ser  Ile  Leu  Gly  Ser  Ile  Cys  Lys  Leu  Val  Phe  Leu
          1595                1600                1605

Lys  Tyr  Leu  Ser  Leu  Arg  Gly  Thr  Asp  Val  Tyr  Gly  Ile  Pro  Lys
          1610                1615                1620

Lys  Val  Lys  Lys  Leu  Gln  Arg  Leu  Glu  Thr  Leu  Asp  Leu  Arg  Asp
          1625                1630                1635

Thr  Arg  Val  Glu  Glu  Leu  Pro  Ile  Gln  Val  Leu  Met  Leu  Pro  Arg
          1640                1645                1650

Leu  Ala  His  Leu  Phe  Gly  Lys  Phe  Glu  Leu  Pro  Pro  Gln  Leu  Lys
          1655                1660                1665

His  Gly  His  Arg  Thr  Ala  Arg  Arg  Arg  Ser  Arg  Leu  Gln  Ala
          1670                1675                1680

Phe  Phe  Ser  Gln  Arg  Ser  Arg  Leu  Gln  Thr  Leu  Ser  Gly  Phe  Val
          1685                1690                1695

Met  Val  Asp  Asp  Ser  Asn  Ser  Phe  Glu  His  Met  Met  Ile  Thr  Ile
          1700                1705                1710

Lys  Ser  Leu  Arg  Lys  Val  Lys  Val  Trp  Cys  Lys  Asn  Ser  Ile  Ser
          1715                1720                1725

Ser  His  Gln  Glu  Arg  His  Leu  Ala  Ser  Ser  Leu  Gln  Gln  Arg  Leu
          1730                1735                1740

Val  Gly  Asn  Ser  Asn  Pro  Leu  Glu  Ser  Leu  Ser  Ile  Asp  Phe  Gly
          1745                1750                1755

Asn  Glu  Ser  Ile  Asn  Phe  Leu  Asn  Asp  Val  Gly  Ala  Thr  Ser  Ala
          1760                1765                1770

Leu  Ile  Gly  Ser  Met  Lys  Leu  Gln  Gly  Arg  Leu  Thr  Ser  Leu  Pro
          1775                1780                1785

Ser  Phe  Met  Thr  Ser  Tyr  Asp  Thr  Thr  Leu  Ser  Gln  Leu  Gln  Leu
          1790                1795                1800

Ser  Ser  Thr  Gly  Leu  Gly  Ile  Glu  Ala  Leu  Ser  Leu  Leu  Gln  Ile
          1805                1810                1815

Leu  Arg  Arg  Leu  Val  Ser  Leu  Lys  Leu  Ala  Gln  Asp  Gly  Asp  Gly
          1820                1825                1830

Phe  Trp  Gly  Asp  Cys  Phe  Ala  Val  Asn  Lys  Asp  Gly  Phe  Pro  Ser
          1835                1840                1845

Leu  Leu  Arg  Leu  Cys  Ile  Gln  Ala  Arg  Glu  Leu  Pro  Gln  Leu  His
          1850                1855                1860

Ile  His  Glu  Gly  Gly  Met  Ser  Ser  Leu  Thr  Ser  Leu  Glu  Leu  Leu
          1865                1870                1875
```

```
Cys Pro Met Phe Ala Ser Arg Gly His Ser Asp Ser Asp Ser Asp
    1880                1885                1890

Ser Asp Leu Gly Lys Thr Tyr Val Glu Thr His Ser Glu Lys Arg
    1895                1900                1905

Ser Lys Gln Val Leu Ser Val Glu Lys Pro Lys Ala Val Asp Pro
    1910                1915                1920

Gly Ile Ser Phe Lys Glu Pro Ser Ser Glu Thr Arg Ser Glu Gly
    1925                1930                1935

Thr Glu Ile Gln Glu Ile Asp Ser Pro Lys Thr Ser Lys Glu Ala
    1940                1945                1950

Gly Pro Ser Ile Gly Phe Lys Asp Ile Ile Leu Pro Glu Asn Thr
    1955                1960                1965

Phe Arg Arg Asn Phe Ser Lys Glu Val Lys Ser Arg Phe Asp Leu
    1970                1975                1980

Lys Gln His Phe Lys Gly Met Glu Tyr Leu Gln Cys Leu Asn Glu
    1985                1990                1995

Leu Val Leu His Cys Ser Val Ser Asp Glu Val Leu Asp Ala Trp
    2000                2005                2010

Thr Lys Arg Ala Ser Ser His Ile Asn Arg Pro Lys Val Thr Arg
    2015                2020                2025

Gln Cys Thr Arg Ala Ala Leu Ser Ile Gly Arg Gly Pro Gly Thr
    2030                2035                2040

Ala Lys His Glu Lys Glu Gly Gln His Arg Ser Gln Leu Met Lys
    2045                2050                2055

Asn Arg Gly Ser Glu Thr Ala Ile His Glu Glu Val Ala Glu Gln
    2060                2065                2070

His Ser Ser Val Gly Thr Ser Arg Glu Glu Ala Gly Leu Phe Gln
    2075                2080                2085

Glu Gln Thr Ser Gly His
    2090

<210> SEQ ID NO 50
<211> LENGTH: 1211
<212> TYPE: PRT
<213> ORGANISM: Zea mays

<400> SEQUENCE: 50

Met Pro Ala Val Gln Arg Leu Asn Val Cys Phe Asn Ala Asn Thr Met
1               5                   10                  15

Gln Gln Tyr Arg Pro Glu Asp Ala Gly Ile Trp Tyr Leu Ser Gly Leu
            20                  25                  30

Gln Val Ile Ser Ala Arg Ile Gly Ala Ala Gly Ile Asp Gln Ala Ser
        35                  40                  45

Arg Glu Ala Ala Lys Ser Arg Leu Leu Asp Ala Ile Leu Ser Asn His
    50                  55                  60

Pro Lys Pro Pro Pro Ile Arg Asn Val Gln Met Val Asp Trp Val Ile
65                  70                  75                  80

His Gly Asp Thr Glu Glu Cys Ser Thr Gly Val Met Ile Arg Lys Asp
                85                  90                  95

Glu Ser Ser Arg Glu His Thr Arg Ser Phe Leu Ser Gln Phe Pro Phe
            100                 105                 110

Arg Arg Arg Pro Leu Leu Pro Ser Ile Phe Thr Arg Arg Gly Gln Asp
        115                 120                 125

Asp Glu Gln His Lys Ile Glu Glu Asn Asp Val Leu Gln Asp Ser Ile
```

```
            130                 135                 140
Ile Leu Arg Glu Ser Ser Ser Leu Met Gln Lys Pro Gly Trp Val Thr
145                 150                 155                 160
Arg Arg Ser Arg Ser Thr Gly Val Gly Leu Leu Met Ala Val Arg Gly
                165                 170                 175
Ser Thr Tyr Met Ile Arg Gln Tyr Ile Lys Glu Pro Gly Phe Asn Ala
            180                 185                 190
Ala Asn Glu Met Ala Ser Ile Asn Gln Glu Ile Arg Gln Ile Gly Arg
        195                 200                 205
Met Val Ile Ser Ser Asn Ile Leu Glu Pro Pro Glu Trp Ile Leu Gln
    210                 215                 220
Ala Gln Asp Leu Ala Cys Asp Val Gln Asp Phe Thr Asp Ile Tyr Thr
225                 230                 235                 240
Trp Leu Gln Ser Lys Ser Arg Arg Ala Leu Ala His Ile Gly Tyr
                245                 250                 255
Ile Ala Gln Leu Lys Asp Arg Ile Ser Ser Leu Arg Glu Trp Gln Gln
            260                 265                 270
Arg Gly Gly Ser Ser Ser Gln Gln Glu Arg Ala Ala Ala Leu Ser
        275                 280                 285
Phe Ser Arg Arg Ser Cys Gly Pro Cys Ala Pro Glu Asp Val Leu Val
    290                 295                 300
Gly Ile Asp Gln Pro Arg Lys Glu Leu Ser Asp Leu Ile Phe Glu Arg
305                 310                 315                 320
Glu Asp Val Val Gln Gln Lys Pro Arg Val Ser Val Val Gly Tyr
                325                 330                 335
Ser Gly Ile Gly Lys Thr Ala Leu Ala Arg Ala Val Tyr Tyr Asp Pro
            340                 345                 350
Ser Val Arg Ser Ala Phe Asn Gly Val Ala Trp Val Val Ala Ser Glu
        355                 360                 365
Cys Asn His Gly Cys Asp Leu Val Ser Lys Ile Cys Gln Gln Val Lys
    370                 375                 380
Asp Glu Gln Ala Gly Asn Gly Ala Val Val Pro Asp Cys Tyr Arg Leu
385                 390                 395                 400
Lys Glu Ile Met Arg Asp Lys Arg Phe Phe Ile Val Ile Asp Asp Leu
                405                 410                 415
Gln Gly Ala Gly Met Trp Asn Asp Ile Lys Gly Val Phe Ser Glu Thr
            420                 425                 430
His Ser Gly Ser Arg Ile Ile Val Thr Thr Ser Ile Gln Ser Val Ala
        435                 440                 445
Ala Ala Cys Thr Pro Glu Pro Arg Tyr Ile Tyr Arg Met Pro Ser Leu
    450                 455                 460
Gly Asn Leu Asp Ser Glu Lys Leu Leu Trp Met Arg Val Gly Arg His
465                 470                 475                 480
Ala Ser Arg Thr Pro Ala Leu Glu His Ala Leu Gly Asn Asp Thr Leu
                485                 490                 495
Lys Lys Cys Gly Gly Leu Pro Leu Ala Leu Ile Ser Val Ala Asn His
            500                 505                 510
Leu Cys Leu Gly Lys Ala Leu Phe Glu Glu Met Asp Arg Val Leu Ala
        515                 520                 525
Lys Cys Tyr Asp Ser Leu Pro Asp Asn Ala His Arg Met Cys Leu Leu
    530                 535                 540
Ser Leu Ser Thr Phe Pro Gln Gly His Val Met Lys Arg Lys Arg Leu
545                 550                 555                 560
```

```
Ile Arg Arg Trp Ile Ala Glu Gly Leu Ala Val Gly Asp Cys Glu Leu
                565                 570                 575

Ser Ala Glu Gln Val Ala Gly Asn Ile Phe Asp Val Leu Ile Asp Arg
            580                 585                 590

Asn Val Thr Glu Pro Val Leu Thr Ala Gly His Gly Ser Ser Ser Lys
        595                 600                 605

Val Lys Ala Cys Leu Val Leu Gly Val Ile Lys Asp Phe Ile Asn Lys
    610                 615                 620

Thr Ala Val Ser Asn Glu Thr Val Ala Ile Ile Gln Asn Asp Glu Leu
625                 630                 635                 640

Leu Leu Pro Asn Arg Met Met Leu Val Ala His Arg Pro Val Arg Arg
                645                 650                 655

Leu Leu Val His Gly Thr Thr Lys Lys Ser Glu Ala Val Ala Lys
                660                 665                 670

Ala Ile Gly Leu Asp Gln Val Arg Ser Leu Thr Ile Cys Asn Ala Val
            675                 680                 685

Pro Phe Asp Phe Gln Gly Cys Trp Leu Leu Arg Val Leu Asp Leu Glu
690                 695                 700

Ala Cys Gln Gly Ile Asp Lys Ser Ile Leu Gly Ser Ile Cys Lys Leu
705                 710                 715                 720

Val Phe Leu Lys Tyr Leu Ser Leu Arg Gly Thr Asp Val Tyr Gly Ile
                725                 730                 735

Pro Lys Lys Val Lys Lys Leu Gln Arg Leu Glu Thr Leu Asp Leu Arg
            740                 745                 750

Asp Thr Arg Val Glu Glu Leu Pro Ile Gln Val Leu Met Leu Pro Arg
        755                 760                 765

Leu Ala His Leu Phe Gly Lys Phe Glu Leu Pro Pro Gln Leu Lys His
    770                 775                 780

Gly His Arg Thr Ala Arg Arg Arg Ser Arg Leu Gln Ala Phe Phe
785                 790                 795                 800

Ser Gln Arg Ser Arg Leu Gln Thr Leu Ser Gly Phe Val Met Val Asp
                805                 810                 815

Asp Ser Asn Ser Phe Glu His Met Met Ile Thr Ile Lys Ser Leu Arg
            820                 825                 830

Lys Val Lys Val Trp Cys Lys Asn Ser Ile Ser Ser His Gln Glu Arg
        835                 840                 845

His Leu Ala Ser Ser Leu Gln Gln Arg Leu Val Gly Asn Ser Asn Pro
    850                 855                 860

Leu Glu Ser Leu Ser Ile Asp Phe Gly Asn Glu Ser Ile Asn Phe Leu
865                 870                 875                 880

Asn Asp Val Gly Ala Thr Ser Ala Leu Ile Gly Ser Met Lys Leu Gln
                885                 890                 895

Gly Arg Leu Thr Ser Leu Pro Ser Phe Met Thr Ser Tyr Asp Thr Thr
            900                 905                 910

Leu Ser Gln Leu Gln Leu Ser Ser Thr Gly Leu Gly Ile Glu Ala Leu
        915                 920                 925

Ser Leu Leu Gln Ile Leu Arg Arg Leu Val Ser Leu Lys Leu Ala Gln
    930                 935                 940

Asp Gly Asp Gly Phe Trp Gly Asp Cys Phe Ala Val Asn Lys Asp Gly
945                 950                 955                 960

Phe Pro Ser Leu Leu Arg Leu Cys Ile Gln Ala Arg Glu Leu Pro Gln
                965                 970                 975
```

```
Leu His Ile His Gly Gly Met Ser Ser Leu Thr Ser Leu Glu Leu
            980                 985                 990

Leu Cys Pro Met Phe Ala Ser Arg Gly His Ser Asp Ser Asp Ser Asp
            995                 1000                1005

Ser Asp Leu Gly Lys Thr Tyr Val Glu Thr His Ser Glu Lys Arg
            1010                1015                1020

Ser Lys Gln Val Leu Ser Val Glu Lys Pro Lys Ala Val Asp Pro
            1025                1030                1035

Gly Ile Ser Phe Lys Glu Pro Ser Ser Glu Thr Arg Ser Glu Gly
            1040                1045                1050

Thr Glu Ile Gln Glu Ile Asp Ser Pro Lys Thr Ser Lys Glu Ala
            1055                1060                1065

Gly Pro Ser Ile Gly Phe Lys Asp Ile Ile Leu Pro Glu Asn Thr
            1070                1075                1080

Phe Arg Arg Asn Phe Ser Lys Glu Val Lys Ser Arg Phe Asp Leu
            1085                1090                1095

Lys Gln His Phe Lys Gly Met Glu Tyr Leu Gln Cys Leu Asn Glu
            1100                1105                1110

Leu Val Leu His Cys Ser Val Ser Asp Glu Val Leu Asp Ala Trp
            1115                1120                1125

Thr Lys Arg Ala Ser Ser His Ile Asn Arg Pro Lys Val Thr Arg
            1130                1135                1140

Gln Cys Thr Arg Ala Ala Leu Ser Ile Gly Arg Gly Pro Gly Thr
            1145                1150                1155

Ala Lys His Glu Lys Glu Gly Gln His Arg Ser Gln Leu Met Lys
            1160                1165                1170

Asn Arg Gly Ser Glu Thr Ala Ile His Glu Glu Val Ala Glu Gln
            1175                1180                1185

His Ser Ser Val Gly Thr Ser Arg Glu Glu Ala Gly Leu Phe Gln
            1190                1195                1200

Glu Gln Thr Ser Asp Thr Gly His
            1205                1210

<210> SEQ ID NO 51
<211> LENGTH: 803
<212> TYPE: PRT
<213> ORGANISM: Zea mays

<400> SEQUENCE: 51

Met Lys Asn Arg Gly Ser Glu Thr Ala Ile His Glu Glu Val Ala Glu
1               5                   10                  15

Gln His Ser Ser Val Gly Thr Ser Arg Glu Glu Ala Gly Leu Phe Gln
                20                  25                  30

Glu Gln Thr Ser Gly His Lys Glu Glu Glu Glu Glu Glu Glu
            35                  40                  45

Cys Thr Ser Glu Asp Arg Ala Leu Asn Gln Pro Cys Asp Met Leu Ile
            50                  55                  60

Gly Met Asp Val Ala Ile Arg Glu Leu Leu Glu Leu Val Asn Leu Glu
65                  70                  75                  80

Glu Phe Gly Val Asp Asp Lys Val Ile Ser Ile Val Gly Cys Pro Gly
                85                  90                  95

Leu Gly Lys Thr Thr Leu Ala Lys Ala Phe Ser Asn Leu Glu Met Ile
            100                 105                 110

Arg Glu Arg Phe Asn Pro Pro Val Trp Val Ser Ala Ser Gln Cys Arg
            115                 120                 125
```

```
Ser Ala Gln Asp Leu Leu Ile Lys Val Ile Arg Gln Ala Ser His Val
    130                 135                 140

His Pro Ala Gln Met Ile Ser Ala Thr Pro Asn Ile Asp Leu Leu Gln
145                 150                 155                 160

Thr Ile Leu Ala Gln Glu Ser Leu Leu Ile Ile Asp Asp Leu Arg
                165                 170                 175

Glu Thr Thr Ala Trp Asn Ser Ile Glu Thr Ala Leu Gly Ser Thr Thr
                180                 185                 190

Ser Thr His Ala Gly Ser Leu Ile Ile Val Thr Thr Arg Ile Gln Ser
            195                 200                 205

Ile Ala Gly Lys Cys Ser Pro His Arg Tyr Ile Tyr Arg Met Pro Gly
    210                 215                 220

Leu Gly His Pro Glu Ser Lys Glu Leu Phe Leu Arg Thr Ala Tyr Gly
225                 230                 235                 240

Asp Ala His Pro Thr Pro Gly Val Ala Asp Ala Val Glu Glu Ile Ser
                245                 250                 255

Gly Ala Cys Asp Gly Leu Pro Leu Ala Leu Val Ser Ala Ala His Asp
                260                 265                 270

Trp Arg Glu Arg Gln Gly Gln Gly Trp Glu Gly Arg Tyr Val Phe Glu
            275                 280                 285

Glu Val Asn Arg Ala Phe Ser Trp Trp Tyr Glu Ser Leu Ala Asp Ala
    290                 295                 300

Ala His Met Leu Ser Leu Gly Ile Phe Pro Tyr Gly His Ser Ile Lys
305                 310                 315                 320

Arg Lys Ser Leu Ile Arg Arg Trp Ile Ala Glu Gly Leu Val Ser Glu
                325                 330                 335

Glu Lys Asp Gly Asp Gln Arg Phe His Glu Leu Val Asp Gln Ser Ile
            340                 345                 350

Val Glu Pro Val Leu Ile Thr Gly Ser Ser Asp Phe Lys Val Lys Arg
    355                 360                 365

Phe Arg Leu Arg Arg Pro Val Leu Glu Phe Ile Val Arg Glu Ser Val
370                 375                 380

Ser Lys Asn Met Val Lys Leu Leu Gln Gly Asp Glu Pro Leu Pro Gly
385                 390                 395                 400

Glu Gly Gly Pro Val Val Ser Ile Tyr Gln Thr Thr Asp Thr Glu
                405                 410                 415

Thr Ser Arg Gly Asn Ile Met Ser Phe Ser Ile Phe Asn Lys Gly Val
            420                 425                 430

Ala Phe Asp Asp Leu Gln Gln Cys Thr Tyr Leu Arg Val Leu Asp Leu
    435                 440                 445

Glu Arg Cys Arg Gly Val Asp His Ser Val Val Ala Gly Ile Cys Lys
450                 455                 460

Leu Ser Leu Leu Arg Tyr Leu Ser Leu Arg Gly Ser Asp Val Arg His
465                 470                 475                 480

Ile Pro Arg Glu Thr Lys Arg Leu Lys Cys Leu Glu Thr Leu Asp Ile
                485                 490                 495

Arg Glu Thr Val Val Asn Asn Leu Pro Val Ala Ala Leu Met Leu Pro
            500                 505                 510

Arg Leu Val His Leu Phe Gly Lys Phe Glu Leu Pro Arg Lys Leu Glu
    515                 520                 525

Asp Glu Arg Ile Arg Gly Lys Leu Glu Arg Phe Phe Arg Glu Glu Ser
530                 535                 540
```

```
Arg Leu Gln Thr Leu Ala Gly Leu Ile Ile Ser Lys Asn Asn Gly Tyr
545                 550                 555                 560

Glu His Ile Val Ile His Ile Arg Leu Leu Arg Lys Ile Lys Ile Trp
                565                 570                 575

Tyr Gln Asn His Leu Leu His Tyr Ser Thr Leu Leu Asn Glu Leu Phe
            580                 585                 590

Ile Arg Asn Thr Ala Leu Asp Ser Leu Ser Val Asp Phe Gly Asp Ser
            595                 600                 605

Leu Met Phe Pro His Ile Ser Asp Ile Phe Gly Pro Cys Met Leu Arg
610                 615                 620

Ser Ile Lys Leu Arg Gly Arg His Trp Pro Leu Pro Thr Ile Ile Ala
625                 630                 635                 640

Ser Ser Ala Asn Tyr Leu Ser Glu Val Gln Leu Ser Ser Thr Val Leu
                645                 650                 655

Pro Leu Arg Tyr Leu Ser Thr Leu Gln Ser Leu Arg Arg Leu Leu Tyr
                660                 665                 670

Leu Lys Leu Val Ala Asp Gly Phe Val Gly Asp Asp Thr Asp Thr Phe
            675                 680                 685

Thr Val Lys Lys Asp Gly Phe Pro Ser Leu Glu Arg Leu Cys Ile Glu
690                 695                 700

Ala Pro Lys Leu Pro His Leu Arg Ile Val Glu Gly Ala Met Pro Ala
705                 710                 715                 720

Leu Thr Ser Leu His Leu Leu Cys Pro Thr Met Thr Met Met Pro Gln
                725                 730                 735

His Pro Gly Gln Met Gly Glu Ile Asp Glu Pro Glu Ala Thr Ser Glu
            740                 745                 750

Thr Lys Leu Gly Lys Glu Trp Gly Ile Glu Tyr Leu Arg Asn Leu Asn
            755                 760                 765

Asp Leu Val Leu Pro Tyr Thr Val Gly Asp Glu Gln Leu Asp Phe Trp
770                 775                 780

Lys Glu Lys Ala Arg Ser Asn Met Asn Arg Pro Lys Val Thr Arg Gln
785                 790                 795                 800

Pro Lys Pro

<210> SEQ ID NO 52
<211> LENGTH: 2859
<212> TYPE: PRT
<213> ORGANISM: Zea mays

<400> SEQUENCE: 52

Met Ser Ile Leu Glu Lys Leu Val Gln Ser Cys Ser Phe Pro Asp Ser
1               5                   10                  15

Trp Arg Gly Pro Pro Asp Ala Glu Val Gln Ala Leu Ile Gly Tyr Leu
                20                  25                  30

Glu Glu Ile Arg Ser Ser Val Leu Asp Leu Ser Lys Glu Asp Glu Asp
            35                  40                  45

Glu Asp Asp Ser Ala Thr Ser Ser Ser Thr Leu Lys Met Ser Leu Thr
        50                  55                  60

Ser Gln Leu Gln Glu Leu Cys Tyr Asp Ala Glu Asp Tyr Leu Glu Met
65                  70                  75                  80

Ala Gln His Ser Arg Gly Gly Cys Ser Trp Gln Ile Ser Trp Val Arg
                85                  90                  95

Ser Lys Ala Thr Arg Gln Arg Pro Ala Leu Ile Ser Ala Lys Asp Leu
            100                 105                 110
```

Ser Gly Leu Ile Ser Arg Val Lys Pro Ala Lys Glu Ile Ala Gln Ala
            115                 120                 125

Tyr Ile Lys Ser Ala Ser Ser Arg Thr Thr Thr Lys Glu Asn Gly Pro
130                 135                 140

Arg Pro Gln Glu Glu Pro Ala Lys Ser Ser Arg Arg Ala Val Tyr
145                 150                 155                 160

Ser Asp Asp Thr Leu Gln Pro Asp Ser His Asp Glu Gln Leu Val Arg
            165                 170                 175

Leu Leu Ala Leu Glu Ser Asp Gln Gln Leu Lys Thr Val Ala Ile His
            180                 185                 190

Gly Leu Pro Gly Val Gly Lys Thr Thr Leu Ala Arg Arg Leu Tyr His
            195                 200                 205

Cys Tyr Glu Gly Arg Phe His Cys Gly Ala Phe Leu Arg Ala Ser Arg
            210                 215                 220

Asn Leu Gln Asp Asp Thr Thr Arg Leu Leu Ala Thr Met Leu Ser Lys
225                 230                 235                 240

Ile Lys Gly Gln Gln Gly Cys Arg Tyr Trp Gly Gly Ser Gly Asp Glu
            245                 250                 255

Gln Asp Leu Ile Asp Ser Ile Arg Gln His Leu Gln Gly Lys Ser Tyr
            260                 265                 270

Phe Ile Val Ile Asp Asp Leu Trp Ala Thr Ser Val Trp Asp Phe Leu
            275                 280                 285

Ser Arg Ala Phe Pro Lys Asp Asn Cys Gly Ser Arg Ile Val Ile Thr
            290                 295                 300

Thr Gln Val Thr Glu Val Ala Phe Ala Cys Cys Asn Asn His Thr Val
305                 310                 315                 320

Asp Ile Phe Asn Met Lys Pro Leu Asp Asp Gln Ser Leu Gln Leu
            325                 330                 335

Phe Tyr Ser Arg Val Lys His Ile Asn Gly Tyr Asn Ala Glu Glu Cys
            340                 345                 350

Lys Ala Ile Ser His Gly Ile Val Ser Asn Cys Gly Asn Leu Ser Pro
            355                 360                 365

Leu Ala Ile Ile Asn Ile Thr Gly Met Leu Ala Gly Trp Ala Asp Phe
            370                 375                 380

Asn Met Asn Asp Trp Glu Tyr Val Ser Lys Cys Cys Thr Phe Thr Ala
385                 390                 395                 400

Asn Leu Thr Thr Glu Glu Ala Met Glu Arg Phe Leu Asn Leu Met Tyr
            405                 410                 415

Asn Lys Leu Pro Ala Lys Leu Lys Thr Cys Leu Leu Tyr Leu Ser Met
            420                 425                 430

Tyr Pro Glu Gly Cys Val Ile Gly Lys Asp Asp Leu Val Arg Gln Trp
            435                 440                 445

Ala Ala Glu Gly Ile Phe Ser Gln Val Val Glu Pro Lys Gly Arg Glu
450                 455                 460

His Glu Val Gly Phe Ile Tyr Phe Asp Glu Leu Leu Lys Arg Gly Leu
465                 470                 475                 480

Ile Gln Pro Val Asp Thr Asp Tyr Asn Asp Gln Val Leu Ser Cys Ile
            485                 490                 495

Val His Gln Val Val Leu Glu Phe Ile Thr Lys Lys Ser Met Gln Glu
            500                 505                 510

Asn Phe Ile Thr Val Val Asp Tyr Arg Glu Thr Gly Thr Val Leu Asp
            515                 520                 525

Asp Asn Lys Val His Arg Leu Ser Ala Arg Phe Glu Gly Ala Lys Ser

```
              530                 535                 540
Ala Gln Ile Pro Arg Ser Phe Arg Val Arg Gln Val Arg Ser Phe Met
545                 550                 555                 560

Phe Ser Gly Phe Phe Lys Ser Leu Pro Ser Leu Leu Lys Tyr Cys Leu
                    565                 570                 575

Val Arg Val Leu Ile Leu Arg Val Trp Ser Asp Asp Gln Gly Lys Thr
                580                 585                 590

Val Val Leu Asp Leu Ser Pro Val Gly Asn Met Leu His Val Arg Tyr
            595                 600                 605

Leu Lys Val Val Ser Asp Met Ile Val Lys Leu Pro Leu Ile Ile Arg
        610                 615                 620

Gly Leu Arg His Leu Glu Thr Leu Glu Val Asp Ala Glu Val Ala
625                 630                 635                 640

Val Pro Leu Asp Val Phe Ile Leu Lys Ser Leu His Leu Arg Leu
                645                 650                 655

Pro Ser Lys Ala Tyr Gln Leu Asp Ser Asp Ile Gln Arg Ile Gly Leu
                660                 665                 670

Thr Asn Thr Phe Pro Leu Ser Phe Leu Pro Phe Val Arg Thr Leu Ser
                675                 680                 685

Ile Leu Phe Leu Trp Arg Ser Leu Leu Ser His Gly His Leu Thr Ser
            690                 695                 700

Leu Gln Ser Leu Gly Tyr Phe Asp Leu Ser Thr Cys Ser Arg Tyr Thr
705                 710                 715                 720

Val Arg Gln Leu Gly Lys Leu Thr Asn Leu Arg Asp Leu His Leu Thr
                725                 730                 735

Cys Ser Ala Val Arg Ser Arg His Arg Ile Ser Asn Ile Gln Cys Leu
                740                 745                 750

Ala Ser Val Leu Gly Lys Cys Thr Ser Leu Glu Ser Leu Thr Ile Arg
            755                 760                 765

Gly Glu Ala Ser Ser Asn Gln Ser Ile Ser Phe Asp Gly Leu Ser Arg
        770                 775                 780

Leu Ser Ser Pro Pro Tyr Asn Leu Val Ser Phe Val Leu Ser Pro Arg
785                 790                 795                 800

Ile Phe Lys Met Ala Lys Leu Pro Lys Trp Ile Gly Gln Leu Ser Arg
                805                 810                 815

Leu Ser Thr Leu Lys Ile Ala Val Gly Glu Leu Ser Ser Glu Asp Val
                820                 825                 830

Asp Ile Leu Lys Glu Leu Ser Ala Leu Thr Ala Leu Ser Leu Tyr Val
            835                 840                 845

Arg Arg Asn Pro Lys Lys Gly Ser Trp Ile Leu Phe Ser Lys Gly Phe
850                 855                 860

Ala Val Leu Lys Tyr Phe Lys Phe Thr Cys Thr Ala Leu Cys Val Lys
865                 870                 875                 880

Phe Ser Glu Gln Ala Met Pro Ala Val Gln Arg Leu Asn Val Cys Phe
                885                 890                 895

Asn Ala Asn Thr Met Gln Gln Tyr Arg Pro Glu Asp Ala Gly Ile Trp
                900                 905                 910

Tyr Leu Ser Gly Leu Gln Val Ile Ser Ala Arg Ile Gly Ala Ala Gly
            915                 920                 925

Ile Asp Gln Ala Ser Arg Glu Ala Ala Lys Ser Arg Leu Leu Asp Ala
        930                 935                 940

Ile Leu Ser Asn His Pro Lys Pro Pro Ile Arg Asn Val Gln Met
945                 950                 955                 960
```

```
Val Asp Trp Val Ile His Gly Asp Thr Glu Glu Cys Ser Thr Gly Val
                965                 970                 975

Met Ile Arg Lys Asp Glu Ser Ser Arg Glu His Thr Arg Ser Phe Leu
                980                 985                 990

Ser Gln Phe Pro Phe Arg Arg Arg Pro Leu Leu Pro Ser Ile Phe Thr
                995                1000                1005

Arg Arg Gly Gln Asp Asp Glu Gln His Lys Ile Glu Glu Asn Asp
   1010                1015                1020

Val Leu Gln Asp Ser Ile Ile Leu Arg Glu Ser Ser Ser Leu Met
   1025                1030                1035

Gln Lys Pro Gly Trp Val Thr Arg Arg Ser Arg Ser Thr Gly Val
   1040                1045                1050

Gly Leu Leu Met Ala Val Arg Gly Ser Thr Tyr Met Ile Arg Gln
   1055                1060                1065

Tyr Ile Lys Glu Pro Gly Phe Asn Ala Ala Asn Glu Met Ala Ser
   1070                1075                1080

Ile Asn Gln Glu Ile Arg Gln Ile Gly Arg Met Val Ile Ser Ser
   1085                1090                1095

Asn Ile Leu Glu Pro Pro Glu Trp Ile Leu Gln Ala Gln Asp Leu
   1100                1105                1110

Ala Cys Asp Val Gln Asp Phe Thr Asp Ile Tyr Thr Trp Leu Gln
   1115                1120                1125

Ser Lys Ser Arg Arg Arg Ala Leu Ala His Ile Gly Tyr Ile Ala
   1130                1135                1140

Gln Leu Lys Asp Arg Ile Ser Ser Leu Arg Glu Trp Gln Gln Arg
   1145                1150                1155

Gly Gly Ser Ser Ser Ser Gln Glu Arg Ala Ala Ala Leu Ser
   1160                1165                1170

Phe Ser Arg Arg Ser Cys Gly Pro Cys Ala Pro Glu Asp Val Leu
   1175                1180                1185

Val Gly Ile Asp Gln Pro Arg Lys Glu Leu Ser Asp Leu Ile Phe
   1190                1195                1200

Glu Arg Glu Asp Val Val Gln Gln Lys Pro Arg Val Val Ser Val
   1205                1210                1215

Val Gly Tyr Ser Gly Ile Gly Lys Thr Ala Leu Ala Arg Ala Val
   1220                1225                1230

Tyr Tyr Asp Pro Ser Val Arg Ser Ala Phe Asn Gly Val Ala Trp
   1235                1240                1245

Val Val Ala Ser Glu Cys Asn His Gly Cys Asp Leu Val Ser Lys
   1250                1255                1260

Ile Cys Gln Gln Val Lys Asp Glu Gln Ala Gly Asn Gly Ala Val
   1265                1270                1275

Val Pro Asp Cys Tyr Arg Leu Lys Glu Ile Met Arg Asp Lys Arg
   1280                1285                1290

Phe Phe Ile Val Ile Asp Leu Gln Gly Ala Gly Met Trp Asn
   1295                1300                1305

Asp Ile Lys Gly Val Phe Ser Glu Thr His Ser Gly Ser Arg Ile
   1310                1315                1320

Ile Val Thr Thr Ser Ile Gln Ser Val Ala Ala Ala Cys Thr Pro
   1325                1330                1335

Glu Pro Arg Tyr Ile Tyr Arg Met Pro Ser Leu Gly Asn Leu Asp
   1340                1345                1350
```

```
Ser Glu Lys Leu Leu Trp Met Arg Val Gly Arg His Ala Ser Arg
    1355                1360                1365

Thr Pro Ala Leu Glu His Ala Leu Gly Asn Asp Thr Leu Lys Lys
    1370                1375                1380

Cys Gly Gly Leu Pro Leu Ala Leu Ile Ser Val Ala Asn His Leu
    1385                1390                1395

Cys Leu Gly Lys Ala Leu Phe Glu Met Asp Arg Val Leu Ala
    1400                1405                1410

Lys Cys Tyr Asp Ser Leu Pro Asp Asn Ala His Arg Met Cys Leu
    1415                1420                1425

Leu Ser Leu Ser Thr Phe Pro Gln Gly His Val Met Lys Arg Lys
    1430                1435                1440

Arg Leu Ile Arg Arg Trp Ile Ala Glu Gly Leu Ala Val Gly Asp
    1445                1450                1455

Cys Glu Leu Ser Ala Glu Gln Val Ala Gly Asn Ile Phe Asp Val
    1460                1465                1470

Leu Ile Asp Arg Asn Val Thr Glu Pro Val Leu Thr Ala Gly His
    1475                1480                1485

Gly Ser Ser Ser Lys Val Lys Ala Cys Leu Val Leu Gly Val Ile
    1490                1495                1500

Lys Asp Phe Ile Asn Lys Thr Ala Val Ser Asn Glu Thr Val Ala
    1505                1510                1515

Ile Ile Gln Asn Asp Glu Leu Leu Pro Asn Arg Met Met Leu
    1520                1525                1530

Val Ala His Arg Pro Val Arg Arg Leu Leu Val His Gly Gly Thr
    1535                1540                1545

Thr Lys Lys Ser Glu Ala Val Ala Lys Ala Ile Gly Leu Asp Gln
    1550                1555                1560

Val Arg Ser Leu Thr Ile Cys Asn Ala Val Pro Phe Asp Phe Gln
    1565                1570                1575

Gly Cys Trp Leu Leu Arg Val Leu Asp Leu Glu Ala Cys Gln Gly
    1580                1585                1590

Ile Asp Lys Ser Ile Leu Gly Ser Ile Cys Lys Leu Val Phe Leu
    1595                1600                1605

Lys Tyr Leu Ser Leu Arg Gly Thr Asp Val Tyr Gly Ile Pro Lys
    1610                1615                1620

Lys Val Lys Lys Leu Gln Arg Leu Glu Thr Leu Asp Leu Arg Asp
    1625                1630                1635

Thr Arg Val Glu Glu Leu Pro Ile Gln Val Leu Met Leu Pro Arg
    1640                1645                1650

Leu Ala His Leu Phe Gly Lys Phe Glu Leu Pro Pro Gln Leu Lys
    1655                1660                1665

His Gly His Arg Thr Ala Arg Arg Arg Ser Arg Leu Gln Ala
    1670                1675                1680

Phe Phe Ser Gln Arg Ser Arg Leu Gln Thr Leu Ser Gly Phe Val
    1685                1690                1695

Met Val Asp Asp Ser Asn Ser Phe Glu His Met Met Ile Thr Ile
    1700                1705                1710

Lys Ser Leu Arg Lys Val Lys Val Trp Cys Lys Asn Ser Ile Ser
    1715                1720                1725

Ser His Gln Glu Arg His Leu Ala Ser Ser Leu Gln Gln Arg Leu
    1730                1735                1740

Val Gly Asn Ser Asn Pro Leu Glu Ser Leu Ser Ile Asp Phe Gly
```

```
            1745                1750                1755
Asn Glu Ser Ile Asn Phe Leu Asn Asp Val Gly Ala Thr Ser Ala
        1760                1765                1770
Leu Ile Gly Ser Met Lys Leu Gln Gly Arg Leu Thr Ser Leu Pro
        1775                1780                1785
Ser Phe Met Thr Ser Tyr Asp Thr Thr Leu Ser Gln Leu Gln Leu
        1790                1795                1800
Ser Ser Thr Gly Leu Gly Ile Glu Ala Leu Ser Leu Leu Gln Ile
        1805                1810                1815
Leu Arg Arg Leu Val Ser Leu Lys Leu Ala Gln Asp Gly Asp Gly
        1820                1825                1830
Phe Trp Gly Asp Cys Phe Ala Val Asn Lys Asp Gly Phe Pro Ser
        1835                1840                1845
Leu Leu Arg Leu Cys Ile Gln Ala Arg Glu Leu Pro Gln Leu His
        1850                1855                1860
Ile His Glu Gly Gly Met Ser Ser Leu Thr Ser Leu Glu Leu Leu
        1865                1870                1875
Cys Pro Met Phe Ala Ser Arg Gly His Ser Asp Ser Asp Ser Asp
        1880                1885                1890
Ser Asp Leu Gly Lys Thr Tyr Val Glu Thr His Ser Glu Lys Arg
        1895                1900                1905
Ser Lys Gln Val Leu Ser Val Glu Lys Pro Lys Ala Val Asp Pro
        1910                1915                1920
Gly Ile Ser Phe Lys Glu Pro Ser Ser Glu Thr Arg Ser Glu Gly
        1925                1930                1935
Thr Glu Ile Gln Glu Ile Asp Ser Pro Lys Thr Ser Lys Glu Ala
        1940                1945                1950
Gly Pro Ser Ile Gly Phe Lys Asp Ile Ile Leu Pro Glu Asn Thr
        1955                1960                1965
Phe Arg Arg Asn Phe Ser Lys Glu Val Lys Ser Arg Phe Asp Leu
        1970                1975                1980
Lys Gln His Phe Lys Gly Met Glu Tyr Leu Gln Cys Leu Asn Glu
        1985                1990                1995
Leu Val Leu His Cys Ser Val Ser Asp Glu Val Leu Asp Ala Trp
        2000                2005                2010
Thr Lys Arg Ala Ser Ser His Ile Asn Arg Pro Lys Val Thr Arg
        2015                2020                2025
Gln Cys Thr Arg Ala Ala Leu Ser Ile Gly Arg Gly Pro Gly Thr
        2030                2035                2040
Ala Lys His Glu Lys Glu Gly Gln His Arg Ser Gln Leu Met Lys
        2045                2050                2055
Asn Arg Gly Ser Glu Thr Ala Ile His Glu Glu Val Ala Glu Gln
        2060                2065                2070
His Ser Ser Val Gly Thr Ser Arg Glu Glu Ala Gly Leu Phe Gln
        2075                2080                2085
Glu Gln Thr Ser Gly His Lys Glu Glu Glu Glu Glu Glu Glu Glu
        2090                2095                2100
Glu Cys Thr Ser Glu Asp Arg Ala Leu Asn Gln Pro Cys Asp Met
        2105                2110                2115
Leu Ile Gly Met Asp Val Ala Ile Arg Glu Leu Leu Glu Leu Val
        2120                2125                2130
Asn Leu Glu Glu Phe Gly Val Asp Asp Lys Val Ile Ser Ile Val
        2135                2140                2145
```

```
Gly Cys Pro Gly Leu Gly Lys Thr Thr Leu Ala Lys Ala Phe Ser
        2150                2155                2160

Asn Leu Glu Met Ile Arg Glu Arg Phe Asn Pro Val Trp Val
        2165                2170                2175

Ser Ala Ser Gln Cys Arg Ser Ala Gln Asp Leu Leu Ile Lys Val
        2180                2185                2190

Ile Arg Gln Ala Ser His Val His Pro Ala Gln Met Ile Ser Ala
        2195                2200                2205

Thr Pro Asn Ile Asp Leu Leu Gln Thr Ile Leu Ala Gln Glu Ser
        2210                2215                2220

Leu Leu Ile Ile Ile Asp Asp Leu Arg Glu Thr Thr Ala Trp Asn
        2225                2230                2235

Ser Ile Glu Thr Ala Leu Gly Ser Thr Thr Ser Thr His Ala Gly
        2240                2245                2250

Ser Leu Ile Ile Val Thr Thr Arg Ile Gln Ser Ile Ala Gly Lys
        2255                2260                2265

Cys Ser Pro His Arg Tyr Ile Tyr Arg Met Pro Gly Leu Gly His
        2270                2275                2280

Pro Glu Ser Lys Glu Leu Phe Leu Arg Thr Ala Tyr Gly Asp Ala
        2285                2290                2295

His Pro Thr Pro Gly Val Ala Asp Ala Val Glu Glu Ile Ser Gly
        2300                2305                2310

Ala Cys Asp Gly Leu Pro Leu Ala Leu Val Ser Ala Ala His Asp
        2315                2320                2325

Trp Arg Glu Arg Gln Gly Gln Gly Trp Glu Gly Arg Tyr Val Phe
        2330                2335                2340

Glu Glu Val Asn Arg Ala Phe Ser Trp Trp Tyr Glu Ser Leu Ala
        2345                2350                2355

Asp Ala Ala His Met Leu Ser Leu Gly Ile Phe Pro Tyr Gly His
        2360                2365                2370

Ser Ile Lys Arg Lys Ser Leu Ile Arg Arg Trp Ile Ala Glu Gly
        2375                2380                2385

Leu Val Ser Glu Glu Lys Asp Gly Asp Gln Arg Phe His Glu Leu
        2390                2395                2400

Val Asp Gln Ser Ile Val Glu Pro Val Leu Ile Thr Gly Ser Ser
        2405                2410                2415

Asp Phe Lys Val Lys Arg Phe Arg Leu Arg Arg Pro Val Leu Glu
        2420                2425                2430

Phe Ile Val Arg Glu Ser Val Ser Lys Asn Met Val Lys Leu Leu
        2435                2440                2445

Gln Gly Asp Glu Pro Leu Pro Gly Glu Gly Gly Pro Val Val
        2450                2455                2460

Ser Ile Tyr Gln Thr Thr Asp Thr Glu Thr Ser Arg Gly Asn Ile
        2465                2470                2475

Met Ser Phe Ser Ile Phe Asn Lys Gly Val Ala Phe Asp Asp Leu
        2480                2485                2490

Gln Gln Cys Thr Tyr Leu Arg Val Leu Asp Leu Glu Arg Cys Arg
        2495                2500                2505

Gly Val Asp His Ser Val Val Ala Gly Ile Cys Lys Leu Ser Leu
        2510                2515                2520

Leu Arg Tyr Leu Ser Leu Arg Gly Ser Asp Val Arg His Ile Pro
        2525                2530                2535
```

Arg Glu Thr Lys Arg Leu Lys Cys Leu Glu Thr Leu Asp Ile Arg
    2540                2545                2550

Glu Thr Val Val Asn Asn Leu Pro Val Ala Ala Leu Met Leu Pro
    2555                2560                2565

Arg Leu Val His Leu Phe Gly Lys Phe Glu Leu Pro Arg Lys Leu
    2570                2575                2580

Glu Asp Glu Arg Ile Arg Gly Lys Leu Glu Arg Phe Phe Arg Glu
    2585                2590                2595

Glu Ser Arg Leu Gln Thr Leu Ala Gly Leu Ile Ile Ser Lys Asn
    2600                2605                2610

Asn Gly Tyr Glu His Ile Val Ile His Ile Arg Leu Leu Arg Lys
    2615                2620                2625

Ile Lys Ile Trp Tyr Gln Asn His Leu Leu His Tyr Ser Thr Leu
    2630                2635                2640

Leu Asn Glu Leu Phe Ile Arg Asn Thr Ala Leu Asp Ser Leu Ser
    2645                2650                2655

Val Asp Phe Gly Asp Ser Leu Met Phe Pro His Ile Ser Asp Ile
    2660                2665                2670

Phe Gly Pro Cys Met Leu Arg Ser Ile Lys Leu Arg Gly Arg His
    2675                2680                2685

Trp Pro Leu Pro Thr Ile Ile Ala Ser Ser Ala Asn Tyr Leu Ser
    2690                2695                2700

Glu Val Gln Leu Ser Ser Thr Val Leu Pro Leu Arg Tyr Leu Ser
    2705                2710                2715

Thr Leu Gln Ser Leu Arg Arg Leu Leu Tyr Leu Lys Leu Val Ala
    2720                2725                2730

Asp Gly Phe Val Gly Asp Asp Thr Asp Thr Phe Thr Val Lys Lys
    2735                2740                2745

Asp Gly Phe Pro Ser Leu Glu Arg Leu Cys Ile Glu Ala Pro Lys
    2750                2755                2760

Leu Pro His Leu Arg Ile Val Glu Gly Ala Met Pro Ala Leu Thr
    2765                2770                2775

Ser Leu His Leu Leu Cys Pro Thr Met Thr Met Met Pro Gln His
    2780                2785                2790

Pro Gly Gln Met Gly Glu Ile Asp Glu Pro Glu Ala Thr Ser Glu
    2795                2800                2805

Thr Lys Leu Gly Lys Glu Trp Gly Ile Glu Tyr Leu Arg Asn Leu
    2810                2815                2820

Asn Asp Leu Val Leu Pro Tyr Thr Val Gly Asp Glu Gln Leu Asp
    2825                2830                2835

Phe Trp Lys Glu Lys Ala Arg Ser Asn Met Asn Arg Pro Lys Val
    2840                2845                2850

Thr Arg Gln Pro Lys Pro
    2855

<210> SEQ ID NO 53
<211> LENGTH: 1803
<212> TYPE: PRT
<213> ORGANISM: Zea mays

<400> SEQUENCE: 53

Met Ala Val Arg Gly Ser Thr Tyr Met Ile Arg Gln Tyr Ile Lys Glu
1               5                   10                  15

Pro Gly Phe Asn Ala Ala Asn Glu Met Ala Ser Ile Asn Gln Glu Ile
            20                  25                  30

```
Arg Gln Ile Gly Arg Met Val Ile Ser Ser Asn Ile Leu Glu Pro Pro
         35                  40                  45
Glu Trp Ile Leu Gln Ala Gln Asp Leu Ala Cys Asp Val Gln Asp Phe
         50                  55                  60
Thr Asp Ile Tyr Thr Trp Leu Gln Ser Lys Ser Arg Arg Arg Ala Leu
65                   70                  75                  80
Ala His Ile Gly Tyr Ile Ala Gln Leu Lys Asp Arg Ile Ser Ser Leu
                     85                  90                  95
Arg Glu Trp Gln Gln Arg Gly Gly Ser Ser Ser Gln Gln Glu Arg
                    100                 105                 110
Ala Ala Ala Leu Ser Phe Ser Arg Arg Ser Cys Gly Pro Cys Ala Pro
                115                 120                 125
Glu Asp Val Leu Val Gly Ile Asp Gln Pro Arg Lys Glu Leu Ser Asp
            130                 135                 140
Leu Ile Phe Glu Arg Glu Asp Val Val Gln Gln Lys Pro Arg Val Val
145                 150                 155                 160
Ser Val Val Gly Tyr Ser Gly Ile Gly Lys Thr Ala Leu Ala Arg Ala
                    165                 170                 175
Val Tyr Tyr Asp Pro Ser Val Arg Ser Ala Phe Asn Gly Val Ala Trp
                180                 185                 190
Val Val Ala Ser Glu Cys Asn His Gly Cys Asp Leu Val Ser Lys Ile
                195                 200                 205
Cys Gln Gln Val Lys Asp Glu Gln Ala Gly Asn Gly Ala Val Val Pro
210                 215                 220
Asp Cys Tyr Arg Leu Lys Glu Ile Met Arg Asp Lys Arg Phe Phe Ile
225                 230                 235                 240
Val Ile Asp Asp Leu Gln Gly Ala Gly Met Trp Asn Asp Ile Lys Gly
                245                 250                 255
Val Phe Ser Glu Thr His Ser Gly Ser Arg Ile Ile Val Thr Thr Ser
                260                 265                 270
Ile Gln Ser Val Ala Ala Ala Cys Thr Pro Glu Pro Arg Tyr Ile Tyr
                275                 280                 285
Arg Met Pro Ser Leu Gly Asn Leu Asp Ser Glu Lys Leu Leu Trp Met
290                 295                 300
Arg Val Gly Arg His Ala Ser Arg Thr Pro Ala Leu Glu His Ala Leu
305                 310                 315                 320
Gly Asn Asp Thr Leu Lys Lys Cys Gly Gly Leu Pro Leu Ala Leu Ile
                325                 330                 335
Ser Val Ala Asn His Leu Cys Leu Gly Lys Ala Leu Phe Glu Glu Met
                340                 345                 350
Asp Arg Val Leu Ala Lys Cys Tyr Asp Ser Leu Pro Asp Asn Ala His
                355                 360                 365
Arg Met Cys Leu Leu Ser Leu Ser Thr Phe Pro Gln Gly His Val Met
370                 375                 380
Lys Arg Lys Arg Leu Ile Arg Arg Trp Ile Ala Glu Gly Leu Ala Val
385                 390                 395                 400
Gly Asp Cys Glu Leu Ser Ala Glu Gln Val Ala Gly Asn Ile Phe Asp
                405                 410                 415
Val Leu Ile Asp Arg Asn Val Thr Glu Pro Val Leu Thr Ala Gly His
                420                 425                 430
Gly Ser Ser Ser Lys Val Lys Ala Cys Leu Val Leu Gly Val Ile Lys
                435                 440                 445
```

-continued

```
Asp Phe Ile Asn Lys Thr Ala Val Ser Asn Glu Thr Val Ala Ile Ile
    450                 455                 460

Gln Asn Asp Glu Leu Leu Leu Pro Asn Arg Met Met Leu Val Ala His
465                 470                 475                 480

Arg Pro Val Arg Arg Leu Leu Val His Gly Gly Thr Thr Lys Lys Ser
                485                 490                 495

Glu Ala Val Ala Lys Ala Ile Gly Leu Asp Gln Val Arg Ser Leu Thr
            500                 505                 510

Ile Cys Asn Ala Val Pro Phe Asp Phe Gln Gly Cys Trp Leu Leu Arg
            515                 520                 525

Val Leu Asp Leu Glu Ala Cys Gln Gly Ile Asp Lys Ser Ile Leu Gly
530                 535                 540

Ser Ile Cys Lys Leu Val Phe Leu Lys Tyr Leu Ser Leu Arg Gly Thr
545                 550                 555                 560

Asp Val Tyr Gly Ile Pro Lys Lys Val Lys Lys Leu Gln Arg Leu Glu
                565                 570                 575

Thr Leu Asp Leu Arg Asp Thr Arg Val Glu Glu Leu Pro Ile Gln Val
            580                 585                 590

Leu Met Leu Pro Arg Leu Ala His Leu Phe Gly Lys Phe Glu Leu Pro
    595                 600                 605

Pro Gln Leu Lys His Gly His Arg Thr Ala Arg Arg Arg Ser Arg
    610                 615                 620

Leu Gln Ala Phe Phe Ser Gln Arg Ser Arg Leu Gln Thr Leu Ser Gly
625                 630                 635                 640

Phe Val Met Val Asp Asp Ser Asn Ser Phe Glu His Met Met Ile Thr
                645                 650                 655

Ile Lys Ser Leu Arg Lys Val Lys Val Trp Cys Lys Asn Ser Ile Ser
            660                 665                 670

Ser His Gln Glu Arg His Leu Ala Ser Ser Leu Gln Gln Arg Leu Val
    675                 680                 685

Gly Asn Ser Asn Pro Leu Glu Ser Leu Ser Ile Asp Phe Gly Asn Glu
    690                 695                 700

Ser Ile Asn Phe Leu Asn Asp Val Gly Ala Thr Ser Ala Leu Ile Gly
705                 710                 715                 720

Ser Met Lys Leu Gln Gly Arg Leu Thr Ser Leu Pro Ser Phe Met Thr
                725                 730                 735

Ser Tyr Asp Thr Thr Leu Ser Gln Leu Gln Leu Ser Ser Thr Gly Leu
            740                 745                 750

Gly Ile Glu Ala Leu Ser Leu Leu Gln Ile Leu Arg Arg Leu Val Ser
    755                 760                 765

Leu Lys Leu Ala Gln Asp Gly Asp Gly Phe Trp Gly Asp Cys Phe Ala
770                 775                 780

Val Asn Lys Asp Gly Phe Pro Ser Leu Leu Arg Leu Cys Ile Gln Ala
785                 790                 795                 800

Arg Glu Leu Pro Gln Leu His Ile His Glu Gly Gly Met Ser Ser Leu
                805                 810                 815

Thr Ser Leu Glu Leu Leu Cys Pro Met Phe Ala Ser Arg Gly His Ser
            820                 825                 830

Asp Ser Asp Ser Asp Ser Asp Leu Gly Lys Thr Tyr Val Glu Thr His
    835                 840                 845

Ser Glu Lys Arg Ser Lys Gln Val Leu Ser Val Glu Lys Pro Lys Ala
850                 855                 860

Val Asp Pro Gly Ile Ser Phe Lys Glu Pro Ser Ser Glu Thr Arg Ser
```

```
              865                 870                 875                 880
Glu Gly Thr Glu Ile Gln Glu Ile Asp Ser Pro Lys Thr Ser Lys Glu
                885                 890                 895
Ala Gly Pro Ser Ile Gly Phe Lys Asp Ile Ile Leu Pro Glu Asn Thr
            900                 905                 910
Phe Arg Arg Asn Phe Ser Lys Glu Val Lys Ser Arg Phe Asp Leu Lys
            915                 920                 925
Gln His Phe Lys Gly Met Glu Tyr Leu Gln Cys Leu Asn Glu Leu Val
        930                 935                 940
Leu His Cys Ser Val Ser Asp Glu Val Leu Asp Ala Trp Thr Lys Arg
945                 950                 955                 960
Ala Ser Ser His Ile Asn Arg Pro Lys Val Thr Arg Gln Cys Thr Arg
                965                 970                 975
Ala Ala Leu Ser Ile Gly Arg Gly Pro Gly Thr Ala Lys His Glu Lys
            980                 985                 990
Glu Gly Gln His Arg Ser Gln Leu Met Lys Asn Arg Gly Ser Glu Thr
            995                 1000                1005
Ala Ile His Glu Glu Val Ala Glu Gln His Ser Ser Val Gly Thr
    1010                1015                1020
Ser Arg Glu Glu Ala Gly Leu Phe Gln Glu Gln Thr Ser Gly His
    1025                1030                1035
Lys Glu Glu Glu Glu Glu Glu Glu Cys Thr Ser Glu Asp
    1040                1045                1050
Arg Ala Leu Asn Gln Pro Cys Asp Met Leu Ile Gly Met Asp Val
    1055                1060                1065
Ala Ile Arg Glu Leu Leu Glu Leu Val Asn Leu Glu Glu Phe Gly
    1070                1075                1080
Val Asp Asp Lys Val Ile Ser Ile Val Gly Cys Pro Gly Leu Gly
    1085                1090                1095
Lys Thr Thr Leu Ala Lys Ala Phe Ser Asn Leu Glu Met Ile Arg
    1100                1105                1110
Glu Arg Phe Asn Pro Pro Val Trp Val Ser Ala Ser Gln Cys Arg
    1115                1120                1125
Ser Ala Gln Asp Leu Leu Ile Lys Val Ile Arg Gln Ala Ser His
    1130                1135                1140
Val His Pro Ala Gln Met Ile Ser Ala Thr Pro Asn Ile Asp Leu
    1145                1150                1155
Leu Gln Thr Ile Leu Ala Gln Glu Ser Leu Leu Ile Ile Ile Asp
    1160                1165                1170
Asp Leu Arg Glu Thr Thr Ala Trp Asn Ser Ile Glu Thr Ala Leu
    1175                1180                1185
Gly Ser Thr Thr Ser Thr His Ala Gly Ser Leu Ile Ile Val Thr
    1190                1195                1200
Thr Arg Ile Gln Ser Ile Ala Gly Lys Cys Ser Pro His Arg Tyr
    1205                1210                1215
Ile Tyr Arg Met Pro Gly Leu Gly His Pro Glu Ser Lys Glu Leu
    1220                1225                1230
Phe Leu Arg Thr Ala Tyr Gly Asp Ala His Pro Thr Pro Gly Val
    1235                1240                1245
Ala Asp Ala Val Glu Glu Ile Ser Gly Ala Cys Asp Gly Leu Pro
    1250                1255                1260
Leu Ala Leu Val Ser Ala Ala His Asp Trp Arg Glu Arg Gln Gly
    1265                1270                1275
```

```
Gln Gly Trp Glu Gly Arg Tyr Val Phe Glu Glu Val Asn Arg Ala
    1280                1285                1290

Phe Ser Trp Trp Tyr Glu Ser Leu Ala Asp Ala Ala His Met Leu
    1295                1300                1305

Ser Leu Gly Ile Phe Pro Tyr Gly His Ser Ile Lys Arg Lys Ser
    1310                1315                1320

Leu Ile Arg Arg Trp Ile Ala Glu Gly Leu Val Ser Glu Glu Lys
    1325                1330                1335

Asp Gly Asp Gln Arg Phe His Glu Leu Val Asp Gln Ser Ile Val
    1340                1345                1350

Glu Pro Val Leu Ile Thr Gly Ser Ser Asp Phe Lys Val Lys Arg
    1355                1360                1365

Phe Arg Leu Arg Arg Pro Val Leu Glu Phe Ile Val Arg Glu Ser
    1370                1375                1380

Val Ser Lys Asn Met Val Lys Leu Leu Gln Gly Asp Glu Pro Leu
    1385                1390                1395

Pro Gly Glu Gly Gly Gly Pro Val Val Ser Ile Tyr Gln Thr Thr
    1400                1405                1410

Asp Thr Glu Thr Ser Arg Gly Asn Ile Met Ser Phe Ser Ile Phe
    1415                1420                1425

Asn Lys Gly Val Ala Phe Asp Asp Leu Gln Gln Cys Thr Tyr Leu
    1430                1435                1440

Arg Val Leu Asp Leu Glu Arg Cys Arg Gly Val Asp His Ser Val
    1445                1450                1455

Val Ala Gly Ile Cys Lys Leu Ser Leu Leu Arg Tyr Leu Ser Leu
    1460                1465                1470

Arg Gly Ser Asp Val Arg His Ile Pro Arg Glu Thr Lys Arg Leu
    1475                1480                1485

Lys Cys Leu Glu Thr Leu Asp Ile Arg Glu Thr Val Val Asn Asn
    1490                1495                1500

Leu Pro Val Ala Ala Leu Met Leu Pro Arg Leu Val His Leu Phe
    1505                1510                1515

Gly Lys Phe Glu Leu Pro Arg Lys Leu Glu Asp Glu Arg Ile Arg
    1520                1525                1530

Gly Lys Leu Glu Arg Phe Phe Arg Glu Glu Ser Arg Leu Gln Thr
    1535                1540                1545

Leu Ala Gly Leu Ile Ile Ser Lys Asn Asn Gly Tyr Glu His Ile
    1550                1555                1560

Val Ile His Ile Arg Leu Leu Arg Lys Ile Lys Ile Trp Tyr Gln
    1565                1570                1575

Asn His Leu Leu His Tyr Ser Thr Leu Leu Asn Glu Leu Phe Ile
    1580                1585                1590

Arg Asn Thr Ala Leu Asp Ser Leu Ser Val Asp Phe Gly Asp Ser
    1595                1600                1605

Leu Met Phe Pro His Ile Ser Asp Ile Phe Gly Pro Cys Met Leu
    1610                1615                1620

Arg Ser Ile Lys Leu Arg Gly Arg His Trp Pro Leu Pro Thr Ile
    1625                1630                1635

Ile Ala Ser Ser Ala Asn Tyr Leu Ser Glu Val Gln Leu Ser Ser
    1640                1645                1650

Thr Val Leu Pro Leu Arg Tyr Leu Ser Thr Leu Gln Ser Leu Arg
    1655                1660                1665
```

```
Arg Leu Leu Tyr Leu Lys Leu Val Ala Asp Gly Phe Val Gly Asp
    1670                1675                1680

Asp Thr Asp Thr Phe Thr Val Lys Lys Asp Gly Phe Pro Ser Leu
    1685                1690                1695

Glu Arg Leu Cys Ile Glu Ala Pro Lys Leu Pro His Leu Arg Ile
    1700                1705                1710

Val Glu Gly Ala Met Pro Ala Leu Thr Ser Leu His Leu Leu Cys
    1715                1720                1725

Pro Thr Met Thr Met Met Pro Gln His Pro Gly Gln Met Gly Glu
    1730                1735                1740

Ile Asp Glu Pro Glu Ala Thr Ser Glu Thr Lys Leu Gly Lys Glu
    1745                1750                1755

Trp Gly Ile Glu Tyr Leu Arg Asn Leu Asn Asp Leu Val Leu Pro
    1760                1765                1770

Tyr Thr Val Gly Asp Glu Gln Leu Asp Phe Trp Lys Glu Lys Ala
    1775                1780                1785

Arg Ser Asn Met Asn Arg Pro Lys Val Thr Arg Gln Pro Lys Pro
    1790                1795                1800

<210> SEQ ID NO 54
<211> LENGTH: 1319
<212> TYPE: PRT
<213> ORGANISM: Zea mays

<400> SEQUENCE: 54

Met Pro Cys Leu Cys Ser Gly Glu Met His Gln Pro Arg Ile Ser Asn
1               5                   10                  15

Tyr Pro Cys Glu Ala Ser Ser Asn Gln Ser Ile Ser Phe Asp Gly Leu
                20                  25                  30

Ser Arg Leu Ser Ser Pro Pro Tyr Asn Leu Val Ser Phe Val Leu Ser
            35                  40                  45

Pro Arg Ile Phe Lys Met Ala Lys Leu Pro Lys Trp Ile Gly Gln Leu
        50                  55                  60

Ser Arg Leu Ser Thr Leu Lys Ile Ala Val Gly Glu Leu Ser Ser Glu
65                  70                  75                  80

Asp Val Asp Ile Leu Lys Glu Leu Ser Ala Leu Thr Ala Leu Ser Leu
                85                  90                  95

Tyr Val Arg Arg Asn Pro Lys Lys Gly Ser Trp Ile Leu Phe Ser Lys
            100                 105                 110

Gly Phe Ala Val Leu Lys Tyr Phe Lys Phe Thr Cys Thr Ala Leu Cys
        115                 120                 125

Val Lys Phe Ser Glu Gln Ala Met Pro Ala Val Gln Arg Leu Asn Val
    130                 135                 140

Cys Phe Asn Ala Asn Thr Met Gln Gln Tyr Arg Pro Glu Asp Ala Gly
145                 150                 155                 160

Ile Trp Tyr Leu Ser Gly Leu Gln Val Ile Ser Ala Arg Ile Gly Ala
                165                 170                 175

Ala Gly Ile Asp Gln Ala Ser Arg Glu Ala Ala Lys Ser Arg Leu Leu
            180                 185                 190

Asp Ala Ile Leu Ser Asn His Pro Lys Pro Pro Ile Arg Asn Val
        195                 200                 205

Gln Met Val Asp Trp Val Ile His Gly Asp Thr Glu Glu Cys Ser Thr
    210                 215                 220

Gly Val Met Ile Arg Lys Asp Glu Ser Ser Arg Glu His Thr Arg Ser
225                 230                 235                 240
```

-continued

Phe Leu Ser Gln Phe Pro Phe Arg Arg Arg Pro Leu Leu Pro Ser Ile
            245                 250                 255

Phe Thr Arg Arg Gly Gln Asp Asp Glu Gln His Lys Ile Glu Glu Asn
            260                 265                 270

Asp Val Leu Gln Asp Ser Ile Ile Leu Arg Glu Ser Ser Ser Leu Met
            275                 280                 285

Gln Lys Pro Gly Trp Val Thr Arg Arg Ser Arg Ser Thr Gly Val Gly
            290                 295                 300

Leu Leu Met Ala Val Arg Gly Ser Thr Tyr Met Ile Arg Gln Tyr Ile
305                 310                 315                 320

Lys Glu Pro Gly Phe Asn Ala Ala Asn Glu Met Ala Ser Ile Asn Gln
            325                 330                 335

Glu Ile Arg Gln Ile Gly Arg Met Val Ile Ser Ser Asn Ile Leu Glu
            340                 345                 350

Pro Pro Glu Trp Ile Leu Gln Ala Gln Asp Leu Ala Cys Asp Val Gln
            355                 360                 365

Asp Phe Thr Asp Ile Tyr Thr Trp Leu Gln Ser Lys Ser Arg Arg Arg
            370                 375                 380

Ala Leu Ala His Ile Gly Tyr Ile Ala Gln Leu Lys Asp Arg Ile Ser
385                 390                 395                 400

Ser Leu Arg Glu Trp Gln Gln Arg Gly Gly Ser Ser Ser Ser Gln Gln
            405                 410                 415

Glu Arg Ala Ala Ala Leu Ser Phe Ser Arg Arg Ser Cys Gly Pro Cys
            420                 425                 430

Ala Pro Glu Asp Val Leu Val Gly Ile Asp Gln Pro Arg Lys Glu Leu
            435                 440                 445

Ser Asp Leu Ile Phe Glu Arg Glu Asp Val Val Gln Gln Lys Pro Arg
            450                 455                 460

Val Val Ser Val Val Gly Tyr Ser Gly Ile Gly Lys Thr Ala Leu Ala
465                 470                 475                 480

Arg Ala Val Tyr Tyr Asp Pro Ser Val Arg Ser Ala Phe Asn Gly Val
            485                 490                 495

Ala Trp Val Val Ala Ser Glu Cys Asn His Gly Cys Asp Leu Val Ser
            500                 505                 510

Lys Ile Cys Gln Gln Val Lys Asp Glu Gln Ala Gly Asn Gly Ala Val
            515                 520                 525

Val Pro Asp Cys Tyr Arg Leu Lys Glu Ile Met Arg Asp Lys Arg Phe
            530                 535                 540

Phe Ile Val Ile Asp Asp Leu Gln Gly Ala Gly Met Trp Asn Asp Ile
545                 550                 555                 560

Lys Gly Val Phe Ser Glu Thr His Ser Gly Ser Arg Ile Ile Val Thr
            565                 570                 575

Thr Ser Ile Gln Ser Val Ala Ala Ala Cys Thr Pro Glu Pro Arg Tyr
            580                 585                 590

Ile Tyr Arg Met Pro Ser Leu Gly Asn Leu Asp Ser Glu Lys Leu Leu
            595                 600                 605

Trp Met Arg Val Gly Arg His Ala Ser Arg Thr Pro Ala Leu Glu His
            610                 615                 620

Ala Leu Gly Asn Asp Thr Leu Lys Lys Cys Gly Gly Leu Pro Leu Ala
625                 630                 635                 640

Leu Ile Ser Val Ala Asn His Leu Cys Leu Gly Lys Ala Leu Phe Glu
            645                 650                 655

```
Glu Met Asp Arg Val Leu Ala Lys Cys Tyr Asp Ser Leu Pro Asp Asn
        660                 665                 670

Ala His Arg Met Cys Leu Leu Ser Leu Ser Thr Phe Pro Gln Gly His
        675                 680                 685

Val Met Lys Arg Lys Arg Leu Ile Arg Arg Trp Ile Ala Glu Gly Leu
        690                 695                 700

Ala Val Gly Asp Cys Glu Leu Ser Ala Glu Gln Val Ala Gly Asn Ile
705                 710                 715                 720

Phe Asp Val Leu Ile Asp Arg Asn Val Thr Glu Pro Val Leu Thr Ala
                725                 730                 735

Gly His Gly Ser Ser Lys Val Lys Ala Cys Leu Val Leu Gly Val
                740                 745                 750

Ile Lys Asp Phe Ile Asn Lys Thr Ala Val Ser Asn Glu Thr Val Ala
                755                 760                 765

Ile Ile Gln Asn Asp Glu Leu Leu Pro Asn Arg Met Met Leu Val
                770                 775                 780

Ala His Arg Pro Val Arg Arg Leu Leu Val His Gly Thr Thr Lys
785                 790                 795                 800

Lys Ser Glu Ala Val Ala Lys Ala Ile Gly Leu Asp Gln Val Arg Ser
                805                 810                 815

Leu Thr Ile Cys Asn Ala Val Pro Phe Asp Phe Gln Gly Cys Trp Leu
                820                 825                 830

Leu Arg Val Leu Asp Leu Glu Ala Cys Gln Gly Ile Asp Lys Ser Ile
                835                 840                 845

Leu Gly Ser Ile Cys Lys Leu Val Phe Leu Lys Tyr Leu Ser Leu Arg
850                 855                 860

Gly Thr Asp Val Tyr Gly Ile Pro Lys Lys Val Lys Lys Leu Gln Arg
865                 870                 875                 880

Leu Glu Thr Leu Asp Leu Arg Asp Thr Arg Val Glu Glu Leu Pro Ile
                885                 890                 895

Gln Val Leu Met Leu Pro Arg Leu Ala His Leu Phe Gly Lys Phe Glu
                900                 905                 910

Leu Pro Pro Gln Leu Lys His Gly His Arg Thr Ala Arg Arg Arg
                915                 920                 925

Ser Arg Leu Gln Ala Phe Phe Ser Gln Arg Ser Arg Leu Gln Thr Leu
930                 935                 940

Ser Gly Phe Val Met Val Asp Asp Ser Asn Ser Phe Glu His Met Met
945                 950                 955                 960

Ile Thr Ile Lys Ser Leu Arg Lys Val Lys Val Trp Cys Lys Asn Ser
                965                 970                 975

Ile Ser Ser His Gln Glu Arg His Leu Ala Ser Ser Leu Gln Gln Arg
                980                 985                 990

Leu Val Gly Asn Ser Asn Pro Leu Glu Ser Leu Ser Ile Asp Phe Gly
        995                 1000                1005

Asn Glu Ser Ile Asn Phe Leu Asn Asp Val Gly Ala Thr Ser Ala
        1010                1015                1020

Leu Ile Gly Ser Met Lys Leu Gln Gly Arg Leu Thr Ser Leu Pro
        1025                1030                1035

Ser Phe Met Thr Ser Tyr Asp Thr Thr Leu Ser Gln Leu Gln Leu
        1040                1045                1050

Ser Ser Thr Gly Leu Gly Ile Glu Ala Leu Ser Leu Leu Gln Ile
        1055                1060                1065

Leu Arg Arg Leu Val Ser Leu Lys Leu Ala Gln Asp Gly Asp Gly
```

```
                         1070                1075                1080

Phe Trp Gly Asp Cys Phe Ala Val Asn Lys Asp Gly Phe Pro Ser
    1085                1090                1095

Leu Leu Arg Leu Cys Ile Gln Ala Arg Glu Leu Pro Gln Leu His
        1100                1105                1110

Ile His Glu Gly Gly Met Ser Ser Leu Thr Ser Leu Glu Leu Leu
    1115                1120                1125

Cys Pro Met Phe Ala Ser Arg Gly His Ser Asp Ser Asp Ser Asp
        1130                1135                1140

Ser Asp Leu Gly Lys Thr Tyr Val Glu Thr His Ser Glu Lys Arg
1145                1150                1155

Ser Lys Gln Val Leu Ser Val Glu Lys Pro Lys Ala Val Asp Pro
    1160                1165                1170

Gly Ile Ser Phe Lys Glu Pro Ser Ser Glu Thr Arg Ser Glu Gly
        1175                1180                1185

Thr Glu Ile Gln Glu Ile Asp Ser Pro Lys Thr Ser Lys Glu Ala
    1190                1195                1200

Gly Pro Ser Ile Gly Phe Lys Asp Ile Ile Leu Pro Glu Asn Thr
    1205                1210                1215

Phe Arg Arg Asn Phe Ser Lys Glu Val Lys Ser Arg Phe Asp Leu
    1220                1225                1230

Lys Gln His Phe Lys Gly Met Glu Tyr Leu Gln Cys Leu Asn Glu
    1235                1240                1245

Leu Val Leu His Cys Ser Val Ser Asp Glu Val Leu Asp Ala Trp
    1250                1255                1260

Thr Lys Arg Ala Ser Ser His Ile Asn Arg Pro Lys Val Thr Arg
    1265                1270                1275

Gln Cys Thr Arg Ala Ala Leu Ser Ile Gly Arg Gly Pro Gly Thr
    1280                1285                1290

Ala Lys His Glu Lys Glu Gly Gln His Arg Ser Gln Leu Met Lys
    1295                1300                1305

Ile Glu Val Gln Lys Gln Gln Ser Met Arg Arg
    1310                1315

<210> SEQ ID NO 55
<211> LENGTH: 1032
<212> TYPE: PRT
<213> ORGANISM: Zea mays

<400> SEQUENCE: 55

Met Val Met Asp Phe Gly Gly Asp Cys Phe Ala Val Asn Lys Asp Gly
1               5                   10                  15

Phe Pro Ser Leu Leu Arg Leu Cys Ile Gln Ala Arg Glu Leu Pro Gln
            20                  25                  30

Leu His Ile His Glu Gly Gly Met Ser Ser Leu Thr Ser Leu Glu Leu
        35                  40                  45

Leu Cys Pro Met Phe Ala Ser Arg Gly His Ser Asp Ser Asp Ser Asp
    50                  55                  60

Ser Asp Leu Gly Lys Thr Tyr Val Glu Thr His Ser Glu Lys Arg Ser
65                  70                  75                  80

Lys Gln Val Leu Ser Val Glu Lys Pro Lys Ala Val Asp Pro Gly Ile
                85                  90                  95

Ser Phe Lys Glu Pro Ser Ser Glu Thr Arg Ser Glu Gly Thr Glu Ile
            100                 105                 110
```

```
Gln Glu Ile Asp Ser Pro Lys Thr Ser Lys Ala Gly Pro Ser Ile
        115                 120                 125

Gly Phe Lys Asp Ile Ile Leu Pro Glu Asn Thr Phe Arg Arg Asn Phe
130                 135                 140

Ser Lys Glu Val Lys Ser Arg Phe Asp Leu Lys Gln His Phe Lys Gly
145                 150                 155                 160

Met Glu Tyr Leu Gln Cys Leu Asn Glu Leu Val Leu His Cys Ser Val
                165                 170                 175

Ser Asp Glu Val Leu Asp Ala Trp Thr Lys Arg Ala Ser Ser His Ile
                180                 185                 190

Asn Arg Pro Lys Val Thr Arg Gln Cys Thr Arg Ala Ala Leu Ser Ile
                195                 200                 205

Gly Arg Gly Pro Gly Thr Ala Lys His Glu Lys Glu Gly Gln His Arg
210                 215                 220

Ser Gln Leu Met Lys Asn Arg Gly Ser Glu Thr Ala Ile His Glu Glu
225                 230                 235                 240

Val Ala Glu Gln His Ser Ser Val Gly Thr Ser Arg Glu Glu Ala Gly
                245                 250                 255

Leu Phe Gln Glu Gln Thr Ser Asp Thr Gly His Lys Glu Glu Glu Glu
                260                 265                 270

Glu Glu Glu Glu Glu Cys Thr Ser Glu Asp Arg Ala Leu Asn Gln Pro
        275                 280                 285

Cys Asp Met Leu Ile Gly Met Asp Val Ala Ile Arg Glu Leu Leu Glu
        290                 295                 300

Leu Val Asn Leu Glu Glu Phe Gly Val Asp Asp Lys Val Ile Ser Ile
305                 310                 315                 320

Val Gly Cys Pro Gly Leu Gly Lys Thr Thr Leu Ala Lys Ala Phe Ser
                325                 330                 335

Asn Leu Glu Met Ile Arg Glu Arg Phe Asn Pro Val Trp Val Ser
                340                 345                 350

Ala Ser Gln Cys Arg Ser Ala Gln Asp Leu Leu Ile Lys Val Ile Arg
                355                 360                 365

Gln Ala Ser His Val His Pro Ala Gln Met Ile Ser Ala Thr Pro Asn
370                 375                 380

Ile Asp Leu Leu Gln Thr Ile Leu Ala Gln Glu Ser Leu Leu Ile Ile
385                 390                 395                 400

Ile Asp Asp Leu Arg Glu Thr Thr Ala Trp Asn Ser Ile Glu Thr Ala
                405                 410                 415

Leu Gly Ser Thr Thr Ser Thr His Ala Gly Ser Leu Ile Ile Val Thr
                420                 425                 430

Thr Arg Ile Gln Ser Ile Ala Gly Lys Cys Ser Pro His Arg Tyr Ile
                435                 440                 445

Tyr Arg Met Pro Gly Leu Gly His Pro Glu Ser Lys Glu Leu Phe Leu
450                 455                 460

Arg Thr Ala Tyr Gly Asp Ala His Pro Thr Pro Gly Val Ala Asp Ala
465                 470                 475                 480

Val Glu Glu Ile Ser Gly Ala Cys Asp Gly Leu Pro Leu Ala Leu Val
                485                 490                 495

Ser Ala Ala His Asp Trp Arg Glu Arg Gln Gly Gln Gly Trp Glu Gly
                500                 505                 510

Arg Tyr Val Phe Glu Glu Val Asn Arg Ala Phe Ser Trp Trp Tyr Glu
                515                 520                 525

Ser Leu Ala Asp Ala Ala His Met Leu Ser Leu Gly Ile Phe Pro Tyr
```

```
            530             535             540
Gly His Ser Ile Lys Arg Lys Ser Leu Ile Arg Arg Trp Ile Ala Glu
545                 550                 555                 560

Gly Leu Val Ser Glu Lys Asp Gly Asp Gln Arg Phe His Glu Leu
                565                 570                 575

Val Asp Gln Ser Ile Val Glu Pro Val Leu Ile Thr Gly Ser Ser Asp
                580                 585                 590

Phe Lys Val Lys Arg Phe Arg Leu Arg Arg Pro Val Leu Glu Phe Ile
                595                 600                 605

Val Arg Glu Ser Val Ser Lys Asn Met Val Lys Leu Leu Gln Gly Asp
            610                 615                 620

Glu Pro Leu Pro Gly Glu Gly Gly Pro Val Val Ser Ile Tyr Gln
625                 630                 635                 640

Thr Thr Asp Thr Glu Thr Ser Arg Gly Asn Ile Met Ser Phe Ser Ile
                645                 650                 655

Phe Asn Lys Gly Val Ala Phe Asp Asp Leu Gln Gln Cys Thr Tyr Leu
                660                 665                 670

Arg Val Leu Asp Leu Glu Arg Cys Arg Gly Val Asp His Ser Val Val
            675                 680                 685

Ala Gly Ile Cys Lys Leu Ser Leu Leu Arg Tyr Leu Ser Leu Arg Gly
690                 695                 700

Ser Asp Val Arg His Ile Pro Arg Glu Thr Lys Arg Leu Lys Cys Leu
705                 710                 715                 720

Glu Thr Leu Asp Ile Arg Glu Thr Val Asn Asn Leu Pro Val Ala
                725                 730                 735

Ala Leu Met Leu Pro Arg Leu Val His Leu Phe Gly Lys Phe Glu Leu
                740                 745                 750

Pro Arg Lys Leu Glu Asp Glu Arg Ile Arg Gly Lys Leu Glu Arg Phe
                755                 760                 765

Phe Arg Glu Glu Ser Arg Leu Gln Thr Leu Ala Gly Leu Ile Ile Ser
                770                 775                 780

Lys Asn Asn Gly Tyr Glu His Ile Val Ile His Ile Arg Leu Leu Arg
785                 790                 795                 800

Lys Ile Lys Ile Trp Tyr Gln Asn His Leu Leu His Tyr Ser Thr Leu
                805                 810                 815

Leu Asn Glu Leu Phe Ile Arg Asn Thr Ala Leu Asp Ser Leu Ser Val
            820                 825                 830

Asp Phe Gly Asp Ser Leu Met Phe Pro His Ile Ser Asp Ile Phe Gly
                835                 840                 845

Pro Cys Met Leu Arg Ser Ile Lys Leu Arg Gly Arg His Trp Pro Leu
850                 855                 860

Pro Thr Ile Ile Ala Ser Ser Ala Asn Tyr Leu Ser Glu Val Gln Leu
865                 870                 875                 880

Ser Ser Thr Val Leu Pro Leu Arg Tyr Leu Ser Thr Leu Gln Ser Leu
                885                 890                 895

Arg Arg Leu Leu Tyr Leu Lys Leu Val Ala Asp Gly Phe Val Gly Asp
                900                 905                 910

Asp Thr Asp Thr Phe Thr Val Lys Lys Asp Gly Phe Pro Ser Leu Glu
            915                 920                 925

Arg Leu Cys Ile Glu Ala Pro Lys Leu Pro His Leu Arg Ile Val Glu
            930                 935                 940

Gly Ala Met Pro Ala Leu Thr Ser Leu His Leu Leu Cys Pro Thr Met
945                 950                 955                 960
```

Thr Met Met Pro Gln His Pro Gly Gln Met Gly Ile Asp Glu Pro
            965                 970                 975

Glu Ala Thr Ser Glu Thr Lys Leu Gly Lys Glu Trp Gly Ile Glu Tyr
        980                 985                 990

Leu Arg Asn Leu Asn Asp Leu Val  Leu Pro Tyr Thr Val Gly Asp Glu
        995                 1000                1005

Gln Leu Asp Phe Trp Lys Glu  Lys Ala Arg Ser Asn  Met Asn Arg
    1010                1015                 1020

Pro Lys Val Thr Arg Gln Pro  Lys Pro
1025                1030

<210> SEQ ID NO 56
<211> LENGTH: 808
<212> TYPE: PRT
<213> ORGANISM: Zea mays

<400> SEQUENCE: 56

Met Arg Asp Lys Arg Phe Phe Ile Val Ile Asp Asp Leu Gln Gly Ala
1               5                   10                  15

Gly Met Trp Asn Asp Ile Lys Gly Val Phe Ser Glu Thr His Ser Gly
            20                  25                  30

Ser Arg Ile Ile Val Thr Thr Ser Ile Gln Ser Val Ala Ala Ala Cys
        35                  40                  45

Thr Pro Glu Pro Arg Tyr Ile Tyr Arg Met Pro Ser Leu Gly Asn Leu
    50                  55                  60

Asp Ser Glu Lys Leu Leu Trp Met Arg Val Gly Arg His Ala Ser Arg
65                  70                  75                  80

Thr Pro Ala Leu Glu His Ala Leu Gly Asn Asp Thr Leu Lys Lys Cys
                85                  90                  95

Gly Gly Leu Pro Leu Ala Leu Ile Ser Val Ala Asn His Leu Cys Leu
            100                 105                 110

Gly Lys Ala Leu Phe Glu Glu Met Asp Arg Val Leu Ala Lys Cys Tyr
        115                 120                 125

Asp Ser Leu Pro Asp Asn Ala His Arg Met Cys Leu Leu Ser Leu Ser
    130                 135                 140

Thr Phe Pro Gln Gly His Val Met Lys Arg Lys Arg Leu Ile Arg Arg
145                 150                 155                 160

Trp Ile Ala Glu Gly Leu Ala Val Gly Asp Cys Glu Leu Ser Ala Glu
                165                 170                 175

Gln Val Ala Gly Asn Ile Phe Asp Val Leu Ile Asp Arg Asn Val Thr
            180                 185                 190

Glu Pro Val Leu Thr Ala Gly His Gly Ser Ser Ser Lys Val Lys Ala
        195                 200                 205

Cys Leu Val Leu Gly Val Ile Lys Asp Phe Ile Asn Lys Thr Ala Val
    210                 215                 220

Ser Asn Glu Thr Val Ala Ile Ile Gln Asn Asp Glu Leu Leu Leu Pro
225                 230                 235                 240

Asn Arg Met Met Leu Val Ala His Arg Pro Val Arg Arg Leu Leu Val
                245                 250                 255

His Gly Gly Thr Thr Lys Lys Ser Glu Ala Val Ala Lys Ala Ile Gly
            260                 265                 270

Leu Asp Gln Val Arg Ser Leu Thr Ile Cys Asn Ala Val Pro Phe Asp
        275                 280                 285

Phe Gln Gly Cys Trp Leu Leu Arg Val Leu Asp Leu Glu Ala Cys Gln

```
                290             295             300
Gly Ile Asp Lys Ser Ile Leu Gly Ser Ile Cys Lys Leu Val Phe Leu
305                 310                 315                 320

Lys Tyr Leu Ser Leu Arg Gly Thr Asp Val Tyr Gly Ile Pro Lys Lys
                325                 330                 335

Val Lys Lys Leu Gln Arg Leu Glu Thr Leu Asp Leu Arg Asp Thr Arg
            340                 345                 350

Val Glu Glu Leu Pro Ile Gln Val Leu Met Leu Pro Arg Leu Ala His
        355                 360                 365

Leu Phe Gly Lys Phe Glu Leu Pro Pro Gln Leu Lys His Gly His Arg
    370                 375                 380

Thr Ala Arg Arg Arg Ser Arg Leu Gln Ala Phe Phe Ser Gln Arg
385                 390                 395                 400

Ser Arg Leu Gln Thr Leu Ser Gly Phe Val Met Val Asp Asp Ser Asn
                405                 410                 415

Ser Phe Glu His Met Met Ile Thr Ile Lys Ser Leu Arg Lys Val Lys
                420                 425                 430

Val Trp Cys Lys Asn Ser Ile Ser Ser His Gln Glu Arg His Leu Ala
            435                 440                 445

Ser Ser Leu Gln Gln Arg Leu Val Gly Asn Ser Asn Pro Leu Glu Ser
450                 455                 460

Leu Ser Ile Asp Phe Gly Asn Glu Ser Ile Asn Phe Leu Asn Asp Val
465                 470                 475                 480

Gly Ala Thr Ser Ala Leu Ile Gly Ser Met Lys Leu Gln Gly Arg Leu
                485                 490                 495

Thr Ser Leu Pro Ser Phe Met Thr Ser Tyr Asp Thr Thr Leu Ser Gln
                500                 505                 510

Leu Gln Leu Ser Ser Thr Gly Leu Gly Ile Glu Ala Leu Ser Leu Leu
                515                 520                 525

Gln Ile Leu Arg Arg Leu Val Ser Leu Lys Leu Ala Gln Asp Gly Asp
            530                 535                 540

Gly Phe Trp Gly Asp Cys Phe Ala Val Asn Lys Asp Gly Phe Pro Ser
545                 550                 555                 560

Leu Leu Arg Leu Cys Ile Gln Ala Arg Glu Leu Pro Gln Leu His Ile
                565                 570                 575

His Glu Gly Gly Met Ser Ser Leu Thr Ser Leu Glu Leu Leu Cys Pro
                580                 585                 590

Met Phe Ala Ser Arg Gly His Ser Asp Ser Asp Ser Asp Ser Asp Leu
            595                 600                 605

Gly Lys Thr Tyr Val Glu Thr His Ser Glu Lys Arg Ser Lys Gln Val
            610                 615                 620

Leu Ser Val Glu Lys Pro Lys Ala Val Asp Pro Gly Ile Ser Phe Lys
625                 630                 635                 640

Glu Pro Ser Ser Glu Thr Arg Ser Glu Gly Thr Glu Ile Gln Glu Ile
                645                 650                 655

Asp Ser Pro Lys Thr Ser Lys Glu Ala Gly Pro Ser Ile Gly Phe Lys
                660                 665                 670

Asp Ile Ile Leu Pro Glu Asn Thr Phe Arg Arg Asn Phe Ser Lys Glu
                675                 680                 685

Val Lys Ser Arg Phe Asp Leu Lys Gln His Phe Lys Gly Met Glu Tyr
                690                 695                 700

Leu Gln Cys Leu Asn Glu Leu Val Leu His Cys Ser Val Ser Asp Glu
705                 710                 715                 720
```

```
Val Leu Asp Ala Trp Thr Lys Arg Ala Ser Ser His Ile Asn Arg Pro
                725                 730                 735

Lys Val Thr Arg Gln Cys Thr Arg Ala Ala Leu Ser Ile Gly Arg Gly
                740                 745                 750

Pro Gly Thr Ala Lys His Glu Lys Glu Gly Gln His Arg Ser Gln Leu
                755                 760                 765

Met Lys Asn Arg Gly Ser Glu Thr Ala Ile His Glu Val Ala Glu
    770                 775                 780

Gln His Ser Ser Val Gly Thr Ser Arg Glu Glu Ala Gly Leu Phe Gln
785                 790                 795                 800

Glu Gln Thr Ser Asp Thr Gly His
                805

<210> SEQ ID NO 57
<211> LENGTH: 497
<212> TYPE: PRT
<213> ORGANISM: Zea mays

<400> SEQUENCE: 57

Met Leu Ser Leu Gly Ile Phe Pro Tyr Gly His Ser Ile Lys Arg Lys
1               5                   10                  15

Ser Leu Ile Arg Arg Trp Ile Ala Glu Gly Leu Val Ser Glu Glu Lys
                20                  25                  30

Asp Gly Asp Gln Arg Phe His Glu Leu Val Asp Gln Ser Ile Val Glu
            35                  40                  45

Pro Val Leu Ile Thr Gly Ser Ser Asp Phe Lys Val Lys Arg Phe Arg
    50                  55                  60

Leu Arg Arg Pro Val Leu Glu Phe Ile Val Arg Glu Ser Val Ser Lys
65                  70                  75                  80

Asn Met Val Lys Leu Leu Gln Gly Asp Glu Pro Leu Pro Gly Glu Gly
                85                  90                  95

Gly Gly Pro Val Val Ser Ile Tyr Gln Thr Thr Asp Thr Glu Thr Ser
            100                 105                 110

Arg Gly Asn Ile Met Ser Phe Ser Ile Phe Asn Lys Gly Val Ala Phe
        115                 120                 125

Asp Asp Leu Gln Gln Cys Thr Tyr Leu Arg Val Leu Asp Leu Glu Arg
    130                 135                 140

Cys Arg Gly Val Asp His Ser Val Val Ala Gly Ile Cys Lys Leu Ser
145                 150                 155                 160

Leu Leu Arg Tyr Leu Ser Leu Arg Gly Ser Asp Val Arg His Ile Pro
                165                 170                 175

Arg Glu Thr Lys Arg Leu Lys Cys Leu Glu Thr Leu Asp Ile Arg Glu
            180                 185                 190

Thr Val Val Asn Asn Leu Pro Val Ala Ala Leu Met Leu Pro Arg Leu
        195                 200                 205

Val His Leu Phe Gly Lys Phe Glu Leu Pro Arg Lys Leu Glu Asp Glu
    210                 215                 220

Arg Ile Arg Gly Lys Leu Glu Arg Phe Phe Arg Glu Glu Ser Arg Leu
225                 230                 235                 240

Gln Thr Leu Ala Gly Leu Ile Ile Ser Lys Asn Gly Tyr Glu His
                245                 250                 255

Ile Val Ile His Ile Arg Leu Leu Arg Lys Ile Lys Ile Trp Tyr Gln
            260                 265                 270

Asn His Leu Leu His Tyr Ser Thr Leu Leu Asn Glu Leu Phe Ile Arg
```

-continued

```
            275                 280                 285
Asn Thr Ala Leu Asp Ser Leu Ser Val Asp Phe Gly Asp Ser Leu Met
    290                 295                 300

Phe Pro His Ile Ser Asp Ile Phe Gly Pro Cys Met Leu Arg Ser Ile
305                 310                 315                 320

Lys Leu Arg Gly Arg His Trp Pro Leu Pro Thr Ile Ile Ala Ser Ser
                325                 330                 335

Ala Asn Tyr Leu Ser Glu Val Gln Leu Ser Ser Thr Val Leu Pro Leu
            340                 345                 350

Arg Tyr Leu Ser Thr Leu Gln Ser Leu Arg Arg Leu Leu Tyr Leu Lys
        355                 360                 365

Leu Val Ala Asp Gly Phe Val Gly Asp Asp Thr Asp Thr Phe Thr Val
    370                 375                 380

Lys Lys Asp Gly Phe Pro Ser Leu Glu Arg Leu Cys Ile Glu Ala Pro
385                 390                 395                 400

Lys Leu Pro His Leu Arg Ile Val Glu Gly Ala Met Pro Ala Leu Thr
                405                 410                 415

Ser Leu His Leu Leu Cys Pro Thr Met Thr Met Pro Gln His Pro
            420                 425                 430

Gly Gln Met Gly Glu Ile Asp Glu Pro Glu Ala Thr Ser Glu Thr Lys
        435                 440                 445

Leu Gly Lys Glu Trp Gly Ile Glu Tyr Leu Arg Asn Leu Asn Asp Leu
    450                 455                 460

Val Leu Pro Tyr Thr Val Gly Asp Glu Gln Leu Asp Phe Trp Lys Glu
465                 470                 475                 480

Lys Ala Arg Ser Asn Met Asn Arg Pro Lys Val Thr Arg Gln Pro Lys
                485                 490                 495

Pro

<210> SEQ ID NO 58
<211> LENGTH: 447
<212> TYPE: PRT
<213> ORGANISM: Zea mays

<400> SEQUENCE: 58

Met Leu Pro Arg Leu Ala His Leu Phe Gly Lys Phe Glu Leu Pro Pro
1               5                   10                  15

Gln Leu Lys His Gly His Arg Thr Ala Arg Arg Arg Ser Arg Leu
                20                  25                  30

Gln Ala Phe Phe Ser Gln Arg Ser Arg Leu Gln Thr Leu Ser Gly Phe
            35                  40                  45

Val Met Val Asp Asp Ser Asn Ser Phe Glu His Met Met Ile Thr Ile
    50                  55                  60

Lys Ser Leu Arg Lys Val Lys Val Trp Cys Lys Asn Ser Ile Ser Ser
65                  70                  75                  80

His Gln Glu Arg His Leu Ala Ser Ser Leu Gln Arg Leu Val Gly
                85                  90                  95

Asn Ser Asn Pro Leu Glu Ser Leu Ser Ile Asp Phe Gly Asn Glu Ser
            100                 105                 110

Ile Asn Phe Leu Asn Asp Val Gly Ala Thr Ser Ala Leu Ile Gly Ser
        115                 120                 125

Met Lys Leu Gln Gly Arg Leu Thr Ser Leu Pro Ser Phe Met Thr Ser
    130                 135                 140

Tyr Asp Thr Thr Leu Ser Gln Leu Gln Leu Ser Ser Thr Gly Leu Gly
```

```
            145                 150                 155                 160
        Ile Glu Ala Leu Ser Leu Leu Gln Ile Leu Arg Arg Leu Val Ser Leu
                        165                 170                 175
        Lys Leu Ala Gln Asp Gly Asp Gly Phe Trp Gly Asp Cys Phe Ala Val
                        180                 185                 190
        Asn Lys Asp Gly Phe Pro Ser Leu Leu Arg Leu Cys Ile Gln Ala Arg
                    195                 200                 205
        Glu Leu Pro Gln Leu His Ile His Glu Gly Met Ser Ser Leu Thr
                210                 215                 220
        Ser Leu Glu Leu Leu Cys Pro Met Phe Ala Ser Arg Gly His Ser Asp
        225                 230                 235                 240
        Ser Asp Ser Asp Ser Asp Leu Gly Lys Thr Tyr Val Glu Thr His Ser
                        245                 250                 255
        Glu Lys Arg Ser Lys Gln Val Leu Ser Val Glu Lys Pro Lys Ala Val
                        260                 265                 270
        Asp Pro Gly Ile Ser Phe Lys Glu Pro Ser Ser Glu Thr Arg Ser Glu
                    275                 280                 285
        Gly Thr Glu Ile Gln Glu Ile Asp Ser Pro Lys Thr Ser Lys Glu Ala
                290                 295                 300
        Gly Pro Ser Ile Gly Phe Lys Asp Ile Ile Leu Pro Glu Asn Thr Phe
        305                 310                 315                 320
        Arg Arg Asn Phe Ser Lys Glu Val Lys Ser Arg Phe Asp Leu Lys Gln
                        325                 330                 335
        His Phe Lys Gly Met Glu Tyr Leu Gln Cys Leu Asn Glu Leu Val Leu
                        340                 345                 350
        His Cys Ser Val Ser Asp Glu Val Leu Asp Ala Trp Thr Lys Arg Ala
                    355                 360                 365
        Ser Ser His Ile Asn Arg Pro Lys Val Thr Arg Gln Cys Thr Arg Ala
                370                 375                 380
        Ala Leu Ser Ile Gly Arg Gly Pro Gly Thr Ala Lys His Glu Lys Glu
        385                 390                 395                 400
        Gly Gln His Arg Ser Gln Leu Met Lys Asn Arg Gly Ser Glu Thr Ala
                        405                 410                 415
        Ile His Glu Glu Val Ala Glu Gln His Ser Ser Val Gly Thr Ser Arg
                        420                 425                 430
        Glu Glu Ala Gly Leu Phe Gln Glu Gln Thr Ser Asp Thr Gly His
                    435                 440                 445
```

METHODS OF IDENTIFYING, SELECTING, AND PRODUCING SOUTHERN CORN RUST RESISTANT CROPS

CROSS REFERENCE TO RELATED APPLICATIONS

This application claims priority to International Patent Application No. PCT/CN2019/115925, filed Nov. 6, 2019, the disclosure of which is hereby expressly incorporated by reference in its entirety.

FIELD OF THE INVENTION

The field is related to plant breeding and methods of identifying and selecting plants with resistance to southern corn rust. Provided are methods to identify novel genes that encode proteins providing plant resistance to southern corn rust and uses thereof. These disease resistant genes are useful in the production of resistant plants through breeding, transgenic modification, or genome editing.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of RTS21631A_Seq_List.txt, a creation date of Oct. 26, 2020, and a size of 377 Kb. The sequence listing filed via EFS-Web is part of the specification and is hereby incorporated in its entirety by reference herein.

BACKGROUND

Corn southern rust (SCR), a fungal disease caused by Puccinia polysora Underw., is a major disease in the tropical regions and southern part of the US and China. If SCR reaches the temperate regions (e.g. US Midwest) at critical points in the growing season and if conditions are favorable for rust development, disease intensity can reach epidemic levels very quickly, resulting in severe yield losses. Temperate maize germplasm is in general susceptible to SCR. The identification and utilization of resistance lines and QTL in breeding programs to develop varieties resistance to SCR represent a cost-effective way in controlling SCR. Alternatively, varieties carrying genes responsible to SCR resistance may be developed by transgenic or genome editing technologies. Identification of resistance QTL and genes would accelerate the development of products resistance to SCR. Resistance lines (e.g. Brewbaker, J. L., et al. "General resistance in maize to southern rust (Puccinia polysora Underw.)." *Crop science* 51, no. 4 (2011): 1393-1409) or QTL (e.g. Jines, M. P., et al. "Mapping resistance to Southern rust in a tropical by temperate maize recombinant inbred topcross population." *Theoretical and Applied Genetics* 114, no. 4 (2007): 659-667. Zhang, Y., et al. "Mapping of southern corn rust-resistant genes in the W2D inbred line of maize (Zea mays L.)." *Molecular breeding* 25, no. 3 (2010): 433-439. Zhou C J, et al. (2007) Characterization and fine mapping of RppQ, a resistance gene to southern corn rust in maize. *Mol Genet Genomics* 278:723-728. Holland, J. B., et al. "Inheritance of resistance to southern corn rust in tropical-by-corn-belt maize populations." *Theoretical and Applied Genetics* 96, no. 2 (1998): 232-241.) have been identified. However, none of the causal genes responsible for SCR resistance have been identified and characterized. There is a continuous need for disease-resistant plants and methods to find disease resistant genes.

SUMMARY

Compositions and methods useful in identifying and selecting plant disease resistance genes, or "R genes," are provided herein. The compositions and methods are useful in selecting disease resistant plants, creating transgenic resistant plants, and/or creating resistant genome edited plants. Plants having newly conferred or enhanced resistance various plant diseases as compared to control plants are also provided herein. In some embodiments, the compositions and methods are useful in selecting corn southern rust (SCR) disease resistant plants, creating transgenic SCR resistant plants, and/or creating SCR resistant genome edited plants.

An SCR resistant plant may be crossed to a second plant in order to obtain a progeny plant that has the resistant gene allele. The disease resistance may be newly conferred or enhanced relative to a control plant that does not have the favorable allele. The SCR R gene allele may be further refined to a chromosomal interval defined by and including defined markers. In some embodiments, the methods for identifying and/or selecting plants having resistance to SCR are presented. In these methods, DNA of a plant is analyzed for the presence of a resistant gene allele on chromosome 4 that is associated with SCR resistance, wherein said resistant gene allele comprises a "T" at PM01-000058W (position 99 of reference sequence SEQ ID NO: 11), a "G" at SOURST-83_1284720 (position 51 of reference sequence SEQ ID NO: 21), a "C" at SOURST-83_1314662 (position 24 of reference sequence SEQ ID NO: 19), a "T" at SOURST-83_1542053 (position 51 of reference sequence SEQ ID NO: 22), an "A" at PZE-104005694 (position 25 of reference sequence SEQ ID NO: 23), a "C" at SOURST-83_III (position 32 of reference sequence SEQ ID NO: 24), a "C" at SOURST-83_1936804 (position 30 of reference sequence SEQ ID NO: 32), a "G" at PZE-104001404 (position 26 of reference sequence SEQ ID NO: 25), a "C" at SOURST-83_1926276 (position 26 of reference sequence SEQ ID NO: 26), a "G" at SOURST-83_1652968 (position 26 of reference sequence SEQ ID NO: 27), an "A" at SOURST-83_2036602 (position 24 of reference sequence SEQ ID NO: 20), a "T" at SOURST-83_2035716 (position 35 of reference sequence SEQ ID NO: 28), a "T" at PZE-104001592 (position 46 of reference sequence SEQ ID NO: 29), a "G" at SOURST-83_2465654 (position 51 of reference sequence SEQ ID NO: 30), and a "T" at SOURST-83_2679982 (position 26 of reference sequence SEQ ID NO: 31), and a plant is identified and/or selected as having SCR resistance if said resistant gene allele is detected. In some embodiments, the methods for identifying and/or selecting plants having resistance to SCR comprise detecting or selecting a genomic region comprising SEQ ID NO: 9 or 10. The SCR resistance may be newly conferred or enhanced relative to a control plant that does not have the favorable allele. In a further embodiment, the SCR resistant region comprises a gene encoding a polypeptide that confers or enhances resistance to SCR. In some embodiments, the polypeptide comprises the amino acid sequence as set forth in SEQ ID NO: 5, 6, 7, or 8.

In another embodiment, methods of identifying and/or selecting plants with SCR resistance are provided in which one or more marker alleles linked to and associated with any of: a "T" at PM01-000058W (position 99 of reference sequence SEQ ID NO: 11), a "G" at SOURST-83_1284720 (position 51 of reference sequence SEQ ID NO: 21), a "C" at SOURST-83_1314662 (position 24 of reference sequence SEQ ID NO: 19), a "T" at SOURST-83_1542053 (position 51 of reference sequence SEQ ID NO: 22), an "A" at PZE-104005694 (position 25 of reference sequence SEQ ID NO: 23), a "C" at SOURST-83_1II (position 32 of reference sequence SEQ ID NO: 24), a "C" at SOURST-83_1936804 (position 30 of reference sequence SEQ ID NO: 32), a "G" at PZE-104001404 (position 26 of reference sequence SEQ ID NO: 25), a "C" at SOURST-83_1926276 (position 26 of reference sequence SEQ ID NO: 26), a "G" at SOURST-83_1652968 (position 26 of reference sequence SEQ ID NO: 27), an "A" at SOURST-83_2036602 (position 24 of reference sequence SEQ ID NO: 20), a "T" at SOURST-83_2035716 (position 35 of reference sequence SEQ ID NO: 28), a "T" at PZE-104001592 (position 46 of reference sequence SEQ ID NO: 29), a "G" at SOURST-83_2465654 (position 51 of reference sequence SEQ ID NO: 30), and a "T" at SOURST-83_2679982 (position 26 of reference sequence SEQ ID NO: 31), are detected in a plant, and a plant having the one or more marker alleles is selected. The one or more marker alleles may be linked by 10 cM, 9 cM, 8 cM, 7 cM, 6 cM, 5 cM, 4 cM, 3 cM, 2 cM, 1 cM, 0.9 cM, 0.8 cM, 0.7 cM, 0.6 cM, 0.5 cM, 0.4 cM, 0.3 cM, 0.2 cM, or 0.1 cM or less on a single meiosis based genetic map. The selected plant may be crossed to a second plant to obtain a progeny plant that has one or more marker alleles linked to and associated with any of a "T" at PM01-000058W (position 99 of reference sequence SEQ ID NO: 11), a "G" at SOURST-83_1284720 (position 51 of reference sequence SEQ ID NO: 21), a "C" at SOURST-83_1314662 (position 24 of reference sequence SEQ ID NO: 19), a "T" at SOURST-83_1542053 (position 51 of reference sequence SEQ ID NO: 22), an "A" at PZE-104005694 (position 25 of reference sequence SEQ ID NO: 23), a "C" at SOURST-83_1II (position 32 of reference sequence SEQ ID NO: 24), a "C" at SOURST-83_1936804 (position 30 of reference sequence SEQ ID NO: 32), a "G" at PZE-104001404 (position 26 of reference sequence SEQ ID NO: 25), a "C" at SOURST-83_1926276 (position 26 of reference sequence SEQ ID NO: 26), a "G" at SOURST-83_1652968 (position 26 of reference sequence SEQ ID NO: 27), an "A" at SOURST-83_2036602 (position 24 of reference sequence SEQ ID NO: 20), a "T" at SOURST-83_2035716 (position 35 of reference sequence SEQ ID NO: 28), a "T" at PZE-104001592 (position 46 of reference sequence SEQ ID NO: 29), a "G" at SOURST-83_2465654 (position 51 of reference sequence SEQ ID NO: 30), and a "T" at SOURST-83_2679982 (position 26 of reference sequence SEQ ID NO: 31).

In another embodiment, methods of introgressing a gene allele associated with SCR resistance are presented herein. In these methods, a population of plants is screened with one or more markers to determine if any of the plants has a gene allele associated with SCR resistance, and at least one plant that has the gene allele associated with SCR resistance is selected from the population. The gene allele comprises a "T" at PM01-000058W (position 99 of reference sequence SEQ ID NO: 11), a "G" at SOURST-83_1284720 (position 51 of reference sequence SEQ ID NO: 21), a "C" at SOURST-83_1314662 (position 24 of reference sequence SEQ ID NO: 19), a "T" at SOURST-83_1542053 (position 51 of reference sequence SEQ ID NO: 22), an "A" at PZE-104005694 (position 25 of reference sequence SEQ ID NO: 23), a "C" at SOURST-83_1II (position 32 of reference sequence SEQ ID NO: 24), a "C" at SOURST-83_1936804 (position 30 of reference sequence SEQ ID NO: 32), a "G" at PZE-104001404 (position 26 of reference sequence SEQ ID NO: 25), a "C" at SOURST-83_1926276 (position 26 of reference sequence SEQ ID NO: 26), a "G" at SOURST-83_1652968 (position 26 of reference sequence SEQ ID NO: 27), an "A" at SOURST-83_2036602 (position 24 of reference sequence SEQ ID NO: 20), a "T" at SOURST-83_2035716 (position 35 of reference sequence SEQ ID NO: 28), a "T" at PZE-104001592 (position 46 of reference sequence SEQ ID NO: 29), a "G" at SOURST-83_2465654 (position 51 of reference sequence SEQ ID NO: 30), and a "T" at SOURST-83_2679982 (position 26 of reference sequence SEQ ID NO: 31).

In some embodiments, introgression of SCR resistant genes from resistant to susceptible lines may be achieved either by marker-assisted trait introgression, transgenic, or genome editing approaches.

Embodiments include an isolated polynucleotide comprising a nucleotide sequence encoding a polypeptide capable of conferring resistance to SCR, wherein the polypeptide encodes an amino acid sequence of at least 50%, at least 75%, at least 80%, at least 85%, at least 90%, at least 95% identity, at least 96% identity, at least 97% identity, at least 98% identity, or at least 99% identity when compared to any one of SEQ ID NOs: 5-8.

Additional embodiments of the present disclosure include a vector comprising a polynucleotide of the disclosure, such as any one of SEQ ID NOs: 1-4, or a recombinant DNA construct comprising a polynucleotide disclosed herein operably linked to at least one regulatory sequence. A plant cell, as well as a plant, each comprising the recombinant DNA construct of an embodiment disclosed herein, and a seed comprising the recombinant DNA construct are also embodied.

In some embodiments, the compositions and methods relate to a modified plant having increased resistance to a disease, wherein the allele causing the increased disease resistance comprises a nucleotide sequence encoding a SCR resistance gene, wherein the SCR resistance gene is at least 50%, at least 75%, at least 80%, at least 85%, at least 90%, and at least 95% identity, at least 96% identity, at least 97% identity, at least 98% identity, or at least 99% identity to the sequence set forth in any one of SEQ ID NOs: 5-8.

The methods embodied by the present disclosure relate to a method for transforming a host cell, including a plant cell, comprising transforming the host cell with the polynucleotide of an embodiment of the present disclosure; a method for producing a plant comprising transforming a plant cell with the recombinant DNA construct of an embodiment of the present disclosure and regenerating a plant from the transformed plant cell, and methods of conferring or enhancing disease resistance, comprising transforming a plant with the recombinant DNA construct disclosed herein.

Methods of altering the level of expression of a protein capable of conferring disease resistance in a plant or plant cell comprising (a) transforming a plant cell with a recombinant DNA construct disclosed herein and (b) growing the transformed plant cell under conditions that are suitable for expression of the recombinant DNA construct wherein expression of the recombinant DNA construct results in production of altered levels of a protein capable of conferring disease resistance in the transformed host are also embodied.

Plants identified and/or selected using any of the methods presented above are also provided.

DESCRIPTION OF SEQUENCES

TABLE 1

Description of the sequences

| SEQ ID NO: | Description |
|---|---|
| 1 | NLR01-3_CDS |
| 2 | NLR01-2_CDS |
| 3 | NLR01-1_CDS |
| 4 | NLR02_CDS |
| 5 | CIMBL83_NLR01-3 protein |
| 6 | CIMBL83_NLR01-2 protein |
| 7 | CIMBL83_NLR01-1 protein |
| 8 | NLR02 protein |
| 9 | NLR01_Genomic (Including UTRs) |
| 10 | NLR02_genomic |
| 11 | PM01-000058W |
| 12 | PM01-00002MH |
| 13 | SOURST-83_1314662 Primer |
| 14 | SOURST-83_1314662 Primer |
| 15 | SOURST-83_1314662 Probe |
| 16 | SOURST-83_2036602 Primer |
| 17 | SOURST-83_2036602 Primer |
| 18 | SOURST-83_2036602 Probe |
| 19 | SOURST-83_1314662 Reference Sequence |
| 20 | SOURST-83_2036602 Reference Sequence |
| 21 | SOURST-83_1284720 Reference Sequence |
| 22 | SOURST-83_1542053 Reference Sequence |
| 23 | PZE-104005694 Reference Sequence |
| 24 | SOURST-83_1II Reference Sequence |
| 25 | PZE-104001404 Reference Sequence |
| 26 | SOURST-83_1926276 Reference Sequence |
| 27 | SOURST-83_1652968 Reference Sequence |
| 28 | SOURST-83_2035716 Reference Sequence |
| 29 | PZE-104001592 Reference Sequence |
| 30 | SOURST-83_2465654 Reference Sequence |
| 31 | SOURST-83_2679982 Reference Sequence |
| 32 | SOURST-83_1936804 Reference Sequence |
| 33 | NLR01-4_CDS |
| 34 | NLR01-5_CDS |
| 35 | NLR01-6_CDS |
| 36 | NLR01-7_CDS |
| 37 | NLR01-8_CDS |
| 38 | NLR01-9_CDS |
| 39 | NLR01-10_CDS |
| 40 | NLR01-11_CDS |
| 41 | NLR01-12_CDS |
| 42 | NLR01-13_CDS |
| 43 | NLR01-14_CDS |
| 44 | NLR01-15_CDS |
| 45 | NLR01-16_CDS |
| 46 | NLR01-4_protein |
| 47 | NLR01-5_protein |
| 48 | NLR01-6_protein |
| 49 | NLR01-7_protein |
| 50 | NLR01-8_protein |
| 51 | NLR01-9_protein |
| 52 | NLR01-10_protein |
| 53 | NLR01-11_protein |
| 54 | NLR01-12_protein |
| 55 | NLR01-13_protein |
| 56 | NLR01-14_protein |
| 57 | NLR01-15_protein |
| 58 | NLR01-16_protein |

DETAILED DESCRIPTION

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof, and so forth. All technical and scientific terms used herein have the same meaning as commonly understood to one of ordinary skill in the art to which this disclosure belongs unless clearly indicated otherwise.

The NBS-LRR ("NLR") group of R-genes is the largest class of R-genes discovered to date. In Arabidopsis thaliana, over 150 are predicted to be present in the genome (Meyers, et al., (2003), *Plant Cell*, 15:809-834; Monosi, et al., (2004), *Theoretical and Applied Genetics*, 109:1434-1447), while in rice, approximately 500 NLR genes have been predicted (Monosi, (2004) supra). The NBS-LRR class of R genes is comprised of two subclasses. Class 1 NLR genes contain a TIR-Toll/Interleukin-1 like domain at their N' terminus; which to date have only been found in dicots (Meyers, (2003) supra; Monosi, (2004) supra). The second class of NBS-LRR contain either a coiled-coil domain or an (nt) domain at their N terminus (Bai, et al. (2002) *Genome Research*, 12:1871-1884; Monosi, (2004) supra; Pan, et al., (2000), *Journal of Molecular Evolution*, 50:203-213). Class 2 NBS-LRR have been found in both dicot and monocot species. (Bai, (2002) supra; Meyers, (2003) supra; Monosi, (2004) supra; Pan, (2000) supra).

The NBS domain of the gene appears to have a role in signaling in plant defense mechanisms (van der Biezen, et al., (1998), *Current Biology: CB*, 8:R226-R227). The LRR region appears to be the region that interacts with the pathogen AVR products (Michelmore, et al., (1998), *Genome Res.*, 8:1113-1130; Meyers, (2003) supra). This LRR region in comparison with the NB-ARC (NBS) domain is under a much greater selection pressure to diversify (Michelmore, (1998) supra; Meyers, (2003) supra; Palomino, et al., (2002), *Genome Research*, 12:1305-1315). LRR domains are found in other contexts as well; these 20-29-residue motifs are present in tandem arrays in a number of proteins with diverse functions, such as hormone-receptor interactions, enzyme inhibition, cell adhesion and cellular trafficking. A number of recent studies revealed the involvement of LRR proteins in early mammalian development, neural development, cell polarization, regulation of gene expression and apoptosis signaling.

An allele is "associated with" a trait when it is part of or linked to a DNA sequence or allele that affects the expression of the trait. The presence of the allele is an indicator of how the trait will be expressed.

As used to herein, "disease resistant" or "have resistance to a disease" refers to a plant showing increase resistance to a disease compared to a control plant. Disease resistance may manifest in fewer and/or smaller lesions, increased plant health, increased yield, increased root mass, increased plant vigor, less or no discoloration, increased growth, reduced necrotic area, or reduced wilting. In some embodiments, an allele may show resistance one or more diseases.

Disease affecting maize plants include, but are not limited to, bacterial leaf blight and stalk rot; bacterial leaf spot; bacterial stripe; chocolate spot; goss's bacterial wilt and blight; holcus spot; purple leaf sheath; seed rot-seedling blight; bacterial wilt; corn stunt; anthracnose leaf blight; anthracnose stalk rot; aspergillus ear and kernel rot; banded leaf and sheath spot; black bundle disease; black kernel rot; borde blanco; brown spot; black spot; stalk rot; cephalosporium kernel rot; charcoal rot; corticium ear rot; curvularia leaf spot; didymella leaf spot; diplodia ear rot and stalk rot; diplodia ear rot; seed rot; corn seedling blight; diplodia leaf spot or leaf streak; downy mildews; brown stripe downy mildew; crazy top downy mildew; green ear downy mildew; graminicola downy mildew; java downy mildew; philippine downy mildew; sorghum downy mildew; spontaneum downy mildew; sugarcane downy mildew; dry ear rot; ergot; horse's tooth; corn eyespot; fusarium ear and stalk rot;

fusarium blight; seedling root rot; gibberella ear and stalk rot; gray ear rot; gray leaf spot; cercospora leaf spot; helminthosporium root rot; hormodendrum ear rot; cladosporium rot; hyalothyridium leaf spot; late wilt; northern leaf blight; white blast; crown stalk rot; corn stripe; northern leaf spot; helminthosporium ear rot; penicillium ear rot; corn blue eye; blue mold; phacocytostroma stalk rot and root rot; phacosphacria leaf spot; physalospora ear rot; botryosphaeria ear rot; pyrenochacta stalk rot and root rot; pythium root rot; pythium stalk rot; red kernel disease; rhizoctonia ear rot; sclerotial rot; rhizoctonia root rot and stalk rot; rostratum leaf spot; common corn rust; southern corn rust; tropical corn rust; sclerotium ear rot; southern blight; selenophoma leaf spot; sheath rot; shuck rot; silage mold; common smut; false smut; head smut; southern corn leaf blight and stalk rot; southern leaf spot; tar spot; trichoderma ear rot and root rot; white ear rot, root and stalk rot; yellow leaf blight; zonate leaf spot; american wheat striate (wheat striate mosaic); barley stripe mosaic; barley yellow dwarf; brome mosaic; cereal chlorotic mottle; lethal necrosis (maize lethal necrosis disease); cucumber mosaic; johnsongrass mosaic; maize bushy stunt; maize chlorotic dwarf; maize chlorotic mottle; maize dwarf mosaic; maize leaf fleck; maize pellucid ringspot; maize rayado fino; maize red leaf and red stripe; maize red stripe; maize ring mottle; maize rough dwarf; maize sterile stunt; maize streak; maize stripe; maize tassel abortion; maize vein enation; maize wallaby ear; maize white leaf; maize white line mosaic; millet red leaf; and northern cercal mosaic.

Disease affecting plants include, but are not limited to, bacterial blight; bacterial leaf streak; foot rot; grain rot; sheath brown rot; blast; brown spot; crown sheath rot; downy mildew; eyespot; false smut; kernel smut; leaf smut; leaf scald; narrow brown leaf spot; root rot; seedling blight; sheath blight; sheath rot; sheath spot; alternaria leaf spot; and stem rot.

Disease affecting soybean plants include, but are not limited to, alternaria leaf spot; anthracnose; black leaf blight; black root rot; brown spot; brown stem rot; charcoal rot; choanephora leaf blight; downy mildew; drechslera blight; frogeye leaf spot; leptosphacrulina leaf spot; mycoleptodiscus root rot; neocosmospora stem rot; phomopsis seed decay; phytophthora root and stem rot; phyllosticta leaf spot; phymatotrichum root rot; pod and stem blight; powdery mildew; purple seed stain; pyrenochacta leaf spot; pythium rot; red crown rot; dactuliophora leaf spot; rhizoctonia aerial blight; rhizoctonia root and stem rot; rust; scab; sclerotinia stem rot; sclerotium blight; stem canker; stemphylium leaf blight; sudden death syndrome; target spot; yeast spot; lance nematode; lesion nematode; pin nematode; reniform nematode; ring nematode; root-knot nematode; sheath nematode; cyst nematode; spiral nematode; sting nematode; stubby root nematode; stunt nematode; alfalfa mosaic; bean pod mottle; bean yellow mosaic; brazilian bud blight; chlorotic mottle; yellow mosaic; peanut mottle; peanut stripe; peanut stunt; chlorotic mottle; crinkle leaf; dwarf; severe stunt; and tobacco ringspot or bud blight.

Disease affecting canola plants include, but are not limited to, bacterial black rot; bacterial leaf spot; bacterial pod rot; bacterial soft rot; scab; crown gall; alternaria black spot; anthracnose; black leg; black mold rot; black root; brown girdling root rot; cercospora leaf spot; clubroot; downy mildew; fusarium wilt; gray mold; head rot; leaf spot; light leaf spot; pod rot; powdery mildew; ring spot; root rot; sclerotinia stem rot; seed rot, damping-off; root gall smut; southern blight; verticillium wilt; white blight; white leaf spot; staghead; yellows; crinkle virus; mosaic virus; yellows virus;

Disease affecting sunflower plants include, but are not limited to, apical chlorosis; bacterial leaf spot; bacterial wilt; crown gall; erwinia stalk rot and head rot; lternaria leaf blight, stem spot and head rot; botrytis head rot; charcoal rot; downy mildew; fusarium stalk rot; fusarium wilt; myrotheciem leaf and stem spot; phialophora yellows; phoma black stem; phomopsis brown stem canker; phymatotrichum root rot; phytophthora stem rot; powdery mildew; pythium seedling blight and root rot; rhizoctonia seedling blight; rhizopus head rot; sunflower rust; sclerotium basal stalk and root rot; septoria leaf spot; verticillium wilt; white rust; yellow rust; dagger; pin; lesion; reniform; root knot; and chlorotic mottle;

Disease affecting sorghum plants include, but are not limited to, bacterial leaf spot; bacterial leaf streak; bacterial leaf stripe; acremonium wilt; anthracnose; charcoal rot; crazy top downy mildew; damping-off and seed rot; ergot; fusarium head blight, root and stalk rot; grain storage mold; gray leaf spot; latter leaf spot; leaf blight; milo disease; oval leaf spot; pokkah boeng; pythium root rot; rough leaf spot; rust; seedling blight and seed rot; smut, covered kernel; smut, head; smut, loose kernel; sooty stripe; downy mildew; tar spot; target leaf spot; and zonate leaf spot and sheath blight.

A plant having disease resistance may have 5, 10, 15, 20, 25, 30, 35, 40, 45, 50, 55, 60, 65, 70, 75, 80, 85, 90, 95, or 100% increased resistance to a disease compared to a control plant. In some embodiments, a plant may have 5, 10, 15, 20, 25, 30, 35, 40, 45, 50, 55, 60, 65, 70, 75, 80, 85, 90, 95, or 100% increased plant health in the presence of a disease compared to a control plant.

As used herein, the term "chromosomal interval" designates a contiguous linear span of genomic DNA that resides in planta on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM (centimorgan), or alternatively, less than or equal to 10 cM, 9 cM, 8 cM, 7 cM, 6 cM, 5 cM, 4 cM, 3 cM, 2 cM, or 1 cM. That is, two genetic elements within a single chromosomal interval undergo recombination at a frequency of less than or equal to 20% at 20 cM, 10% at 10 cM, or 5% at 5 cM.

The phrase "closely linked", in the present application, means that recombination between two linked loci occurs with a frequency of equal to or less than about 10% (i.e., are separated on a genetic map by not more than 10 cM). Put another way, the closely linked loci co-segregate at least 90% of the time. Marker loci are especially useful with respect to the subject matter of the current disclosure when they demonstrate a significant probability of co-segregation (linkage) with a desired trait (e.g., resistance to southern corn rust). Closely linked loci such as a marker locus and a second locus can display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination a frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. In some cases, two different markers can have the same genetic map coordinates. In that case, the two markers are in such close proximity to each other that recombination occurs between them with such low frequency that it is undetectable.

The term "crossed" or "cross" refers to a sexual cross and involved the fusion of two haploid gametes via pollination to produce diploid progeny (e.g., cells, seeds or plants). The term encompasses both the pollination of one plant by another and selfing (or self-pollination, e.g., when the pollen and ovule are from the same plant).

An "elite line" is any line that has resulted from breeding and selection for superior agronomic performance.

An "exotic strain," a "tropical line," or an "exotic germplasm" is a strain derived from a plant not belonging to an available elite line or strain of germplasm. In the context of a cross between two plants or strains of germplasm, an exotic germplasm is not closely related by descent to the elite germplasm with which it is crossed. Most commonly, the exotic germplasm is not derived from any known elite line, but rather is selected to introduce novel genetic elements (typically novel alleles) into a breeding program.

A "favorable allele" is the allele at a particular locus (a marker, a QTL, a gene etc.) that confers, or contributes to, an agronomically desirable phenotype, e.g., disease resistance, and that allows the identification of plants with that agronomically desirable phenotype. A favorable allele of a marker is a marker allele that segregates with the favorable phenotype.

"Genetic markers" are nucleic acids that are polymorphic in a population and where the alleles of which can be detected and distinguished by one or more analytic methods, e.g., RFLP, AFLP, isozyme, SNP, SSR, and the like. The term also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also known for the detection of expressed sequence tags (ESTs) and SSR markers derived from EST sequences and randomly amplified polymorphic DNA (RAPD).

"Germplasm" refers to genetic material of or from an individual (e.g., a plant), a group of individuals (e.g., a plant line, variety or family), or a clone derived from a line, variety, species, or culture, or more generally, all individuals within a species or for several species (e.g., maize germplasm collection or Andean germplasm collection). The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells, that can be cultured into a whole plant.

A "haplotype" is the genotype of an individual at a plurality of genetic loci, i.e. a combination of alleles. Typically, the genetic loci described by a haplotype are physically and genetically linked, i.e., on the same chromosome segment.

The term "heterogeneity" is used to indicate that individuals within the group differ in genotype at one or more specific loci.

The heterotic response of material, or "heterosis", can be defined by performance which exceeds the average of the parents (or high parent) when crossed to other dissimilar or unrelated groups.

A "heterotic group" comprises a set of genotypes that perform well when crossed with genotypes from a different heterotic group (Hallauer et al. (1998) Corn breeding, p. 463-564. In G. F. Sprague and J. W. Dudley (ed.) *Corn and corn improvement*). Inbred lines are classified into heterotic groups, and are further subdivided into families within a heterotic group, based on several criteria such as pedigree, molecular marker-based associations, and performance in hybrid combinations (Smith et al. (1990) *Theor. Appl. Gen.* 80:833-840). The two most widely used heterotic groups in the United States are referred to as "Iowa Stiff Stalk Synthetic" (also referred to herein as "stiff stalk") and "Lancaster" or "Lancaster Sure Crop" (sometimes referred to as NSS, or non-Stiff Stalk).

Some heterotic groups possess the traits needed to be a female parent, and others, traits for a male parent. For example, in maize, yield results from public inbreds released from a population called BSSS (Iowa Stiff Stalk Synthetic population) has resulted in these inbreds and their derivatives becoming the female pool in the central Corn Belt. BSSS inbreds have been crossed with other inbreds, e.g. SD 105 and Maiz Amargo, and this general group of materials has become known as Stiff Stalk Synthetics (SSS) even though not all of the inbreds are derived from the original BSSS population (Mikel and Dudley (2006) *Crop Sci;* 46:1193-1205). By default, all other inbreds that combine well with the SSS inbreds have been assigned to the male pool, which for lack of a better name has been designated as NSS, i.e. Non-Stiff Stalk. This group includes several major heterotic groups such as Lancaster Surecrop, Iodent, and Leaming Corn.

The term "homogeneity" indicates that members of a group have the same genotype at one or more specific loci.

The term "hybrid" refers to the progeny obtained between the crossing of at least two genetically dissimilar parents.

The term "inbred" refers to a line that has been bred for genetic homogeneity.

The term "indel" refers to an insertion or deletion, wherein one line may be referred to as having an inserted nucleotide or piece of DNA relative to a second line, or the second line may be referred to as having a deleted nucleotide or piece of DNA relative to the first line.

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., detected by a marker that is associated with a phenotype, at a QTL, a transgene, or the like. Offspring comprising the desired allele may be repeatedly backcrossed to a line having a desired genetic background and selected for the desired allele, to result in the allele becoming fixed in a selected genetic background.

The process of "introgressing" is often referred to as "backcrossing" when the process is repeated two or more times.

A "line" or "strain" is a group of individuals of identical parentage that are generally inbred to some degree and that are generally homozygous and homogeneous at most loci (isogenic or near isogenic). A "subline" refers to an inbred subset of descendants that are genetically distinct from other similarly inbred subsets descended from the same progenitor.

As used herein, the term "linkage" is used to describe the degree with which one marker locus is associated with another marker locus or some other locus. The linkage relationship between a molecular marker and a locus affecting a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units (or cM) of a single meiosis map (a genetic map based on a population that has undergone one round of meiosis, such as e.g. an $F_2$; the IBM2 maps consist of multiple meiosis). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "in proximity to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency. Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same linkage group.) As used herein, linkage can be between two markers, or alternatively between a marker and a locus affecting a phenotype. A marker locus can be "associated with" (linked to) a trait. The degree of linkage of a marker locus and a locus affecting a phenotypic trait is measured, e.g., as a statistical probability of co-segregation of that molecular marker with the phenotype (e.g., an F statistic or LOD score).

Linkage disequilibrium is most commonly assessed using the measure $r^2$, which is calculated using the formula described by Hill, W. G. and Robertson, A, Theor. Appl. Genet. 38:226-231(1968). When $r^2=1$, complete LD exists between the two marker loci, meaning that the markers have not been separated by recombination and have the same allele frequency. The $r^2$ value will be dependent on the population used. Values for $r^2$ above ⅓ indicate sufficiently strong LD to be useful for mapping (Ardlie et al., Nature Reviews Genetics 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

A "locus" is a position on a chromosome, e.g. where a nucleotide, gene, sequence, or marker is located.

The "logarithm of odds (LOD) value" or "LOD score" (Risch, Science 255:803-804 (1992)) is used in genetic interval mapping to describe the degree of linkage between two marker loci. A LOD score of three between two markers indicates that linkage is 1000 times more likely than no linkage, while a LOD score of two indicates that linkage is 100 times more likely than no linkage. LOD scores greater than or equal to two may be used to detect linkage. LOD scores can also be used to show the strength of association between marker loci and quantitative traits in "quantitative trait loci" mapping. In this case, the LOD score's size is dependent on the closeness of the marker locus to the locus affecting the quantitative trait, as well as the size of the quantitative trait effect.

The term "plant" includes whole plants, plant cells, plant protoplast, plant cell or tissue culture from which plants can be regenerated, plant calli, plant clumps and plant cells that are intact in plants or parts of plants, such as seeds, flowers, cotyledons, leaves, stems, buds, roots, root tips and the like. As used herein, a "modified plant" means any plant that has a genetic change due to human intervention. A modified plant may have genetic changes introduced through plant transformation, genome editing, or conventional plant breeding A "marker" is a means of finding a position on a genetic or physical map, or else linkages among markers and trait loci (loci affecting traits). The position that the marker detects may be known via detection of polymorphic alleles and their genetic mapping, or else by hybridization, sequence match or amplification of a sequence that has been physically mapped. A marker can be a DNA marker (detects DNA polymorphisms), a protein (detects variation at an encoded polypeptide), or a simply inherited phenotype (such as the 'waxy' phenotype). A DNA marker can be developed from genomic nucleotide sequence or from expressed nucleotide sequences (e.g., from a spliced RNA or a cDNA). Depending on the DNA marker technology, the marker may consist of complementary primers flanking the locus and/or complementary probes that hybridize to polymorphic alleles at the locus. A DNA marker, or a genetic marker, may also be used to describe the gene, DNA sequence or nucleotide on the chromosome itself (rather than the components used to detect the gene or DNA sequence) and is often used when that DNA marker is associated with a particular trait in human genetics (e.g. a marker for breast cancer). The term marker locus is the locus (gene, sequence or nucleotide) that the marker detects.

Markers can be defined by the type of polymorphism that they detect and also the marker technology used to detect the polymorphism. Marker types include but are not limited to, e.g., detection of restriction fragment length polymorphisms (RFLP), detection of isozyme markers, randomly amplified polymorphic DNA (RAPD), amplified fragment length polymorphisms (AFLPs), detection of simple sequence repeats (SSRs), detection of amplified variable sequences of the plant genome, detection of self-sustained sequence replication, or detection of single nucleotide polymorphisms (SNPs). SNPs can be detected e.g. via DNA sequencing, PCR-based sequence specific amplification methods, detection of polynucleotide polymorphisms by allele specific hybridization (ASH), dynamic allele-specific hybridization (DASH), molecular beacons, microarray hybridization, oligonucleotide ligase assays, Flap endonucleases, 5' endonucleases, primer extension, single strand conformation polymorphism (SSCP) or temperature gradient gel electrophoresis (TGGE). DNA sequencing, such as the pyrosequencing technology has the advantage of being able to detect a series of linked SNP alleles that constitute a haplotype. Haplotypes tend to be more informative (detect a higher level of polymorphism) than SNPs.

A "marker allele", alternatively an "allele of a marker locus", can refer to one of a plurality of polymorphic nucleotide sequences found at a marker locus in a population.

"Marker assisted selection" (of MAS) is a process by which individual plants are selected based on marker genotypes.

"Marker assisted counter-selection" is a process by which marker genotypes are used to identify plants that will not be selected, allowing them to be removed from a breeding program or planting.

A "marker haplotype" refers to a combination of alleles at a marker locus.

A "marker locus" is a specific chromosome location in the genome of a species where a specific marker can be found. A marker locus can be used to track the presence of a second linked locus, e.g., one that affects the expression of a phenotypic trait. For example, a marker locus can be used to monitor segregation of alleles at a genetically or physically linked locus.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution. Some of the markers described herein are also referred to as hybridization markers when located on an indel region, such as the non-collinear region described herein. This is because the insertion region is, by definition, a polymorphism vis a vis a plant without the insertion. Thus, the marker need only indicate whether the indel region is present or absent. Any suitable marker detection technology may be used to identify such a hybridization marker, e.g. SNP technology is used in the examples provided herein.

An allele "negatively" correlates with a trait when it is linked to it and when presence of the allele is an indicator that a desired trait or trait form will not occur in a plant comprising the allele.

The term "phenotype", "phenotypic trait", or "trait" can refer to the observable expression of a gene or series of genes. The phenotype can be observable to the naked eye, or by any other means of evaluation, e.g., weighing, counting, measuring (length, width, angles, etc.), microscopy, biochemical analysis, or an electromechanical assay. In some cases, a phenotype is directly controlled by a single gene or genetic locus, i.e., a "single gene trait" or a "simply inherited trait". In the absence of large levels of environmental variation, single gene traits can segregate in a population to give a "qualitative" or "discrete" distribution, i.e. the phenotype falls into discrete classes. In other cases, a phenotype is the result of several genes and can be considered a "multigenic trait" or a "complex trait". Multigenic traits segregate in a population to give a "quantitative" or "continuous" distribution, i.e. the phenotype cannot be separated into discrete classes. Both single gene and multigenic traits can be affected by the environment in which they are being expressed, but multigenic traits tend to have a larger environmental component.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination (that can vary in different populations).

A "polymorphism" is a variation in the DNA between two or more individuals within a population. A polymorphism preferably has a frequency of at least 1% in a population. A useful polymorphism can include a single nucleotide polymorphism (SNP), a simple sequence repeat (SSR), or an insertion/deletion polymorphism, also referred to herein as an "indel".

A "production marker" or "production SNP marker" is a marker that has been developed for high-throughput purposes. Production SNP markers are developed to detect specific polymorphisms and are designed for use with a variety of chemistries and platforms.

The term "quantitative trait locus" or "QTL" refers to a region of DNA that is associated with the differential expression of a quantitative phenotypic trait in at least one genetic background, e.g., in at least one breeding population. The region of the QTL encompasses or is closely linked to the gene or genes that affect the trait in question.

A "reference sequence" or a "consensus sequence" is a defined sequence used as a basis for sequence comparison. The reference sequence for a marker is obtained by sequencing a number of lines at the locus, aligning the nucleotide sequences in a sequence alignment program (e.g. Sequencher), and then obtaining the most common nucleotide sequence of the alignment. Polymorphisms found among the individual sequences are annotated within the consensus sequence. A reference sequence is not usually an exact copy of any individual DNA sequence, but represents an amalgam of available sequences and is useful for designing primers and probes to polymorphisms within the sequence.

An "unfavorable allele" of a marker is a marker allele that segregates with the unfavorable plant phenotype, therefore providing the benefit of identifying plants that can be removed from a breeding program or planting.

The term "yield" refers to the productivity per unit area of a particular plant product of commercial value. Yield is affected by both genetic and environmental factors. "Agronomics", "agronomic traits", and "agronomic performance" refer to the traits (and underlying genetic elements) of a given plant variety that contribute to yield over the course of growing season. Individual agronomic traits include emergence vigor, vegetative vigor, stress tolerance, disease resistance or tolerance, herbicide resistance, branching, flowering, seed set, seed size, seed density, standability, threshability and the like. Yield is, therefore, the final culmination of all agronomic traits.

Marker loci that demonstrate statistically significant co-segregation with a disease resistance trait that confers broad resistance against a specified disease or diseases are provided herein. Detection of these loci or additional linked loci and the resistance gene may be used in marker assisted selection as part of a breeding program to produce plants that have resistance to a disease or diseases.

Genetic Mapping

It has been recognized for quite some time that specific genetic loci correlating with particular phenotypes, such as disease resistance, can be mapped in an organism's genome. The plant breeder can advantageously use molecular markers to identify desired individuals by detecting marker alleles that show a statistically significant probability of co-segregation with a desired phenotype, manifested as linkage disequilibrium. By identifying a molecular marker or clusters of molecular markers that co-segregate with a trait of interest, the breeder is able to rapidly select a desired phenotype by selecting for the proper molecular marker allele (a process called marker-assisted selection, or MAS).

A variety of methods are available for detecting molecular markers or clusters of molecular markers that co-segregate with a trait of interest, such as a disease resistance trait. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference. Two such methods used to detect trait loci of interest are: 1) Population-based association analysis (i.e. association mapping) and 2) Traditional linkage analysis.

Association Mapping

Understanding the extent and patterns of linkage disequilibrium (LD) in the genome is a prerequisite for developing efficient association approaches to identify and map quantitative trait loci (QTL). Linkage disequilibrium (LD) refers to the non-random association of alleles in a collection of individuals. When LD is observed among alleles at linked loci, it is measured as LD decay across a specific region of a chromosome. The extent of the LD is a reflection of the recombinational history of that region. The average rate of LD decay in a genome can help predict the number and density of markers that are required to undertake a genome-wide association study and provides an estimate of the resolution that can be expected.

Association or LD mapping aims to identify significant genotype-phenotype associations. It has been exploited as a powerful tool for fine mapping in outcrossing species such as humans (Corder et al. (1994) "Protective effect of apolipoprotein-E type-2 allele for late-onset Alzheimer-disease," *Nat Genet* 7:180-184; Hastbacka et al. (1992) "Linkage disequilibrium mapping in isolated founder populations: diastrophic dysplasia in Finland," *Nat Genet* 2:204-211; Kerem et al. (1989) "Identification of the cystic fibrosis gene: genetic analysis," *Science* 245:1073-1080) and maize (Remington et al., (2001) "Structure of linkage disequilibrium and phenotype associations in the maize genome," *Proc Natl Acad Sci* USA 98:11479-11484; Thornsberry et al. (2001) "Dwarf8 polymorphisms associate with variation in flowering time," *Nat Genet* 28:286-289; reviewed by Flint-Garcia et al. (2003) "Structure of linkage disequilibrium in plants," *Annu Rev Plant Biol.* 54:357-374), where recombination among heterozygotes is frequent and results in a rapid decay of LD. In inbreeding species where recombination among homozygous genotypes is not genetically detectable, the extent of LD is greater (i.e., larger blocks of linked markers are inherited together) and this dramatically enhances the detection power of association mapping (Wall and Pritchard (2003) "Haplotype blocks and linkage disequilibrium in the human genome," *Nat Rev Genet* 4:587-597).

The recombinational and mutational history of a population is a function of the mating habit as well as the effective size and age of a population. Large population sizes offer enhanced possibilities for detecting recombination, while older populations are generally associated with higher levels of polymorphism, both of which contribute to observably accelerated rates of LD decay. On the other hand, smaller effective population sizes, e.g., those that have experienced a recent genetic bottleneck, tend to show a slower rate of LD decay, resulting in more extensive haplotype conservation (Flint-Garcia et al. (2003) "Structure of linkage disequilibrium in plants," *Annu Rev Plant Biol.* 54:357-374).

Elite breeding lines provide a valuable starting point for association analyses. Association analyses use quantitative phenotypic scores (e.g., disease tolerance rated from one to nine for each line) in the analysis (as opposed to looking only at tolerant versus resistant allele frequency distributions in intergroup allele distribution types of analysis). The availability of detailed phenotypic performance data collected by breeding programs over multiple years and environments for a large number of elite lines provides a valuable dataset for genetic marker association mapping analyses. This paves the way for a seamless integration between research and application and takes advantage of historically accumulated data sets. However, an understanding of the relationship between polymorphism and recombination is useful in developing appropriate strategies for efficiently extracting maximum information from these resources.

This type of association analysis neither generates nor requires any map data, but rather is independent of map position. This analysis compares the plants' phenotypic score with the genotypes at the various loci. Subsequently, any suitable map (for example, a composite map) can optionally be used to help observe distribution of the identified QTL markers and/or QTL marker clustering using previously determined map locations of the markers.

Traditional Linkage Analysis

The same principles underlie traditional linkage analysis; however, LD is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, *Genetics* 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait of interest at that position on the genetic map (which will fall between two particular marker loci).

Marker loci that demonstrate statistically significant co-segregation with a disease resistance trait, as determined by traditional linkage analysis and by whole genome association analysis, are provided herein. Detection of these loci or additional linked loci can be used in marker assisted breeding programs to produce plants having disease resistance.

Activities in marker assisted breeding programs may include but are not limited to: selecting among new breeding populations to identify which population has the highest frequency of favorable nucleic acid sequences based on historical genotype and agronomic trait associations, selecting favorable nucleic acid sequences among progeny in breeding populations, selecting among parental lines based on prediction of progeny performance, and advancing lines in germplasm improvement activities based on presence of favorable nucleic acid sequences.

Chromosomal Intervals

Chromosomal intervals that correlate with the disease resistance trait are provided. A variety of methods are available for identifying chromosomal intervals. The boundaries of such chromosomal intervals are drawn to encompass markers that will be linked to the gene(s) controlling the trait of interest. In other words, the chromosomal interval is drawn such that any marker that lies within that interval (including the terminal markers that define the boundaries of the interval) can be used as a marker for a disease resistance trait.

Conversely, e.g., if two markers in close proximity show co-segregation with the desired phenotypic trait, it is sometimes unclear if each of those markers identify the same gene or two different gene or multiple genes. Regardless, knowledge of how many genes are in a particular physical/genomic interval is not necessary to make or practice that which is presented in the current disclosure.

The chromosome 4 interval may encompass any of the markers identified herein as being associated with the SCR resistance trait including a "T" at PM01-000058W (position 99 of reference sequence SEQ ID NO: 11), a "G" at SOURST-83_1284720 (position 51 of reference sequence SEQ ID NO: 21), a "C" at SOURST-83_1314662 (position 24 of reference sequence SEQ ID NO: 19), a "T" at SOURST-83_1542053 (position 51 of reference sequence SEQ ID NO: 22), an "A" at PZE-104005694 (position 25 of reference sequence SEQ ID NO: 23), a "C" at SOURST-83_1II (position 32 of reference sequence SEQ ID NO: 24), a "C" at SOURST-83_1936804 (position 30 of reference sequence SEQ ID NO: 32), a "G" at PZE-104001404 (position 26 of reference sequence SEQ ID NO: 25), a "C" at SOURST-83_1926276 (position 26 of reference sequence SEQ ID NO: 26), a "G" at SOURST-83_1652968 (position 26 of reference sequence SEQ ID NO: 27), an "A" at SOURST-83_2036602 (position 24 of reference sequence SEQ ID NO: 20), a "T" at SOURST-83_2035716 (position 35 of reference sequence SEQ ID NO: 28), a "T" at PZE-104001592 (position 46 of reference sequence SEQ ID NO: 29), a "G" at SOURST-83_2465654 (position 51 of reference sequence SEQ ID NO: 30), and a "T" at SOURST-83_2679982 (position 26 of reference sequence SEQ ID NO: 31). Any marker located within these intervals can find use as a marker for SCR resistance and can be used in the context of the methods presented herein to identify and/or select plants that have resistance to SCR, whether it is newly conferred or enhanced compared to a control plant. In certain embodiments, markers located upstream and downstream of SCR resistance gene position are very tightly linked genetically and physically and hence may be used to select the SCR resistance gene for trait introgression and products development.

Chromosomal intervals can also be defined by markers that are linked to (show linkage disequilibrium with) a disease resistant gene, and $r^2$ is a common measure of linkage disequilibrium (LD) in the context of association studies. If the $r^2$ value of LD between a chromosome 7 marker locus in an interval of interest and another chromosome 7 marker locus in close proximity is greater than ⅓ (Ardlie et al., *Nature Reviews Genetics* 3:299-309 (2002)), the loci are in linkage disequilibrium with one another.

Markers and Linkage Relationships

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation.

The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

Although particular marker alleles can co-segregate with the disease resistance trait, it is important to note that the marker locus is not necessarily responsible for the expression of the disease resistance phenotype. For example, it is not a requirement that the marker polynucleotide sequence be part of a gene that is responsible for the disease resistant phenotype (for example, is part of the gene open reading frame). The association between a specific marker allele and the disease resistance trait is due to the original "coupling" linkage phase between the marker allele and the allele in the ancestral line from which the allele originated. Eventually, with repeated recombination, crossing over events between the marker and genetic locus can change this orientation. For this reason, the favorable marker allele may change depending on the linkage phase that exists within the parent having resistance to the disease that is used to create segregating populations. This does not change the fact that the marker can be used to monitor segregation of the phenotype. It only changes which marker allele is considered favorable in a given segregating population.

Methods presented herein include detecting the presence of one or more marker alleles associated with disease resistance in a plant and then identifying and/or selecting plants that have favorable alleles at those marker loci. Markers have been identified herein as being associated with the disease resistance trait and hence can be used to predict disease resistance in a plant. Any marker within 50 cM, 40 cM, 30 cM, 20 cM, 15 cM, 10 cM, 9 cM, 8 cM, 7 cM, 6 cM, 5 cM, 4 cM, 3 cM, 2 cM, 1 cM, 0.75 cM, 0.5 cM or 0.25 cM (based on a single meiosis based genetic map) could also be used to predict disease resistance in a plant.

Marker Assisted Selection

Molecular markers can be used in a variety of plant breeding applications (e.g. see Staub et al. (1996) *Hortscience* 31: 729-741; Tanksley (1983) *Plant Molecular Biology Reporter.* 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true where the phenotype is hard to assay. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. In some embodiments, the methods disclosed herein produce a marker in a disease resistance gene, wherein the gene was identified by inferring genomic location from clustering of conserved domains or a clustering analysis.

When a gene is introgressed by MAS, it is not only the gene that is introduced but also the flanking regions (Gepts. (2002). *Crop Sci;* 42: 1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite line. This is also sometimes referred to as "yield drag." The size of the flanking region can be decreased by additional backcrossing, although this is not always successful, as breeders do not have control over the size of the region or the recombination breakpoints (Young et al. (1998) *Genetics* 120:579-585). In classical breeding it is usually only by chance that recombinations are selected that contribute to a reduction in the size of the donor segment (Tanksley et al. (1989). *Biotechnology* 7: 257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will allow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The key components to the implementation of MAS are: (i) Defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. The markers described in this disclosure, as well as other marker types such as SSRs and FLPs, can be used in marker assisted selection protocols.

SSRs can be defined as relatively short runs of tandemly repeated DNA with lengths of 6 bp or less (Tautz (1989) *Nucleic Acid Research* 17: 6463-6471; Wang et al. (1994) *Theoretical and Applied Genetics,* 88:1-6) Polymorphisms arise due to variation in the number of repeat units, probably caused by slippage during DNA replication (Levinson and Gutman (1987) *Mol Biol Evol* 4: 203-221). The variation in repeat length may be detected by designing PCR primers to the conserved non-repetitive flanking regions (Weber and May (1989) *Am J Hum Genet.* 44:388-396). SSRs are highly suited to mapping and MAS as they are multi-allelic, codominant, reproducible and amenable to high throughput automation (Rafalski et al. (1996) Generating and using DNA markers in plants. In: *Non-mammalian genomic analysis: a practical guide.* Academic press. pp 75-135).

Various types of SSR markers can be generated, and SSR profiles can be obtained by gel electrophoresis of the amplification products. Scoring of marker genotype is based on the size of the amplified fragment.

Various types of FLP markers can also be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals, and such indels are known to occur frequently in maize (Bhattramakki et al. (2002). *Plant Mol Biol* 48, 539-547; Rafalski (2002b), supra).

SNP markers detect single base pair nucleotide substitutions. Of all the molecular marker types, SNPs are the most abundant, thus having the potential to provide the highest genetic map resolution (Bhattramakki et al. 2002 *Plant Molecular Biology* 48:539-547). SNPs can be assayed at an even higher level of throughput than SSRs, in a so-called 'ultra-high-throughput' fashion, as SNPs do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing, and coded spheres. Such methods have been reviewed in: Gut (2001) *Hum Mutat* 17 pp. 475-492; Shi (2001) *Clin Chem* 47, pp. 164-172; Kwok (2000) *Pharmacogenomics* 1, pp. 95-100; and Bhattramakki and Rafalski (2001) Discovery and application of single nucleotide polymorphism markers in plants. In: R. J. Henry, Ed. *Plant Genotyping: The DNA Fingerprinting of Plants,* CABI Publishing, Wallingford. A wide range of commercially available technologies utilize these and other methods to interrogate SNPs including Masscode.TM. (Qiagen), INVADER®. (Third Wave Technologies) and Invader PLUS®, SNAPSHOT®. (Applied Biosystems), TAQMAN®. (Applied Biosystems) and BEADARRAYS®. (Illumina).

A number of SNPs together within a sequence, or across linked sequences, can be used to describe a haplotype for any particular genotype (Ching et al. (2002), *BMC Genet.* 3:19 pp Gupta et al. 2001, Rafalski (2002b), *Plant Science* 162:329-333). Haplotypes can be more informative than single SNPs and can be more descriptive of any particular genotype. For example, a single SNP may be allele "T" for a specific line or variety with disease resistance, but the allele 'T' might also occur in the breeding population being utilized for recurrent parents. In this case, a haplotype, e.g. a combination of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high throughput marker detection platforms makes this process highly efficient and effective.

Many of the markers presented herein can readily be used as single nucleotide polymorphic (SNP) markers to select for the SCR resistance gene. Using PCR, the primers are used to amplify DNA segments from individuals (preferably inbred) that represent the diversity in the population of interest. The PCR products are sequenced directly in one or both directions. The resulting sequences are aligned and polymorphisms are identified. The polymorphisms are not limited to single nucleotide polymorphisms (SNPs), but also include indels, CAPS, SSRs, and VNTRs (variable number of tandem repeats). Specifically, with respect to the fine map information described herein, one can readily use the information provided herein to obtain additional polymorphic SNPs (and other markers) within the region amplified by the primers disclosed herein. Markers within the described map region can be hybridized to BACs or other genomic libraries, or electronically aligned with genome sequences, to find new sequences in the same approximate location as the described markers.

In addition to SSR's, FLPs and SNPs, as described above, other types of molecular markers are also widely used, including but not limited to expressed sequence tags (ESTs), SSR markers derived from EST sequences, randomly amplified polymorphic DNA (RAPD), and other nucleic acid based markers.

Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) *Plant Molecular Biology Reporter* 1:3-8).

Sequence alignments or contigs may also be used to find sequences upstream or downstream of the specific markers listed herein. These new sequences, close to the markers described herein, are then used to discover and develop functionally equivalent markers. For example, different physical and/or genetic maps are aligned to locate equivalent markers not described within this disclosure but that are within similar regions. These maps may be within the species, or even across other species that have been genetically or physically aligned.

In general, MAS uses polymorphic markers that have been identified as having a significant likelihood of co-segregation with a trait such as the SCR disease resistance trait. Such markers are presumed to map near a gene or genes that give the plant its disease resistant phenotype, and are considered indicators for the desired trait, or markers. Plants are tested for the presence of a desired allele in the marker, and plants containing a desired genotype at one or more loci are expected to transfer the desired genotype, along with a desired phenotype, to their progeny. Thus, plants with SCR disease resistance may be selected for by detecting one or more marker alleles, and in addition, progeny plants derived from those plants can also be selected. Hence, a plant containing a desired genotype in a given chromosomal region (i.e. a genotype associated with disease resistance) is obtained and then crossed to another plant. The progeny of such a cross would then be evaluated genotypically using one or more markers and the progeny plants with the same genotype in a given chromosomal region would then be selected as having disease resistance.

The SNPs could be used alone or in combination (i.e. a SNP haplotype) to select for a favorable resistant gene allele associated with SCR disease resistance. For example, a SNP haplotype at the a "T" at PM01-000058W (position 99 of reference sequence SEQ ID NO: 11), a "G" at SOURST-83_1284720 (position 51 of reference sequence SEQ ID NO: 21), a "C" at SOURST-83_1314662 (position 24 of reference sequence SEQ ID NO: 19), a "T" at SOURST-83_1542053 (position 51 of reference sequence SEQ ID NO: 22), an "A" at PZE-104005694 (position 25 of reference sequence SEQ ID NO: 23), a "C" at SOURST-83_1II (position 32 of reference sequence SEQ ID NO: 24), a "C" at SOURST-83_1936804 (position 30 of reference sequence SEQ ID NO: 32), a "G" at PZE-104001404 (position 26 of reference sequence SEQ ID NO: 25), a "C" at SOURST- 83_1926276 (position 26 of reference sequence SEQ ID NO: 26), a "G" at SOURST-83_1652968 (position 26 of reference sequence SEQ ID NO: 27), an "A" at SOURST-83_2036602 (position 24 of reference sequence SEQ ID NO: 20), a "T" at SOURST-83_2035716 (position 35 of reference sequence SEQ ID NO: 28), a "T" at PZE-104001592 (position 46 of reference sequence SEQ ID NO: 29), a "G" at SOURST-83_2465654 (position 51 of reference sequence SEQ ID NO: 30), and a "T" at SOURST-83_2679982 (position 26 of reference sequence SEQ ID NO: 31), or a combination thereof.

The skilled artisan would expect that there might be additional polymorphic sites at marker loci in and around a chromosome marker identified by the methods disclosed herein, wherein one or more polymorphic sites is in linkage disequilibrium (LD) with an allele at one or more of the polymorphic sites in the haplotype and thus could be used in a marker assisted selection program to introgress a gene allele or genomic fragment of interest. Two particular alleles at different polymorphic sites are said to be in LD if the presence of the allele at one of the sites tends to predict the presence of the allele at the other site on the same chromosome (Stevens, *Mol. Diag.* 4:309-17 (1999)). The marker loci can be located within 5 cM, 2 cM, or 1 cM (on a single meiosis based genetic map) of the disease resistance trait QTL.

The skilled artisan would understand that allelic frequency (and hence, haplotype frequency) can differ from one germplasm pool to another. Germplasm pools vary due to maturity differences, heterotic groupings, geographical distribution, etc. As a result, SNPs and other polymorphisms may not be informative in some germplasm pools.

Plant Compositions

Plants identified, modified, and/or selected by any of the methods described above are also of interest.

Proteins and Variants and Fragments Thereof

SCR resistance polypeptides are encompassed by the disclosure. "SCR resistance polypeptide" and "SCR resistance protein" as used herein interchangeably refers to a polypeptide(s) having SCR resistance activity, and is sufficiently identical to the SCR resistance polypeptide of any one of SEQ ID NOs: 5-8. A variety of SCR resistance polypeptides are contemplated.

"Sufficiently identical" is used herein to refer to an amino acid sequence that has at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity. In some embodiments the sequence identity is against the full length sequence of a polypeptide. The term "about" when used herein in context with percent sequence identity means +/−1.0%.

A "recombinant protein" is used herein to refer to a protein that is no longer in its natural environment, for example in vitro or in a recombinant bacterial or plant host cell; a protein that is expressed from a polynucleotide that has been edited from its native version; or a protein that is expressed from a polynucleotide in a different genomic position relative to the native sequence.

"Substantially free of cellular material" as used herein refers to a polypeptide including preparations of protein having less than about 30%, 20%, 10% or 5% (by dry weight) of non-target protein (also referred to herein as a "contaminating protein").

"Fragments" or "biologically active portions" include polypeptide or polynucleotide fragments comprising sequences sufficiently identical to an SCR resistance polypeptide or polynucleotide, respectively, and that exhibit disease resistance when expressed in a plant.

"Variants" as used herein refers to proteins or polypeptides having an amino acid sequence that is at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater identical to the parental amino acid sequence.

In some embodiments a SCR resistance polypeptide comprises an amino acid sequence having at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity to the full length or a fragment of the amino acid sequence of any one of SEQ ID NOs: 5-8, wherein the SCR resistance polypeptide has SCR resistance when expressed in a plant.

Methods for such manipulations are generally known in the art. For example, amino acid sequence variants of a SCR resistance polypeptide may be prepared by mutations in the DNA. This may also be accomplished by one of several forms of mutagenesis, such as for example site-specific double strand break technology, and/or in directed evolution. In some aspects, the changes encoded in the amino acid sequence will not substantially affect the function of the protein. Such variants will possess the desired activity. However, it is understood that the ability of an SCR resistance polypeptide to confer disease resistance may be improved by the use of such techniques upon the compositions of this disclosure.

Nucleic Acid Molecules and Variants and Fragments Thereof

Isolated or recombinant nucleic acid molecules comprising nucleic acid sequences encoding SCR resistance polypeptides or biologically active portions thereof, as well as nucleic acid molecules sufficient for use as hybridization probes to identify nucleic acid molecules encoding proteins with regions of sequence homology are provided. As used herein, the term "nucleic acid molecule" refers to DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule (or DNA) is used herein to refer to a nucleic acid sequence (or DNA) that is no longer in its natural environment, for example in vitro. A "recombinant" nucleic acid molecule (or DNA) is used herein to refer to a nucleic acid sequence (or DNA) that is in a recombinant bacterial or plant host cell; has been edited from its native sequence; or is located in a different location than the native sequence. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the disclosure, "isolated" or "recombinant" when used to refer to nucleic acid molecules excludes isolated chromosomes. For example, in various embodiments, the recombinant nucleic acid molecules encoding SCR resistance polypeptides can contain less than about 5 kb, 4 kb, 3 kb, 2 kb, 1 kb, 0.5 kb or 0.1 kb of nucleic acid sequences that naturally flank the nucleic acid molecule in genomic DNA of the cell from which the nucleic acid is derived.

In some embodiments an isolated nucleic acid molecule encoding SCR resistance polypeptides has one or more change in the nucleic acid sequence compared to the native or genomic nucleic acid sequence. In some embodiments the change in the native or genomic nucleic acid sequence includes but is not limited to: changes in the nucleic acid sequence due to the degeneracy of the genetic code; changes in the nucleic acid sequence due to the amino acid substitution, insertion, deletion and/or addition compared to the native or genomic sequence; removal of one or more intron; deletion of one or more upstream or downstream regulatory regions; and deletion of the 5' and/or 3' untranslated region associated with the genomic nucleic acid sequence. In some embodiments the nucleic acid molecule encoding an SCR resistance polypeptide is a non-genomic sequence.

A variety of polynucleotides that encode SCR resistance polypeptides or related proteins are contemplated. Such polynucleotides are useful for production of SCR resistance polypeptides in host cells when operably linked to a suitable promoter, transcription termination and/or polyadenylation sequences. Such polynucleotides are also useful as probes for isolating homologous or substantially homologous polynucleotides that encode SCR resistance polypeptides or related proteins.

In some embodiments the nucleic acid molecule encoding an SCR resistance polypeptide is a polynucleotide having the sequence set forth in any one of SEQ ID NOs: 5-8, and variants, fragments and complements thereof. "Complement" is used herein to refer to a nucleic acid sequence that is sufficiently complementary to a given nucleic acid sequence such that it can hybridize to the given nucleic acid sequence to thereby form a stable duplex. "Polynucleotide sequence variants" is used herein to refer to a nucleic acid sequence that except for the degeneracy of the genetic code encodes the same polypeptide.

In some embodiments the nucleic acid molecule encoding the SCR resistance polypeptide is a non-genomic nucleic acid sequence. As used herein a "non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments the non-genomic nucleic acid molecule is a synthetic nucleic acid sequence.

In some embodiments the nucleic acid molecule encoding an SCR resistance polypeptide disclosed herein is a non-genomic polynucleotide having a nucleotide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity, to the nucleic acid sequence of any one of SEQ ID NOs: 5-8, wherein the SCR resistance polypeptide has SCR resistance activity when expressed in a plant.

In some embodiments the nucleic acid molecule encodes an SCR resistance polypeptide variant comprising one or more amino acid substitutions to the amino acid sequence of any one of SEQ ID NOS: 5-8.

Nucleic acid molecules that are fragments of these nucleic acid sequences encoding SCR resistance polypeptides are also encompassed by the embodiments. "Fragment" as used herein refers to a portion of the nucleic acid sequence encoding an SCR resistance polypeptide. A fragment of a nucleic acid sequence may encode a biologically active portion of an SCR resistance polypeptide or it may be a fragment that can be used as a hybridization probe or PCR primer using methods disclosed below. Nucleic acid molecules that are fragments of a nucleic acid sequence encoding an SCR resistance polypeptide comprise at least about 150, 180, 210, 240, 270, 300, 330, 360, 400, 450, or 500 contiguous nucleotides or up to the number of nucleotides present in a full-length nucleic acid sequence encoding a SCR resistance polypeptide identified by the methods disclosed herein, depending upon the intended use. "Contiguous nucleotides" is used herein to refer to nucleotide residues that are immediately adjacent to one another. Fragments of the nucleic acid sequences of the embodiments will encode protein fragments that retain the biological activity of the SCR resistance polypeptide and, hence, retain disease resistance. "Retains disease resistance" is used herein to refer to a polypeptide having at least about 10%, at least about 30%, at least about 50%, at least about 70%, 80%, 90%, 95% or higher of the disease resistance of the full-length SCR resistance polypeptide as set forth in any one of sSEQ ID NOs: 5-8.

"Percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways, for instance, using publicly available computer software such as BLAST, BLAST-2. Those skilled in the art can determine appropriate parameters for aligning sequences, including any algorithms needed to achieve maximal alignment over the full length of the sequences being compared. The percent identity between the two sequences is a function of the number of identical positions shared by the sequences (e.g., percent identity of query sequence=number of identical positions between query and subject sequences/total number of positions of query sequence×100).

In some embodiments a SCR resistance polynucleotide encodes a SCR resistance polypeptide comprising an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of any one of SEQ ID NOs: 5-8.

The embodiments also encompass nucleic acid molecules encoding SCR resistance polypeptide variants. "Variants" of SCR resistance polynucleotides encoding polypeptide sequences include those sequences that encode the SCR resistance polypeptides identified by the methods disclosed herein, but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleic acid sequences also include synthetically derived nucleic acid sequences that have been generated, for example, by using site-directed mutagenesis but which still encode the SCR resistance polypeptides disclosed herein.

The skilled artisan will further appreciate that changes can be introduced by mutation of the nucleic acid sequences thereby leading to changes in the amino acid sequence of the encoded SCR resistance polypeptides, without altering the biological activity of the proteins. Thus, variant nucleic acid molecules can be created by introducing one or more nucleotide substitutions, additions and/or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present disclosure.

Alternatively, variant nucleic acid sequences can be made by introducing mutations randomly along all or part of the coding sequence, such as by saturation mutagenesis, and the resultant mutants can be screened for ability to confer activity to identify mutants that retain activity. Following mutagenesis, the encoded protein can be expressed recombinantly, and the activity of the protein can be determined using standard assay techniques.

The polynucleotides of the disclosure and fragments thereof are optionally used as substrates for a variety of recombination and recursive recombination reactions, in addition to standard cloning methods as set forth in, e.g., Ausubel, Berger and Sambrook, i.e., to produce additional polypeptide homologues and fragments thereof with desired properties. A variety of such reactions are known. Methods for producing a variant of any nucleic acid listed herein comprising recursively recombining such polynucleotide with a second (or more) polynucleotide, thus forming a library of variant polynucleotides are also embodiments of the disclosure, as are the libraries produced, the cells comprising the libraries and any recombinant polynucleotide produced by such methods. Additionally, such methods optionally comprise selecting a variant polynucleotide from such libraries based on activity, as is wherein such recursive recombination is done in vitro or in vivo.

A variety of diversity generating protocols, including nucleic acid recursive recombination protocols are available. The procedures can be used separately, and/or in combination to produce one or more variants of a nucleic acid or set of nucleic acids, as well as variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties or that encode proteins with or which confer desirable properties. Following diversification by one or more of the methods herein or otherwise available to one of skill, any nucleic acids that are produced can be selected for a desired activity or property, e.g. such activity at a desired pH, etc. This can include identifying any activity that can be detected, for example, in an automated or automatable format, by any of the assays in the art. A variety of related (or even unrelated) properties can be evaluated, in serial or in parallel, at the discretion of the practitioner.

The nucleotide sequences of the embodiments can also be used to isolate corresponding sequences from a different source. In this manner, methods such as PCR, hybridization, and the like can be used to identify such sequences based on their sequence homology to the sequences identified by the methods disclosed herein. Sequences that are selected based on their sequence identity to the entire sequences set forth herein or to fragments thereof are encompassed by the embodiments. Such sequences include sequences that are orthologs of the sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein.

In a PCR approach, oligonucleotide primers can be designed for use in PCR reactions to amplify corresponding DNA sequences from cDNA or genomic DNA extracted from any organism of interest. Methods for designing PCR primers and PCR cloning are disclosed in Sambrook, et al., (1989) *Molecular Cloning: A Laboratory Manual* (2d ed., Cold Spring Harbor Laboratory Press, Plainview, New York), hereinafter "Sambrook". See also, Innis, et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization methods, all or part of the nucleic acid sequence can be used to screen cDNA or genomic libraries. Methods for construction of such cDNA and genomic libraries are disclosed in Sambrook and Russell, (2001), supra. The so-called hybridization probes may be genomic DNA fragments, cDNA fragments, RNA fragments or other oligonucleotides and may be labeled with a detectable group such as 32P or any other detectable marker, such as other radioisotopes, a fluorescent compound, an enzyme or an enzyme co-factor. Probes for hybridization can be made by labeling synthetic oligonucleotides based on the known polypeptide-encoding nucleic acid sequences disclosed herein. Degenerate primers designed on the basis of conserved nucleotides or amino acid residues in the nucleic acid sequence or encoded amino acid sequence can additionally be used. The probe typically comprises a region of nucleic acid sequence that hybridizes under stringent conditions to at least about 12, at least about 25, at least about 50, 75, 100, 125, 150, 175 or 200 consecutive nucleotides of nucleic acid sequences encoding polypeptides or a fragment or variant thereof. Methods for the preparation of probes for hybridization and stringency conditions are disclosed in Sambrook and Russell, (2001), supra.

Nucleotide Constructs, Expression Cassettes and Vectors

The use of the term "nucleotide constructs" herein is not intended to limit the embodiments to nucleotide constructs comprising DNA. Those of ordinary skill in the art will recognize that nucleotide constructs, particularly polynucleotides and oligonucleotides composed of ribonucleotides and combinations of ribonucleotides and deoxyribonucleotides, may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures and the like.

A further embodiment relates to a transformed organism such as an organism selected from plant cells, bacteria, yeast, baculovirus, protozoa, nematodes and algae. The transformed organism comprises a DNA molecule of the embodiments, an expression cassette comprising the DNA molecule or a vector comprising the expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and/or a regulatory sequence and a second sequence, wherein the promoter and/or regulatory sequence initiates, mediates, and/or affects transcription of the DNA sequence corresponding to the second sequence. Generally, operably linked means that the nucleic acid sequences being linked are contiguous and where necessary to join two protein coding regions in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the polypeptide gene sequence of the disclosure to be under the transcriptional regulation of the regulatory regions. The DNA construct may additionally contain selectable marker genes.

The DNA construct will generally include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter or regulatory sequence may be the natural sequence or alternatively a synthetic sequence. The term "foreign" as used herein indicates that the promoter is not found in the native organism into which the promoter is introduced. As used herein, the term "heterologous" in reference to a sequence means a sequence that originates from a foreign species or, if from the same species, is substantially modified from its native form in composition and/or genomic locus by deliberate human intervention. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

In some embodiments the DNA construct comprises a polynucleotide encoding an SCR resistance polypeptide of the embodiments. In some embodiments the DNA construct comprises a polynucleotide encoding a fusion protein comprising an SCR resistance polypeptide of the embodiments.

In some embodiments the DNA construct may also include a transcriptional enhancer sequence. As used herein, the term an "enhancer" refers to a DNA sequence which can stimulate promoter activity, and may be an innate element of the promoter or a heterologous element inserted to enhance the level or tissue-specificity of a promoter. Various enhancers include, for example, introns with gene expression enhancing properties in plants (US Patent Application Publication Number 2009/0144863, the ubiquitin intron (i.e., the maize ubiquitin intron 1 (see, for example, NCBI sequence S94464)), the omega enhancer or the omega prime enhancer (Gallie, et al., (1989) *Molecular Biology of RNA* ed. Cech (Liss, New York) 237-256 and Gallie, et al., (1987) *Gene* 60:217-25), the CaMV 35S enhancer (see, e.g., Benfey, et al., (1990) *EMBO J.* 9:1685-96) and the enhancers of U.S. Pat. No. 7,803,992 may also be used. The above list of transcriptional enhancers is not meant to be limiting. Any appropriate transcriptional enhancer can be used in the embodiments.

The termination region may be native with the transcriptional initiation region, may be native with the operably linked DNA sequence of interest, may be native with the plant host or may be derived from another source (i.e., foreign or heterologous to the promoter, the sequence of interest, the plant host or any combination thereof).

Convenient termination regions are available from the Ti-plasmid of *A. tumefaciens,* such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903 and Joshi, et al., (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri, (1990) *Plant Physiol.* 92:1-11 for a discussion of host-preferred usage. For example, although nucleic acid sequences of the embodiments may be expressed in both monocotyledonous and dicotyledonous plant species, sequences can be modified to account for the specific preferences and GC content preferences of monocotyledons or dicotyledons as these preferences have been shown to differ (Murray et al. (1989) *Nucleic Acids Res.* 17:477-498). Thus, the plant-preferred for a particular amino acid may be derived from known gene sequences from plants.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as *E. coli* or eukaryotic cells such as yeast, insect, amphibian or mammalian cells or monocotyledonous or dicotyledonous plant cells. An example of a monocotyledonous host cell is a maize host cell. When possible, the sequence is modified to avoid predicted hairpin secondary mRNA structures.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

A number of promoters can be used in the practice of the embodiments. The promoters can be selected based on the desired outcome. The nucleic acids can be combined with constitutive, tissue-preferred, inducible or other promoters for expression in the host organism.

Plant Transformation

The methods of the embodiments involve introducing a polypeptide or polynucleotide into a plant. "Introducing" is as used herein means presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide(s) or polypeptide(s) gains access to the interior of at least one cell of the plant. Methods for introducing polynucleotide(s) or polypeptide(s) into plants include, but are not limited to, stable transformation methods, transient transformation methods, and virus-mediated methods.

"Stable transformation" as used herein means that the nucleotide construct introduced into a plant integrates into the genome of the plant and is capable of being inherited by the progeny thereof. "Transient transformation" as used herein means that a polynucleotide is introduced into the plant and does not integrate into the genome of the plant or a polypeptide is introduced into a plant. "Plant" as used herein refers to whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells and pollen).

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), Agrobacterium-mediated transformation (U.S. Pat. Nos. 5,563,055 and 5,981,840), direct gene transfer (Paszkowski, et al., (1984) *EMBO J.* 3:2717-2722) and ballistic particle acceleration (see, for example, U.S. Pat. Nos. 4,945,050; 5,879,918; 5,886,244 and 5,932,782; Tomes, et al., (1995) in *Plant Cell, Tissue, and Organ Culture: Fundamental Methods,* ed. Gamborg and Phillips, (Springer-Verlag, Berlin) and McCabe, et al., (1988) *Bio-technology* 6:923-926) and Lec1 transformation (WO 00/28058). For potato transformation see, Tu, et al., (1998) *Plant Molecular Biology* 37:829-838 and Chong, et al., (2000) *Transgenic Research* 9:71-78. Additional transformation procedures can be found in Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature (London)* 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues,* ed. Chapman, et al., (Longman, New York), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*).

Methods to Introduce Genome Editing Technologies into Plants

In some embodiments, polynucleotide compositions can be introduced into the genome of a plant using genome editing technologies, or previously introduced polynucleotides in the genome of a plant may be edited using genome editing technologies. For example, the identified polynucleotides can be introduced into a desired location in the genome of a plant through the use of double-stranded break technologies such as TALENs, meganucleases, zinc finger nucleases, CRISPR-Cas, and the like. For example, the identified polynucleotides can be introduced into a desired location in a genome using a CRISPR-Cas system, for the purpose of site-specific insertion. The desired location in a plant genome can be any desired target site for insertion, such as a genomic region amenable for breeding or may be a target site located in a genomic window with an existing trait of interest. Existing traits of interest could be either an endogenous trait or a previously introduced trait.

In some embodiments, where an SCR resistance gene allele has been identified in a genome, genome editing technologies may be used to alter or modify the polynucleotide sequence. Site specific modifications that can be introduced into the desired SCR resistance gene allele polynucleotide include those produced using any method for introducing site specific modification, including, but not limited to, through the use of gene repair oligonucleotides (e.g. US Publication 2013/0019349), or through the use of double-stranded break technologies such as TALENs, meganucleases, zinc finger nucleases, CRISPR-Cas, and the like. Such technologies can be used to modify the previously introduced polynucleotide through the insertion, deletion or substitution of nucleotides within the introduced polynucleotide. Alternatively, double-stranded break technologies can be used to add additional nucleotide sequences to the introduced polynucleotide. Additional sequences that may be added include, additional expression elements, such as enhancer and promoter sequences. In another embodiment, genome editing technologies may be used to position additional disease resistant proteins in close proximity to the SCR resistance polynucleotide compositions within the genome of a plant, in order to generate molecular stacks disease resistant proteins.

An "altered target site," "altered target sequence." "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

EXAMPLES

The following examples are offered to illustrate, but not to limit, the claimed subject matter. It is understood that the examples and embodiments described herein are for illustrative purposes only, and persons skilled in the art will recognize various reagents or parameters that can be altered without departing from the spirit of the disclosure or the scope of the appended claims.

Example 1. QTL Mapping

Southern Corn Rust (SCR) is a disease of maize caused by the fungal pathogen Puccinia polysora. CIMBL83, an inbred line resistant to SCR, was crossed with a susceptible line. The F1 progeny from this cross were then back-crossed to the susceptible line to create a BC1F1 population with the susceptible line as the recurrent parent. A mapping population of 117 recombinant inbred lines (RILs) was developed through single seed decent from the BC1F1 population.

The RILs were planted in 2016 and 2017 at the Changge station in Henan province and in 2017 at the Ledong station in Hainan province in China. Natural infection of the SCR pathogen was used to evaluate the resistance level of the plants in the field. Disease severity was assessed at 30-35 days post-pollination using a scale from 1 (the most resistant phenotype) to 9 (the most susceptible phenotype). The resistant parent, CIMBL83 was completely resistant (score of 1) while the susceptible parent exhibited a mean score of 7.4. For the RILs, the mean score for the plot was used for subsequent analysis. Plants were genotyped with 9,433 SNPs using the MaizeSNP9.4k BeadChip and composite interval mapping was done using QTL Cartographer. A QTL was identified on chromosome 4 in bin 4.01 (qSCR4.01). This QTL was reproducible across multiple years and locations, and explain 48-65% of the phenotypic variations.

Example 2. QTL Fine Mapping and Candidate Gene Identification

To develop a population for fine mapping, a RIL line that was heterozygous for qSCR4.01 was self-pollinated to develop a near isogenic line (NIL) F2 population. A total of 1289 NIL F2 individuals were used for fine mapping. These plants were genotyped using two SNP markers, PM01-000058W (SEQ ID NO: 11) and PM01-00002MH (SEQ ID NO: 12), which flank the QTL interval. A total of 449 recombinants were identified. These recombinants were grown, genotyped with newly developed markers, and selfed. The progeny of 70 of these F3 families were grown in Ledong, Hainan and evaluated for SCR resistance. Based on the analysis of the phenotypes, combined with the genotypes of the F2 NILs, the qSCR4.01 was delimited to an interval flanked by the markers SOURST-83_1314662 (SEQ ID NO: 19) and SOURST-83_2036602 (SEQ ID NO: 20).

TABLE 2

SNP Markers for QTL Mapping

| Marker Name | Reference Sequence | Type | Resistant | Susceptible | B73v4 SNP Position |
|---|---|---|---|---|---|
| PM01-000058W | SEQ ID NO: 11 | SNP Marker | T | A | 1279994 |
| PM01-00002MH | SEQ ID NO: 12 | SNP Marker | T | C | 3248271 |

TABLE 3

Primers and Probes for Markers for QTL Mapping

| Marker Name | Forward Primer (5'-3') | Reverse Primer (5'-3') | Probe | Type | Resistant | Susceptible | B73v4 SNP Position |
|---|---|---|---|---|---|---|---|
| SOURST-83_1314662 | SEQ ID NO: 13 | SEQ ID NO: 14 | SEQ ID NO: 15 | KASP Marker | G | A | 1546133 |
| SOURST-83_2036602 | SEQ ID NO: 16 | SEQ ID NO: 17 | SEQ ID NO: 18 | KASP Marker | A | T | 2537720 |

To identify genes in the qSCR4.01 QTL interval, the CIMBL83 genome was sequenced. RNA-seq data from infected and non-infected leaf tissues were generated to facilitate gene annotation and expression analysis. In CIMBL83, the qSCR4.01 interval between SOURST-83_1314662 and SOURST-83_2036602 is approximately 668 kb. Two R genes were annotated within the interval. The leading candidate gene, NLR01, appears to be a fusion of three NLRs with multiple transcriptional start sites which result in a single NLR (NLR01-1, SEQ ID NO: 7), 2-NLR fusion (NLR01-2, SEQ ID NO: 6), and a 3-NLR fusion (NLR01-3, SEQ ID NO: 5). The second gene, NLR02 (SEQ ID NO: 8), has an NB-ARC domain but lacks a leucine-rich repeat domain. Through Iso-Seq (Full-Length Isoform Sequencing) and additional RNA-seq, more NLR01 transcript isoforms were identified (SEQ ID NO 33-58).

TABLE 4

Candidate R Gene Sequences

| SEQ ID NO: | Description of SEQ ID NO: |
|---|---|
| 1 | NLR01-3 CDS |
| 2 | NLR01-2 CDS |
| 3 | NLR01-1 CDS |
| 4 | NLR02 CDS |
| 5 | NLR01-3 Amino Acid |
| 6 | NLR01-2 Amino Acid |
| 7 | NLR01-1 Amino Acid |
| 8 | NLR02 Amino Acid |
| 33 | NLR01-4_CDS |
| 34 | NLR01-5_CDS |
| 35 | NLR01-6_CDS |
| 36 | NLR01-7_CDS |
| 37 | NLR01-8_CDS |
| 38 | NLR01-9_CDS |
| 39 | NLR01-10_CDS |
| 40 | NLR01-11_CDS |
| 41 | NLR01-12_CDS |
| 42 | NLR01-13_CDS |
| 43 | NLR01-14_CDS |
| 44 | NLR01-15_CDS |
| 45 | NLR01-16_CDS |
| 46 | NLR01-4_protein |
| 47 | NLR01-5_protein |
| 48 | NLR01-6_protein |
| 49 | NLR01-7_protein |
| 50 | NLR01-8_protein |
| 51 | NLR01-9_protein |
| 52 | NLR01-10_protein |
| 53 | NLR01-11_protein |
| 54 | NLR01-12_protein |
| 55 | NLR01-13_protein |
| 56 | NLR01-14_protein |
| 57 | NLR01-15_protein |
| 58 | NLR01-16_protein |

Primers were designed in our mapping interval based on SNPs from various maize lines. Primer Picker was used to design primers for KASP markers. Several SNPs were able to distinguish between the resistant and susceptible genotypes in our mapping population. These markers were used to narrow the chromosomal interval. To get the CIMBL83 haplotype, after the CIMBL83 genome sequence was obtained, the primers sequences for the KASP markers were used for mapping to the CIMBL83 genome sequence. The SNP present in CIMBL83 was recorded as the resistant allele. The other SNP as assayed by the KASP primers as the susceptible allele. Table 5 shows the KASP markers for the CIMBL83 resistant haplotype.

TABLE 5

CIMBL83 QTL and Fine Mapping Markers

| Marker | Chromosome | B73 v4 Pos | CIMBL83 | Susceptible | Reference Sequence SEQ ID NO: |
|---|---|---|---|---|---|
| PM01-000058W | Chr4 | 1279994 | T | A | 11 |
| SOURST-83_1284720 | Chr4 | 1518539 | G | A | 21 |
| SOURST-83_1314662 | Chr4 | 1546133 | C | T | 19 |
| SOURST-83_1542053 | Chr4 | 1751040 | T | G | 22 |
| PZE-104005694 | Chr4 | 1768240 | A | G | 23 |
| SOURST-83_1II | Chr4 | 1785157 | C | T | 24 |
| SOURST-83_1936804 | Chr4 | 2462979 | C | G | 32 |
| PZE-104001404 | Chr4 | 2432052 | G | A | 25 |
| SOURST-83_1926276 | Chr4 | 2430969 | C | T | 26 |
| SOURST-83_1652968 | Chr4 | 1864853 | G | C | 27 |
| SOURST-83_2036602 | Chr4 | 2537720 | A | T | 20 |
| SOURST-83_2035716 | Chr4 | 2538606 | T | C | 28 |
| PZE-104001592 | Chr4 | 2541019 | T | C | 29 |
| SOURST-83_2465654 | Chr4 | 3000813 | G | A | 30 |
| SOURST-83_2679982 | Chr4 | 3227087 | T | C | 31 |

Example 3. Transgenic Validation of SCR Resistance Causal Gene

The genomic sequence of the whole NLR01 fragment (SEQ ID NO 9), as well as NLR01-1. NLR01-2 and NLR01-3 gene (including the promoter region) is synthesized and cloned into a binary vector for transformation in HC69. Single copy quality events are crossed to PHR03 to generate segregating T1 seeds. T1 plants are inoculated with the Puccinia polysora urediospores and kept in the greenhouse for 10 days. Greenhouse disease scoring is done visually as susceptible (S) or resistant (R) based on presence or absence of erupted uredia (a sporulating pustule), respectively. About 30 T1 plants with a single copy of transgene and 30 T1 plants without the transgene, all from the same 6 events, are tested for SCR resistance in the greenhouse. All the 30 transgene positive plants are expected to give the resistant phenotype, while all the transgene negative plants are expected to score as susceptible.

What is claimed is:

1. A method of producing a plant with a haplotype associated with increased resistance to southern corn rust, said method comprising: a) crossing a first maize plant and second maize plant to produce progeny plants, wherein the first maize plant comprises an interval on chromosome 4 comprising a haplotype associated with increased resistance to southern corn rust wherein said haplotype comprises a "T" at position 99 of SEQ ID NO: 11, a "G" at position 51 of SEQ ID NO: 21, a "C" at position 24 of SEQ ID NO: 19, a "T" at position 51 of SEQ ID NO: 22, an "A" at position 25 of SEQ ID NO: 23, a "C" at position 32 of SEQ ID NO: 24, a "C" at position 30 of SEQ ID NO: 32, a "G" at position 26 of SEQ ID NO: 25, a "C" at position 26 SEQ ID NO: 26, a "G" at position 26 SEQ ID NO: 27, an "A" at position 24 of SEQ ID NO: 20, a "T" position 35 of SEQ ID NO: 28, a "T" at position 46 of SEQ ID NO: 29, a "G" at position 51 of SEQ ID NO: 30, and a "T" at position 26 of SEQ ID NO: 31; and b) screening said progeny plants for the presence of the haplotype associated with increased resistance to southern corn rust; and c) selecting said progeny plants having the haplotype associated with increased resistance to southern corn rust.

2. The method of claim 1, further comprising counter-selecting progeny plants that do not have the haplotype associated with increased resistance to southern corn rust.

3. The method of claim 1, wherein screening said progeny plants for the presence of the haplotype comprises: detecting in the genome of said progeny plants a polynucleotide encoding a polypeptide having the amino acid sequence set forth in SEQ ID NO: 7 and selecting said progeny plants comprising said polynucleotide.

* * * * *